US012735498B2

(12) United States Patent
Beaumont et al.

(10) Patent No.: US 12,735,498 B2
(45) Date of Patent: Sep. 15, 2026

(54) EPITHELIAL CADHERIN-SPECIFIC ANTIBODIES

(71) Applicant: Kling Biotherapeutics B.V., Amsterdam (NL)

(72) Inventors: Tim Beaumont, Ouderkerk aan de Amstel (NL); Sabrina Julia Louisa Merat, 's-Hertogenbosch (NL); Mark Jeroen Kwakkenbos, Amsterdam (NL); Martijn Kedde, Amsterdam (NL); Hergen Spits, Bergen (NL)

(73) Assignee: Kling Biotherapeutics B.V., Amsterdam (NL)

( * ) Notice: Subject to any disclaimer, the term of this patent is extended or adjusted under 35 U.S.C. 154(b) by 1063 days.

(21) Appl. No.: 17/789,940

(22) PCT Filed: Jan. 8, 2021

(86) PCT No.: PCT/NL2021/050009

§ 371 (c)(1), (2) Date: Jun. 29, 2022

(87) PCT Pub. No.: WO2021/141492

PCT Pub. Date: Jul. 15, 2021

(65) Prior Publication Data

US 2024/0317880 A1 Sep. 26, 2024

(30) Foreign Application Priority Data

Jan. 10, 2020 (EP) .................................... 20151325

(51) Int. Cl.

| | |
|---|---|
| ***C07K 16/28*** | (2006.01) |
| ***A61K 39/00*** | (2006.01) |
| ***A61K 39/395*** | (2006.01) |
| ***A61K 47/68*** | (2017.01) |
| ***A61P 35/00*** | (2006.01) |
| ***C07K 16/22*** | (2006.01) |
| ***C12N 5/0783*** | (2010.01) |

(52) U.S. Cl.

CPC ...... *C07K 16/2896* (2013.01); *A61K 47/6803* (2017.08); *C07K 16/22* (2013.01); *C07K 16/2809* (2013.01); *C12N 5/0636* (2013.01); *A61K 2039/505* (2013.01); *C07K 2317/24* (2013.01); *C07K 2317/31* (2013.01); *C07K 2317/34* (2013.01); *C07K 2317/41* (2013.01); *C07K 2317/52* (2013.01); *C07K 2317/55* (2013.01); *C07K 2317/565* (2013.01); *C07K 2317/77* (2013.01); *C07K 2317/92* (2013.01)

(58) Field of Classification Search

CPC .......... A61K 47/6803; A61K 2039/505; A61K 39/395; C07K 2317/55; C07K 2317/565

See application file for complete search history.

(56) References Cited

U.S. PATENT DOCUMENTS

| | | | |
|---|---|---|---|
| 4,681,581 | A | 7/1987 | Coates |
| 4,735,210 | A | 4/1988 | Goldenberg |
| 5,101,827 | A | 4/1992 | Goldenberg |
| 5,102,990 | A | 4/1992 | Rhodes |
| 5,648,471 | A | 7/1997 | Buttram et al. |
| 5,697,902 | A | 12/1997 | Goldenberg |
| 9,534,058 | B2 | 1/2017 | Stull et al. |
| 2015/0337048 | A1 | 11/2015 | Stull et al. |

FOREIGN PATENT DOCUMENTS

| | | | |
|---|---|---|---|
| CN | 105848671 | A | 8/2016 |
| CN | 108738324 | A | 11/2018 |
| EP | 2634194 | A1 | 4/2013 |
| JP | 2018070589 | A | 5/2018 |
| WO | 2010087994 | A2 | 8/2010 |
| WO | 2011157741 | A2 | 12/2011 |
| WO | 2012058418 | A2 | 5/2012 |
| WO | 2013081463 | A2 | 6/2013 |
| WO | 2013138790 | A1 | 9/2013 |
| WO | 2015093949 | A2 | 6/2015 |
| WO | 2018190719 | A2 | 10/2018 |
| WO | 2018210793 | A2 | 11/2018 |

OTHER PUBLICATIONS

Oosterhoff et al. Trends in Immunology. 43(10): 800-814; Published: Aug. 22, 2022 (Year: 2002).*
Damschroder et al. Molecular Immunology. 41(10): 985-1000; Published: Aug. 2004 (Year: 2004).*
Rudikoff et al. Proc. Nat.l Acad. Sci. U.S.A. 79(6): 1979-1983; Published: Mar. 1982 (Year: 1982).*
MacCallum et al. Journal of Molecular Biology. 262: 732-745; Published: 1996 (Year: 1996).*
Casset et al. Biochemical and Biophysical Research Communications. 307: 198-205; Published: 2003 (Year: 2003).*
Vajdos et al. Journal of Molecular Biology. 320: 415-428; Published: 2002 (Year: 2002).*
Wu et al. Journal of Molecular Biology. 294: 151-162; Published: 1999 (Year: 1999).*
Padlan et al. PNAS. 86: 5938-5942; Published: 1989 (Year: 1989).*
Lamminmaki et al. JBC. 276: 36687-36694; Published: 2001 (Year: 2001).*
Murphy et al. Journal of Immunological Methods. 463: 127-133; Published: Oct. 12, 2018 (Year: 2018).*
Lommel et al. PNAS. 110(52): 21024-21029; Published: Dec. 24, 2013 (Year: 2013).*
Larsen et al. Current Opinion in Structural Biology. 56: 171-178; Published: Apr. 15, 2019 (Year: 2019).*
Carvalho et al. Oncotarget. 7(40): 65231-65246: Published: Aug. 12, 2016 (Year: 2016).*
Matsuyoshi et al. Biochemical and Biophysical Research Communications. 235(2): 355-358; Published: Jun. 18, 1997 (Year: 1997).*
Pitot et al. Cancer. 73(3): 962-970; Published: Aug. 1, 1993 (Year: 1993).*

(Continued)

*Primary Examiner* — Juliet C Switzer
*Assistant Examiner* — Katherine Ann Holtzman
(74) *Attorney, Agent, or Firm* — Adams & Reese, LLP

(57) ABSTRACT

The present invention relates to epithelial cadherin-specific antibodies, as well as uses thereof in the diagnosis and treatment of diseases such as cancer.

27 Claims, 27 Drawing Sheets

Figure 2A:
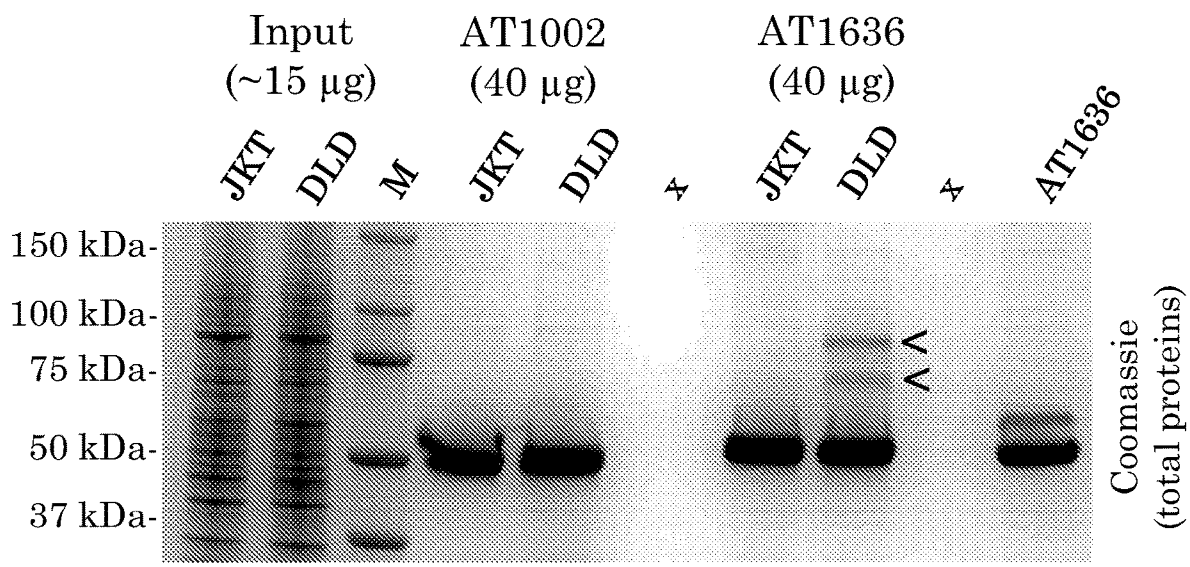

Specification includes a Sequence Listing.

(56) References Cited

OTHER PUBLICATIONS

Hanahan et al. Cell. 144(5): 646-674; Published: Mar. 4, 2011 (Year: 2011).*
Larsen et al. PNAS. 114(42): 11163-11168; Published: Oct. 17, 2017 (Year: 2017).*
Junghans et al., "Antibodies", Cancer Chemotherapy and Biotherapy: Principles and Practice, 5th Edition, Chapter 25, pp. 1-63 (2011).
Kedde, M. et al., "Abstract 5163: A colon cancer survivor-derived antibody recognizes a previously unidentified truncated, O-mannosylated 70kDa variant of E-cadherin", Cancer Res., (2020), 80 (16_Supplement); doi.org/10.1158/1538-7445.AM2020-5163.
Kedde, M. et al., "A colon cancer survivor-derived antibody recognizes a previously unidentified truncated, O-mannosylated 70kDa variant of E-cadherin", AACR Cancer Therapeutic Targets poster #5163, (2020), Originally published online at www.globenewswire.com/news-release/2020/06/22/2051291/0/en/AIMM-Therapeutics-Presents-Preclinical-Data-on-its-Four-Oncology-Therapies-at-AACR-s-Annual-Meeting-Session-on-Antibody-Technologies.html.
Brouxhon et al., "Monoclonal Antibody against the Ectodomain of E-Cadherin (DECMA-1) Suppresses Breast Carcinogenesis: Involvement of HER/PI3K/Akt/mTOR and IAP Pathways", Clinical Cancer Research, Jun. 15, 2013 American Association for Cancer Research, (2013) US-ISSN 1078-0432, vol. 19, Nr:12, pp. 3234-3246.
Aiello et al., "EMT Subtype Influences Epithelial Plasticity and Mode of Cell Migration", Developmental Cell 2018; 45:681-695.
Atwell et al., "Stable heterodimers from remodeling the domain interface of a homodimer using a phage display library", Journal of Molecular Biology 1997; 270: 26-35.
Baeuerle et al., "Synthetic TRUC receptors engaging the complete T cell receptor for potent anti-tumor response", Nature Communications (2019)10: 2087, 12 pages.
Barretina et al., "The Cancer Cell Line Encyclopedia enables predictive modelling of anticancer drug sensitivity", Nature 2012; 483: 603-607.
Bartels et al., "Protein O-mannosylation in the murine brain: Occurrence of mono-O-mannosyl glycans and identification of new substrates", PLoS One 11:e0166119; (2016) 23 pages.
Bartels et al., "A Chemo-enzymatically Linked Bispecific Antibody Retargets T Cells to a Sialylated Epitope on CD43 in Acute Myeloid Leukemia", Cancer Research 2019; 79: 3372-3382.
Bartels et al., "Preparation of bispecific antibody-protein adducts by site-specific chemo-enzymatic conjugation", Methods 154 (2019) 93-101.
Carvalho et al., "O-mannosylation and N-glycosylation: Two coordinated mechanisms regulating the tumour suppressor functions of E-cadherin in cancer", Oncotarget 7:65231-65246 (2016).
Chau et al., "Antibody-drug conjugates for cancer", Lancet 2019: 394: 793-804.
Chen et al., "Selection and Analysis of an Optimized Anti-VEGF Antibody: Crystal Structure of an Affinity-matured Fab in Complex with Antigen", J. Mol. Biol. 293:865-881 (1999).
De Jong et al., "A Novel Platform for the Potentiation of Therapeutic Antibodies Based on Antigen-Dependent Formation of IgG Hexamers at the Cell Surface", PLoS Biol 14(1), 24 pages (2016).
Gauthier et al., "Multifunctional Natural Killer Cell Engager Targeting NKp46 Trigger Protective Tumor Immunity", 2019) Cell 177, 1701-1713.
De Groot et al., "De-immunization of Therapeutic Proteins by T-cell Epitope Modification", (2005) Dev. Biol. 122: 171-194.
Guedan et al., "Engineering and Design of Chimeric Antigen Receptors", (2019) Molecular Therapy: Methods & Clinical Development. vol. 12: 145-156.
Hanly et al., "Review of Polyclonal Antibody Production Procedures in Mammals and Poultry", (1995) ILAR Journal. 37(3): 93-118.
Idusogie et al., "Engineered Antibodies with Increased Activity to Recruit Complement", (2001) J. Immunol. 166: 2571-2575.
Ovid: Cancer Chemotherapy and Biotherapy: Principles and Practice, 5th Edition, Junghans et al., Chapter 25: Antibodies, 2011; pp. 465-494, Retrieved from ovidsp.dc1.ovid.com/ovid-b/ovidweb.cgi.
Kwakkenbos et al., "Genetic manipulation of B cells for the isolation of rare therapeutic antibodies from the human repertoire", Methods 2013; 1-6.
Larsen et al., "Discovery of an O-mannosylation pathway selectively serving cadherins and protocadherins", Proc Natl Acad Sci USA 2017; 114: 11163-11168.
Lazar et al., "Engineered antibody Fc variants with enhanced effector function", (2006) Proc. Natl. Acad. Sci. USA 103: 4005-4010.
Lommel et al., "Protein O-mannosylation is crucial for E-cadherin-mediated cell adhesion", Proc Natl Acad Sci USA 110:21024-21029 (2013).
Lund et al., "Multiple binding sites on the CH2 domain of IgG for Mouse FcyR11", (1992) Mol. Immunol. 29: 53-59.
Merchant et al., "An efficient route to human bispecific IgG", Nature Biotechnology, (1998); 16: 677-681.
Moore et al., "Engineered Fc variant antibodies with enhanced ability to recruit complement and mediate effector functons", (2010) MAbs 2(2): 181-189.
Padmanaban et al., "E-cadherin is required for metastasis in multiple models of breast cancer", Nature 2019; 1-31.
Patnaik et al., "Lectin-Resistant CHO Glycosylation Mutants", (2006) Methods Enzymol. 416: 159-182.
Racapé et al., "The Involcement of SMILE/TMTC3 in Endoplasmic Reticulum Stress Response", PLoS ONE (2011); 6: e19321, 11 pages.
Rafiq et al., "Engineering strategies to overcome the current roadblocks in CAR T cell therapy", Nature Reviews, Clinical Oncology, vol. 17, (2020) pp. 147-167.
Shields et al., "High resolution mapping of the binding site on human IgG1 for FcγRI, FcγRII, FcγRIII, and FcRn and design of IgG1 variants with improved binding to the FcγR", (2001) J. Biol Chem 276: 6591-6604.
Stravenhagen et al., "Fc Optimization of Therapeutic Antibodies Enhances Their Ability to Kill Tumor Cells In vitro and Controls Tumor Expansion In vivo via Low-Affinity Activating Fcγ Receptors", (2007) Cancer Res. 67: 8882-8890.
Sunryd et al., "TMTC1 and TMTC2 are novel endoplasmic reticulum tetratricopeptide repeat-containing adapter proteins involved in calcium homeostasis", Journal of Biological Chemistry 2014; 289: 16085-16099.
Suurs et al., "A review of bispecific antibodies and antibody constructs in oncology and clinical challenges", (2019) Pharmacology & Therapeutics 201: 103-119.
Tauriello et al., "TGFβ drives immune evasion in genetically reconstituted colon cancer metastasis", Nature (2018);554: 538-543.
Tsuchikama et al., "Antibody-drug conjugates: recent advances in conjugation and linker chemistries", (2018). Protein Cell 9(1):33-46.
Vester-Christensen et al., "Mining the O-mannose glycoproteome reveals cadherins as major O-mannosylated glycoproteins", Proc Natl Acad Sci USA 2013; 110: 21018-21023.
Yamane-Ohnuki et al., "Establishment of FUT8 knockout Chinese hamster ovary cells: An ideal host cell line for producing completely defucosylated antibodies with enhanced antibody-dependent cellular cytotoxicity", Biotechnology and Bioengineering, 87: 614-622.
First office action dated Jan. 25, 2025 received for related Japanese patent application 2022-542247; English Translation Ref. No. F88162A1 Mailing No. 023144 Mailing Date: Jan. 25, 2025.
First office action dated Jun. 27, 2025 received for related Chinese patent application 202211674336.7; English Translation Issue serial No. 2025062700338460 Issue Date: Jun. 27, 2025.

* cited by examiner

| 10 | 20 | 30 | 40 | 50 |
|---|---|---|---|---|
| MGPWSRSLSA | LLLLLQVSSW | LCQEPEPCHP | GFDAESYTFT | VPRRHLERGR |
| 60 | 70 | 80 | 90 | 100 |
| VLGRVNFEDC | TGRQRTAYFS | LDTRFKVGTD | GVITVKRPLR | FHNPQIHFLV |
| 110 | 120 | 130 | 140 | 150 |
| YAWDSTYRKF | STKVTLNTVG | HHHRPPPHQA | SVSGIQAELL | TFPNSSPGLR |
| 160 | 170 | 180 | 190 | 200 |
| RQKRDWVIPP | ISCPENEKGP | FPKNLVQIKS | NKDKEGKVFY | SITGQGADTP |
| 210 | 220 | 230 | 240 | 250 |
| PVGVFIIERE | TGWLKVTEPL | DRERIATYTL | FSHAVSSNGN | AVEDPMEILI |
| 260 | 270 | 280 | 290 | 300 |
| TVTDQNDNKP | EFTQEVFKGS | VMEGALPGTS | VMEVTATDAD | DDVNTYNAAI |
| 310 | 320 | 330 | 340 | 350 |
| AYTILSQDPE | LPDKNMFTIN | RNTGVISVVT | TGLDRESFPT | YTLVVQAADL |
| 360 | 370 | 380 | 390 | 400 |
| QGEGLSTTAT | AVITVTDTND | NPPIFNPTTY | KGQVPENEAN | VVITTLKVTD |
| 410 | 420 | 430 | 440 | 450 |
| ADAPNTPAWE | AVYTILNDDG | GQFVVTTNPV | NNDGILKTAK | GLDFEAKQQY |
| 460 | 470 | 480 | 490 | 500 |
| ILHVAVTNVV | PFEVSLTTST | ATVTVDVLDV | NEAPIFVPPE | KRVEVSEDFG |
| 510 | 520 | 530 | 540 | 550 |
| VGQEITSYTA | QEPDTFMEQK | ITYRIWRDTA | NWLEINPDTG | AISTRAELDR |
| 560 | 570 | 580 | 590 | 600 |
| EDFEHVKNST | YTALIIATDN | GSPVATGTGT | LLLILSDVND | NAPIPEPRTI |
| 610 | 620 | 630 | 640 | 650 |
| FFCERNPKPQ | VINIIDADLP | PNTSPFTAEL | THGASANWTI | QYNDPTQESI |
| 660 | 670 | 680 | 690 | 700 |
| ILKPKMALEV | GDYKINLKLM | DNQNKDQVTT | LEVSVCDCEG | AAGVCRKAQP |
| 710 | 720 | 730 | 740 | 750 |
| VEAGLQIPAI | LGILGGILAL | LILILLLLLF | LRRRAVVKEP | LLPPEDDTRD |
| 760 | 770 | 780 | 790 | 800 |
| NVYYYDEEGG | GEEDQDFDLS | QLHRGLDARP | EVTRNDVAPT | LMSVPRYLPR |
| 810 | 820 | 830 | 840 | 850 |
| PANPDEIGNF | IDENLKAADT | DPTAPPYDSL | LVFDYEGSGS | EAASLSSLNS |
| 860 | 870 | 880 | | |
| SESDKDQDYD | YLNEWGNRFK | KLADMYGGGE | DD | |

Fig. 1A

Signal peptide:
MGPWSRSLSALLLLLQVSSWLCQEPEP

Precursor sequence:
CHPGFDAESYTFTVPRRHLERGRVLGRVNFEDCTGRQRTAYFSLDTRFKVGTDGVIT
VKRPLRFHNPQIHFLVYAWDSTYRKFSTKVTLNTVGHHHRPPPHQASVSGIQAELLT
FPNSSPGLRRQKR EC1 domain:
DWVIPPISCPENEKGPFPKNLVQIKSNKDKEGKVFYSITGQGADTPPVGVFIIERETGW
LKVTEPLDRERIATYTLFSHAVSSNGNAVEDPMEILITVTDQNDNKPEF EC2 domain:
TQEVFKGSVMEGALPGTSVMEVTATDADDDVNTYNAAIAYTILSQDPELPDKNMFT
INRNTGVISVVTTGLDRESFPTYTLVVQAADLQGEGLSTTATAVITVTDTNDNPPIF EC3 domain:
NPTTYKGQVPENEANVVITTLKVTDADAPNTPAWEAVYTILNDDGGQFVVTTNPVN
NDGILKTAKGLDFEAKQQYILHVAVTNVVPFEVSLTTSTATVTVDVLDVNEAPIF EC4 domain:
VPPEKRVEVSEDFGVGQEITSYTAQEPDTFMEQKITYRIWRDTANWLEINPDTGAIST
RAELDREDFEHVKNSTYTALIIATDNGSPVATGTGTLLLILSDVNDNAPIP EC5 domain:
EPRTIFFCERNPKPQVINIIDADLPPNTSPFTAELTHGASANWTIQYNDPTQESIILKPK
MALEVGDYKINLKLMDNQNKDQVTTLEVSVCDCEGAAGVCRKAQPVEAGL TM domain:
QIPAILGILGGILALLILILLLLLFL Cytoplasmic domain 1:
RRRAVVKEPLLPPEDDTRDNVYYYDEEGGGEEDQDFDLSQLHRGLDARPEVTRNDV
APTLMSVPRYLPRPA Cytoplasmic domain 2:
NPDEIGNFIDENLKAADTDPTAPPYDSLLVFDYEGSGSEAASLSSLNSSESDKDQDYD
YLNEWGNRFKKLADMYGGGEDD

Fig. 1B

EVSLTTSTATVTVDVLDVNEAPIFVPPEKRVEVSEDFG
VGQEITSYTAQEPDTFMEQKITYRIWRDTANWLEIN
PDTGAISTRAELDREDFEHVKNSTYTALIIATDNGSPV
ATGTGTLLLILSDVNDNAPIPEPRTIFFCERNPKPQVIN
IIDADLPPNTSPFTAELTHGASANWTIQYNDPTQESII
LKPKMALEVGDYKINLKLMDNQNKDQVTTLEVSVC
DCEGAAGVCRKAQPVEAGL*QIPAILGILGGILALLILILL*
*LLLFL*RRRAVVKEPLLPPEDDTRDNVYYYDEEGGGEE
DQDFDLSQLHRGLDARPEVTRNDVAPTLMSVPRYL
PRPANPDEIGNFIDENLKAADTDPTAPPYDSLLVFDY
EGSGSEAASLSSLNSSESDKDQDYDYLNEWGNRFKK
LADMYGGGEDD

Fig. 1C

A431 d7 fibro
TGFß AT1636IYN

A431 d7 fibro
TGFß

EPITHELIAL CADHERIN-SPECIFIC ANTIBODIES

FIELD OF THE INVENTION

The present invention relates to the fields of biology, medicine and immunology.

BACKGROUND OF THE INVENTION

The transmembrane protein epithelial cadherin (E-cadherin; also referred to as, amongst other things, CD324, cadherin-1, CAM 120/80 and uvomorulin), is a member of the cadherin superfamily. E-cadherin is known in the art as a calcium-dependent cell-cell adhesion glycoprotein with a molecular weight of about 120 kDa, composed of five extracellular cadherin (EC) repeats (EC1-EC5), a transmembrane region and a highly conserved cytoplasmic tail. E-cadherin is an important type of cell-cell adhesion protein to hold epithelial cells tight together. E-cadherin downregulation decreases the strength of cellular adhesion within a tissue, which may result in an increase in cellular motility and epithelial-mesenchymal transition (EMT). Loss of E-cadherin function or expression has been implicated in cancer progression and metastasis.

SUMMARY OF THE INVENTION

In a first aspect, the invention provides E-cadherin specific antibodies and antigen binding fragments thereof comprising the structural and functional features specified herein.

In various embodiments, the invention provides an antibody or antigen binding fragment thereof that specifically binds one or more O-mannosylated threonine residues of E-cadherin, wherein said one or more O-mannosylated threonine residues are present within amino acid positions 467-472 of the E-cadherin sequence as depicted in FIG. 1A. In preferred embodiments, the binding of said antibody or antigen binding fragment to said E-cadherin is influenced by the presence of an O-mannosylated threonine residue at position 467, an O-mannosylated threonine residue at position 468, an O-mannosylated threonine residue at position 470, an O-mannosylated threonine residue at position 472, the glutamic acid residue at position 463, the serine residue at position 465, the serine residue at position 469, and/or the valine residue at position 477, of the E-cadherin sequence as depicted in FIG. 1A, particularly on the presence of an O-mannosylated threonine residue at position 467 and/or an O-mannosylated threonine residue at position 468 and/or an O-mannosylated threonine residue at position 470 of the E-cadherin sequence as depicted in FIG. 1A. In some embodiments, said serine residue at position 465 and/or 469 is O-mannosylated. In preferred embodiments, said antibody or antigen binding fragment binds O-mannosylated truncated 70 kDa E-cadherin better than O-mannosylated full length E-cadherin. In preferred embodiments, said antibody or antigen binding fragment binds O-mannosylated truncated 70 kDa E-cadherin at least 2 fold better, more preferably at least 3 fold better, more preferably at least 4 fold better, more preferably at least 5 fold better, than O-mannosylated full length E-cadherin.

In various embodiments, the invention provides an antibody or antigen binding fragment thereof that is able to bind O-mannosylated E-cadherin, wherein said antibody or antigen binding fragment comprises one or more, and optionally each, of:

a. a heavy chain variable region CDR1 comprising the amino acid sequence GF$X_1$FS$X_2$AW (SEQ ID NO:59), wherein $X_1$ is T or I and wherein $X_2$ is N or Y;

or a heavy chain variable region CDR1 comprising an amino acid sequence differing from said GF$X_1$FS$X_2$AW sequence by 1, 2 or 3 conservative substitutions;

b. a heavy chain variable region CDR2 comprising the amino acid sequence IKSKIDG XT $X_2$, (SEQ ID NO:60), wherein $X_1$ is G or E and wherein $X_2$ is T or I;

or a heavy chain variable region CDR2 comprising an amino acid sequence differing from said IKSKIDG $X_1$T $X_2$ sequence by 1, 2 or 3 conservative substitutions;

c. a heavy chain variable region CDR3 comprising the amino acid sequence TPGVG$X_1$N$X_2$PYYFDR (SEQ ID NO:61), wherein $X_1$ is A or T and wherein $X_2$ is D or N;

or a heavy chain variable region CDR3 comprising an amino acid sequence differing from said TPGVG$X_1$N$X_2$PYYFDR sequence by 1, 2 or 3 conservative substitutions;

d. a light chain variable region CDR1 comprising the amino acid sequence QSVLCRSNNKNC (SEQ ID NO:62);

or a light chain variable region CDR1 comprising an amino acid sequence differing from said QSVLCRSNNKNC sequence by 1, 2 or 3 conservative substitutions;

e. a light chain variable region CDR2 comprising the amino acid sequence WA$X_1$, wherein $X_1$ is S or C;

or a light chain variable region CDR2 comprising an amino acid sequence differing from said WA$X_1$ sequence by 1, 2 or 3 conservative substitutions;

f. a light chain variable region CDR3 comprising the amino acid sequence QQYSNTPQT (SEQ ID NO:63);

or a light chain variable region CDR3 comprising an amino acid sequence differing from said QQYSNTPQT sequence by 1, 2 or 3 conservative substitutions.

In certain embodiments, the antibody or antigen binding fragment comprises a heavy chain variable region comprising a sequence having at least 80% sequence identity with a VH sequence selected from the group consisting of SEQ ID NOs: 1-17; and/or a light chain variable region comprising a sequence having at least 80% sequence identity with a VL sequence selected from the group consisting of SEQ ID NOs: 18-22, as depicted in Table 1. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions.

In various embodiments an antibody or antigen binding fragment according to the present invention is a full length antibody.

In various embodiments an antibody or antigen binding fragment according to the present invention is a human antibody or an antigen binding fragment thereof.

In various embodiments an antibody or antigen binding fragment according to the present invention is of the IgA isotype. In various embodiments an antibody or antigen binding fragment according to the present invention is of the IgM isotype. In various embodiments an antibody or antigen binding fragment according to the present invention is of the IgD isotype. In certain embodiments the antibody or antigen binding fragment is a human IgA, IgM or IgD.

In various embodiments an antibody or antigen binding fragment according to the present invention is of the IgG isotype. In certain embodiments the antibody or antigen binding fragment is an IgG1, IgG2, IgG3 or IgG4, preferably an IgG1. In certain embodiments the antibody or antigen binding fragment is a human IgG1, IgG2, IgG3 or IgG4, preferably a human IgG1.

In various embodiments an antibody or antigen binding fragment according to the present invention is afucosylated.

Certain embodiments provide an antibody or antigen binding fragment thereof that competes with an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN for binding to O-mannosylated E-cadherin, preferably to O-mannosylated truncated 70 kDa E-cadherin.

In certain embodiments, an antibody or antigen binding fragment according to the present invention has one or more, and preferably each of, the following characteristics:

- binds to the extracellular 3 (EC3) domain of O-mannosylated E-cadherin;
- binds O-mannosylated truncated 70 kDa E-cadherin better, preferably at least 2 fold better, more preferably at least 3 fold better, more preferably at least 4 fold better, more preferably at least 5 fold better, than O-mannosylated full length E-cadherin; and
- binds tumor cells that co-express E-cadherin and an O-mannosyltransferase, preferably TMTC3.

In some embodiments, said antibody or antigen binding fragment further comprises at least one of the following characteristics:

- binds colon cancer subtypes CMS1, CMS2, CMS3 and CMS4;
- binds colon carcinoma cell line SW948 better than healthy medullary thymic epithelial cells or dendritic cells or Langerhans cells.

In certain embodiments, an antibody or antigen binding fragment according to the invention is coupled to another compound. In certain embodiments, said other compound is a therapeutic compound. In certain embodiments, said other compound is a compound selected from the group consisting of an immunomodulatory compound, a T cell-binding compound, a natural killer cell (NK cell)-binding compound, a natural killer T cell (NKT cell)-binding compound, a gamma-delta T cell-binding compound, a CD3-specific binding compound, a TGFβ-specific binding compound, a cytokine, a second antibody or antigen binding part thereof, a detectable label, a drug, a chemotherapeutic drug, a cytotoxic agent, a toxic moiety, a hormone, an enzyme and a radioactive compound. In some embodiments, said immunomodulatory compound is not the Fc tail of an antibody according to the invention. In some embodiments, said immunomodulatory compound is a non-natural immunomodulatory compound.

An antibody or antigen binding fragment according to the invention that is directly or indirectly coupled to a therapeutic compound is also referred to herein as an antibody-drug conjugate (ADC) according to the invention.

The invention also provides a bispecific or multispecific binding compound, preferably a bispecific or multispecific antibody or antigen binding fragment thereof, that is able to bind O-mannosylated E-cadherin, comprising:

- an antibody or antigen binding fragment according to the invention; and
- an immunomodulatory compound.

In some embodiments, said immunomodulatory compound is not the Fc tail of an antibody according to the invention. In some embodiments, said immunomodulatory compound is a non-natural immunomodulatory compound.

The invention also provides a bispecific or multispecific binding compound, preferably a bispecific or multispecific antibody or antigen binding fragment thereof, that is able to bind O-mannosylated E-cadherin, comprising:

- an antibody or antigen binding fragment according to the invention; and
- a T cell-binding compound or a natural killer cell (NK cell)-binding compound or a natural killer T cell (NKT cell)-binding compound or a gamma-delta T cell-binding compound.

The invention also provides a bispecific or multispecific binding compound, preferably a bispecific or multispecific antibody or antigen binding fragment thereof, that is able to bind O-mannosylated E-cadherin, comprising:

- an antibody or antigen binding fragment according to the invention; and
- a CD3-specific binding compound.

The invention also provides a bispecific or multispecific binding compound, preferably a bispecific or multispecific antibody or antigen binding fragment thereof, that is able to bind O-mannosylated E-cadherin, comprising:

- an antibody or antigen binding fragment according to the invention; and
- a KLRG1-specific binding compound.

The invention also provides a bispecific or multispecific binding compound, preferably a bispecific or multispecific antibody or antigen binding fragment thereof, that is able to bind O-mannosylated E-cadherin, comprising:

- an antibody or antigen binding fragment according to the invention; and
- a CD103-specific binding compound.

The invention also provides a bispecific or multispecific binding compound, preferably a bispecific or multispecific antibody or antigen binding fragment thereof, that is able to bind O-mannosylated E-cadherin, comprising:

- an antibody or antigen binding fragment according to the invention; and
- a TGFβ-specific binding compound.

Also provided is a bispecific antibody or antigen binding fragment thereof that is able to bind O-mannosylated E-cadherin, comprising:

- one Fab fragment of an antibody or antigen binding fragment according to the invention; and
- one Fab fragment of another antibody, preferably specific for a T cell, an NK cell, an NKT cell or a gamma-delta T cell.

Also provided is a bispecific antibody or antigen binding fragment thereof that is able to bind O-mannosylated E-cadherin, comprising:

- one Fab fragment of an antibody or antigen binding fragment according to the invention; and
- one Fab fragment of another antibody that is specific for CD3.

Also provided is a bispecific antibody or antigen binding fragment thereof that is able to bind O-mannosylated E-cadherin, comprising:

one Fab fragment of an antibody or antigen binding fragment according to the invention; and one Fab fragment of another antibody that is specific for KLRG1 or CD103.

Also provided is a bispecific antibody or antigen binding fragment thereof that is able to bind O-mannosylated E-cadherin, comprising:

one Fab fragment of an antibody or antigen binding fragment according to the invention; and one Fab fragment of another antibody that is specific for TGFβ.

Certain embodiments provide a chimeric antigen receptor (CAR) T cell that is able to bind O-mannosylated E-cadherin, wherein the CAR T cell comprises the heavy chain CDR1, CDR2 and CDR3 sequences of an antibody according to the invention. Said CAR T cell preferably also comprises the light chain CDR1, CDR2 and CDR3 sequences of an antibody according to the invention. Preferably, said CDR1-3 sequences are present at the surface of said CAR T cell in a single chain format.

The invention also provides nucleic acids comprising the structural and functional features specified herein. In various embodiments, the invention provides an isolated, synthetic or recombinant nucleic acid encoding an antibody or antigen binding fragment according to the present invention, or encoding at least the heavy chain variable region and/or the light chain variable region of an antibody or antigen binding fragment according to the present invention.

In certain embodiments, the invention provides a nucleic acid comprising a sequence that has at least 80% sequence identity with a sequence selected from the group consisting of SEQ ID NOs: 23-39, and/or comprising a sequence that has at least 80% sequence identity with a sequence selected from the group consisting of SEQ ID NOs: 40-44, as depicted in Table 1. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations are located outside the CDR regions.

In certain embodiments, a nucleic acid according to the present invention comprises DNA or RNA.

In certain embodiments, a nucleic acid according to the present invention comprises cDNA, peptide nucleic acid (PNA), locked nucleic acid (LNA), or a DNA/RNA helix.

In certain embodiments, a nucleic acid according to the present invention is codon optimized for expression in a non-human host cell.

In certain embodiments, a nucleic acid according to the present invention is codon optimized for expression in HEK293T cells or CHO cells.

The invention further provides a vector comprising a nucleic acid according to the present invention. In some embodiments, said vector is a CAR T cell vector, comprising a nucleic acid sequence encoding an antigen recognition domain and a T cell activating domain. In some embodiments, said CAR T cell vector further comprises a nucleic acid sequence encoding a transmembrane domain.

The invention further provides an isolated or recombinant host cell, or a non-human animal, comprising an antibody, antigen binding fragment, nucleic acid, vector, ADC or CAR T cell according the present invention. In certain embodiments, said host cell is a mammalian cell, a bacterial cell, a plant cell, a HEK293T cell or a CHO cell.

The invention also provides a composition comprising an antibody, antigen binding fragment, nucleic acid molecule, vector, ADC, CAR T cell or host cell according to the present invention. In various embodiments, said composition is a pharmaceutical composition that also comprises a pharmaceutically acceptable carrier, diluent or excipient.

The invention also provides a kit of parts comprising an antibody, antigen binding fragment, nucleic acid molecule, vector, ADC, CAR T cell or host cell according to the invention.

In certain embodiments, a composition or kit of parts according to the invention further comprises at least one other therapeutic agent.

The invention also provides a method for producing an antibody or antigen binding fragment according to the invention, the method comprising culturing a host cell comprising a nucleic acid or vector according to the invention and allowing said host cell to translate said nucleic acid or vector, thereby producing said antibody or antigen binding fragment according to the invention. Said method preferably further comprises recovering said antibody or antigen binding fragment from said host cell and/or from the culture medium. In some embodiments, said host cell is provided with a vector that comprises both a nucleic acid sequence encoding the heavy chain of said antibody and a nucleic acid sequence encoding the light chain of said antibody. In some embodiments said host cell is provided with at least two different vectors, wherein one vector comprises a nucleic acid sequence encoding the heavy chain of said antibody and a second vector comprises a nucleic acid sequence encoding the light chain of said antibody.

Also provided is an antibody or antigen binding fragment when obtained by a method according to the invention.

The invention also provides an antibody or antigen binding fragment or bispecific antibody or multispecific antibody or ADC or CAR T cell or nucleic acid or vector or host cell according to the invention for use as a medicament or prophylactic agent or diagnostic agent.

Also provided is an antibody or antigen binding fragment or bispecific antibody or multispecific antibody or ADC or CAR T cell or nucleic acid or vector or host cell according to the invention for use in a method for treating or preventing a disorder that is associated with cells, preferably tumor cells, that express E-cadherin and an O-mannosyltransferase, preferably TMTC3. In some preferred embodiments, said disorder is an E-cadherin-positive and TMTC3-positive cancer. In some embodiments, said cancer also comprises tumor cells that express TGFβ.

Various embodiments provide an antibody or antigen binding fragment or bispecific antibody or multispecific antibody or ADC or CAR T cell or nucleic acid or vector or host cell for use according to the invention, whereby said antibody or antigen binding fragment or bispecific antibody or multispecific antibody or ADC or CAR T cell or nucleic acid or vector or host cell is combined with another therapeutic agent useful in the treatment and/or prevention of a disorder that is associated with cells, preferably tumor cells, that express E-cadherin and an O-mannosyltransferase, preferably TMTC3.

The invention also provides a use of an antibody or antigen binding fragment or bispecific antibody or multispecific antibody or ADC or CAR T cell or nucleic acid or vector or host cell according to the invention for the manufacture of a medicament.

Also provided is a use of an antibody or antigen binding fragment or bispecific antibody or multispecific antibody or ADC or CAR T cell or nucleic acid or vector or host cell according to the invention for the manufacture of a medicament for treating or preventing a disorder that is associated with cells that express E-cadherin and an O-mannosyltransferase. In particular embodiments, said cells are tumor cells. In particular embodiments, said O-mannosyltransferase is TMTC3. Also provided is a use of an antibody or antigen binding fragment or bispecific antibody or multispecific antibody or ADC or CAR T cell or nucleic acid or vector or host cell according to the invention for the preparation of a medicament for treating or preventing E-cadherin-positive and TMTC3-positive cancer. In particular embodiments, said E-cadherin-positive and TMTC3-positive cancer is an epithelial cancer. In some embodiments, said E-cadherin-positive and TMTC3-positive cancer is selected from the group consisting of adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer.

In some embodiments, said E-cadherin-positive and TMTC3-positive cancer is selected from the group consisting of colorectal cancer, colon cancer, colon cancer subtype CMS1, colon cancer subtype CMS2, colon cancer subtype CMS3, colon cancer subtype CMS4, laryngeal cancer, head and neck cancer, breast cancer, pancreatic cancer, esophageal cancer, bladder cancer, lung cancer, stomach cancer, urinary tract cancer, prostate cancer and ovary cancer.

The invention also provides a method for treating and/or preventing a disorder that is associated with cells, preferably tumor cells, that express E-cadherin and an O-mannosyltransferase, comprising administering to an individual in need thereof a therapeutically effective amount of an antibody or antigen binding fragment according to the invention, and/or a bispecific antibody or multispecific antibody or ADC or CAR T cell according to the invention, and/or a nucleic acid according to the invention, and/or a vector or cell according to the invention, and/or a composition or kit of parts according to the invention. Further provided is a method for at least in part treating and/or preventing an E-cadherin-positive and TMTC3-positive cancer, comprising administering to an individual in need thereof a therapeutically effective amount of an antibody or antigen binding fragment according to the invention, and/or a bispecific antibody or multispecific antibody or ADC or CAR T cell according to the invention, and/or a nucleic acid according to the invention, and/or a vector or cell according to the invention, and/or a composition or kit of parts according to the invention. Said composition is preferably a pharmaceutical composition according to the invention.

The invention also provides a use of an antibody or antigen binding fragment or bispecific antibody or multispecific antibody or ADC or CAR T cell according to the invention for determining whether a sample comprises cells, preferably tumor cells, that comprise O-mannosylated E-cadherin.

Also provided is a method for determining whether cells, preferably tumor cells, that comprise O-mannosylated E-cadherin are present in a sample, the method comprising:

contacting said sample with an antibody or antigen binding fragment or bispecific antibody or multispecific antibody or ADC or CAR T cell according to the invention, and allowing said antibody or antigen binding fragment or bispecific antibody or multispecific antibody or ADC or CAR T cell to bind to O-mannosylated E-cadherin-comprising cells, preferably O-mannosylated E-cadherin-comprising tumor cells, if present, and determining whether or not cells are bound to said antibody or antigen binding fragment or bispecific antibody or multispecific antibody or ADC or CAR T cell, thereby determining whether or not O-mannosylated E-cadherin-comprising cells, preferably O-mannosylated E-cadherin-comprising tumor cells, are present in said sample.

Also provided is a method for determining whether cells, preferably tumor cells, that express E-cadherin and an O-mannosyltransferase, preferably TMTC3, are present in a sample, the method comprising:

contacting said sample with an antibody or antigen binding fragment or bispecific antibody or multispecific antibody or ADC or CAR T cell according to the invention, and allowing said antibody or antigen binding fragment or bispecific antibody or multispecific antibody or ADC or CAR T cell to bind to cells, preferably tumor cells, that express E-cadherin and an O-mannosyltransferase, preferably TMTC3, if present, and determining whether or not cells are bound to said antibody or antigen binding fragment or bispecific antibody or multispecific antibody or ADC or CAR T cell, thereby determining whether or not cells, preferably tumor cells, that express E-cadherin and an O-mannosyltransferase, preferably TMTC3, are present in said sample.

The invention also provides a method for determining whether a human or non-human individual is suffering from a cancer that is positive for O-mannosylated E-cadherin, the method comprising:

contacting tumor cells of said individual with an antibody or antigen binding fragment or bispecific antibody or multispecific antibody or ADC or CAR T cell according to the invention, allowing said antibody or antigen binding fragment or bispecific antibody or multispecific antibody or ADC or CAR T cell to bind O-mannosylated E-cadherin-comprising tumor cells, if present, and determining whether or not tumor cells are bound to said antibody or antigen binding fragment or bispecific antibody or multispecific antibody or ADC or CAR T cell, thereby determining whether or nor said individual is suffering from a cancer that is positive for O-mannosylated E-cadherin.

In some embodiments, said method is an ex vivo method. In other embodiments, said method is performed in vivo.

FIGURE LEGENDS

FIG. 1. (A) Shown is the full length E-cadherin amino acid sequence (SEQ ID NO:45) (Uniprot Q9UII7) including numbering as used throughout the text. (B) The different domains of E-cadherin are indicated. Adopted from Berx et al. Genomics 1995. In bold the predicted binding epitope of AT1636. The sequence identifiers are: Signal peptide, SEQ ID NO:45; Precursor peptide SEQ ID NO:47; EC1 domain, SEQ ID NO:48; EC2 domain, SEQ ID NO:49; EC3 domain, SEQ ID NO:50; EC4 domain, SEQ ID NO:51; EC5 domain, SEQ ID NO:52; TM domain, SEQ ID NO:53; Cytoplasmic domain 1, SEQ ID NO: 54; Cytoplasmic domain 2, SEQ ID NO:55. (C) The truncated 70 kDa protein, further indicated in the Examples as p70, is shown including the transmembrane (italics) and intracellular domains (SEQ ID NO:56).

FIG. 2. (A) SDS-PAGE resolving the immunoprecipitation samples of AT1002 and AT1636 antibodies. Arrows indicate protein bands' that were immunoprecipitated by AT1636 and analyzed by mass spectrometry, JKT=Jurkat a negative ctrl T cell line, DLD1 is a colon carcinoma cell line, M=molecular weight marker, IP=immune precipitation and AT1002 is a negative control antibody. (B) western blot showing the immunoprecipitation of full length E-cadherin by the EP700Y rabbit antibody (Abcam) and the C-tail intracellular directed antibody (BD Biosciences) and the immunoprecipitation of the p70 protein by AT1636 from DLD1 cells. EP700Y; binds extracellular membrane proximal EC5 domain; C-tail intra, a mouse anti-E-cadherin specific for the C-terminal intracellular domain of E-cadherin (BD Bioscience) and was used for detection also and AT1636 reacts with an epitope which is preferentially exposed on the p70 E-cadherin form.

Figure 3:
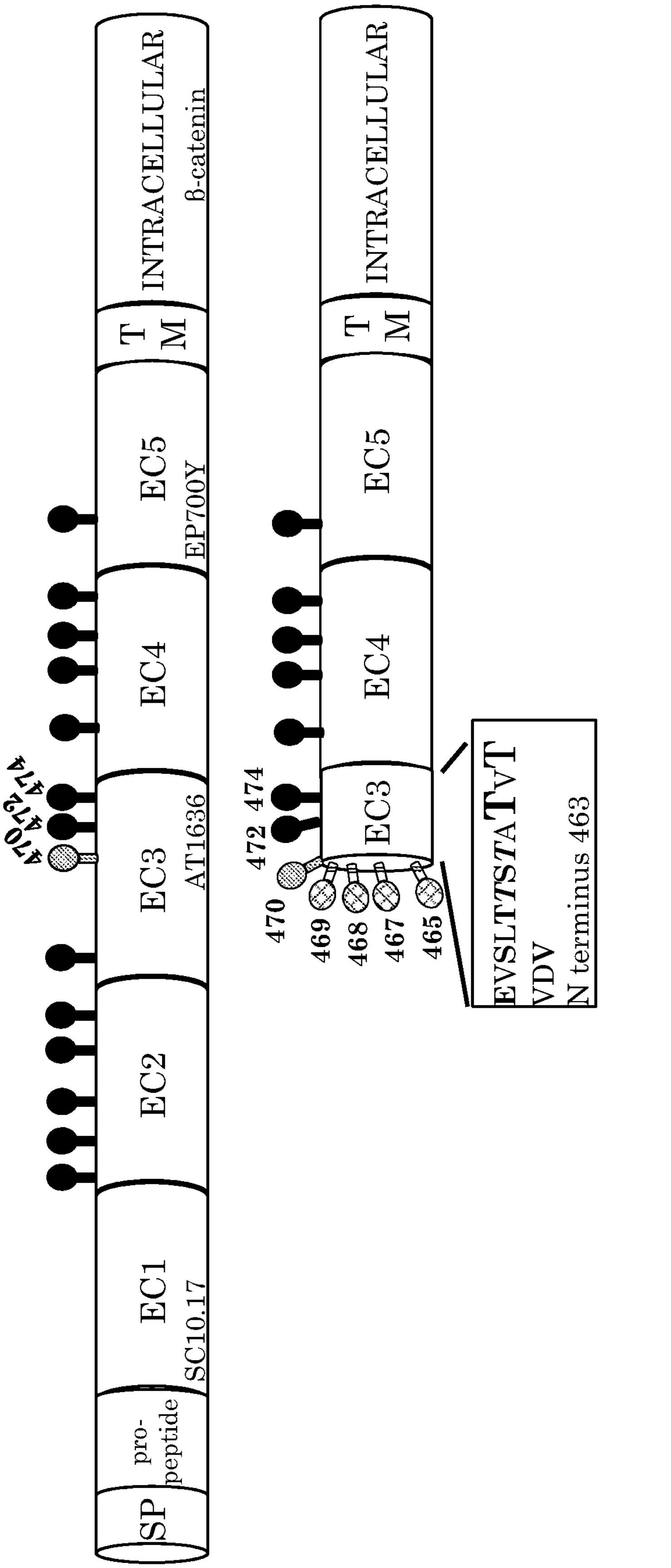

FIG. 3. Graphic overview presenting the full length and truncated p70 E-cadherin. The black lollypops depict the reported O-mannose glycosylation sites (Larsen PNAS (2017) and Vester-Christensen, PNAS (2013)), while the dark grey lollypop describes a predicted O-mannose glycosylation site and the light grey lollypops describe sites that we identified by potentially mannosylated by mass spectrometry of AT1636 immunoprecipitated p70 E-cadherin. Amino acid residues indicated in bold are important for AT1636 binding as determined by alanine scanning. Uppercase residues 472 and 474 are known to be O-mannosylated and 470 is predicted to be mannosylated as described by Larsen et al 2017 and Vester-Christensen et al 2013. In the full length E-cadherin (top) the antibody binding regions of SC10.17 (anti-CD324 monoclonal antibodies and uses thereof, U.S. Pat. No. 9,534,058 (B2)) and EP700Y and the β-catenin binding region are depicted.

Figure 4:
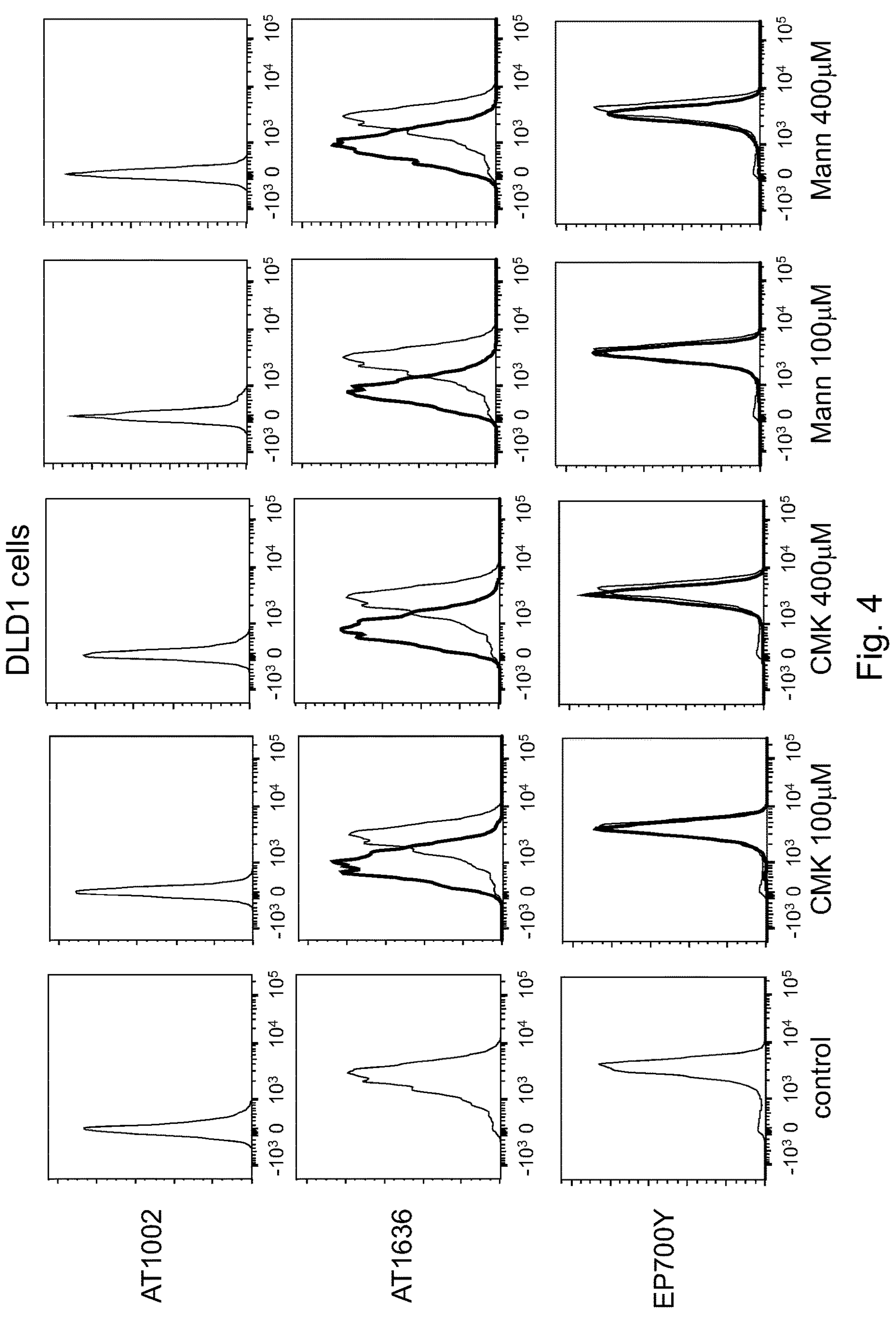

FIG. 4. Flow cytometry analysis of binding of AT1636 to DLD1 cells that had been pretreated with different inhibitors. Indicated are the histograms (solid lines, open histogram) of AT1636 and control antibodies AT1002 and EP700Y at 5 μg/ml on DLD1 cells pretreated for 48 hrs with Mann (mannosyltransferase Inhibitor: 4-Oxo-2-thioxo-3-thiazolidinylacetic acid (Sigma)) or CMK (Furin including convertases inhibitor: Decanoyl-RVKR-CMK (Tocris)) inhibitors. Filled histograms indicate binding to non-treated cells.

Figure 5:
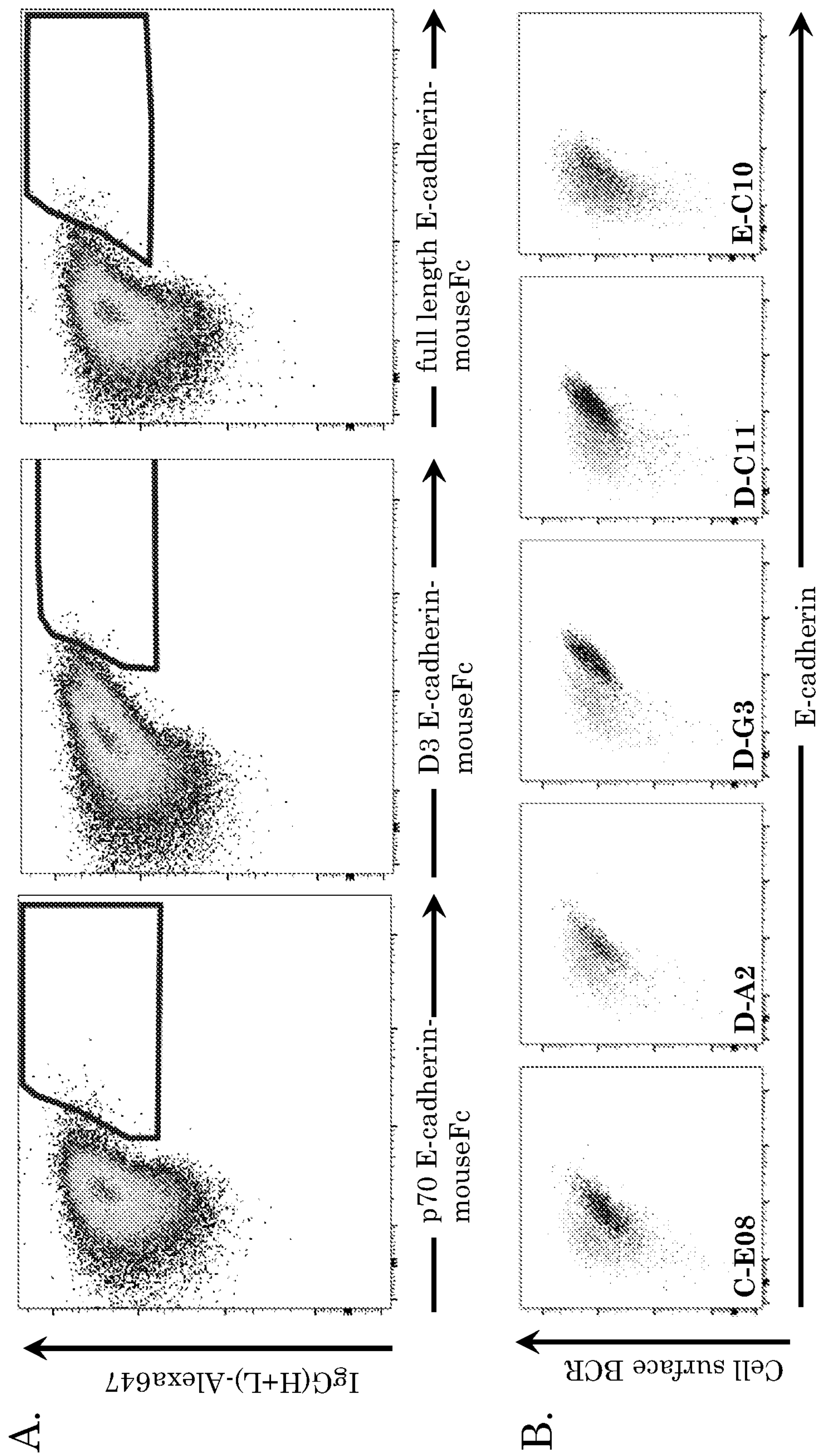

FIG. 5. (A) Selection and isolation of subclones (red box) with increased binding to E-cadherin recombinant protein as compared to the average binding of the E-cadherin clone parental clone, 7G02. Cells were stained with recombinant E-cadherin proteins and IgG(H+L)-Alexa647 and anti-mouse-Fc-PE antibody. Single cell cloning of gated cells was performed with a cell sorter (FACS ARIA, BD). (B) Selection of subclones with increased E-cadherin antigen binding compared to the parental 7G02 clone. AT1636 GFP-low parental cells were mixed with GFP-high subclone cells. This mix of cells was stained for E-cadherin binding and BCR expression. Shown is the intensity of antigen binding related to the BCR expression of the subclones (Blue) compared to the parental 7G02 cells (Orange).

FIG. 6. (A) Indicated are the binding curves of AT1636 and AT1636 high affinity variants to the human CRC cell line DLD1, the breast epithelial cell line MCF10a and the mouse CRC cell line CMT93 as detected by flow cytometry (depicted is the mean fluorescent intensity (MFI) of the Alexa647 dye conjugated to the goat anti-human secondary antibody (Invitrogen)). EP700Y and SC10.17 antibodies are not cross-reactive to mouse E-cadherin. (B) Indicated is the binding ratio of the AT1636 and AT1636-YN and -IYN variants to the control antibody AT1002 as detected by flow cytometry on skin epithelial cell line A431, the lung A546 and mouse CMT93 cell line.

FIG. 7. (A) SPR binding of AT1636, AT1636-NY and -IYN variants to soluble p70 E-cadherin. 5.0 μg/ml antibody injected on a spot immobilized with 2.0 μg/ml p70 E-cadherin. As a control the EP700Y rabbit anti-human E-cadherin was used that is specific for the EC5 domain. Binding is detected using the IBIS multiplex SPR imaging (B) ELISA assay to determine binding of AT1636 and AT1636-IYN variant to recombinant, immobilized full length E-cadherin (left panel), p70 E-cadherin (middle panel) and the E-cadherin D3 domain containing the M470A substitution (preventing mannosylation of this residue) (right panel). SC10.17 antibody is used as a control antibody for binding to full length (EC1 domain) but not to the p70 and D3 domain. AT1002 is a negative human control antibody specific for influenza. (C) ELISA assay using a wide-concentration range of AT1636 and its variants to bind to recombinant, immobilized full length E-cadherin (left panel), p70 E-cadherin (middle panel) and the E-cadherin D3 domain containing the M470A substitution (preventing mannosylation of this residue) (right panel). AT1002 is a negative human control antibody specific for influenza.

FIG. 8. (A) Western blot showing the input and flow-through (FT) after an AT1636 immunoprecipitation and the specific elution of p70 from AT1636 immunoprecipitates using high levels of Mannopyranoside. (B) ELISA demonstrating AT1636 binding to full length E-cadherin (Sino Biological) derived from HEK cells (left panel) and the lack of binding of AT1636 to *E. coli* derived E-cadherin (Lsbio) (right panel). *E. coli* produced E-cadherin is recognized by the EP700Y antibody.

Figure 9:
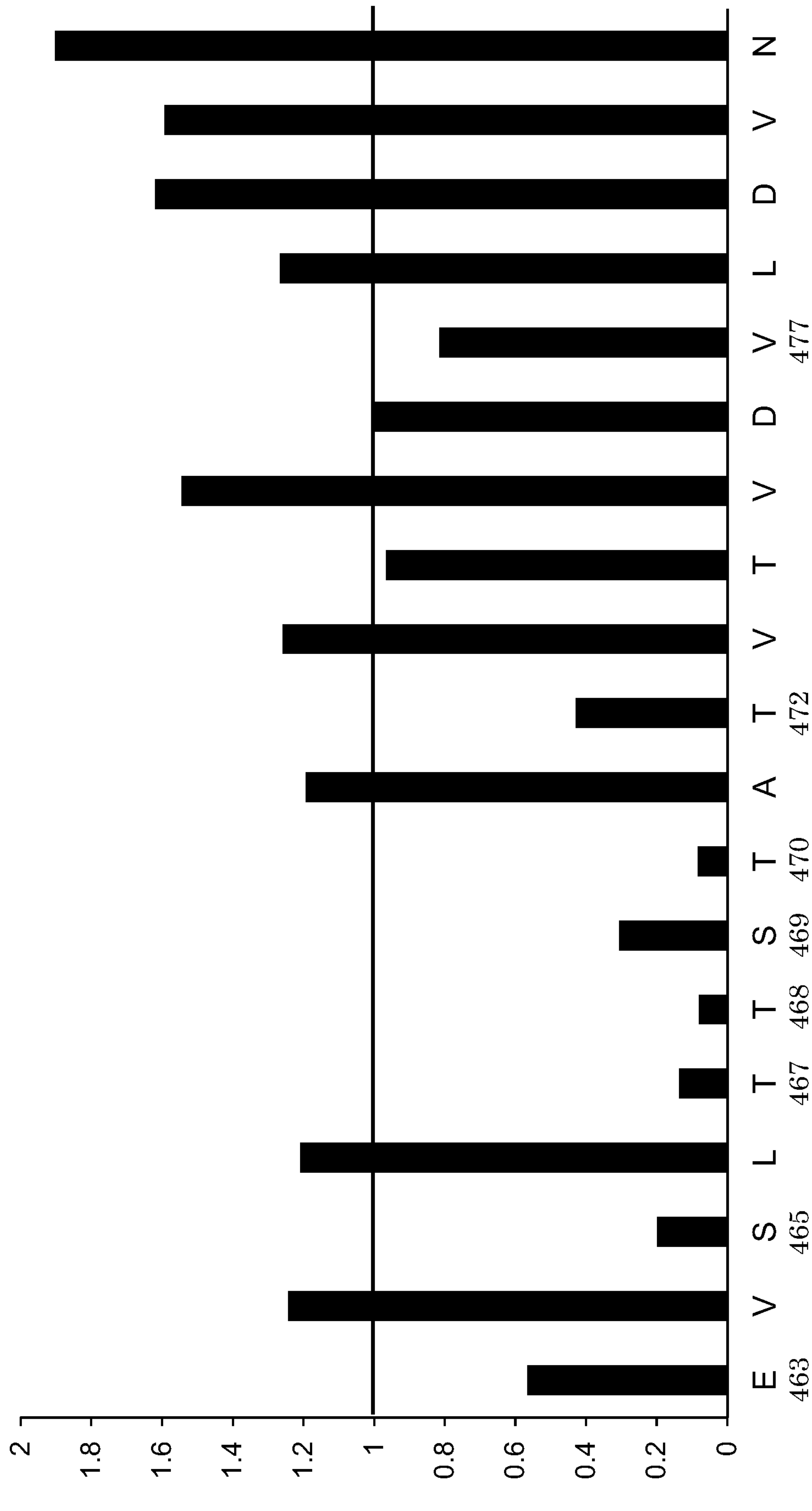

FIG. 9. Alanine substitution of E-cadherin p70 truncated EC3 domain (D3) reveals several amino acids that are essential for binding of AT1636. Binding of AT1636 to recombinant small scale D3-FLAG-mouseFc fusion proteins was studied by ELISA upon anti-mouse Fc capture. All proteins were expressed in similar amounts in culture supernatants and D3-wildtype binding is set to 1, and all are normalized to anti-FLAG detection.

Figure 10:
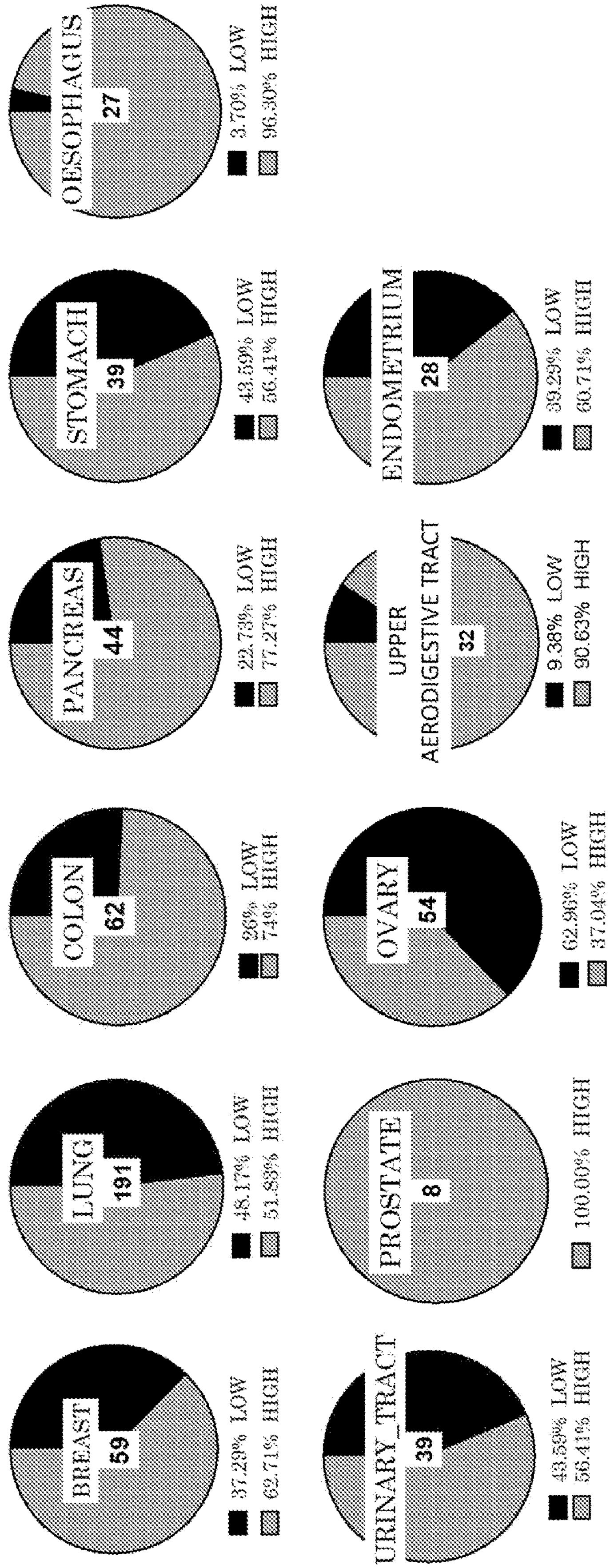

FIG. 10. Computational analysis depicted is the combined mRNA expression of TMTC3 and E-cadherin in several tumor specific cell lines; in the middle of the circle is the number of tumor cell lines included per tissue type. In light grey the percentage of tumor cell-lines that are high (≥7 fold) for both E-cadherin and TMTC3 expression and thus predicted to be recognized by AT1636. The cut-off value of 7 was selected based on flow cytometry analysis that demonstrated that such cell lines can be bound by AT1636 antibody, see Table 3. Tissues normally negative for both TMTC3 and E-cadherin are hematopoietic and lymphoid tissue, bone and soft tissue. (data obtained from the Broad Institute: https://portals.broadinstitute.org/ccle, J. Barretina, Nature (2012)).

Figure 11:
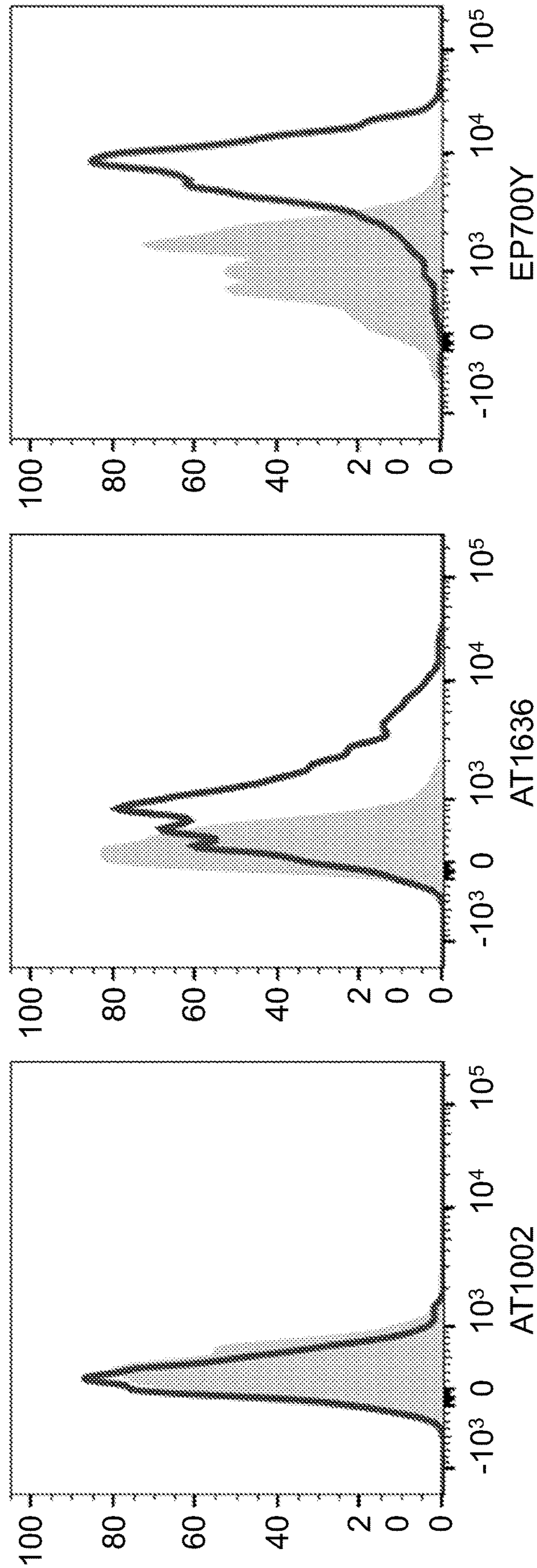

FIG. 11. Flow cytometry analysis indicating the binding of AT1636 is increased to SK-MEL-5 cells transduced with a construct containing full length E-cadherin. SK-MEL-5 are normally negative for E-cadherin but do express TMTC3. AT1636 (solid line) is not binding SK-MEL-5 (left) but does bind when E-cadherin is overexpressed (middle). Also EP700Y (right) is now binding SK-MEL-5. Light grey curve is background staining of isotype control.

Figure 12:
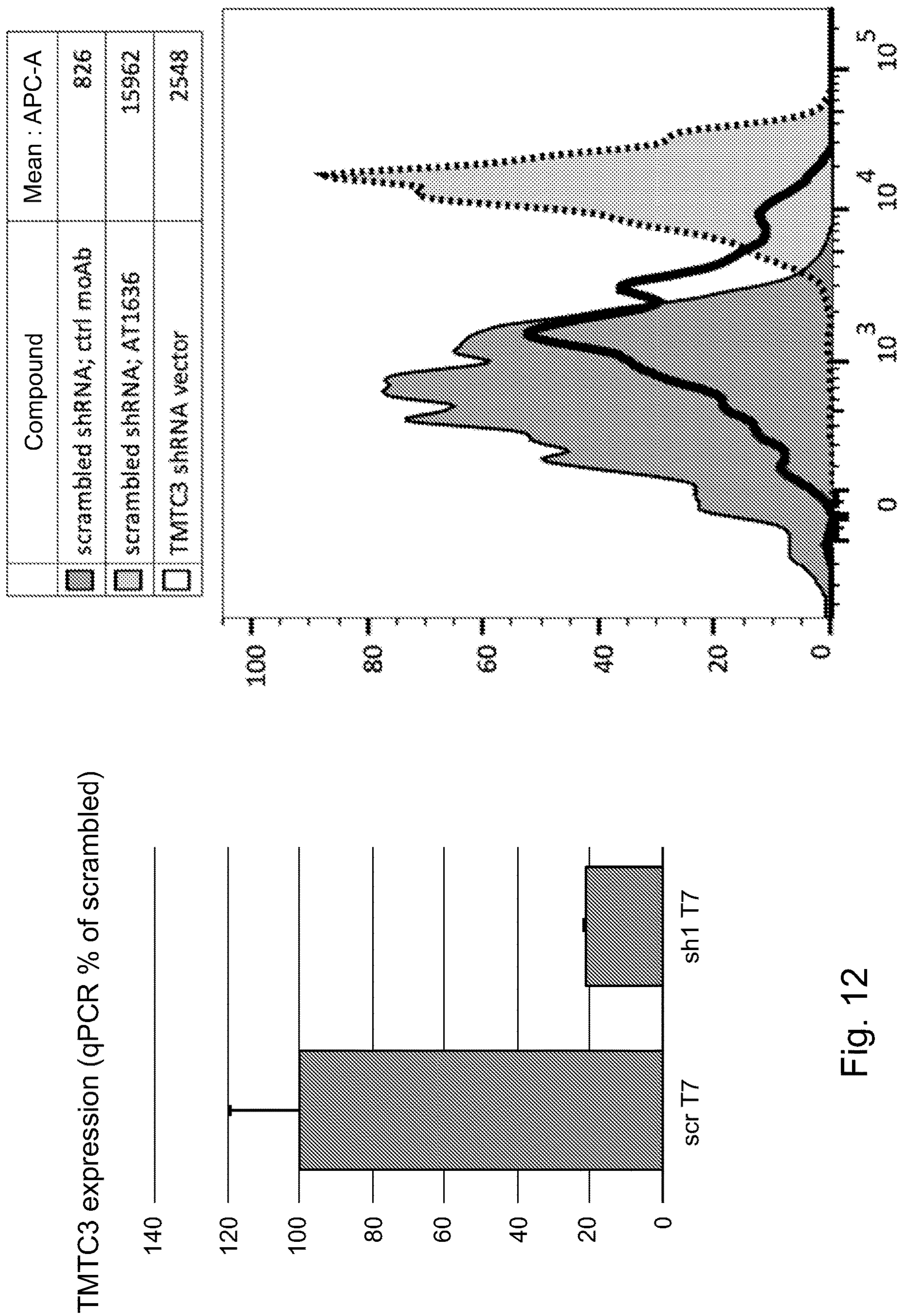

FIG. 12. shRNA induced TMTC3 knockdown results in reduced AT1636 binding as determined by flow cytometry. Besides a control scrambled shRNA vector, a TMTC3 targeting shRNA probe was developed and tested. TMTC3 expression is strongly reduced as determined by qPCR (left). TMTC3 knock-down resulted in a >3-fold reduction in AT1636 binding (right panel, solid line).

FIG. 13. (A) graphic representation of the structure of the monovalent T cell engager (mTCE) consisting of AT1636 or AT1636-IYN fused to anti-CD3 UCHT1. (B) Compounds were tested in a 2D cell-culture model where Luciferase and GFP positive CRC cell lines DLD1, HT29 and HCT116, were cultured O/N at 5000 c/w (96w) before being incubated for 2 days with non-stimulated total PBMC as effector cells. Cell cytotoxicity was establish by measurement of luciferase expressed over the course of the 48 hours. (C) Graphic representation of the structure of the Knob-in-Hole (KiH) bispecific format monovalent for both AT1636, AT1636-IYN or AT1002 and CD3e scFv originating from the UCHT1 antibody. (D) Compounds were tested in a 2D cell-culture model where Luciferase and GFP positive CRC cell lines DLD1 and HT29 and the melanoma cell line A375, were cultured O/N at 5000 c/w (96w) before being incubated with the KiH bispecific monovalent AT1636, AT1636-IYN and AT1002 with the UCHT1 scFv CD3e and subsequently cultured for 2 days with non-stimulated total PBMC as effector cells. Cell cytotoxicity was assessed by measurement of luciferase activity at the end of the 48 hours incubation time.

Figure 14:
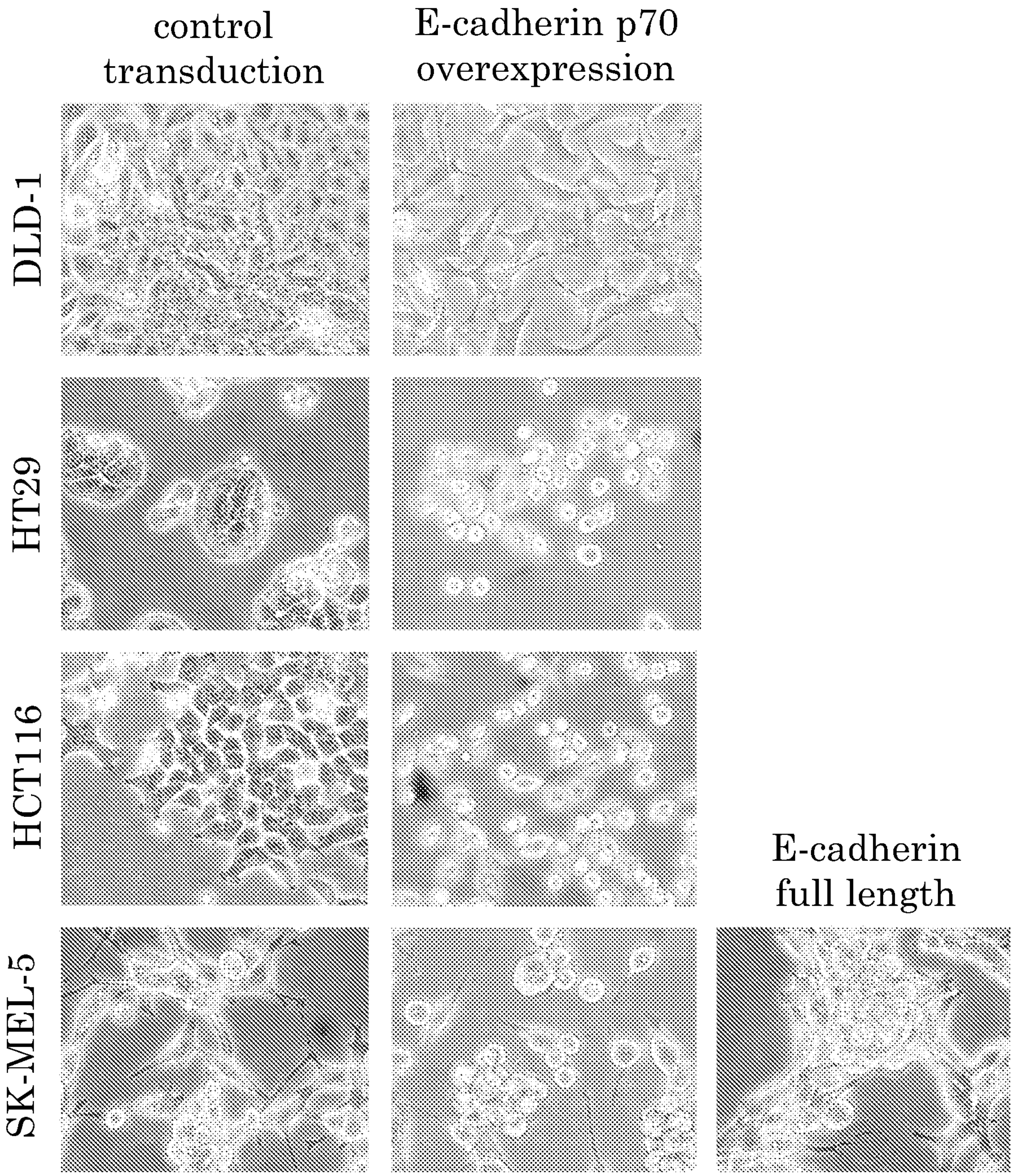

FIG. 14. Stable overexpression of the p70 E-cadherin and full length E-cadherin in cell lines normally expressing E-cadherin (DLD1, HCT116, and HT29) and cells normally negative for E-cadherin (SK-MEL-5). The left column shows cells transduced with an empty vector. Upon overexpression of p70 E-cadherin, all cells demonstrate a de-adhesion morphological phenotype (suggestive of EMT phenotype).

Figure 15:
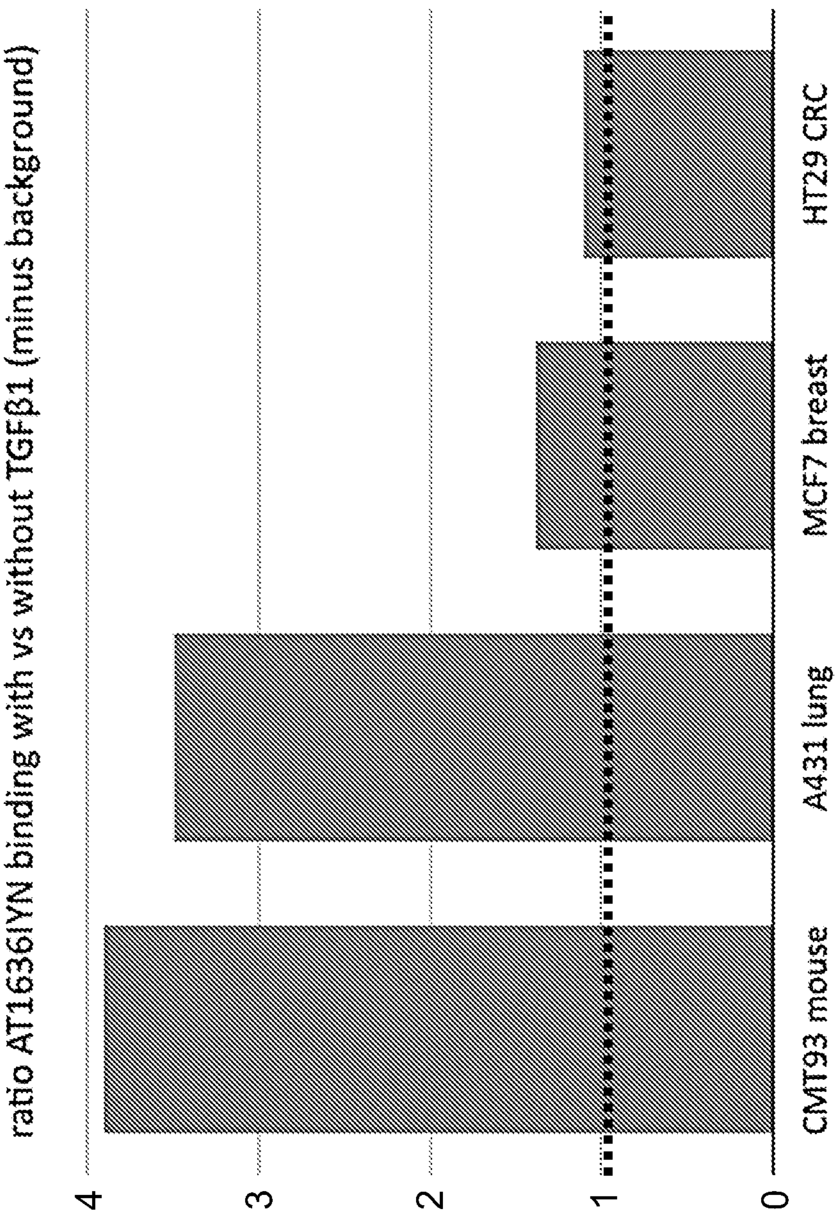

FIG. 15. Flow cytometric analysis of AT1636 binding to DLD1 cells cultured for a prolonged period with TGFβ compared to cells cultured in the absence of TGFβ.

Figure 16A:
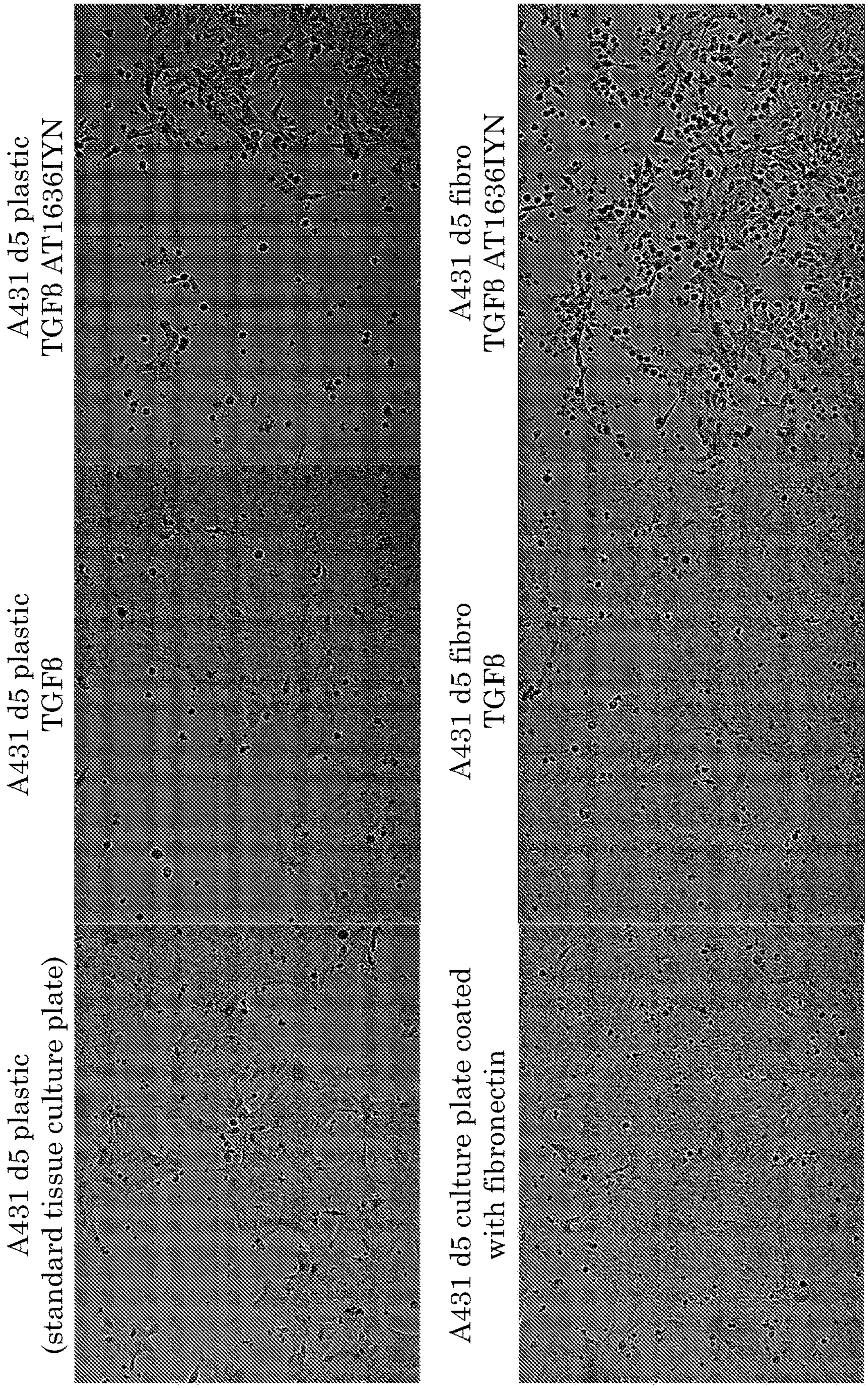
Figure 16B:
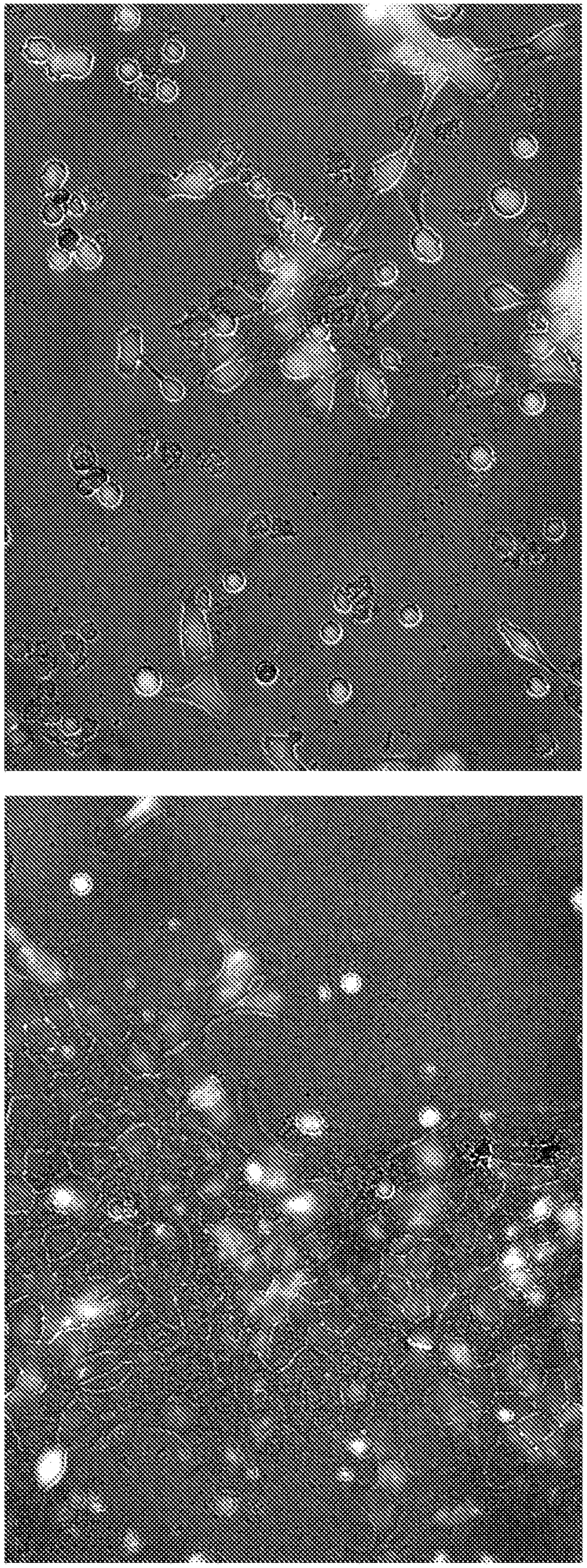

FIG. 16. Decreased cell growth and cell numbers after addition of TGFβ and AT1636-IYN. (A) A431 cell cultures in the absence and presence of TGFβ and AT1636 and the AT1636-IYN variant. The top row panel shows A431 cells cultured for 5 days on tissue culture treated plastic, the bottom row panels cells A431 cells cultured on fibronectin coated plastic using a 10× magnification. The left panels show cells cultured in culture medium, middle panels in the presence of TGFβ and on the right with TGFβ and AT1636-IYN. In the wells cultured in the presence of TGFβ and AT1636-IYN, reduced (viable) cells were observed and less adherent cells. No differences were observed between cells cultured in plastic or fibronectin coated plates and no effect was observed for AT1636-wt or a the AT1002 control antibody (not shown). (B) Detailed representative overview using 20× magnification of A431 cells cultured in fibronectin coated wells after 7d culture in the presence of TGFβ (left panel) and TGFβ and AT1636-IYN (right panel). In the right panel more rounded, dying single-cells are observed and less adherent cells.

Figure 17:
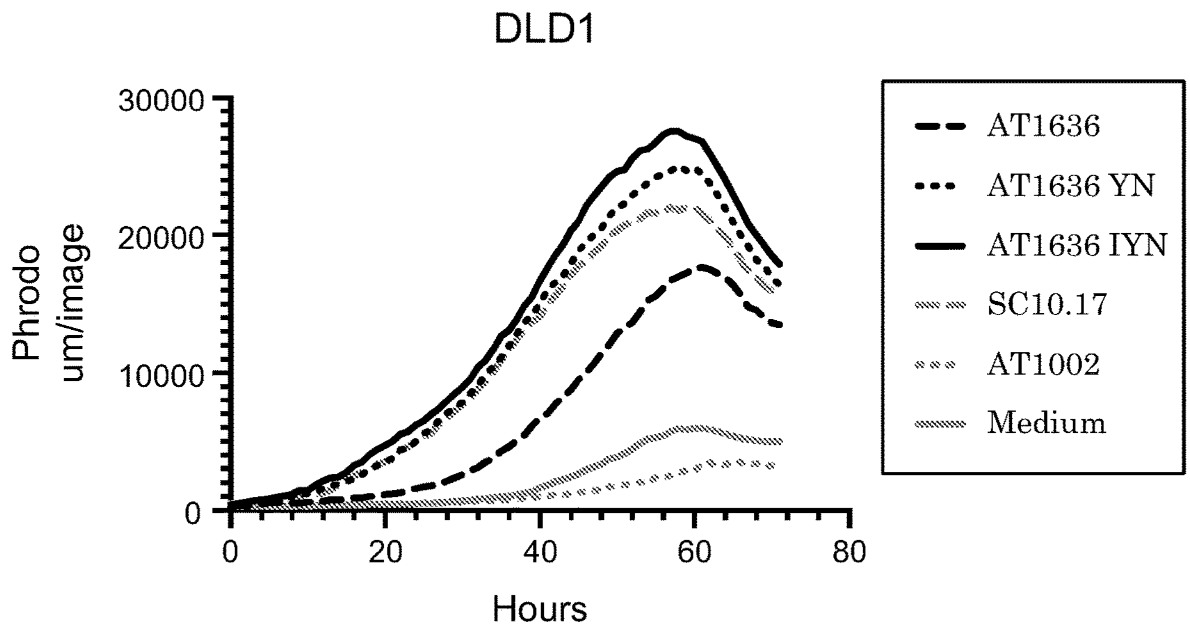

FIG. 17. Time course analysis of the internalization of AT1636 and it variants in DLD1 cells detected with the fluorescent microscope (Incucyte) using the pH sensitive Zenon pHrodo iFL dye. All antibodies except the negative control AT1002 are internalized.

Figure 18:
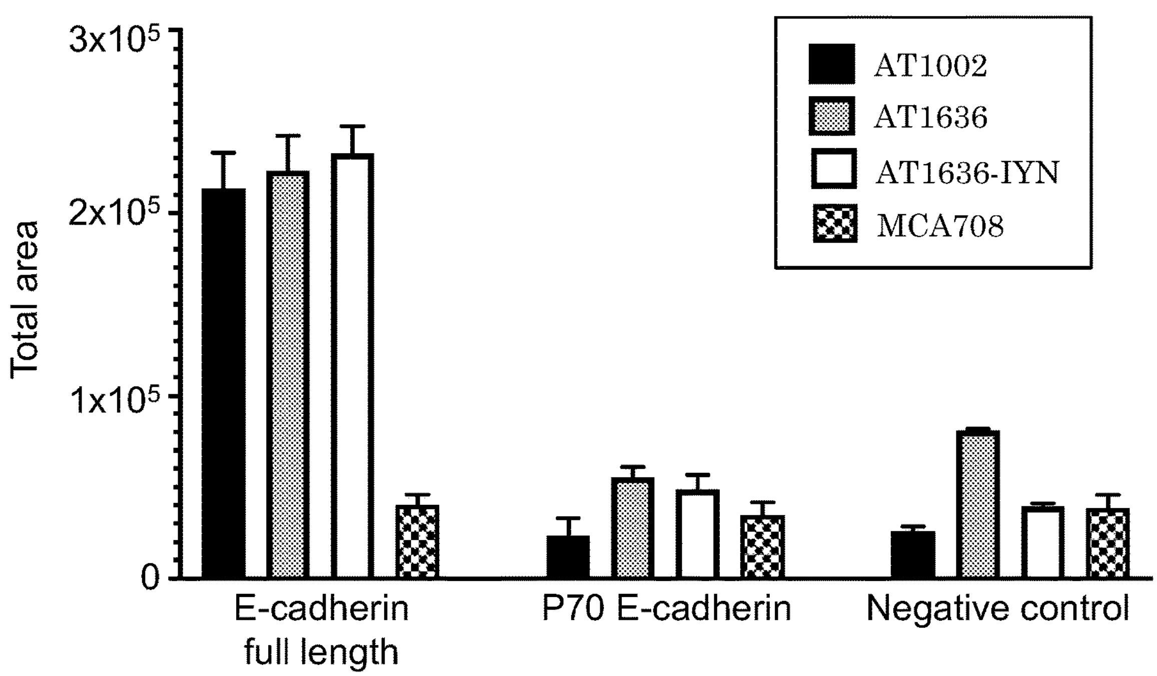

FIG. 18. Indicated is the cell surface coverage of CFSE labelled CD103+ T cells incubated on plate bound full length and p70 E-cadherin protein after being incubated with AT1636 and its variants and a CD103 specific antibody (MCA708).

DETAILED DESCRIPTION

E-Cadherin

E-Cadherin is in humans encoded by the CDH1 gene, which is also referred to as CD324. The amino acid sequence of human E-cadherin as currently known is depicted in FIG. 1A. E-Cadherin is a 120-kDa transmembrane glycoprotein that is localized in the adherens junctions of epithelial cells. E-cadherin is a member of a large family of Cadherins that can be classified into several subtypes: type I classical cadherins such as E-cadherin (CDH1), N-cadherin (CDH2), and P-cadherin (CDH3); type II classical cadherins such as VE-cadherin (CDH5) and OB-cadherin (CDH11); the desmosomal cadherins; the seven-pass transmembrane cadherins; FAT and dachsous (DCHS) group cadherins; and protocadherins (PCDHs). E-cadherin is a transmembrane protein with three components: (1) an extracellular cadherin domain (EC) responsible for homotypic cadherin-cadherin interaction (2) a single-pass transmembrane domain or a seven-pass transmembrane and (3) a cytoplasmic domain that acts as a connector between cell surface, the associated cytoplasmic catenin proteins and the cytoskeleton. Cadherins are involved in growth of organisms (embryogenesis), would healing and tumor invasion and metastasis.

In addition to being a calcium-dependent adhesion molecule, E-Cadherin is also a critical regulator of epithelial junction formation. Its association with catenins is required for cell-cell adhesion and the polarization of epithelial cells/epithelial sheets between the lateral and apical membrane. Tyrosine phosphorylation can disrupt these complexes, leading to changes in cell adhesion properties. E-Cadherin expression is often down-regulated in highly invasive, poorly differentiated carcinomas. Increased expression of E-cadherin in these cells reduces invasiveness. Thus, loss of expression or function of E-cadherin appears to be an important step in tumorigenic progression. Furthermore, cadherins play a vital role in the invasion and migration of cells through the epithelial-mesenchymal transition (EMT), a reversable process. EMT is a very diverse process that can be orchestrated by many external signals (inflammation, stress, hypoxia, immune responses etc). It is generally accepted that especially the strong regulation of EMT inducing transcription factors (Snail, E47, Twist and Zeb families) is the basis of EMT, which by for example the binding of TGFβ, Wnt, integrins and growth factors to the cells, will result in down-regulation of E-cadherin, ZO-1, desmoplakin and upregulation of Vimentin, fibronectin, N-cadherin among others. The cells go through a process in which they resemble a more 'stemness' like phenotype. More recently this model has been changing because it was observed that cells could also 'show' EMT without down or up regulation of the known EMT markers. This has been named partial EMT, hybrid EMT/MET and quasi-EMT, most of the new models propose a system in which the cells are able to regulate protein expression (for example protein internalization, high/low protein turnover) or cells together (clusters) have a different mode of activity/invasiveness. E-cadherin plays a dominant role in those processes and in this respect E-cadherin O-mannosylation is thought to be an additional tool for tumor cells to regulate adhesion and morphology changes while interacting with the surrounding matrix.

Anti E-Cadherin Antibodies and Antigen Binding Fragments Thereof

The present invention provides antibodies and antigen binding fragments thereof that are able to specifically bind O-mannosylated E-cadherin. In some embodiments, the antibodies are isolated. In other embodiments, the antibodies are synthetic or recombinant. Interestingly, the invention provides antibodies and antigen binding fragments thereof comprising VH and VL sequences that are based on the VH and VL sequences of a human antibody that was derived from a human individual who suffered from stage IV colon carcinoma with metastases but who has been in complete remission for years after chemotherapy. In contrast, many currently known therapeutic antibodies are typically obtained by immunizing non human animals such as mice, rats, camelids, rabbits or goats, optionally followed by a humanization process. Such humanized antibodies still involve the risk of adverse side effects due to an immune reaction of the recipient against non-human sequences. In addition, many prior art therapeutic antibodies or fragments thereof are derived from artificial phage display libraries where immunoglobulin heavy and light chains are randomly paired. In contrast, the present invention provides antibodies and antigen binding fragments with naturally paired heavy and light chains, based on the sequences of an antibody that has evolved in vivo in a human patient who is in complete remission.

As E-cadherin is broadly expressed in many epithelial tissues, before the present invention it was not considered in the art as an antigen of choice for therapeutic applications, especially in view of the fact the E-cadherin is often down-regulated in tumor cells in order to promote EMT. The present invention, however, provides antibodies and antigen binding fragments thereof that are able to specifically bind a truncated form of E-cadherin, with a molecular weight of about 70 kDa, which is often upregulated in tumor cells.

The term “antibody”, as used herein, embraces proteinaceous molecules as well as any antigen-binding fragments thereof. Said proteinaceous molecules are preferably immunoglobulin proteins, meaning that they belong to the immunoglobulin class of proteins. In some embodiments an antibody or antigen binding fragment thereof comprises one or more domains that bind an epitope on an antigen, where such domains are preferably derived from or share sequence homology with the variable domain of an antibody.

Complementary-determining regions (CDRs) are the hypervariable regions present in heavy chain variable domains and light chain variable domains. In case of full length antibodies, the CDRs 1-3 of a heavy chain and the CDRs 1-3 of the connected light chain together form an antigen-binding site.

The fragment crystallizable (Fc) region of a natural antibody is composed of the CH2 and CH3 domains of two heavy chains.

Typically, an antigen binding fragment of an antibody is capable of binding the same antigen as said antibody, albeit not necessarily to the same extent. In some embodiments, an antigen binding fragment comprises at least the heavy chain CDR3 region of an antibody. In some embodiments, an antigen binding fragment comprises at least the heavy chain CDR3 region and the light chain CDR3 region of an antibody. In some embodiments, said heavy and light chain CDR3 regions are paired with each other.

In various embodiments, an antigen binding fragment of an antibody comprises at least the heavy chain CDR1, CDR2 and CDR3 regions of an antibody. In various embodiments, an antigen binding fragment of an antibody comprises at least a VH domain. In various embodiments, an antigen binding fragment of an antibody comprises at least the heavy chain CDR1, CDR2 and CDR3 regions and the light chain CDR1, CDR2 and CDR3 regions of an antibody. In various embodiments, an antigen binding fragment of an antibody comprises at least a VL domain. In various embodiments, an antigen binding fragment of an antibody comprises at least a VH and VL domain.

Non-limiting examples of antibodies or antigen binding fragments according to the invention are a full length antibody, a DuoBody® (a bispecific antibody containing two different IgG1s), a single domain antibody or a nanobody (containing a single VH or VL domain), a single chain variable fragment (scFv; containing a VH domain and a VL domain, typically connected by a short linker peptide), a Fv fragment (containing a VH domain and a VL domain, typically without a linker), an Unibody™, a Fd fragment (containing a VH domain and a CH1 domain), a diabody (containing two VH domains and two VL domains, wherein a VH is linked to a VL by such short linker that they cannot pair to each other but pair with a VL and VH of another chain, thereby creating two antigen binding sites), a Fab fragment (containing the heavy chain constant domain CH1, the light chain constant domain CL and the heavy and light chain variable domains VH and VL) and a $F(ab')_2$ fragment (containing two Fab fragments linked by a disulfide bridge).

In various embodiments an antibody or antigen binding fragment of the invention comprises a heavy chain variable region (VH) and a light chain variable region (VL). In some embodiments, said VH is paired with said VL.

Antibodies for therapeutic use are preferably as close to natural antibodies of the subject to be treated as possible (for instance human antibodies for human subjects). In various embodiments an antibody of the invention is a full length antibody, preferably an IgG or IgM or IgA full length antibody. As used herein, an IgG full length antibody is a bivalent molecule comprising two heavy chains of the gamma class and two light chains. As is well known by the skilled person, a heavy chain of an antibody is the larger of the two types of chains making up an immunoglobulin molecule. A natural heavy chain typically comprises a constant domain CH, which comprises constant regions CH1, CH2 and CH3, and a variable domain (VH), which variable domain is involved in antigen binding. A light chain of an antibody is the smaller of the two types of chains making up an immunoglobulin molecule. A natural light chain typically comprises a constant domain (CL) and a variable domain (VL). The light chain variable domain is often, but not always, together with the variable domain of the heavy chain involved in antigen binding.

A full length IgD antibody is a bivalent molecule comprising two heavy chains of the delta class and two light chains.

A full length antibody in the case of an IgM is a decavalent or dodecavalent molecule comprising 5 or 6 linked immunoglobulins in which immunoglobulin each monomer has two antigen binding sites formed of a heavy and light chain.

A full length antibody in the case of an IgA can be monomeric or dimeric.

In some embodiments an antibody or antigen binding fragment according to the invention is a human antibody or antigen binding fragment thereof. The presence of human amino acid sequences diminishes the chance of adverse side effects during therapeutic use in human patients, as opposed to murine or humanized antibodies, wherein the non-human CDR or variable region or constant region sequences involve a risk of an anti-murine immune response in human recipients.

In various embodiments, an antibody or antigen binding fragment according to the invention is of the IgG isotype, preferably IgG1. This is beneficial for medical applications in humans, for instance because IgG1 antibodies typically have a favorable half life upon in vivo administration to human individuals. Furthermore, the Fc tail of an IgG1 allows for effector functions like antibody-dependent cell-mediated cytotoxicity (ADCC), complement-dependent cytotoxicity (CDC) and antibody-dependent cellular phagocytosis (ADCP). In some embodiments, an antibody or antigen binding fragment according to the invention is a human IgG, preferably a human IgG1.

In some embodiments, an antibody or antigen binding fragment according to the invention is of the IgG2 isotype. In some embodiments, an antibody or antigen binding fragment according to the invention is of the IgG3 isotype. some embodiments, an antibody or antigen binding fragment according to the invention is of the IgG4 isotype.

In some embodiments, an antibody or antigen binding fragment according to the invention is of the IgM isotype. In some embodiments, an antibody or antigen binding fragment according to the invention is of the IgA isotype. In some embodiments, an antibody or antigen binding fragment according to the invention is of the IgD isotype.

In various embodiments, an antibody or antigen binding fragment thereof comprises one or more mutations. Such mutations for instance include amino acid substitutions, insertions or deletions. As used herein, full length antibodies wherein one or several, preferably at most 20, amino acid residues are deleted, without essentially altering the binding characteristics of the resulting antibody are still considered a full length antibody.

In some embodiments, an antibody or antigen binding fragment according to the invention has a modified Fc tail. In some embodiments, said Fc tail has been modified by one or more amino acid replacement(s) and/or by glycosylation alterations. In some embodiments, said Fc tail has been modified in order to reduce ADCC activity. In some embodiments, said Fc tail has been modified in order to enhance ADCC activity. In some embodiments, an antibody or antigen binding fragment according to the invention is afucosylated, thereby enhancing ADCC activity.

The terms “able to bind”, “specific for”, “able to specifically bind”, “capable of specifically binding” and “binds” are used herein interchangeably and refer to the interaction between an antibody, or an antigen binding fragment thereof, and its target (also referred to as its antigen). This means that said antibody or antigen binding fragment preferentially binds to said antigen over other antigens or amino acid sequences. Thus, although the antibody or antigen binding fragment may non-specifically bind to other antigens or amino acid sequences, the binding affinity of said antibody or antigen binding fragment for its antigen is significantly higher than the non-specific binding affinity of said antibody or antigen binding fragment for other antigens or amino acid sequences.

Typically, an antibody or antigen binding fragment of the invention which is modified in some way retains at least 50% of its binding activity (when compared to the parental antibody). Preferably, an antibody or antigen binding fragment of the invention retains at least 60%, 70%, 80%, 90%, 95% or 100% of its binding activity as compared to the parental antibody.

In some embodiments, an antibody or antigen binding fragment of the invention comprises conservative or non-conservative amino acid substitutions that do not substantially alter its biologic activity (the resulting variant being referred to herein as a “conservative variant” or “function conserved variant”, respectively). In some embodiments, such conservative variant or function conserved variant retains at least 80%, 90%, 95% or 100% of its binding activity as compared to the parental antibody.

As used herein, conservative substitutions are substitutions whereby an amino acid residue is substituted by another residue with generally similar properties (size, hydrophobicity, etc.), such that the overall functioning of the antibody is essentially not affected. Typically, substitutions of amino acid residues within the same class, depicted in Table 2, are considered conservative amino acid substitutions.

An antibody or antigen binding fragment according to the invention that is able to bind O-mannosylated E-cadherin can also be specific for another compound if the O-mannosylated E-cadherin epitope that is bound by said antibody or antigen binding fragment also happens to be present in said other compound. In such case an antibody or antigen binding fragment referred to herein as being specific for O-mannosylated E-cadherin is also specific for such other compound comprising the same kind of O-mannosylated epitope. Such other O-mannosylated epitope may have been produced in vivo by another O-mannosyltransferase than the O-mannosyltransferases that produce O-mannosylated E-cadherin in vivo. Hence, the term “binding” or “specific for” does not exclude binding of an antibody or antigen binding fragment of the invention to another protein or protein(s) that contain the same kind of O-mannosylated epitope.

“Binding affinity” refers to the strength of the total sum of the noncovalent interactions between a single binding site of an antibody or antigen binding fragment and its binding partner (e.g., an antigen). Unless indicated otherwise, as used herein, “binding affinity” refers to intrinsic binding affinity which reflects a 1:1 interaction between members of a binding pair (e.g., antibody and antigen). The affinity can generally be represented by the equilibrium dissociation constant ($K_D$), which is calculated as the $k_a$ to $k_d$ ratio, see, e.g., Chen, Y., et al., (1999) *J. Mol Biol* 293:865-881. Affinity can be measured by common methods known in the art, such as for instance a Surface Plasmon Resonance (SPR) assay such as BiaCore (GE Healthcare), Octet (Fortebio) or IBIS-iSPR instrument at IBIS Technologies BV (Hengelo, the Netherlands) or solution phase assays, such as Kinexa.

As used herein, the terms “nucleic acid” and “nucleic acid molecule” are used interchangeably. In some embodiments, a nucleic acid or nucleic acid molecule according to the invention comprises a chain of nucleotides, more preferably DNA, cDNA or RNA. In some embodiments, a nucleic acid or nucleic acid molecule according to the invention comprises non-natural nucleotides, modified nucleotides and/or non-nucleotide building blocks which exhibit the same function as natural nucleotides, such as for instance a DNA/RNA helix, peptide nucleic acid (PNA) and/or locked nucleic acid (LNA).

The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. Methods and computer programs for the alignment are well known in the art, for example "Align 2".

As used herein, the singular term "a" encompasses the term "one or more".

Exemplary E-Cadherin Specific Antibodies

The present invention provides antibodies and antigen binding fragments thereof that are specific for O-mannosylated E-cadherin and that have specified structural and functional features, as well as therapeutic uses thereof for the treatment or prevention of disease. A non-limiting example of such disease is an O-mannosylated E-cadherin comprising cancer.

As used herein, the term "O-mannosylated E-cadherin" refers to an E-cadherin protein that comprises at least one threonine or serine residue with an O-linked mannose, meaning that a mannose is attached to the oxygen atom of said threonine or serine. In some embodiments, said E-cadherin protein comprises at least one single O-mannosylated threonine or serine residue. The term "single O-mannosylated threonine residue" refers to a threonine residue that contains an O-linked mannose without attachment of another sugar moiety to said O-linked mannose. The term "single O-mannosylated serine residue" refers to a serine residue that contains an O-linked mannose without attachment of another sugar moiety to said O-linked mannose.

Various embodiments provide an antibody or antigen binding fragment according to the invention that is specific for O-mannosylated E-cadherin, wherein the binding of said antibody or antigen binding fragment to said E-cadherin is dependent on the presence of an O-mannosylated threonine residue at position 467, an O-mannosylated threonine residue at position 468, an O-mannosylated threonine residue at position 470, an O-mannosylated threonine residue at position 472, the glutamic acid residue at position 463, the serine residue at position 465, the serine residue at position 469, and/or the valine residue at position 477, of the E-cadherin sequence as depicted in FIG. 1A.

Some embodiments provide antibodies, and antigen binding fragments thereof, that are specific for O-mannosylated E-cadherin and wherein the binding of said antibody or antigen binding fragment to said E-cadherin is dependent on the presence of one or more O-mannosylated threonine residues within the E-cadherin amino acid region 467-472, as depicted in FIG. 1A. In some embodiments, said antibody or antigen binding fragment is dependent on the presence of an O-mannosylated threonine residue at position 467 and/or an O-mannosylated threonine residue at position 468 and/or an O-mannosylated threonine residue at position 470 and/or an O-mannosylated threonine residue at position 472 of the E-cadherin sequence as depicted in FIG. 1A. In some embodiments, said antibody or antigen binding fragment is dependent on the presence of an O-mannosylated threonine residue at position 468 and an O-mannosylated threonine residue at position 470 of the E-cadherin sequence as depicted in FIG. 1A. In some embodiments, said antibody or antigen binding fragment is dependent on the presence of an O-mannosylated threonine residue at position 467 and an O-mannosylated threonine residue at position 468 and an O-mannosylated threonine residue at position 470 of the E-cadherin sequence as depicted in FIG. 1A. In some embodiments, said antibody or antigen binding fragment is dependent on the presence of an O-mannosylated threonine residue at position 467 and an O-mannosylated threonine residue at position 468 and an O-mannosylated threonine residue at position 470 and an O-mannosylated threonine residue at position 472 of the E-cadherin sequence as depicted in FIG. 1A. In some embodiments, the binding of said antibody or antigen binding fragment to said E-cadherin is further dependent on the presence of the glutamic acid residue at position 463, and/or the serine residue at position 465, and/or the serine residue at position 469, and/or the valine residue at position 477 of the E-cadherin sequence, as depicted in FIG. 1A. In some embodiments, said serine residue at position 465 and/or 469 is O-mannosylated.

As used herein, binding of an antibody or antigen binding fragment is "dependent on" a certain amino acid residue if replacement of said amino acid residue by alanine reduces binding of said antibody or antigen binding fragment to its antigen by at least 40%, preferably by at least 50%, preferably by at least 60%, preferably by at least 70%, preferably by at least 80%, preferably by at least 85%, more preferably by at least 90%, more preferably by at least 95%.

Some embodiments provide an antibody or antigen binding fragment according to the invention that is specific for O-mannosylated E-cadherin and that specifically binds an O-mannosylated threonine residue at position 467, and/or an O-mannosylated threonine residue at position 468, and/or an O-mannosylated threonine residue at position 470, and/or an O-mannosylated threonine residue at position 472, and/or the glutamic acid residue at position 463, and/or the serine residue at position 465, and/or the serine residue at position 469, and/or the valine residue at position 477, of the E-cadherin sequence as depicted in FIG. 1A. In some embodiments, said serine residue at position 465 and/or 469 is O-mannosylated.

Some embodiments of the present invention provide an antibody or antigen binding fragment thereof that is specific for O-mannosylated E-cadherin and that specifically binds one or more O-mannosylated threonine residues of E-cadherin, wherein said one or more O-mannosylated threonine residues are present within amino acid positions 467-472 of the E-cadherin sequence as depicted in FIG. 1A.

Some embodiments provide antibodies and antigen binding fragments thereof that specifically bind one or more O-mannosylated threonine residues selected from the group consisting of an O-mannosylated threonine residue at position 467, an O-mannosylated threonine residue at position 468, an O-mannosylated threonine residue at position 470, and an O-mannosylated threonine residue at position 472 of the E-cadherin sequence as depicted in FIG. 1A. Some embodiments provide antibodies and antigen binding fragments thereof that specifically bind an O-mannosylated threonine residue at position 467 of the E-cadherin sequence as depicted in FIG. 1A. Some embodiments provide antibodies and antigen binding fragments thereof that specifically bind an O-mannosylated threonine residue at position 468 of the E-cadherin sequence as depicted in FIG. 1A. Some embodiments provide antibodies and antigen binding fragments thereof that specifically bind an O-mannosylated threonine residue at position 470 of the E-cadherin sequence as depicted in FIG. 1A. Some embodiments provide antibodies and antigen binding fragments thereof that specifically bind an O-mannosylated threonine residue at position 472 of the E-cadherin sequence as depicted in FIG. 1A of the E-cadherin sequence as depicted in FIG. 1A.

Some embodiments provide antibodies and antigen binding fragments thereof that specifically bind an O-mannosylated threonine residue at position 468 and an O-mannosylated threonine residue at position 470 of the E-cadherin sequence as depicted in FIG. 1A.

Some embodiments provide antibodies and antigen binding fragments thereof that specifically bind an O-mannosylated threonine residue at position 467 and an O-mannosylated threonine residue at position 468 and an O-mannosylated threonine residue at position 470 of the E-cadherin sequence as depicted in FIG. 1A.

Some embodiments provide antibodies and antigen binding fragments thereof that specifically bind an O-mannosylated threonine residue at position 467 and an O-mannosylated threonine residue at position 468 and an O-mannosylated threonine residue at position 470 and an O-mannosylated threonine residue at position 472 of the E-cadherin sequence as depicted in FIG. 1A.

Some embodiments provide antibodies and antigen binding fragments thereof that specifically bind a region of E-cadherin comprising T468 and T470 of the E-cadherin sequence as depicted in FIG. 1A, wherein at least one of said threonine residues is O-mannosylated. In some embodiments, both threonine residues are O-mannosylated.

Some embodiments provide antibodies and antigen binding fragments thereof that specifically bind a region of E-cadherin comprising T467, T468 and T470 of the E-cadherin sequence as depicted in FIG. 1A, wherein at least one of said threonine residues is O-mannosylated. In some embodiments, two of said threonine residues are O-mannosylated. In some embodiments, all three threonine residues are O-mannosylated.

Some embodiments provide antibodies and antigen binding fragments thereof that specifically bind a region of E-cadherin comprising T467, T468, T470 and T472 of the E-cadherin sequence as depicted in FIG. 1A, wherein said threonine residues are O-mannosylated. In some embodiments, two of said threonine residues are O-mannosylated. In some embodiments, three of said threonine residues are O-mannosylated. In some embodiments, all four threonine residues are O-mannosylated.

Some embodiments provide antibodies and antigen binding fragments thereof that specifically bind a region of E-cadherin comprising T468, S469 and T470 of the E-cadherin sequence as depicted in FIG. 1A, wherein at least one of said threonine residues is O-mannosylated. In some embodiments, both threonine residues are O-mannosylated. In some embodiments, said serine residue is O-mannosylated.

Some embodiments provide antibodies and antigen binding fragments thereof that specifically bind a region of E-cadherin comprising T467, T468, S469 and T470 of the E-cadherin sequence as depicted in FIG. 1A, wherein at least one of said threonine residues is O-mannosylated. In some embodiments, at least two of said threonine residues are O-mannosylated. In some embodiments, all of said threonine residues are O-mannosylated. In some embodiments, said serine residue is O-mannosylated.

Some embodiments provide antibodies and antigen binding fragments thereof that specifically bind a region of E-cadherin comprising S465, T467, T468, S469 and T470 of the E-cadherin sequence as depicted in FIG. 1A, wherein at least one of said threonine residues is O-mannosylated. In some embodiments, at least two of said threonine residues are O-mannosylated. In some embodiments, all of said threonine residues are O-mannosylated. In some embodiments, at least one serine residue is O-mannosylated. In some embodiments, both serine residue are O-mannosylated.

Some embodiments provide antibodies and antigen binding fragments thereof that specifically bind a region of E-cadherin comprising S465, T467, T468, S469, T470 and T472 of the E-cadherin sequence as depicted in FIG. 1A, wherein at least one of said threonine residues is O-mannosylated. In some embodiments, at least two of said threonine residues are O-mannosylated. In some embodiments, at least three of said threonine residues are O-mannosylated. In some embodiments, all of said threonine residues are O-mannosylated. In some embodiments, at least one serine residue is O-mannosylated. In some embodiments, both serine residue are O-mannosylated.

Some embodiments provide antibodies and antigen binding fragments thereof that specifically bind a region of E-cadherin comprising E463, S465, T467, T468, S469, T470 and T472 of the E-cadherin sequence as depicted in FIG. 1A, wherein at least one of said threonine residues is O-mannosylated. In some embodiments, at least two of said threonine residues are O-mannosylated. In some embodiments, at least three of said threonine residues are O-mannosylated. In some embodiments, all of said threonine residues are O-mannosylated. In some embodiments, at least one serine residue is O-mannosylated. In some embodiments, both serine residue are O-mannosylated.

Some embodiments provide antibodies and antigen binding fragments thereof that specifically bind a region of E-cadherin comprising E463, S465, T467, T468, S469, T470, T472 and V477 of the E-cadherin sequence as depicted in FIG. 1A, wherein at least one of said threonine residues is O-mannosylated. In some embodiments, at least two of said threonine residues are O-mannosylated. In some embodiments, at least three of said threonine residues are O-mannosylated. In some embodiments, all of said threonine residues are O-mannosylated. In some embodiments, at least one serine residue is O-mannosylated. In some embodiments, both serine residue are O-mannosylated.

Some embodiments provide antibodies and antigen binding fragments thereof that specifically bind an epitope of E-cadherin comprising the sequence TST, wherein at least one of said threonine residues is O-mannosylated. In some embodiments, both threonine residues are O-mannosylated. In some embodiments, said serine residue is O-mannosylated.

Some embodiments provide antibodies and antigen binding fragments thereof that specifically bind an epitope of E-cadherin comprising the sequence TTST, wherein at least one of said threonine residues is O-mannosylated. In some embodiments, at least two of said threonine residues are O-mannosylated. In some embodiments, all of said threonine residues are O-mannosylated. In some embodiments, said serine residue is O-mannosylated.

Some embodiments provide antibodies and antigen binding fragments thereof that specifically bind an epitope of E-cadherin comprising the sequence STTST, wherein at least one of said threonine residues is O-mannosylated. In some embodiments, at least two of said threonine residues are O-mannosylated. In some embodiments, all of said threonine residues are O-mannosylated. In some embodiments, at least one serine residue is O-mannosylated. In some embodiments, both serine residue are O-mannosylated.

Some embodiments provide antibodies and antigen binding fragments thereof that specifically bind an epitope of E-cadherin comprising the sequence STTSTT, wherein at least one of said threonine residues is O-mannosylated. In some embodiments, at least two of said threonine residues are O-mannosylated. In some embodiments, at least three of said threonine residues are O-mannosylated. In some embodiments, all of said threonine residues are O-mannosylated. In some embodiments, at least one serine residue is O-mannosylated. In some embodiments, both serine residue are O-mannosylated.

Some embodiments provide antibodies and antigen binding fragments thereof that specifically bind an epitope of E-cadherin comprising the sequence ESTTSTT, wherein at least one of said threonine residues is O-mannosylated. In some embodiments, at least two of said threonine residues are O-mannosylated. In some embodiments, at least three of said threonine residues are O-mannosylated. In some embodiments, all of said threonine residues are O-mannosylated. In some embodiments, at least one serine residue is O-mannosylated. In some embodiments, both serine residue are O-mannosylated.

Some embodiments provide antibodies and antigen binding fragments thereof that specifically bind an epitope of E-cadherin comprising the sequence ESTTSTTV, wherein at least one of said threonine residues is O-mannosylated. In some embodiments, at least two of said threonine residues are O-mannosylated. In some embodiments, at least three of said threonine residues are O-mannosylated. In some embodiments, all of said threonine residues are O-mannosylated. In some embodiments, at least one serine residue is O-mannosylated. In some embodiments, both serine residue are O-mannosylated.

E-cadherin is known in the art as a product of the CDH1 gene, which in humans has a molecular weight of about 120 kDa. The present invention, however, provides the surprising insight that an O-mannosylated truncated E cadherin form also exists in nature. This truncated form, with a molecular weight of about 70 kDa, lacks extracellular domains EC1 and EC2 of the full length E-cadherin. Extracellular domains 5, 4 and a part of extracellular domain EC3 are still present in the truncated 70 kDa form. The present inventors have provided the insight that this truncated 70 kDa form of E-cadherin is present on the surface of many kinds of epithelial cells, and is often upregulated on tumor cells. Without being bound to any theory, it is believed that upregulation of the 70 kDa form of E-cadherin contributes to tumor growth, amongst other things because the truncated 70 kDa form stimulates epithelial to mesenchymal transition (EMT), as shown in the Examples, thereby increasing tumor cell migration and metastasis. Moreover, it is believed that upregulation of the 70 kDa form of E-cadherin contributes to a tumor's immune escape mechanism, as the truncated 70 kDa form of E-cadherin is less able to bind immune cells as compared to the 120 kDa full length form of E-cadherin. According to the present invention, over-representation of the O-mannosylated 70 kDa E-cadherin form can facilitate escape from immune cell recognition via CD3 or KLRG1 or CD103 and promote EMT without completely down-regulation of E-cadherin. Upregulation of the 70 kDa truncated form on tumor cells could thus diminish interactions between these tumor cells and immune cells, thereby assisting the tumor in escaping from an immune response.

In some embodiments, the present invention provides antibodies and antigen binding parts thereof that bind the above mentioned O-mannosylated truncated 70 kDa E-cadherin better than the well known O-mannosylated full length E-cadherin of about 120 kDa. Preferred embodiments provide antibodies and antigen binding parts thereof that bind the O-mannosylated truncated 70 kDa E-cadherin at least 2 fold better, more preferably at least 3 fold better, more preferably at least 4 fold better, more preferably at least 5 fold better, than O-mannosylated full length E-cadherin. This characteristic allows for an increase of tumor-specificity and a decrease of adverse side effects caused by healthy tissue binding in cases wherein the truncated 70 kDa E-cadherin form is significantly upregulated on tumor cells. As used herein, the term "full length E-cadherin" refers to the known CDH1 gene product which in humans has a molecular weight of about 120 kDa, as for instance depicted in FIG. 1A. The term "truncated 70 kDa E-cadherin" or "70 kDa E-cadherin form" refers to the smaller E-cadherin form with a molecular weight of between 60 and 80 kDa, typically about 70 kDa, that also occurs in nature on the surface of epithelial cells. As shown in FIG. 1C, this naturally occurring truncated E-cadherin form with a molecular weight of between 60 and 80 kDa lacks extracellular domains EC1 and EC2 of the full length E-cadherin. Extracellular domains 5, 4 and a part of extracellular domain EC3 are still present in this truncated 70 kDa form. The term "O-mannosylated truncated 70 kDa E-cadherin" refers to the above mentioned truncated 70 kDa E-cadherin protein that comprises at least one O-mannosylated threonine or serine residue, preferably at least an O-mannosylated threonine residue at position 467 and/or position 468 and/or position 470 as depicted in FIG. 1A.

In certain embodiments, an anti E-cadherin antibody or antigen binding fragment of the invention comprises:

a heavy chain variable region CDR3 comprising the amino acid sequence $TPGVGX_1NX_2PYYFDR$ (SEQ ID NO:61), wherein $X_1$ is A or T and wherein $X_2$ is D or N; and a light chain variable region CDR3 comprising the amino acid sequence QQYSNTPQT (SEQ ID NO:63).

Certain embodiments provide an antibody or antigen binding fragment thereof that is able to bind O-mannosylated E-cadherin, wherein said antibody or antigen binding fragment comprises one or more, and optionally each, of:

a. a heavy chain variable region CDR1 comprising the amino acid sequence $GFX_1FSX_2AW$ (SEQ ID NO:59), wherein $X_1$ is T or I and wherein $X_2$ is N or Y;

b. a heavy chain variable region CDR2 comprising the amino acid sequence IKSKIDG $X_1$T $X_2$ (SEQ ID NO:60), wherein $X_1$ is G or E and wherein $X_2$ is T or I;

c. a heavy chain variable region CDR3 comprising the amino acid sequence $TPGVGX_1NX_2PYYFDR$ (SEQ ID NO:61), wherein $X_1$ is A or T and wherein $X_2$ is D or N;

d. a light chain variable region CDR1 comprising the amino acid sequence QSVLCRSNNKNC (SEQ ID NO:62);

e. a light chain variable region CDR2 comprising the amino acid sequence $WAX_1$, wherein $X_1$ is S or C;

f. a light chain variable region CDR3 comprising the amino acid sequence QQYSNTPQT (SEQ ID NO:63);

or a light chain variable region CDR3 comprising an amino acid sequence differing from said QQYSNTPQT sequence by 1, 2 or 3 conservative substitutions.

Optionally, conservative amino acid substitution is applied to at least one of the above mentioned CDR sequences. In some embodiments, said conservative substitution comprises the substitution of one or more amino acid residues of an amino acid class as depicted in Table 2 by another amino acid residue of the same amino acid class. Non-limiting examples of conservative amino acid substitutions include the substitution of one hydrophobic residue such as isoleucine, valine, leucine or methionine by another hydrophobic residue, and the substitution of one polar residue by another polar residue, such as the substitution of arginine by lysine, glutamic acid by aspartic acid, or glutamine by asparagine. Preferably, after conservative amino acid substitution the favorable E-cadherin-binding characteristic of the parental antibody is maintained or even improved. Preferably, the CDR sequences of such variants differ in no more than three, preferably in no more than two, preferably in no more than one amino acid from the parental sequences.

Some embodiments therefore provide an anti E-cadherin antibody or antigen binding fragment of the invention comprises:

a heavy chain variable region CDR3 comprising the amino acid sequence $TPGVGX_1NX_2PYYFDR$ (SEQ ID NO:61), wherein $X_1$ is A or T and wherein $X_2$ is D or N; or a heavy chain variable region CDR3 comprising an amino acid sequence differing from said $TPGVGX_1NX_2PYYFDR$ sequence by 1, 2 or 3 conservative substitutions; and a light chain variable region CDR3 comprising the amino acid sequence QQYSNTPQT (SEQ ID NO:63) or a light chain variable region CDR3 comprising an amino acid sequence differing from said QQYSNTPQT sequence by 1, 2 or 3 conservative substitutions.

Also provided is an antibody or antigen binding fragment thereof that is able to bind O-mannosylated E-cadherin, wherein said antibody or antigen binding fragment comprises one or more, and optionally each, of:

a. a heavy chain variable region CDR1 comprising the amino acid sequence $GFX_1FSX_2AW$ (SEQ ID NO:59), wherein $X_1$ is T or I and wherein $X_2$ is N or Y;

or a heavy chain variable region CDR1 comprising an amino acid sequence differing from said $GFX_1FSX_2AW$ sequence by 1, 2 or 3 conservative substitutions;

b. a heavy chain variable region CDR2 comprising the amino acid sequence $IKSKIDGX_1TX_2$, (SEQ ID NO:60), wherein $X_1$ is G or E and wherein $X_2$ is T or I; or a heavy chain variable region CDR2 comprising an amino acid sequence differing from said $IKSKIDGX_1TX_2$ sequence by 1, 2 or 3 conservative substitutions;

c. a heavy chain variable region CDR3 comprising the amino acid sequence $TPGVGX_1NX_2PYYFDR$ (SEQ ID NO:61), wherein $X_1$ is A or T and wherein $X_2$ is D or N; or a heavy chain variable region CDR3 comprising an amino acid sequence differing from said $TPGVGX_1NX_2PYYFDR$ sequence by 1, 2 or 3 conservative substitutions;

d. a light chain variable region CDR1 comprising the amino acid sequence QSVLCRSNNKNC (SEQ ID NO:62);

or a light chain variable region CDR1 comprising an amino acid sequence differing from said QSVLCRSNNKNC sequence by 1, 2 or 3 conservative substitutions;

e. a light chain variable region CDR2 comprising the amino acid sequence $WAX_1$, wherein $X_1$ is S or C;

or a light chain variable region CDR2 comprising an amino acid sequence differing from said $WAX_1$ sequence by 1, 2 or 3 conservative substitutions;

f. a light chain variable region CDR3 comprising the amino acid sequence QQYSNTPQT (SEQ ID NO:63);

or a light chain variable region CDR3 comprising an amino acid sequence differing from said QQYSNTPQT sequence by 1, 2 or 3 conservative substitutions.

Table 1 provide sequences of preferred antibodies according to the invention. These preferred antibodies are referred to herein as antibodies AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN. These antibodies bind O-mannosylated E-cadherin, in particular the newly discovered truncated E-cadherin form of about 70 kDa as described herein before. The heavy and light chain CDR sequences of these preferred antibodies are according to the CDR sequences $GFX_1FSX_2AW$, $IKSKIDGX_1TX_2$, $TPGVGX_1NX_2PYYFDR$, QSVLCRSNNKNC, $WAX_1$ and QQYSNTPQT as described above under a) to f).

As used herein, the terms "AT1636", "E-C06", "D-H04", "D-A02", "D-E09", "E-A04", "E-B09", "C-A05", "C-A03", "C-B02", "C-D04-A", "C-D04-B", "F-C08", "D-G03", "D-F10", "C-E08", "D-B06", "D-G05", "D-H08", "C-H01", "D-C12", "D-C11", "E-C10", "AT1636-I", "AT1636-Y", "AT1636-E", "AT1636-N", "AT1636-YN", "AT1636-IYN" and "AT1636-IYEN" encompass all antibodies and antigen binding fragments having at least the heavy and light chain CDR1-3 regions, preferably the heavy and light chain variable regions, of these antibodies as depicted in Table 1.

Based on the antibodies depicted in Table 1, it is possible to produce an antibody or antigen binding fragment thereof that binds O-mannosylated E-cadherin and that comprises at least one CDR sequence of an antibody depicted in Table 1. Provided is therefore an antibody or an antigen binding fragment thereof, comprising at least one CDR sequence of an antibody as depicted in Table 1. Said CDR sequence is preferably a CDR3 sequence of an antibody as depicted in Table 1. In some embodiments, an antibody or antigen binding fragment is provided that comprises the heavy chain CDR3 sequence and the light chain CDR3 sequence of an antibody as depicted in Table 1. Some embodiments thus provide an antibody or antigen binding fragment comprising the heavy and light chain CDR3 sequences of an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN.

Some embodiments provide an antibody or antigen binding fragment thereof that binds O-mannosylated E-cadherin and that comprises the heavy chain CDR 1-3 sequences of one or more antibodies depicted in Table 1.

In some embodiments, an antibody or antigen binding fragment is provided that comprises the heavy chain CDR1, CDR2 and CDR3 sequences of the same antibody indicated in Table 1. Hence, according to this embodiment, the heavy chain CDR1, CDR2 and CDR3 sequences of antibody AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN or AT1636-IYEN are jointly present in one antibody or antigen binding fragment. Such antibody or antigen binding fragment may further comprise a common light chain, which is defined herein as a light chain that is able to functionally pair with a plurality of different heavy chains, whereby the antigen specificity of said heavy chains is maintained. This approach is based on the well-known fact that the heavy chain is often the main driver for affinity and specificity. Pairing of a common light chain with a given heavy chain typically provides a favorable conformation, while such common light chain does not significantly contribute to antigen specificity.

In some embodiments, an antibody or antigen binding fragment according to the invention comprises all three heavy chain CDRs and all three light chain CDRs of the same antibody depicted in Table 1. Further provided is therefore an antibody or antigen binding fragment comprising the heavy and light chain CDR1-3 sequences of an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN.

The heavy chain variable region (VH) and light chain variable region (VL) sequences of antibodies AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN are also depicted in Table 1. Based on these VH and/or VL sequences, it is further possible to produce an antibody or antigen binding fragment thereof that binds O-mannosylated E-cadherin and that comprises the heavy chain variable region (VH) and/or the light chain variable region (VL) of an antibody depicted in Table 1, or sequences having at least 80% sequence identity thereto. Typically, VH and VL sequence variations between 80 and 99% are tolerated while maintaining antigen specificity, especially when the CDR regions remain unaltered. Antibodies and antigen binding fragments comprising a VH or VL sequence that has at least 80% sequence identity to a VH or VL sequence as depicted in table 1 are therefore also provided herein.

Provided is therefore an antibody, or an antigen binding fragment thereof, comprising the heavy chain variable region (VH) of an antibody depicted in Table 1, or a sequence having at least 80% sequence identity thereto. Also provided is an antibody, or an antigen binding fragment thereof, comprising the light chain variable region (VL) of an antibody depicted in Table 1, or a sequence having at least 80% sequence identity thereto. Some embodiments provide an antibody, or an antigen binding fragment thereof, comprising the heavy chain variable region (VH) and the light chain variable region (VL) of an antibody depicted in Table 1, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody, or an antigen binding fragment thereof, comprising the heavy chain variable region (VH) and/or the light chain variable region (VL) of an antibody depicted in Table 1, or sequences having at least 80% sequence identity thereto, wherein said antibody or antigen binding fragment comprises the heavy chain CDR3 sequence and the light chain CDR3 sequence of an antibody as depicted in Table 1. Preferably, said antibody or antigen binding fragment comprises the heavy chain CDR 1-3 sequences and the light chain CDR 1-3 sequences of an antibody as depicted in Table 1.

For instance, in some embodiments one or more framework residues of a VH or VL sequence depicted in Table 1 are modified in order to decrease immunogenicity and/or in order to increase binding efficacy or stability of the resulting antibody or antigen binding fragment. Framework sequences are for instance optimized by mutating a nucleic acid molecule encoding such framework sequence where after the characteristics of the resulting antibody—or antigen binding fragment thereof—are preferably tested. This way, it is possible to obtain improved binding compounds.

In some embodiments, one or more framework residues are mutated back to the germline sequence from which antibody AT1636 is derived in order to decrease immunogenicity. Methods for comparing a framework region of a given antibody with the germline sequence from which the antibody is derived are well known in the art.

In some embodiments, one or more framework residues of a VH or VL sequence depicted in Table 1 are modified in order to remove one or more T cell epitopes, thereby decreasing the potential immunogenicity of the resulting antibody or antigen binding fragment. This is referred to as deimmunization. Methods for deimmunizing a framework region of a given antibody or antigen binding fragment are also well known in the art, as for instance described in De Groot et al, 2005.

In some embodiments, at most 10 amino acid residues of the framework residues of a VH or VL sequence as depicted in Table 1 are modified as compared to said VH or VL sequence as depicted in Table 1. In some embodiments, at most 8 amino acid residues of the framework residues of a VH or VL sequence as depicted in Table 1 are modified. In some embodiments, at most 5 amino acid residues of the framework residues of a VH or VL sequence as depicted in Table 1 are modified. In some embodiments, at most 3 or 2 amino acid residues of the framework residues of a VH or VL sequence as depicted in Table 1 are modified. In some embodiments, 1 amino acid residue of the framework residues of a VH or VL sequence as depicted in Table 1 is modified.

Some embodiments provide an antibody or antigen binding fragment according to the invention that is able to bind O-mannosylated E-cadherin, comprising:

- a heavy chain variable region comprising a sequence having at least 80% sequence identity with a VH sequence selected from the group consisting of SEQ ID NOs: 1-17; and/or
- a light chain variable region comprising a sequence having at least 80% sequence identity with a VL sequence selected from the group consisting of SEQ ID NOs: 18-22.

A preferred antibody according to the present invention is antibody AT1636. This antibody is preferred because it is capable of binding O-mannosylated E-cadherin expressed on tumor cells, in particular the newly discovered truncated E-cadherin form of about 70 kDa as described herein before. A particular advantage of AT1636 is the fact that it binds this truncated 70 kDa E-cadherin form better than full length E-cadherin of about 120 kDa. This characteristic of AT1636 typically allows for an increase of tumor-specificity in cases wherein O-mannosylated truncated 70 kDa E-cadherin is upregulated on tumor cells. A further advantage of that AT1636 has a preference for truncated 70 kDa E-cadherin form is that full length E-cadherin is broadly expressed. Hence, in the absence of a preference for the truncated 70 kDa E-cadherin form, the broadly expressed full length E-cadherin can work as a sink and/or introduce undesirable effects. Furthermore, the expression levels of full length E-cadherin are very high and therefore often not distinguishable between healthy and tumor epithelial cells, while a preference for the truncated 70 kDa E-cadherin form allows for more tumor specificity. In addition, E-cadherin has an important barrier function, so that it is preferable to avoid significant interference with the healthy function of E-cadherin.

Furthermore, AT1636 is derived from a human individual who suffered from stage IV colon carcinoma with metastases but who has been in complete remission for many years after chemotherapy, suggestive of therapeutic efficacy. Interestingly, AT1636 is of the IgG3 isotype. The presence of human amino acid sequences diminishes the chance of adverse side effects during therapeutic use in human patients.

In addition, AT1636 was selected by virtue of its ability to bind O-mannosylated E-cadherin-expressing colon cancer subtypes CMS1, CMS2, CMS3 and CMS4. AT1636 binds to tumor cells, specifically epithelial tumor cells, more specifically O-mannosylated E-cadherin-expressing cancer cells, such as for instance O-mannosylated E-cadherin-expressing colon cancer cells, breast cancer cells, pancreatic cancer cells, bladder cancer cells, endometrium cancer cells, lung cancer cells and esophagus cancer cells, as shown in the Examples. Antibody AT1636 is, therefore, particularly suitable for treatment and/or diagnosis of a disorder that is associated with the presence of cells that express O-mannosylated E-cadherin, such as O-mannosylated E-cadherin-expressing cancer cells, particularly cancer cells that express the newly discovered truncated E-cadherin form of about 70 kDa.

Antibodies E-C10, D-C12 and D-C11, depicted in Table 1, have the same heavy and light chain CDR 1-3 sequences as AT1636 and have, therefore, the same binding specificity. These antibodies are also preferred antibodies according to the invention, amongst other things because they are capable of binding O-mannosylated E-cadherin expressed on cells, in particular the newly discovered truncated E-cadherin form of about 70 kDa as described herein, more particularly one or more O-mannosylated threonine residues that are present within amino acid positions 467-472 of the E-cadherin sequence as depicted in FIG. 1A (SEQ ID NO:45), and they are therefore very suitable for treatment and/or diagnosis of a disorder that is associated with the presence of such O-mannosylated E-cadherin-expressing cells, particularly cancer cells. The presence of human amino acid sequences diminishes the chance of adverse side effects during therapeutic use in human patients.

The heavy chain CDR1-3 sequences of antibodies AT1636, E-C10, D-C12 and D-C11, as depicted in Table 1, are GFTFSNAW (SEQ ID NO:69), IKSKIDGGTT (SEQ ID NO: 70) and TPGVGANDPYYFDR (SEQ ID NO: 71). The light chain CDR1-3 sequences of these antibodies AT1636, E-C10, D-C12 and D-C11 are QSVLCRSNNKNC (SEQ ID NO: 62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSNAW (SEQ ID NO: 69) and a heavy chain CDR2 comprising the sequence IKSKIDGGTT (SEQ ID NO: 70) and a heavy chain CDR3 comprising the sequence TPGVGANDPYYFDR (SEQ ID NO: 71) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO:63).

The VH sequence of antibody AT1636 is depicted in Table 1 as SEQ ID NO: 1. The VL sequence of antibody AT1636 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 1 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 1 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody AT1636 as depicted in Table 1.

The VH sequence of antibody E-C10 is depicted in Table 1 as SEQ ID NO: 1. The VL sequence of antibody E-C10 is depicted in Table 1 as SEQ ID NO: 22. Some embodiments therefore provide an antibody or antigen binding fragment that is able to bind O-mannosylated E-cadherin, comprising a VH sequence as depicted in SEQ ID NO: 1 and a VL sequence as depicted in SEQ ID NO: 22, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 1 and a VL sequence as depicted in SEQ ID NO: 22, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody E-C10 as depicted in Table 1.

The VH sequence of antibody D-C12 is depicted in Table 1 as SEQ ID NO: 13. The VL sequence of antibody D-C12 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 13 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 13 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody D-C12 as depicted in Table 1.

The VH sequence of antibody D-C11 is depicted in Table 1 as SEQ ID NO: 14. The VL sequence of antibody D-C11 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 14 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 14 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody D-C11 as depicted in Table 1.

Further provided is an antibody or antigen binding fragment thereof that competes with antibody AT1636 or E-C10 or D-C12 or D-C11 for binding to O-mannosylated E-cadherin, preferably for binding to one or more O-mannosylated threonine residues that are present within amino acid positions 467-472 of the E-cadherin sequence as depicted in FIG. 1A.

Further provided is an antibody or antigen binding fragment thereof that competes with antibody AT1636 or E-C10 or D-C12 or D-C11 for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody AT1636 or E-C10 or D-C12 or D-C11 for binding to cells, preferably tumor cells, that express E-cadherin and an O-mannosyltransferase, preferably TMTC3.

Antibodies E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, AT1636-I, AT1636-Y, AT1636-E and AT1636-N, depicted in Table 1, are also preferred antibodies according to the invention. These antibodies are also capable of binding O-mannosylated E-cadherin expressed on cells, in particular the newly discovered truncated E-cadherin form of about 70 kDa, more particularly one or more O-mannosylated threonine residues that are present within amino acid positions 467-472 of the E-cadherin sequence as depicted in FIG. 1A, and are therefore very suitable for treatment and/or diagnosis of a disorder that is associated with the presence of such O-mannosylated E-cadherin-expressing cells, particularly cancer cells. The presence of human amino acid sequences in these antibodies diminishes the chance of adverse side effects during therapeutic use in human patients.

The heavy chain CDR1-3 sequences of antibodies E-C06, D-H04, D-A02, D-E09, E-A04, E-B09 and AT1636-I, depicted in Table 1, are GFIFSNAW (SEQ ID NO:72), IKSKIDGGTT (SEQ ID NO:70) and TPGVGANDPYYFDR (SEQ ID NO:71). The light chain CDR1-3 sequences of these antibodies E-C06, D-H04, D-A02, D-E09, E-A04, E-B09 and AT1636-I are QSVLCRSNNKNC (SEQ ID NO:62), WAS and QQYSNTPQT (SEQ ID NO: 63). Some embodiments therefore provide an antibody or antigen binding fragment that is able to bind O-mannosylated E-cadherin, comprising a heavy chain CDR1 comprising the sequence GFIFSNAW (SEQ ID NO:72) and a heavy chain CDR2 comprising the sequence IKSKIDGGTT (SEQ ID NO:70) and a heavy chain CDR3 comprising the sequence TPGVGANDPYYFDR (SEQ ID NO:61) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO:63).

The VH sequence of antibodies E-C06 and D-H04 is depicted in Table 1 as SEQ ID NO: 2. The VL sequence of antibodies E-C06 and D-H04 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 2 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 2 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody E-C06 or D-H04 as depicted in Table 1.

The VH sequence of antibodies D-A02, D-E09, E-A04, E-B09 and AT1636-I is depicted in Table 1 as SEQ ID NO: 3. The VL sequence of antibodies D-A02, D-E09, E-A04, E-B09 and AT1636-I is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 3 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 3 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody D-A02, D-E09, E-A04, E-B09 or AT1636-I as depicted in Table 1.

Further provided is an antibody or antigen binding fragment thereof that competes with antibody E-C06 or D-H04 or D-A02 or D-E09 or E-A04 or E-B09 or AT1636-I for binding to O-mannosylated E-cadherin, preferably for binding to one or more O-mannosylated threonine residues that are present within amino acid positions 467-472 of the E-cadherin sequence as depicted in FIG. 1A.

Further provided is an antibody or antigen binding fragment thereof that competes with antibody E-C06 or D-H04 or D-A02 or D-E09 or E-A04 or E-B09 or AT1636-I for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody E-C06 or D-H04 or D-A02 or D-E09 or E-A04 or E-B09 or AT1636-I for binding to cells, preferably tumor cells, that express E-cadherin and an O-mannosyltransferase, preferably TMTC3.

The heavy chain CDR1-3 sequences of antibody C-A05, depicted in Table 1, are GFIFSNAW (SEQ ID NO:72), IKSKIDGETT (SEQ ID NO:76) and TPGVGANDPYYFDR (SEQ ID NO:77). The light chain CDR1-3 sequences of this antibody C-A05 are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFIFSNAW (SEQ ID NO:72) and a heavy chain CDR2 comprising the sequence IKSKIDGETT (SEQ ID NO:76) and a heavy chain CDR3 comprising the sequence TPGVGANDPYYFDR (SEQ ID NO:74) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO: 63).

The VH sequence of antibody C-A05 is depicted in Table 1 as SEQ ID NO: 4. The VL sequence of antibody C-A05 is depicted in Table 1 as SEQ ID NO: 19. Some embodiments therefore provide an antibody or antigen binding fragment that is able to bind O-mannosylated E-cadherin, comprising a VH sequence as depicted in SEQ ID NO: 4 and a VL sequence as depicted in SEQ ID NO: 19, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 4 and a VL sequence as depicted in SEQ ID NO: 19, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody C-A05 as depicted in Table 1.

Further provided is an antibody or antigen binding fragment thereof that competes with antibody C-A05 for binding to O-mannosylated E-cadherin, preferably for binding to one or more O-mannosylated threonine residues that are present within amino acid positions 467-472 of the E-cadherin sequence as depicted in FIG. 1A (SEQ ID NO: 45).

Further provided is an antibody or antigen binding fragment thereof that competes with antibody C-A05 for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody C-A05 for binding to cells, preferably tumor cells, that express E-cadherin and an O-mannosyltransferase, preferably TMTC3.

The heavy chain CDR1-3 sequences of antibodies C-A03, C-B02 and AT1636-E, depicted in Table 1, are GFTFSNAW (SEQ ID NO:69), IKSKIDGETT (SEQ ID NO:76) and TPGVGANDPYYFDR (SEQ ID NO:77). The light chain CDR1-3 sequences of these antibodies C-A03, C-B02 and AT1636-E are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSNAW (SEQ ID NO:69) and a heavy chain CDR2 comprising the sequence IKSKIDGETT (SEQ ID NO:76) and a heavy chain CDR3 comprising the sequence TPGVGANDPYYFDR (SEQ ID NO:77) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO:63).

The VH sequence of antibodies C-A03, C-B02 and AT1636-E is depicted in Table 1 as SEQ ID NO: 5. The VL sequence of antibodies C-A03, C-B02 and AT1636-E is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 5 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 5 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody C-A03 or C-B02 or AT1636-E as depicted in Table 1.

Further provided is an antibody or antigen binding fragment thereof that competes with antibody C-A03 or C-B02 or AT1636-E for binding to O-mannosylated E-cadherin, preferably for binding to one or more O-mannosylated threonine residues that are present within amino acid positions 467-472 of the E-cadherin sequence as depicted in FIG. 1A.

Further provided is an antibody or antigen binding fragment thereof that competes with antibody C-A03 or C-B02 or AT1636-E for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody C-A03 or C-B02 or AT1636-E for binding to cells, preferably tumor cells, that express E-cadherin and an O-mannosyltransferase, preferably TMTC3.

The heavy chain CDR1-3 sequences of antibody C-D04-A, depicted in Table 1, are GFTFSNAW (SEQ ID NO:69), IKSKIDGETT (SEQ ID NO:76) and TPGVGANNPYYFDR (SEQ ID NO:77). The light chain CDR1-3 sequences of this antibody C-D04-A are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSNAW (SEQ ID NO:69) and a heavy chain CDR2 comprising the sequence IKSKIDGETT (SEQ ID NO:76) and a heavy chain CDR3 comprising the sequence TPGVGANNPYYFDR (SEQ ID NO:77) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO: 63).

The VH sequence of antibody C-D04-A is depicted in Table 1 as SEQ ID NO: 6. The VL sequence of antibody C-D04-A is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 6 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 6 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody C-D04-A as depicted in Table 1.

Further provided is an antibody or antigen binding fragment thereof that competes with antibody C-D04-A for binding to O-mannosylated E-cadherin, preferably for binding to one or more O-mannosylated threonine residues that are present within amino acid positions 467-472 of the E-cadherin sequence as depicted in FIG. 1A (SEQ ID NO: 45).

Further provided is an antibody or antigen binding fragment thereof that competes with antibody C-D04-A for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody C-D04-A for binding to cells, preferably tumor cells, that express E-cadherin and an O-mannosyltransferase, preferably TMTC3.

The heavy chain CDR1-3 sequences of antibody C-D04-B, depicted in Table 1, are GFTFSNAW (SEQ ID NO:69), IKSKIDGETT (SEQ ID NO:76) and TPGVGANNPYYFDR (SEQ ID NO:77). The light chain CDR1-3 sequences of this antibody C-D04-B are QSVLCRSNNKNC (SEQ ID NO:62), WAC and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSNAW (SEQ ID NO:69) and a heavy chain CDR2 comprising the sequence IKSKIDGETT (SEQ ID NO:76) and a heavy chain CDR3 comprising the sequence TPGVGANNPYYFDR (SEQ ID NO:77) and a light chain CDR1 comprising the sequence QSVLCRSNNKNC (SEQ ID NO:62) and a light chain CDR2 comprising the sequence WAC and a light chain CDR3 comprising the sequence QQYSNTPQT (SEQ ID NO: 63).

The VH sequence of antibody C-D04-B is depicted in Table 1 as SEQ ID NO: 6. The VL sequence of antibody C-D04-B is depicted in Table 1 as SEQ ID NO: 20. Some embodiments therefore provide an antibody or antigen binding fragment that is able to bind O-mannosylated E-cadherin, comprising a VH sequence as depicted in SEQ ID NO: 6 and a VL sequence as depicted in SEQ ID NO: 20, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 6 and a VL sequence as depicted in SEQ ID NO: 20, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody C-D04-B as depicted in Table 1.

Further provided is an antibody or antigen binding fragment thereof that competes with antibody C-D04-B for binding to O-mannosylated E-cadherin, preferably for binding to one or more O-mannosylated threonine residues that are present within amino acid positions 467-472 of the E-cadherin sequence as depicted in FIG. 1A (SEQ ID NO: 45).

Further provided is an antibody or antigen binding fragment thereof that competes with antibody C-D04-B for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody C-D04-B for binding to cells, preferably tumor cells, that express E-cadherin and an O-mannosyltransferase, preferably TMTC3.

The heavy chain CDR1-3 sequences of antibodies F-C08, D-G03 and AT1636-N, depicted in Table 1, are GFTFSNAW (SEQ ID NO:69), IKSKIDGGTT (SEQ ID NO:70) and TPGVGANNPYYFDR (SEQ ID NO:83). The light chain CDR1-3 sequences of these antibodies F-C08, D-G03 and AT1636-N are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSNAW (SEQ ID NO:69) and a heavy chain CDR2 comprising the sequence IKSKIDGGTT (SEQ ID NO:70) and a heavy chain CDR3 comprising the sequence TPGVGANNPYYFDR (SEQ ID NO:80) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO:63).

The VH sequence of antibody F-C08 is depicted in Table 1 as SEQ ID NO: 7. The VL sequence of antibody F-C08 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 7 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 7 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody F-C08 as depicted in Table 1.

The VH sequence of antibodies D-G03 and AT1636-N is depicted in Table 1 as SEQ ID NO: 8. The VL sequence of antibodies D-G03 and AT1636-N is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 8 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 8 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody D-G03 or AT1636-N as depicted in Table 1.

Further provided is an antibody or antigen binding fragment thereof that competes with antibody F-C08 or D-G03 or AT1636-N for binding to O-mannosylated E-cadherin, preferably for binding to one or more O-mannosylated threonine residues that are present within amino acid positions 467-472 of the E-cadherin sequence as depicted in FIG. 1A (SEQ ID NO:45).

Further provided is an antibody or antigen binding fragment thereof that competes with antibody F-C08 or D-G03 or AT1636-N for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody F-C08 or D-G03 or AT1636-N for binding to cells, preferably tumor cells, that express E-cadherin and an O-mannosyltransferase, preferably TMTC3.

The heavy chain CDR1-3 sequences of antibody D-F10, depicted in Table 1, are GFTFSNAW (SEQ ID NO:69), IKSKIDGGTT (SEQ ID NO:70) and TPGVGTNNPYYFDR (SEQ ID NO:92). The light chain CDR1-3 sequences of this antibody C-A05 are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSNAW (SEQ ID NO:69) and a heavy chain CDR2 comprising the sequence IKSKIDGGTT (SEQ ID NO:70) and a heavy chain CDR3 comprising the sequence TPGVGTNNPYYFDR (SEQ ID NO:92) and a light chain CDR1 comprising the sequence QSVLCRSNNKNC SEQ ID NO:62) and a light chain CDR2 comprising the sequence WAS and a light chain CDR3 comprising the sequence QQYSNTPQT (SEQ ID NO: 63).

The VH sequence of antibody D-F10 is depicted in Table 1 as SEQ ID NO: 9. The VL sequence of antibody D-F10 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 9 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 9 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody D-F10 as depicted in Table 1.

Further provided is an antibody or antigen binding fragment thereof that competes with antibody D-F10 for binding to O-mannosylated E-cadherin, preferably for binding to one or more O-mannosylated threonine residues that are present within amino acid positions 467-472 of the E-cadherin sequence as depicted in FIG. 1A (SEQ ID NO: 45).

Further provided is an antibody or antigen binding fragment thereof that competes with antibody D-F10 for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody D-F10 for binding to cells, preferably tumor cells, that express E-cadherin and an O-mannosyltransferase, preferably TMTC3.

The heavy chain CDR1-3 sequences of antibodies C-E08, D-B06, D-G05, AT1636-Y and D-H08, depicted in Table 1, are GFTFSYAW (SEQ ID NO:93), IKSKIDGGTT (SEQ ID NO:94) and TPGVGANDPYYFDR (SEQ ID NO:95). The light chain CDR1-3 sequences of these antibodies C-E08, D-B06, D-G05 and D-H08 are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSYAW (SEQ ID NO:93) and a heavy chain CDR2 comprising the sequence IKSKIDGGTT (SEQ ID NO:94) and a heavy chain CDR3 comprising the sequence TPGVGANDPYYFDR (SEQ ID NO:95) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO: 63).

The VH sequence of antibodies C-E08, D-B06 and AT1636-Y is depicted in Table 1 as SEQ ID NO: 10. The VL sequence of antibodies C-E08, D-B06 and AT1636-Y is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 10 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 10 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody C-E08 or D-B06 or AT1636-Y as depicted in Table 1.

The VH sequence of antibody D-G05 is depicted in Table 1 as SEQ ID NO: 10. The VL sequence of antibody D-G05 is depicted in Table 1 as SEQ ID NO: 21. Some embodiments therefore provide an antibody or antigen binding fragment that is able to bind O-mannosylated E-cadherin, comprising a VH sequence as depicted in SEQ ID NO: 10 and a VL sequence as depicted in SEQ ID NO: 21, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 10 and a VL sequence as depicted in SEQ ID NO: 21, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody D-G05 as depicted in Table 1.

The VH sequence of antibody D-H08 is depicted in Table 1 as SEQ ID NO: 11. The VL sequence of antibody D-H08 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 11 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 11 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody D-H08 as depicted in Table 1.

Further provided is an antibody or antigen binding fragment thereof that competes with antibody C-E08 or D-B06 or D-G05 or D-H08 or AT1636-Y for binding to O-mannosylated E-cadherin, preferably for binding to one or more O-mannosylated threonine residues that are present within amino acid positions 467-472 of the E-cadherin sequence as depicted in FIG. 1A (SEQ ID NO:45).

Further provided is an antibody or antigen binding fragment thereof that competes with antibody C-E08 or D-B06 or D-G05 or D-H08 or AT1636-Y for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody C-E08 or D-B06 or D-G05 or D-H08 or AT1636-Y for binding to cells, preferably tumor cells, that express E-cadherin and an O-mannosyltransferase, preferably TMTC3.

The heavy chain CDR1-3 sequences of antibody C-H01, depicted in Table 1, are GFTFSNAW (SEQ ID NO:96), IKSKIDGGTI (SEQ ID NO:97) and TPGVGANDPYYFDR (SEQ ID NO:98). The light chain CDR1-3 sequences of this antibody C-H01 are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSNAW (SEQ ID NO:96) and a heavy chain CDR2 comprising the sequence IKSKIDGGTI (SEQ ID NO:97) and a heavy chain CDR3 comprising the sequence TPGVGANDPYYFDR (SEQ ID NO:98) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO: 63).

The VH sequence of antibody C-H01 is depicted in Table 1 as SEQ ID NO: 12. The VL sequence of antibody C-H01 is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 12 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 12 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody C-H01 as depicted in Table 1.

Further provided is an antibody or antigen binding fragment thereof that competes with antibody C-H01 for binding to O-mannosylated E-cadherin, preferably for binding to one or more O-mannosylated threonine residues that are present within amino acid positions 467-472 of the E-cadherin sequence as depicted in FIG. 1A (SEQ ID NO: 45).

Further provided is an antibody or antigen binding fragment thereof that competes with antibody C-H01 for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody C-H01 for binding to cells, preferably tumor cells, that express E-cadherin and an O-mannosyltransferase, preferably TMTC3.

Another preferred antibody according to the present invention is antibody AT1636-YN. This antibody is preferred because it is capable of binding O-mannosylated E-cadherin expressed on tumor cells, in particular the newly discovered truncated E-cadherin form of about 70 kDa. A particular advantage of AT1636-YN is the fact that it binds this truncated 70 kDa E-cadherin form better than full length E-cadherin of about 120 kDa. As described herein before, this characteristic typically allows for an increase of tumor-specificity in cases wherein O-mannosylated truncated 70 kDa E-cadherin is upregulated on tumor cells. A further advantage of that AT1636-YN has a preference for truncated 70 kDa E-cadherin form is that full length E-cadherin is broadly expressed. Hence, in the absence of a preference for the truncated 70 kDa E-cadherin form, the broadly expressed full length E-cadherin can work as a sink and/or introduce undesirable effects. Furthermore, the expression levels of full length E-cadherin are very high and therefore often not distinguishable between healthy and tumor epithelial cells, while a preference for the truncated 70 kDa E-cadherin form allows for more tumor specificity. In addition, E-cadherin has an important barrier function, so that it is preferable to avoid significant interference with the healthy function of E-cadherin.

In addition, AT1636-YN is able to bind O-mannosylated E-cadherin-expressing colon cancer subtypes CMS1, CMS2, CMS3 and CMS4. AT1636-YN binds to tumor cells, specifically epithelial tumor cells, more specifically O-mannosylated E-cadherin-expressing cancer cells, such as for instance O-mannosylated E-cadherin-expressing colon cancer cells, breast cancer cells, pancreatic cancer cells, bladder cancer cells, endometrium cancer cells, lung cancer cells and esophagus cancer cells. Antibody AT1636-YN is, therefore, particularly suitable for treatment and/or diagnosis of a disorder that is associated with the presence of cells that express O-mannosylated E-cadherin, such as O-mannosylated E-cadherin-expressing cancer cells, particularly cancer cells that express the newly discovered truncated E-cadherin form of about 70 kDa. The presence of human amino acid sequences diminishes the chance of adverse side effects during therapeutic use in human patients.

Figure 6A:
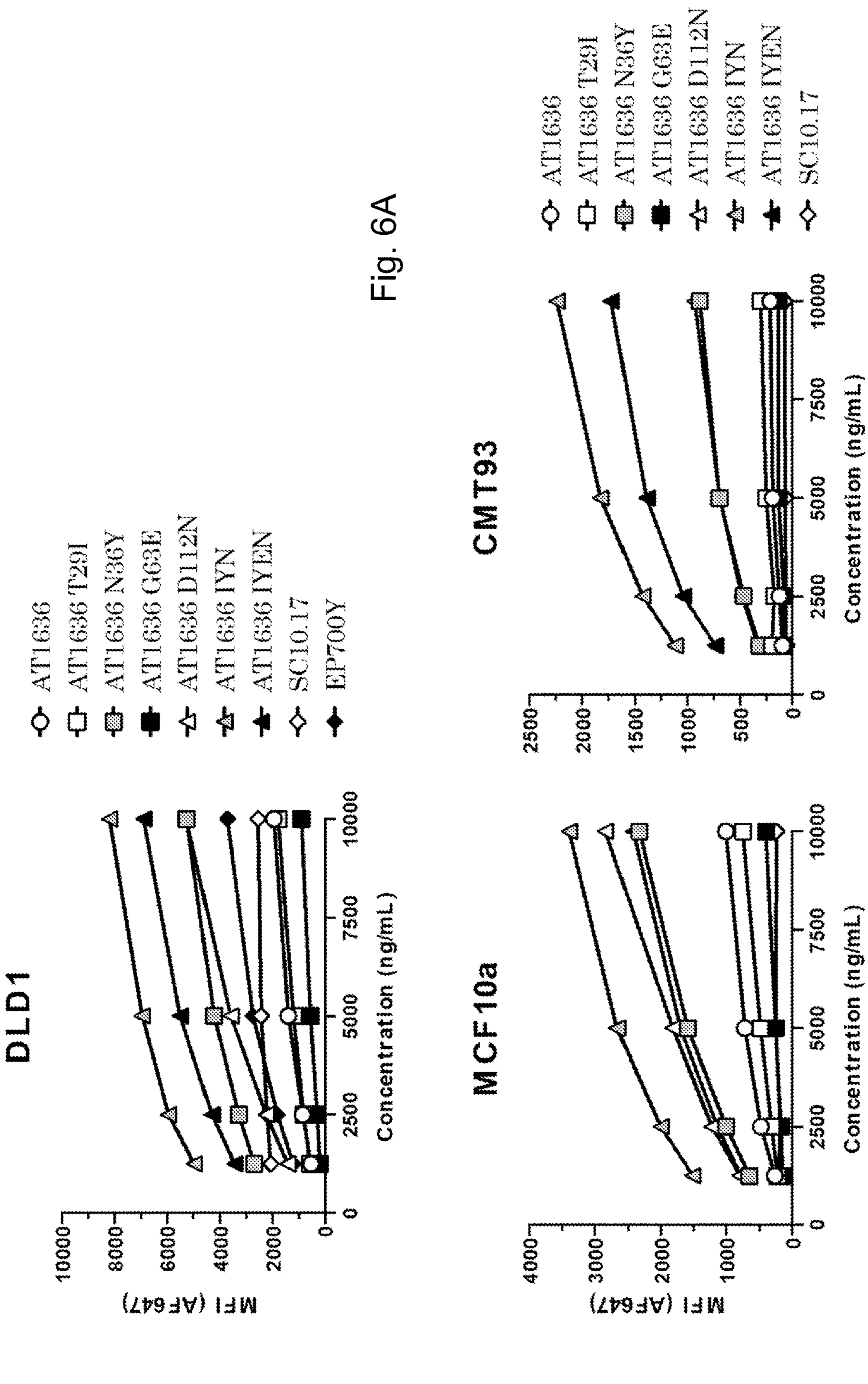
Figure 6B:
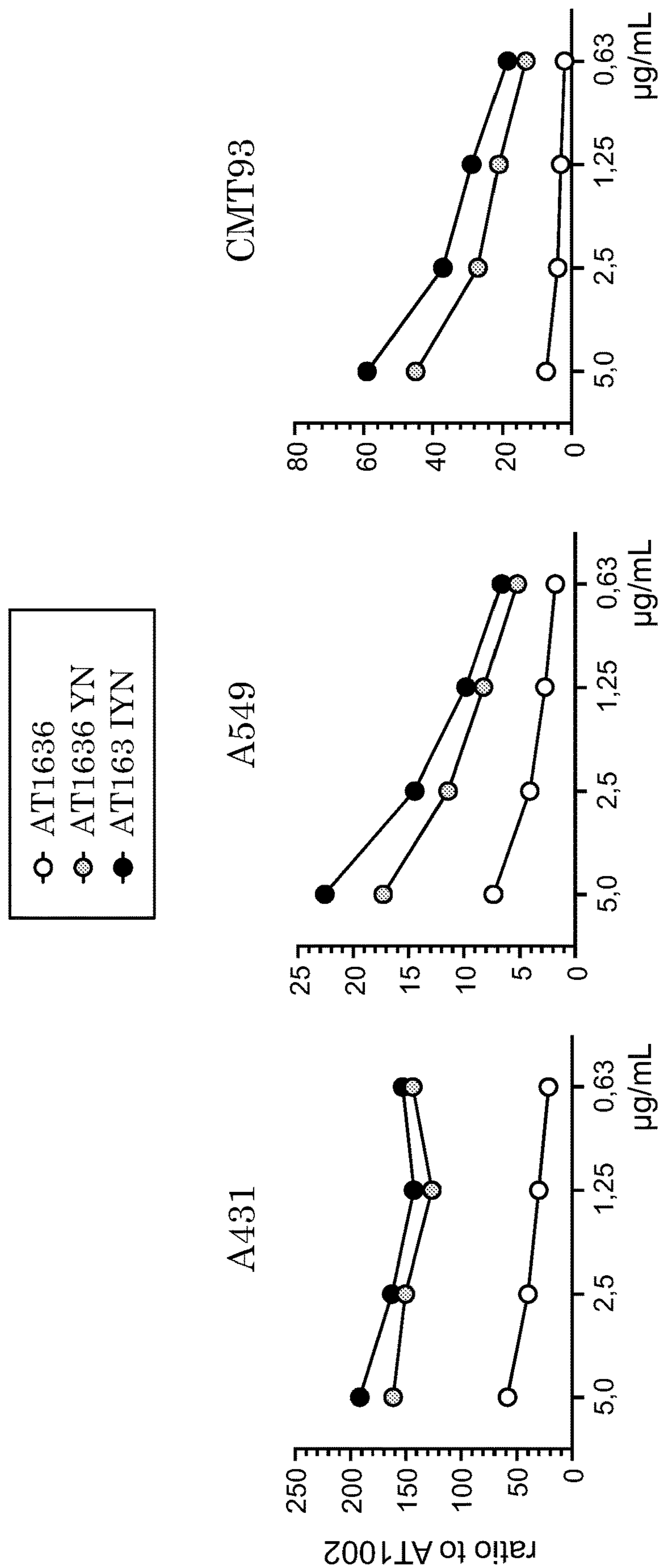

Furthermore, antibody AT1636-YN binds epidermoid carcinoma cell line A431, lung cancer cell line A549 and mouse tumor cell line CMT93 better than antibody AT1636 (see FIG. 6B).

The heavy chain CDR1-3 sequences of antibody AT1636-YN, depicted in Table 1, are GFTFSYAW (SEQ ID NO:99), IKSKIDGGTT (SEQ ID NO: 100) and TPGVGANNPYYFDR (SEQ ID NO:101). The light chain CDR1-3 sequences of this antibody AT1636-YN are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFTFSYAW (SEQ ID NO:99) and a heavy chain CDR2 comprising the sequence IKSKIDGGTT (SEQ ID NO:100) and a heavy chain CDR3 comprising the sequence TPGVGANNPYYFDR (SEQ ID NO:101) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO:63).

The VH sequence of antibody AT1636-YN is depicted in Table 1 as SEQ ID NO: 15. The VL sequence of antibody AT1636-YN is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 15 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 15 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody AT1636-YN as depicted in Table 1.

Further provided is an antibody or antigen binding fragment thereof that competes with antibody AT1636-YN for binding to O-mannosylated E-cadherin, preferably for binding to one or more O-mannosylated threonine residues that are present within amino acid positions 467-472 of the E-cadherin sequence as depicted in FIG. 1A (SEQ ID NO:45).

Further provided is an antibody or antigen binding fragment thereof that competes with antibody AT1636-YN for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody AT1636-YN for binding to cells, preferably tumor cells, that express E-cadherin and an O-mannosyltransferase, preferably TMTC3.

Another preferred antibody according to the present invention is antibody AT1636-IYN. This antibody is preferred because it is capable of binding O-mannosylated E-cadherin expressed on tumor cells, in particular the newly discovered truncated E-cadherin form of about 70 kDa. A particular advantage of AT1636-IYN is the fact that it binds this truncated 70 kDa E-cadherin form better than full length E-cadherin of about 120 kDa. As described herein before, this characteristic typically allows for an increase of tumor-specificity in cases wherein O-mannosylated truncated 70 kDa E-cadherin is upregulated on tumor cells. A further advantage of that AT1636-IYN has a preference for truncated 70 kDa E-cadherin form is that full length E-cadherin is broadly expressed. Hence, in the absence of a preference for the truncated 70 kDa E-cadherin form, the broadly expressed full length E-cadherin can work as a sink and/or introduce undesirable effects. Furthermore, the expression levels of full length E-cadherin are very high and therefore often not distinguishable between healthy and tumor epithelial cells, while a preference for the truncated 70 kDa E-cadherin form allows for more tumor specificity. In addition, E-cadherin has an important barrier function, so that it is preferable to avoid significant interference with the healthy function of E-cadherin.

In addition, AT1636-IYN is able to bind O-mannosylated E-cadherin-expressing colon cancer subtypes CMS1, CMS2, CMS3 and CMS4. AT1636-IYN binds to tumor cells, specifically epithelial tumor cells, more specifically O-mannosylated E-cadherin-expressing cancer cells, such as for instance O-mannosylated E-cadherin-expressing colon cancer cells, breast cancer cells, pancreatic cancer cells, bladder cancer cells, endometrium cancer cells, lung cancer cells and esophagus cancer cells. Antibody AT1636-IYN is, therefore, particularly suitable for treatment and/or diagnosis of a disorder that is associated with the presence of cells that express O-mannosylated E-cadherin, such as O-mannosylated E-cadherin-expressing cancer cells, particularly cancer cells that express the newly discovered truncated E-cadherin form of about 70 kDa. The presence of human amino acid sequences diminishes the chance of adverse side effects during therapeutic use in human patients.

Furthermore, antibody AT1636-IYN binds colon cell line DLD1, breast epithelial cell line MCF10a, epidermoid carcinoma cell line A431, lung cancer cell line A549 and mouse tumor cell line CMT93 better than antibody AT1636 (see FIGS. 6A and 6B).

The heavy chain CDR1-3 sequences of antibody AT1636-IYN, depicted in Table 1, are GFIFSYAW (SEQ ID NO:102), IKSKIDGGTT (SEQ ID NO:103) and TPGVGANNPYYFDR (SEQ ID NO:104). The light chain CDR1-3 sequences of this antibody AT1636-IYN are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFIFSYAW (SEQ ID NO:102) and a heavy chain CDR2 comprising the sequence IKSKIDGGTT (SEQ ID NO:103) and a heavy chain CDR3 comprising the sequence TPGVGANNPYYFDR (SEQ ID NO:104) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO:63).

The VH sequence of antibody AT1636-IYN is depicted in Table 1 as SEQ ID NO: 16. The VL sequence of antibody AT1636-IYN is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 16 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 16 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody AT1636-IYN as depicted in Table 1.

Further provided is an antibody or antigen binding fragment thereof that competes with antibody AT1636-IYN for binding to O-mannosylated E-cadherin, preferably for binding to one or more O-mannosylated threonine residues that are present within amino acid positions 467-472 of the E-cadherin sequence as depicted in FIG. 1A (SEQ ID NO:45).

Further provided is an antibody or antigen binding fragment thereof that competes with antibody AT1636-IYN for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody AT1636-IYN for binding to cells, preferably tumor cells, that express E-cadherin and an O-mannosyltransferase, preferably TMTC3.

Another preferred antibody according to the present invention is antibody AT1636-IYEN. This antibody is preferred because it is capable of binding O-mannosylated E-cadherin expressed on tumor cells, in particular the newly discovered truncated E-cadherin form of about 70 kDa. A particular advantage of AT1636-IYEN is the fact that it binds this truncated 70 kDa E-cadherin form better than full length E-cadherin of about 120 kDa. As described herein before, this characteristic typically allows for an increase of tumor-specificity in cases wherein O-mannosylated truncated 70 kDa E-cadherin is upregulated on tumor cells. A further advantage of that AT1636-IYEN has a preference for truncated 70 kDa E-cadherin form is that full length E-cadherin is broadly expressed. Hence, in the absence of a preference for the truncated 70 kDa E-cadherin form, the broadly expressed full length E-cadherin can work as a sink and/or introduce undesirable effects. Furthermore, the expression levels of full length E-cadherin are very high and therefore often not distinguishable between healthy and tumor epithelial cells, while a preference for the truncated 70 kDa E-cadherin form allows for more tumor specificity. In addition, E-cadherin has an important barrier function, so that it is preferable to avoid significant interference with the healthy function of E-cadherin.

In addition, AT1636-IYEN is able to bind O-mannosylated E-cadherin-expressing colon cancer subtypes CMS1, CMS2, CMS3 and CMS4 AT1636-IYEN binds to tumor cells, specifically epithelial tumor cells, more specifically O-mannosylated E-cadherin-expressing cancer cells, such as for instance O-mannosylated E-cadherin-expressing colon cancer cells, breast cancer cells, pancreatic cancer cells, bladder cancer cells, endometrium cancer cells, lung cancer cells and esophagus cancer cells. Antibody AT1636-IYEN is, therefore, particularly suitable for treatment and/or diagnosis of a disorder that is associated with the presence of cells that express O-mannosylated E-cadherin, such as O-mannosylated E-cadherin-expressing cancer cells, particularly cancer cells that express the newly discovered truncated E-cadherin form of about 70 kDa. The presence of human amino acid sequences diminishes the chance of adverse side effects during therapeutic use in human patients.

Furthermore, antibody AT1636-IYEN binds colon cell line DLD1, breast epithelial cell line MCF10a and mouse tumor cell line CMT93 better than antibody AT1636 (see FIG. 6A).

The heavy chain CDR1-3 sequences of antibody AT1636-IYEN, depicted in Table 1, are GFIFSYAW (SEQ ID NO:105), IKSKIDGETT (SEQ ID NO: 106) and TPGVGANNPYYFDR (SEQ ID NO:107). The light chain CDR1-3 sequences of this antibody AT1636-IYEN are QSVLCRSNNKNC (SEQ ID NO:62), WAS and QQYSNTPQT (SEQ ID NO:63). Some embodiments therefore provide an antibody or antigen binding fragment that is able to bind O-mannosylated E-cadherin, comprising a heavy chain CDR1 comprising the sequence GFIFSYAW (SEQ ID NO:105) and a heavy chain CDR2 comprising the sequence IKSKIDGETT (SEQ ID NO:106) and a heavy chain CDR3 comprising the sequence TPGVGANNPYYFDR (SEQ ID NO:107) and a light chain CDR1 comprising the sequence QSVLCRSNNKNC (SEQ ID NO:62) and a light chain CDR2 comprising the sequence WAS and a light chain CDR3 comprising the sequence QQYSNTPQT (SEQ ID NO:63).

The VH sequence of antibody AT1636-IYEN is depicted in Table 1 as SEQ ID NO: 17. The VL sequence of antibody AT1636-IYEN is depicted in Table 1 as SEQ ID NO: 18. Some embodiments therefore provide an antibody or antigen binding fragment that is able to bind O-mannosylated E-cadherin, comprising a VH sequence as depicted in SEQ ID NO: 17 and a VL sequence as depicted in SEQ ID NO: 18, or sequences having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions. Some embodiments therefore provide an antibody or antigen binding fragment that is able to bind O-mannosylated E-cadherin, comprising a VH sequence as depicted in SEQ ID NO: 17 and a VL sequence as depicted in SEQ ID NO: 18, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto, wherein said antibody or antigen binding fragment comprises the heavy chain CDR 1-3 sequences and the light chain CDR 1-3 sequences of antibody AT1636-IYEN as depicted in Table 1.

Further provided is an antibody or antigen binding fragment thereof that competes with antibody AT1636-IYEN for binding to O-mannosylated E-cadherin, preferably for binding to one or more O-mannosylated threonine residues that are present within amino acid positions 467-472 of the E-cadherin sequence as depicted in FIG. 1A (SEQ ID NO:45).

Further provided is an antibody or antigen binding fragment thereof that competes with antibody AT1636-IYEN for binding to O-mannosylated E-cadherin-comprising cells, preferably to O-mannosylated E-cadherin positive tumor cells. Said cells preferably express O-mannosylated E-cadherin on their surface.

Further provided is an antibody or antigen binding fragment thereof that competes with antibody AT1636-IYEN for binding to cells, preferably tumor cells, that express E-cadherin and an O-mannosyltransferase, preferably TMTC3.

In some embodiments, the heavy and light chain CDR1-3 sequences of the above described antibodies consist of the recited heavy and light chain CDR1-3 sequences.

In some embodiments, the heavy chain and light chain CDR1-3 sequences of antibody AT1636, E-C06, D-H04, D-A02, D-E09, E-A04, E-B09, C-A05, C-A03, C-B02, C-D04, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN or AT1636-IYEN are grafted onto a framework sequence of a different antibody. Said framework sequence is preferably a human framework sequence. The sequences of human framework regions are available from public DNA databases. In some preferred embodiments, human germline sequences are used for framework regions in antibodies and antigen binding fragments according to the invention. The use of human germline sequences minimizes the risk of immunogenicity of said antibodies, because these germline sequences are typically devoid of somatic hypermutations that may cause an immunogenic response.

In some embodiments, an antibody or antigen binding fragment according to the invention is a human antibody or antigen binding fragment thereof. The presence of human amino acid sequences diminishes the chance of adverse side effects during therapeutic use in human patients, as compared to non-human antibodies.

Some embodiments provide an antibody according to the invention that is a full length antibody. Full length antibodies are advantageous because of their favourable half life. An antibody of the invention is preferably of the IgG isotype. In particular, IgG1 is favoured based on its long circulatory half life in humans. Furthermore, IgG1 antibodies are easily produced commercially and their Fc tail allows for effector functions like antibody-dependent cell-mediated cytotoxicity (ADCC), complement-dependent cytotoxicity (CDC) and antibody-dependent cellular phagocytosis (ADCP). In order to prevent immunogenicity in humans it is preferred that an antibody according to the invention is a human antibody, or an antigen binding fragment thereof.

As described hereinbefore, antibody AT1636 is of the IgG3 isotype. As antibodies of IgG3 isotype are challenging to develop commercially since they have a tendency to aggregate, some embodiments provide an antibody of IgG1 isotype that comprises the heavy chain CDR1-3 and the light chain CDR1-3 sequences of antibody AT1636. Some embodiments provide an IgG1 antibody that comprises the heavy chain CDR1-3 and the light chain CDR1-3 sequences of an antibody selected from the group consisting of antibody AT1636-I, AT1636-Y, AT1636-E, AT1636-N, AT1636-YN, AT1636-IYN and AT1636-IYEN.

Some embodiments provide an IgG1 antibody that comprises the VH sequence and the VL sequence of an antibody selected from the group consisting of antibody AT1636, AT1636-I, AT1636-Y, AT1636-E, AT1636-N, AT1636-YN, AT1636-IYN and AT1636-IYEN, or sequences having at least 80%, preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% sequence identity thereto. Preferably, said sequence variations of said VH and/or VL regions are located outside the CDR regions.

Full length IgG antibodies according to the invention encompass antibodies wherein mutations are present that provide desired characteristics. Such mutations should not be deletions of substantial portions of any of the antibody regions. However, as described herein before, antibodies wherein one or several amino acid residues are deleted, without essentially altering the binding characteristics of the resulting antibody, are embraced within the term "full length antibody". For instance, an IgG antibody can have 1-20 amino acid residue insertions, deletions or a combination thereof in the constant region. For instance, glycosylation can be reduced and ADCC or CDC activity can be altered, as described herein below.

In some embodiments, an antibody or antigen binding fragment according to the invention comprises one or more, and preferably each of, the following characteristics:

- binds to the extracellular (EC) 3 domain of O-mannosylated E-cadherin;
- binds O-mannosylated truncated 70 kDa E-cadherin better, preferably at least 2 fold better, more preferably at least 3 fold better, more preferably at least 4 fold better, more preferably at least 5 fold better, than O-mannosylated full length E-cadherin;
- binds tumor cells that co-express E-cadherin and an O-mannosyltransferase, preferably TMTC3.

In some embodiments, said antibody or antigen binding fragment further comprises at least one of the following characteristics:

- binds colon cancer subtypes CMS1, CMS2, CMS3 and CMS4;
- binds colon carcinoma cell line SW948 better than healthy medullary thymic epithelial cells or dendritic cells or Langerhans cells.

Some preferred embodiments provide an antibody and antigen binding fragment according to the invention that has each of the characteristics listed above. Such antibodies and antigen binding fragments have a broad anti-tumor applicability in view of their ability to bind different cancer types and different colon cancer subtypes. Moreover, as explained in detail herein before, in view of their preference for the truncated 70 kDa E-cadherin as compared to full length E-cadherin, such antibodies and antigen binding fragments are suitable for increasing tumor-specificity in cases wherein the truncated 70 kDa E-cadherin form is significantly upregulated on tumor cells.

As shown in the Examples, antibodies are provided that specifically bind one or more O-mannosylated threonine and/or serine residues of E-cadherin, wherein said one or more O-mannosylated threonine and/or serine residues are present within amino acid positions 467-472 of the E-cadherin sequence as depicted in FIG. 1A. Now that this is known, it has become possible to obtain or generate further antibodies that compete for the same epitope of O-mannosylated E-cadherin. This can for instance be done by immunizing a non-human animal with an O-mannosylated E-cadherin peptide comprising the above mentioned amino acid residues 467-472 of the E-cadherin sequence as depicted in FIG. 1A, or with an immunogenic compound comprising such peptide, or with a nucleic acid molecule encoding such peptide, preferably followed by one or more booster administrations. Alternatively, non-human animals can be immunized with cells expressing TMTC3 and E-cadherin to express O-mannosylated E-cadherin on the surface of the cells. Also, non-human animals can be immunized with nucleic acids like for instance cDNAs, expressing both TMTC3 and E-cadherin by so-called DNA immunization technologies.

Subsequently, antibodies and/or B cells that are specific for said epitopes or peptides can be harvested from said non-human animal. In some embodiments, obtained antibodies are humanized in order to optimize them for human therapy. In some embodiments, obtained antibodies or B cells are tested for competition with an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, for binding to said peptide or to O-mannosylated E-cadherin or to the 70 kDa truncated form thereof.

Animal immunization protocols, including suitable administration procedures and adjuvants, procedures for obtaining and purifying antibodies and/or immune cells from such immunized animals, competition experiments and humanization procedures of non-human antibodies are well known in the art. Reference is for instance made to Hanly et al, 1995.

Alternatively, or additionally, said peptide or TMCT3-E-cadherin co-expressing cell is used to screen a phage display library in order to identify and/or isolate O-mannosylated E-cadherin-specific immunoglobulins, typically Fab fragments. Obtained antibodies, B cells or Fab fragments will typically compete with an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or with an antigen binding fragment thereof, for binding to said peptide or to O-mannosylated E-cadherin or to the 70 kDa truncated form thereof. In some embodiments, a competition assay is performed.

Also provided herewith are nucleic acid molecules and vectors that encode at least one CDR sequence of an antibody or antigen binding fragment according to the invention. Some embodiments thus provide an isolated, synthetic or recombinant nucleic acid, or a vector, encoding at least one CDR sequence of an antibody or antigen binding fragment according to the invention. In some embodiments, at least the heavy chain CDR3 sequence and the light chain CDR3 sequence of an antibody or antigen binding fragment according to the invention are encoded. Further provided is therefore an isolated, synthetic or recombinant nucleic acid, or a vector, encoding at least the heavy chain CDR3 sequence and the light chain CDR3 sequence of an antibody or antigen binding fragment according to the invention. Preferably, at least the heavy chain CDR1-3 sequences and the light chain CDR 1-3 sequences of an antibody or antigen binding fragment according to the invention are encoded. Further provided is therefore an isolated, synthetic or recombinant nucleic acid, or a vector, encoding at least the heavy chain CDR1-3 sequences and the light chain CDR1-3 sequences of an antibody or antigen binding fragment according to the invention. Preferably, said CDR sequences are the CDR sequences of an antibody as depicted in Table 1.

Particular embodiments provide an isolated, synthetic or recombinant nucleic acid encoding at least the heavy chain variable region and/or the light chain variable region of an antibody or antigen binding fragment according to the invention. In some embodiments, said nucleic acid encodes both the heavy chain variable region and the light chain variable region of an antibody or antigen binding fragment according to the invention. Such nucleic acids are particularly suitable for the production of antibodies or antigen binding fragments of the invention in producer cells. In some embodiments, said nucleic acids comprise nucleic acid sequences that have been codon optimized for a certain producer cell, such as for instance for *E. coli*, Chinese hamster ovary (CHO), NSO (a mouse myeloma) or T293 cells, enabling efficient production of antibodies or antigen binding fragments of the invention in these producer cells. It should be noted that antibody production can be done by any recombinant antibody production system; the four producer cell systems mentioned above are only a few examples of the many systems that are available to date. As used herein, the term "codon" means a triplet of nucleotides that encode a specific amino acid residue. The term "codon optimized" means that one or more codons from an original, preferably human, nucleic acid sequence is replaced by one or more codons that are preferred by a certain producer cell. These replacement codons preferably encode the same amino acid residue as the original codon that has been replaced. Alternatively, one or more replacement codons encode(s) a different amino acid residue. This preferably results in conservative amino acid substitution, although this is not necessary. In constant regions and framework regions, one or more amino acid substitutions are generally allowed. In CDR regions, it is preferred to use codons that encode the same amino acid residue as the original codon that has been replaced, so that the resulting product has the same CDR amino acid sequences as the original antibody.

VH and VL amino acid and nucleotide sequences of preferred antibodies according to the present invention are listed in Table 1. Since many amino acid residues are encoded by more than one different nucleic acid codons, different codons can be used for a certain amino acid residue, for instance to optimize the codon usage for a certain producer cell, as explained above. Furthermore, some nucleic acid sequence variations resulting in different amino acid residues are also typically tolerated, in particular outside the CDR encoding sequences. Particular embodiments therefore provide an isolated, synthetic or recombinant nucleic acid encoding at least the heavy chain variable region and/or the light chain variable region of an antibody depicted in Table 1. Some embodiments provide an isolated, synthetic or recombinant nucleic acid encoding a heavy chain variable region amino acid sequence selected from the group consisting of SEQ ID NOs 1-17, or encoding an amino acid sequence that has at least 80% sequence identity thereto. Preferably, said sequence identity is at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH regions are located outside the CDR regions. Some embodiments provide an isolated, synthetic or recombinant nucleic acid encoding a light chain variable region amino acid sequence selected from the group consisting of SEQ ID NOs 18-22, or encoding an amino acid sequence that has at least 80% sequence identity thereto. Preferably, said sequence identity is at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VL regions are located outside the CDR regions. Some embodiments provide an isolated, synthetic or recombinant nucleic acid encoding a heavy chain variable region amino acid sequence selected from the group consisting of SEQ ID NOs 1-17 and a light chain variable region amino acid sequence selected from the group consisting of SEQ ID NOs 18-22, or encoding amino acid sequences that have at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions.

Some embodiments provide an isolated, synthetic or recombinant nucleic acid that has at least 80% sequence identity with a VH or a VL sequence as depicted in Table 1. VH nucleic acid sequences of preferred antibodies according to the present invention are listed in Table 1 as SEQ ID Nos 23-39. VL nucleic acid sequences of preferred antibodies according to the present invention are listed in Table 1 as SEQ ID Nos 40-44. Further provided is therefore a nucleic acid comprising a sequence that has at least 80% sequence identity with a sequence selected from the group consisting of SEQ ID Nos 23-39, and/or comprising a sequence that has at least 80% sequence identity with a sequence selected from the group consisting of SEQ ID Nos 40-44. Preferably, a nucleic acid molecule according to the invention comprises a variable heavy chain encoding sequence as well as a variable light chain encoding sequence of the same antibody as depicted in Table 1. Also provided is therefore a nucleic acid comprising a sequence that has at least 80% sequence identity with a sequence selected from the group consisting of SEQ ID Nos 23-39, and comprising a sequence that has at least 80% sequence identity with a sequence selected from the group consisting of SEQ ID Nos 40-44. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions.

In some embodiments, nucleic acid molecules are provided that encode an antibody or antigen binding fragment according to the invention. Further provided is a nucleic acid molecule that encodes an antibody selected from the group consisting of antibodies AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN. In some embodiments, said nucleic acid is codon optimized for expression in a non-human host cell.

Further provided is a vector comprising a nucleic acid molecule according to the invention. As used herein "a vector comprising a nucleic acid molecule according to the invention" is also referred to as "a vector according to the invention".

Methods for constructing vectors comprising one or more nucleic acid molecule(s) according to the invention are well known in the art. Non-limiting examples of suitable vectors and production platforms are retroviral and lentiviral vectors, bacterial or yeast plasmids, SV40 vectors, baculoviral vectors, phage DNA vectors, pUC vectors, plasmid vectors like pBR322, vectors manufactured by Lonza like for instance the pCon plus vectors, production systems manufactured by Rentschler Biopharma like for instance the TurboCell™ expression platform and expression platforms of Fujifilm Diosynth like for instance the Apollo™ mammalian expression platform.

In some embodiments, a vector according to the invention comprises nucleic acid sequences encoding the VH and VL sequences of an antibody as depicted in Table 1. The VH nucleic acid sequences of these antibodies are listed in Table 1 as SEQ ID Nos 23-39 and the VL nucleic acid sequences of these antibodies are listed in Table 1 as SEQ ID Nos 40-44. Further provided is therefore a vector comprising a nucleic acid sequence that has at least 80% sequence identity with a sequence selected from the group consisting of SEQ ID Nos 23-39, and/or comprising a nucleic acid sequence that has at least 80% sequence identity with a sequence selected from the group consisting of SEQ ID Nos 40-44. Preferably, a vector according to the invention comprises a variable heavy chain encoding sequence as well as a variable light chain encoding sequence of an antibody as depicted in Table 1. Also provided is therefore a vector comprising a nucleic acid sequence that has at least 80% sequence identity with a sequence selected from the group consisting of SEQ ID Nos 23-39, and comprising a nucleic acid sequence that has at least 80% sequence identity with a sequence selected from the group consisting of SEQ ID Nos 40-44. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions of said antibodies.

Some embodiments provide a vector that comprises:

- a VH encoding nucleic acid sequence as depicted in SEQ ID NO: 23 and a VL encoding nucleic acid sequence as depicted in SEQ ID NO: 40, or sequences having at least 80% sequence identity thereto; or
- a VH encoding nucleic acid sequence as depicted in SEQ ID NO: 23 and a VL encoding nucleic acid sequence as depicted in SEQ ID NO: 44, or sequences having at least 80% sequence identity thereto; or a VH encoding nucleic acid sequence as depicted in SEQ ID NO: 24 and a VL encoding nucleic acid sequence as depicted in SEQ ID NO: 40, or sequences having at least 80% sequence identity thereto a VH encoding nucleic acid sequence as depicted in SEQ ID NO: 25 and a VL encoding nucleic acid sequence as depicted in SEQ ID NO: 40, or sequences having at least 80% sequence identity thereto; or a VH encoding nucleic acid sequence as depicted in SEQ ID NO: 26 and a VL encoding nucleic acid sequence as depicted in SEQ ID NO: 41, or sequences having at least 80% sequence identity thereto; or a VH encoding nucleic acid sequence as depicted in SEQ ID NO: 27 and a VL encoding nucleic acid sequence as depicted in SEQ ID NO: 40, or sequences having at least 80% sequence identity thereto; or a VH encoding nucleic acid sequence as depicted in SEQ ID NO: 28 and a VL encoding nucleic acid sequence as depicted in SEQ ID NO: 40, or sequences having at least 80% sequence identity thereto; or a VH encoding nucleic acid sequence as depicted in SEQ ID NO: 28 and a VL encoding nucleic acid sequence as depicted in SEQ ID NO: 42, or sequences having at least 80% sequence identity thereto; or a VH encoding nucleic acid sequence as depicted in SEQ ID NO: 29 and a VL encoding nucleic acid sequence as depicted in SEQ ID NO: 40, or sequences having at least 80% sequence identity thereto; or a VH encoding nucleic acid sequence as depicted in SEQ ID NO: 30 and a VL encoding nucleic acid sequence as depicted in SEQ ID NO: 40, or sequences having at least 80% sequence identity thereto; or a VH encoding nucleic acid sequence as depicted in SEQ ID NO: 31 and a VL encoding nucleic acid sequence as depicted in SEQ ID NO: 40, or sequences having at least 80% sequence identity thereto; or a VH encoding nucleic acid sequence as depicted in SEQ ID NO: 32 and a VL encoding nucleic acid sequence as depicted in SEQ ID NO: 40, or sequences having at least 80% sequence identity thereto; or a VH encoding nucleic acid sequence as depicted in SEQ ID NO: 32 and a VL encoding nucleic acid sequence as depicted in SEQ ID NO: 43, or sequences having at least 80% sequence identity thereto; or a VH encoding nucleic acid sequence as depicted in SEQ ID NO: 33 and a VL encoding nucleic acid sequence as depicted in SEQ ID NO: 40, or sequences having at least 80% sequence identity thereto; or a VH encoding nucleic acid sequence as depicted in SEQ ID NO: 34 and a VL encoding nucleic acid sequence as depicted in SEQ ID NO: 40, or sequences having at least 80% sequence identity thereto; or a VH encoding nucleic acid sequence as depicted in SEQ ID NO: 35 and a VL encoding nucleic acid sequence as depicted in SEQ ID NO: 40, or sequences having at least 80% sequence identity thereto; or a VH encoding nucleic acid sequence as depicted in SEQ ID NO: 36 and a VL encoding nucleic acid sequence as depicted in SEQ ID NO: 40, or sequences having at least 80% sequence identity thereto; or a VH encoding nucleic acid sequence as depicted in SEQ ID NO: 37 and a VL encoding nucleic acid sequence as depicted in SEQ ID NO: 40, or sequences having at least 80% sequence identity thereto; or a VH encoding nucleic acid sequence as depicted in SEQ ID NO: 38 and a VL encoding nucleic acid sequence as depicted in SEQ ID NO: 40, or sequences having at least 80% sequence identity thereto; or a VH encoding nucleic acid sequence as depicted in SEQ ID NO: 39 and a VL encoding nucleic acid sequence as depicted in SEQ ID NO: 40, or sequences having at least 80% sequence identity thereto.

Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions.

In some embodiments, a vector according to the invention is a CAR T cell vector, comprising a nucleic acid sequence encoding an antigen recognition domain and a T cell activating domain. In some embodiments said antigen recognition domain comprises at least the heavy chain CDR1-3 sequences of an antibody according to the invention. In some embodiments said antigen recognition domain comprises at least the light chain CDR1-3 sequences of an antibody according to the invention. In some embodiments said antigen recognition domain comprises the heavy chain CDR1-3 sequences and the light chain CDR1-3 sequences of an antibody according to the invention. In some embodiments said antigen recognition domain comprises the VH sequence of an antibody according to the invention, or a sequence having at least 80% sequence identity thereto.

In some embodiments said antigen recognition domain comprises the VL sequence of an antibody according to the invention, or a sequence having at least 80% sequence identity thereto. In some embodiments said antigen recognition domain comprises the VH and the VL sequences of an antibody according to the invention, or a sequence having at least 80% sequence identity thereto. Preferably, said sequence identities are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Preferably, said sequence variations of said VH and/or VL regions are located outside the CDR regions.

In some embodiments, said antigen recognition domain is in a single chain format. In some embodiments, said CAR T cell vector further comprises a nucleic acid sequence encoding a transmembrane domain.

A vector according to the invention is for instance useful for in vitro production of antibodies or antigen binding fragments or CAR T cells of the invention. This is for instance done by introducing such nucleic acid molecule or vector into a cell so that the cell's nucleic acid translation machinery will produce the encoded antibodies or antigen binding fragments or CAR T cells. In some embodiments, at least one nucleic acid molecule or vector according to the invention is expressed in so called producer cells, such as for instance *E. coli*, CHO, NSO or T293 cells, some of which are adapted to commercial antibody production. As described herein before, in such cases it is preferred to use nucleic acid molecules wherein the original human sequences as provided herein are codon optimized for the producer cell. Proliferation of said producer cells results in a producer cell line capable of producing antibodies or antigen binding fragments according to the invention. Preferably, said producer cell line is suitable for producing antibodies for use in humans. Hence, said producer cell line is preferably free of pathogenic agents such as pathogenic micro-organisms. In some embodiments, antibodies consisting of human sequences are generated by such producer cell line.

In some embodiments a CAR T cell vector according to the invention is introduced into a T cell in order to produce a CAR T cell.

Further provided is therefore an isolated or recombinant host cell, comprising at least one antibody, or antigen binding fragment, or nucleic acid molecule, or vector according to the invention. Such cell is preferably an antibody producer cell, capable of large scale antibody production. In some embodiments, said cell is a mammalian cell, a T cell, a bacterial cell, a plant cell, a HEK293T cell, a CHO cell, a production system manufactured by Lonza like for instance the pCon plus production system, a production system manufactured by Rentschler Biopharma like for instance the TurboCell™ expression platform, or an expression platform of Fujifilm Diosynth like for instance the Apollo™ mammalian expression platform.

Further provided is a method for producing an antibody or antigen binding fragment according to the invention, the method comprising culturing a host cell comprising a nucleic acid or vector according to the invention and allowing said host cell to translate said nucleic acid or vector, thereby producing said antibody or antigen binding fragment according to the invention. Said method according to the invention preferably further comprises a step of recovering said antibody or antigen binding fragment from said host cell and/or from the culture medium. In some embodiments, said antibody or antigen binding fragment is an antibody as depicted in Table 1, preferably an antibody selected from the group consisting of AT1636, AT1636-I, AT1636-Y, AT1636-E, AT1636-N, AT1636-YN, AT1636-IYN and AT1636-IYEN, and antigen binding fragments thereof. In some preferred embodiments, said antibody or antigen binding fragment is an antibody selected from the group consisting of AT1636-YN, AT1636-IYN and AT1636-IYEN, and antigen binding fragments thereof.

An antibody or antigen binding fragment when obtained by a method according to the invention is also provided herewith. Obtained binding compounds according to the invention are for instance suitable for use in human therapy or diagnostics, optionally after additional purifying, isolation or processing steps.

In some embodiments, at least one nucleic acid molecule or vector according to the invention is introduced into a non-human animal, for instance for in vivo antibody production. Further provided is therefore an isolated or recombinant non-human animal, comprising an antibody, antigen binding fragment, nucleic acid molecule or vector according to the invention. Methods for producing transgenic non-human animals are known in the art.

Additional Antibody Modifications

Further provided are antibodies according to the invention wherein one or more amino acid residues of the constant region are modified. In some embodiments, one or more amino acids in the Fc region are modified in order to reduce glycosylation. N-glycosylation is a commonly found post-translational modification of antibodies and is known to occur at glycosylation motifs containing the consensus sequence N-X-S or N-X-T, wherein N represents an asparagine, X represents any amino acid residue, S represents a serine and T represents a threonine. Fc glycosylation influences the structural characteristics of an antibody's Fc part, thereby influencing effector functions and pharmacokinetics. As Fc glycosylation may result in a decreased half life and/or increased immunogenicity, glycosylation may be undesired for a therapeutic antibody. In some embodiments, one or more amino acids in a Fc glycosylation region are modified, as compared to the original parental antibody, in order to diminish or avoid glycosylation. For instance, at least one of the N, S and T residues of the above mentioned glycosylation motifs is altered. In some embodiments, the asparagine residue at position 47 (N47) of the CH2 region is altered. In some embodiments, the threonine at position 95 (T95) of the CH2 region is altered.

Alternatively, or additionally, one or more glycosylation sites in the variable framework region of an antibody according to the invention are altered in order to diminish or avoid glycosylation.

The constant domains of antibodies play a role in various antibody characteristics like antibody-dependent cell-mediated cytotoxicity (ADCC), antibody-dependent cellular phagocytosis (ADCP), and complement-dependent cytotoxicity (CDC). Fc regions mediate antibody function by binding to different receptors on immune effector cells such as macrophages, natural killer cells, B-cells and neutrophils. Some of these receptors, such as CD16A (FcγRIIIA) and CD32A (FcγRIIA), activate the immune effector cells to build a response against antigens. Other receptors, such as CD32B, inhibit the activation of immune cells. In some embodiments, an antibody according to the invention is engineered to enhance ADCC activity. One technique for enhancing ADCC activity of an antibody is afucosylation. Further provided is therefore an antibody or antigen binding fragment according to the invention, which is afucosylated.

Any means known in the art for obtaining afucosylated antibodies can be applied. Afucosylated antibodies are for instance obtained by the use of producer cell lines with a reduced capacity of fucosylation, such as for instance the Lec13 CHO mutant (Patnaik & Stanley, 2006). It is also possible to knock out the FUT8 gene encoding the alpha1, 6-fucosyltransferase in cell lines such as CHO (Potelligent® technology) (Yamane-Ohnuki et al, 2004).

Alternatively, an antibody producing cell line can be used wherein N-acetylglucosaminyltransferase III (GnT III) is overexpressed, resulting in non-fucosylated antibodies (GlycoMAb™ technology).

Alternatively, or additionally, multiple other strategies can be used to achieve ADCC enhancement, for instance including glycoengineering (Kyowa Hakko/Biowa, GlycArt (Roche) and Eureka Therapeutics) and mutagenesis (Xencor and Macrogenics), all of which seek to improve Fc binding to low-affinity activating FcγRIIIa, and/or to reduce binding to the low affinity inhibitory FcγRIIb. Chemo-enzymatic modification has also been used for modifications of Fc-bound N-glycans.

Besides fucose, other sugar moieties are also known to play a role in ADCC activity. In some embodiments, an antibody or antigen binding fragment according to the invention is hypergalactosylated in order to enhance ADCC.

In some embodiments, at least one amino acid of an FcγR binding site within the Fc domain of an antibody of the invention is modified in order to manipulate Fc/FcR interactions. In some embodiments, amino acid mutations S298A, E333A and K334A are introduced into the Fc domain of an antibody of the invention. These mutations are reported to enhance ADCC activity (Shields et al, 2001). In some embodiments, ADCC activity of an antibody of the invention is enhanced by introducing the amino acid mutations S239D and I332E, optionally in combination with the amino acid mutation A330L (Lazar et al, 2006). In some embodiments, ADCC activity of an antibody of the invention is enhanced by introducing the amino acid mutations L235V, F243L, R292P, Y300L and P396L (Stavenhagen et al, 2007). Further provided is therefore an antibody or antigen binding fragment according to the invention, comprising amino acid mutations selected from the group of:

S298A, E333A, K334A;
S239D, I332E;
S239D, I332E, A330L; and
L235V, F243L, R292P, Y300L, P396L.

Several in vitro methods exist for determining the efficacy of antibodies in eliciting ADCC. Among these are chromium-51 [Cr51] release assays, europium [Eu] release assays and sulfur-35 [S35] release assays. Usually, a labeled target cell line expressing a certain surface-exposed antigen is incubated with an antibody specific for that antigen. After washing, effector cells expressing Fc receptor CD16 are typically co-incubated with the antibody-labeled target cells. Target cell lysis is subsequently typically measured by release of intracellular label, for instance by a scintillation counter or spectrophotometry. Alternatively, a luciferase-based cytotoxicity assay can be used, wherein target cells expressing firefly luciferase are incubated with an antibody, such as for instance a bispecific or multispecific antibody. After washing, effector cells are added and co-incubated. Target cell kill is subsequently typically measured by lysing the remaining target cells and measuring luciferin luminescence by spectrophotometry.

In some embodiments, an antibody according to the invention is engineered to enhance CDC activity. One way to enhance CDC is the introduction of amino acid mutation K326W and/or E333S into the Fc domain (Idusogie et al, 2001). In some embodiments, amino acid mutations S267E, H268F and S324T are introduced into the Fc domain of an antibody of the invention in order to enhance CDC activity. As these mutations are reported to diminish ADCC activity, amino acid substitutions G236A and I332E are preferably also introduced in order to restore ADCC activity (Moore et al, 2010).

In some embodiments, amino acid mutation E345R is introduced into the Fc domain of an antibody of the invention in order to enhance CDC activity. In some embodiments, amino acid mutations E345K and/or E430G are introduced into the Fc domain of an antibody of the invention in order to enhance CDC and ADCC activity (De Jong et al, 2016).

Further provided is therefore an antibody or antigen binding fragment according to the invention, comprising one or more amino acid mutations selected from the group of:

K326W;
E333S;
K326W, E333S;
E345R;
E345K;
E430G;
E345K, E430G;
S267E, H268F, S324T; and
S267E, H268F, S324T, G236A, I332E.

While immune effector functions like ADCC and CDC are beneficial in many therapeutic applications, in other applications it is beneficial to diminish them. Such applications for instance include therapeutic approaches where the mechanism of action particularly lies in the Fab arms or other moieties fused to the Fc region. In such cases, reduction of Fc/FcR and/or Fc/C1q interactions may be beneficial to reduce tissue damage caused by immune effector functions. Reduction of immune effector functions may therefore be preferred in cases where the use of antibodies according to the invention does not require ADCC or CDC. Effector functions of an antibody according to the invention may for instance be diminished by the use of an IgG2 or IgG4 format, which have reduced effector functions as compared to IgG1. In some embodiments, effector functions of an antibody according to the invention are diminished by introduction of a L235E mutation in the Fc region, or by introduction of one or more other mutations within amino acid positions 234-237. In some embodiments, an IgG1 antibody of the invention is provided with amino acid substitutions L234A and L235A (LALA mutations) in order to diminish effector functions (Lund et al, 1992). In some embodiments, an IgG1 antibody of the invention is provided with amino acid substitutions L234A, L235A and P329G (LALA-PG mutations) in order to diminish effector functions. In some embodiments, an IgG4 antibody of the invention is provided with amino acid substitutions S228P and L235E (SPLE mutations). Introduction of amino acid substitution P329G is also beneficial for diminishing effector functions.

Further provided is therefore an antibody or antigen binding fragment according to the invention, comprising one or more amino acid mutations selected from the group of:

L235E;
L234A, L235A;
L234A, L235A, P329G;
S228P, L235E; and
S228P, L235E, P329G.

Bispecific or Multispecific Binding Compounds

Another aspect of the invention provides an antibody or antigen binding fragment according to the invention, that is coupled to another compound. In some embodiments, an antibody or antigen binding fragment according to the invention is coupled to another therapeutic moiety, such as for instance a drug, a chemotherapeutic drug, a toxic moiety, a cytotoxic agent or a radioactive compound, to form a so called "antibody-drug conjugate" (ADC).

Some embodiments provide an ADC wherein the ADC comprises an antibody or antigen binding fragment according to the invention and a cytostatic or cytotoxic drug unit. The drug unit may for instance disrupt DNA strands (eg, duocarmycins, calicheamicins, pyrrolobenzodiazepines [PBDs], and SN-38 [the active metabolite of irinotecan]) or microtubules (eg, maytansines and auristatins), or exerts topoisomerase or RNA polymerase inhibition, leading to cell death (Chau et al, 2019). In some embodiments, said ADC comprises a chemical linker unit between the cytostatic or cytotoxic drug unit and the antibody unit (Tsuchikama, 2018). In some embodiments, the linker is cleavable under intracellular conditions, such that the cleavage of the linker releases the drug unit from the antibody or antigen binding fragment in the intracellular environment. In some embodiments, the linker unit is not cleavable, and the drug is for instance released by antibody degradation. In some embodiments, the linker is cleavable by a cleavable agent that is present in the intracellular environment (e. g. within a lysosome or endosome or caveola). Non-limiting examples of cleavable linkers include disulfide-containing linkers that are cleavable through disulfide exchange, acid-labile linkers that are cleavable at acidic pH, and linkers that are cleavable by hydrolases, esterases, peptidases and glucuronidases In some embodiments, an antibody or antigen binding fragment is conjugated to a nucleic acid, which may be a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In some embodiments, an antibody or antigen binding fragment is conjugated to an aptamer or a ribozyme instead of an auristatin or a functional peptide analog or derivate thereof.

In some embodiments, an antibody drug conjugate according to the invention comprises one or more radiolabeled amino acids, which are useful for both diagnostic and therapeutic purposes, Methods for preparing radiolabeled amino acids and related peptide derivatives are known in the art (see for instance Junghans et al. 1996, U.S. Pat. Nos. 4,681,581, 4,735,210, 5,101,827, 5,102,990 (US RE35, 50G), U.S. Pat. Nos. 5,648,471 and 5,697,902). In some embodiments, an antibody or antigen binding fragment according to the invention is conjugated to a radioisotope or to a radioisotope-containing chelate.

The antibodies and antigen-binding fragments thereof disclosed herein may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, 51To, 226Ra, 60Co, 59Fe, 51Se, 152Eu, 67CU, 2nCi, 211At, 212Pb, 47Sc, 109Pd, 234Th, and 4oK, 151Gd, 55Mn, 52Tr, and 56Fe.

In some embodiments, a moiety that is coupled to an antibody or antigen binding fragment according to the invention is an immunomodulatory compound. A preferred example of such immunomodulatory compound is a T cell-binding compound, an NK cell-binding compound, an NKT cell-binding compound, or a gamma-delta T cell-binding compound. In some preferred embodiments, said T cell-binding compound is a CD3-specific binding compound, a KLRG1-specific binding compound or a CD103-specific binding compound. If coupled to an antibody or antigen binding fragment according to the invention, such T cell-binding compound will target T cells to cells, such as cancer cells, that express E-cadherin and an O-mannosyltransferase, thereby inducing or enhancing a cytotoxic T-cell response against said (cancer) cells.

Likewise, an NK cell-binding compound, an NKT cell-binding compound, or a gamma-delta T cell-binding compound is suitable for targeting NK cells, NKT cells or gamma-delta-T cells, respectively, to attract them to cells that express E-cadherin and an O-mannosyltransferase and induce cytotoxicity or other immune-mediated activity.

In some preferred embodiments, said T cell-binding compound is a CD3-specific binding compound. In some preferred embodiments, said T cell-binding compound is a KLRG1-specific binding compound. In some preferred embodiments, said T cell-binding compound is a CD103-specific binding compound.

In some embodiments, an antibody or antigen binding fragment according to the invention is coupled to a TGFβ-specific binding compound. This is particularly useful for targeting an antibody or antigen binding fragment according to the invention to cells, preferably disease-specific cells such as tumor cells, that comprise O-mannosylated E-cadherin and TGFβ. As shown in the Examples, an antibody or antigen binding fragment according to the invention is particularly well capable of inhibiting tumor cell growth and/or increasing tumor cell death when said tumor expresses both O-mannosylated E-cadherin and TGFβ.

A review of bispecific antibodies and antibody constructs in oncology is provided in Suurs et al, 2019.

Some embodiments therefore provide a bispecific or multispecific binding compound, comprising an antibody or antigen binding fragment according to the present invention and an immunomodulatory molecule.

Some embodiments provide a bispecific or multispecific binding compound, comprising an antibody or antigen binding fragment according to the present invention and a compound selected from the group consisting of a T cell-binding compound, an NK cell-binding compound, an NKT cell-binding compound and a gamma-delta T cell-binding compound.

Some embodiments provide a bispecific or multispecific binding compound, comprising an antibody or antigen binding fragment according to the invention and a CD3-specific binding compound.

Some embodiments provide a bispecific or multispecific binding compound, comprising an antibody or antigen binding fragment according to the invention and a CD103-specific binding compound.

Some embodiments provide a bispecific or multispecific binding compound, comprising an antibody or antigen binding fragment according to the invention and a KLRG1-specific binding compound.

Some embodiments provide a bispecific or multispecific binding compound, comprising an antibody or antigen binding fragment according to the invention and a TGFβ-specific binding compound.

Some embodiments provide an antibody or antigen binding fragment according to the invention that is coupled to another tumor-binding compound. Such bispecific or multispecific compounds allow, for instance, for increased binding or more specific binding of tumor cells, especially when the two or more coupled binding compounds are specific for different epitopes on tumor cells. Such bispecific or multispecific compound is thus very suitable for therapeutic or diagnostic applications.

In some embodiments, an antibody or antigen binding fragment according to the present invention is coupled to a label. This allows detection of E-cadherin-containing cells, such as for instance E-cadherin-positive cancer cells, using such labeled binding compound. In some embodiments, an antibody or antigen binding fragment according to the present invention is coupled to a hormone or an enzyme. This allows the targeting of such hormone or enzyme to E-cadherin-containing (cancer) cells. Other embodiments provide an antibody or antigen binding fragment according to the invention that is coupled to a second antibody or antigen binding fragment thereof.

Some embodiments thus provide an antibody or antigen binding fragment according to the invention that is coupled to another compound, preferably to a compound selected from the group consisting of an immunomodulatory compound, a T cell-binding compound, an NK cell-binding compound, an NKT cell-binding compound and a gamma-delta T cell-binding compound, a CD3-specific binding compound, a TGFβ-specific binding compound, a cytokine, a second antibody or antigen binding fragment thereof, a detectable label, a drug, a chemotherapeutic drug, a cytotoxic agent, a toxic moiety, a hormone, an enzyme, and a radioactive compound.

In some embodiments, said second antibody or antigen binding fragment thereof is also specific for O-mannosylated E-cadherin. Provided is therefore a bispecific or multispecific binding compound comprising an antibody or antigen binding fragment according to the invention and a second antibody or antigen binding fragment thereof that is also specific for O-mannosylated E-cadherin. The resulting binding compound is monospecific for E-Cadherin, and each Fab arm will typically bind its own E-Cadherin epitope. In some embodiments, the epitopes recognized by the Fab fragments are different from each other. In other embodiments, the epitopes are the same. The Fab arms may bind the epitopes with different affinity. Alternatively, the Fab arms bind their epitopes with essentially the same affinity, meaning that the $K_D$ of the Fab arms differ no more than 30%, preferably no more than 20% or no more than 10% from each other.

In some embodiments, said second antibody or antigen binding fragment thereof is also an antibody or antigen binding fragment according to the present invention. Provided is therefore a bispecific or multispecific binding compound comprising at least two antibodies or antigen binding fragments according to the invention. In some embodiments, said at least two antibodies or antigen binding fragments according to the invention are coupled to each other. In some embodiments, said bispecific or multispecific binding compound comprises at least two AT1636 antibodies or antigen binding parts thereof. In some embodiments, said bispecific or multispecific binding compound comprises at least two AT1636-I antibodies or antigen binding parts thereof. In some embodiments, said bispecific or multispecific binding compound comprises at least two AT1636-E antibodies or antigen binding parts thereof. In some embodiments, said bispecific or multispecific binding compound comprises at least two AT1636-N antibodies or antigen binding parts thereof. In some embodiments, said bispecific or multispecific binding compound comprises at least two AT1636-Y antibodies or antigen binding parts thereof. In some embodiments, said bispecific or multispecific binding compound comprises at least two AT1636-YN antibodies or antigen binding parts thereof. In some embodiments, said bispecific or multispecific binding compound comprises at least two AT1636-IYN antibodies or antigen binding parts thereof. In some embodiments, said bispecific or multispecific binding compound comprises at least two AT1636-IYEN antibodies or antigen binding parts thereof.

Some embodiments provide a binding compound that is able to bind O-mannosylated E-cadherin, wherein said compound comprises an antibody or antigen binding fragment according to the present invention and a therapeutic drug or a radioactive compound or a toxic moiety.

In some embodiments, an antibody or antigen binding fragment according to the invention is coupled to another E-cadherin-specific binding compound, such as for instance a currently known anti E-cadherin antibody or antigen binding fragment thereof, in order to produce a bispecific or multispecific compound. In some embodiments, a heavy chain of an antibody or antigen binding fragment according to the invention is paired with a heavy chain of another E-cadherin-specific antibody, in order to produce a bispecific antibody or antigen binding fragment thereof. Bispecific or multispecific compounds according to the invention allow, for instance, for increased binding to E-cadherin-containing cells. Such bispecific or multispecific compound is thus very suitable for therapeutic or diagnostic applications. It is also possible to use bispecific or multispecific compounds according to the invention in assays wherein different E-cadherin-containing cells are bound to the same bispecific or multispecific binding compound.

Some embodiments provide a bispecific antibody, or an antigen binding fragment thereof, that comprises one Fab fragment of an antibody according to the present invention and one Fab fragment of another antibody. In some embodiments, such bispecific antibody comprises one Fab fragment of an antibody according to the invention and one Fab fragment of another antibody, preferably specific for a T cell, an NK cell, an NKT cell or a gamma-delta T cell, such as for instance a Fab fragment that is specific for CD3, KLRG1 or CD103.

Some embodiments therefore provide a bispecific antibody or antigen binding fragment thereof that is able to bind O-mannosylated E-cadherin, comprising:

- one Fab fragment of an antibody or antigen binding fragment according to the invention; and
- one Fab fragment of another antibody, preferably specific for a T cell, an NK cell, an NKT cell or a gamma-delta T cell.

Also provided is a bispecific antibody or antigen binding fragment thereof that is able to bind O-mannosylated E-cadherin, comprising:

- one Fab fragment of an antibody or antigen binding fragment according to the invention; and
- one Fab fragment of another antibody that is specific for CD3.

Also provided is a bispecific antibody or antigen binding fragment thereof that is able to bind O-mannosylated E-cadherin, comprising:

- one Fab fragment of an antibody or antigen binding fragment according to the invention; and
- one Fab fragment of another antibody that is specific for KLRG1.

Also provided is a bispecific antibody or antigen binding fragment thereof that is able to bind O-mannosylated E-cadherin, comprising:

- one Fab fragment of an antibody or antigen binding fragment according to the invention; and
- one Fab fragment of another antibody that is specific for CD103.

Also provided is a bispecific antibody or antigen binding fragment thereof that is able to bind O-mannosylated E-cadherin, comprising:

- one Fab fragment of an antibody or antigen binding fragment according to the invention; and
- one Fab fragment of another antibody that is specific for TGFβ.

An antibody or antigen binding fragment according to the invention may be coupled to another moiety, such as for example a drug or immunomodulatory compound or a label, via a linker such as for instance an acid-labile hydrazone linker, or via a peptide linker like citrulline-valine, or through a thioether linkage, or by sortase catalyzed transamidation, which is described in detail in WO 2010/087994.

Sortase catalyzed transamidation involves engineering of a sortase recognition site (LPETGG) on the heavy chain of an antibody, preferably on the C-terminal part of the heavy chain, and on the moiety to be coupled to said antibody. The antibody and the moiety further typically contain a GGGGS sequence and a tag for purification purposes, such as a HIS tag. Subsequently sortase mediated transamidation is performed followed by click chemistry linkage. In a sortase catalyzed transamidation, "click chemistry linkage" typically involves chemical coupling of, for instance, an alkyne-containing reagent and, for instance, an azide-containing reagent which are added by sortase through addition of glycines to the sortase motif on the heavy chain of the antibody and to a sortase motif on the moiety (such as a protein, peptide or antibody) to be coupled to the antibody. In one embodiment, the invention therefore provides an antibody according to the invention wherein a sortase recognition site (LPETGG) is engineered on the heavy chain of the antibody, preferably on the C-terminal part of the heavy chain, the antibody preferably further containing a GGGGS sequence and a purification tag, such as a HIS tag.

In some embodiments, an antibody or antigen binding fragment according to the invention is coupled to another moiety via a thioether linkage. In such cases, one or more cysteines are preferably incorporated into an antibody or antigen binding fragment according to the invention. Cysteines contain a thiol group and, therefore, incorporation of one or more cysteines into an antibody or antigen binding fragment according to the invention, or replacement of one or more amino acids by one or more cysteines, enable coupling of said antibody or antigen binding fragment to another moiety. Said one or more cysteines are preferably introduced at a position where it does not significantly influence folding of said antibody or antigen binding fragment, and does not significantly alter antigen binding or effector function. The invention therefore also provides an antibody or antigen binding fragment according to the invention that comprises a heavy chain sequence of an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, wherein at least one amino acid of said antibody (other than cysteine) has been replaced by a cysteine.

The present invention further provides chimeric antigen receptor (CAR) T cells that comprise the heavy chain CDR1, CDR2 and CDR3 sequences of an antibody according to the invention. In some embodiments, said CAR T cells further comprise the light chain CDR1, CDR2 and CDR3 sequences of an antibody according to the invention. Chimeric antigen receptors (CARs, also known as chimeric immunoreceptors, chimeric T cell receptors or artificial T cell receptors) are engineered receptor proteins that can give cells ability to bind a new specific target. CARs combine both antigen-binding and cell activating functions into a single receptor. CARs typically have a modular design including an antigen-binding domain and one or more intracellular domains, either directly or indirectly bound, that transmit activation signals. Depending on the number of costimulatory domains, CARs can be classified into first (CD3z only), second (one costimulatory domain+CD3z), or third generation CARs (more than one costimulatory domain+CD3z). Introduction of CAR genes into a T cell successfully redirects the T cell with additional antigen specificity and provides the necessary signals to drive full T cell activation. Alternatively, CAR genes can also be introduced into other immune cells, such as NK, NKT or gamma-delta-T-cells (Rafiq et al. 2019).

The antigen-binding characteristics of a CAR is preferably defined by an extracellular scFv. The format of an scFv is generally two variable domains linked by a flexible peptide sequence, either in the orientation VH-linker-VL or VL-linker-VH. Other formats known in the art include Tandem CAR, Looped Tandem CAR and CARs that bind common adapter molecules. (Guedan et al. Mol Ther 2019).

The intracellular signaling domain of a CAR typically comprises an activation domain and one or more co-stimulatory domains. In the art, the vast majority of CARs activate CAR T cells via CD33-derived immunoreceptor tyrosine-based activation motifs. The most widely studied co-stimulatory domains are derived from costimulatory molecules from the CD28 family (including CD28 and ICOS) or the tumor necrosis factor receptor (TNFR) family of genes (including 4-1BB (CD137), OX40 and CD27). Alternative domains include those derived from MYD88 or killer cell immunoglobulin-like receptor 2DS2 (KIR2DS2; combined with co-expression of TYRO protein tyrosine kinase-binding protein, also known as DAP12). Alternatively, binding domains used for CAR-T cells can be fused to the extracellular N-termini of any of the five other TCR subunits, resulting in the incorporation of the respective TCR fusion constructs (TRuCs) into the TCR complex. (Bauerle et al, 2019).

Strategies being used in the art to genetically modify cells to express CARs include viral- and non-viral-based genetic engineering tools, such as gamma retroviral and lentiviral vectors. Other methods include, for instance, transposon systems like sleeping beauty (SB) and piggyBac, mRNA, non-integrative lentivirus, endonuclease enzymes (Guedan et al. 2019) and DNA nano-carriers for in situ cell programming.

A CAR T cell according to the invention binds O-mannosylated E-cadherin, preferably the 70 kDA truncated form thereof, and is therefore very suitable for use in immunotherapy against O-mannosylated E-cadherin positive cancer cells. Some embodiments therefore provide a chimeric antigen receptor (CAR) T cell that is able to bind O-mannosylated E-cadherin, wherein the CAR T cell comprises the heavy chain CDR1, CDR2 and CDR3 sequences of an antibody according to the invention. In some embodiments, said CAR T cell comprises the heavy chain CDR1, CDR2 and CDR3 sequences of an antibody as depicted in Table 1. In some embodiments, said CAR T cell further comprises the light chain CDR1, CDR2 and CDR3 sequences of an antibody as depicted in Table 1. In some embodiments, said CAR T cell comprises the heavy chain CDR1, CDR2 and CDR3 sequences and the light chain CDR1, CDR2 and CDR3 sequences of an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN.

Some embodiments provide an isolated or recombinant host cell, or a non-human animal, comprising a bispecific antibody or a multispecific antibody or CAR T cell according to the invention.

Therapeutic Uses of Anti E-Cadherin Antibodies

Antibodies or antigen binding fragments or ADCs or CAR T cells according to the invention are suitable for use against cells that express O-mannosylated E-cadherin. Further provided are methods for treating subjects, including human subjects, in need of treatment with antibodies or antigen binding fragments or ADCs or CAR T cells according to the invention. Also provided is a nucleic acid molecule or vector according to the invention, or a cell that comprises a nucleic acid according to the invention, for use as a medicament and/or prophylactic agent. When (a vector comprising) one or more nucleic acid molecule(s) according to the invention is/are administered, the nucleic acid molecule(s) will be translated in situ into an antibody or antigen binding fragment according to the invention. The resulting antibodies or antigen binding fragments according to the invention will subsequently counteract or prevent disorders associated with O-mannosylated E-cadherin-expressing cells, like for instance E-cadherin-positive and TMTC3-positive tumors. Likewise, introduction of a cell according to the invention into a patient in need thereof will result in in vivo generation of therapeutic or prophylactic anti O-mannosylated E-cadherin antibodies or antigen binding fragments according to the invention.

Some embodiments provide an antibody or antigen binding fragment or bispecific antibody or multispecific antibody or ADC or CAR T cell or nucleic acid or vector or host cell according to the invention, for use as a medicament or prophylactic agent. In some embodiments, said medicament or prophylactic agent is against a disorder that is associated with cells that express E-cadherin. In particular embodiments, said cells also express an O-mannosyltransferase, enabling O-mannosylation of E-cadherin and binding thereof by antibodies and antigen binding fragments thereof that are specific for O-mannosylated E-cadherin. Some embodiments therefore provide an antibody or antigen binding fragment or bispecific antibody or multispecific antibody or ADC or CAR T cell or nucleic acid or vector or host cell according to the invention, for use in a method for treating or preventing a disorder that is associated with cells, preferably tumor cells, that express E-cadherin and an O-mannosyltransferase.

In particular embodiments, said O-mannosyltransferase is TMTC3, which is well known for its E-cadherin O-mannosylation activity. Further provided is therefore an antibody or antigen binding fragment or bispecific antibody or multispecific antibody or ADC or CAR T cell or nucleic acid or vector or host cell according to the invention, for use in a method for treating or preventing a disorder that is associated with cells, preferably tumor cells, that express E-cadherin and TMTC3.

In some embodiments, said disorder that is associated with tumor cells that express E-cadherin and an O-mannosyltransferase is epithelial cancer. In some embodiments, said disorder that is associated with tumor cells that express E-cadherin and an O-mannosyltransferase is selected from the group consisting of adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer. In some embodiments, said disorder that is associated with tumor cells that express E-cadherin and an O-mannosyltransferase is selected from the group consisting of colorectal cancer, colon cancer, colon cancer subtype CMS1, colon cancer subtype CMS2, colon cancer subtype CMS3, colon cancer subtype CMS4, laryngeal cancer, head and neck cancer, breast cancer, pancreatic cancer, esophageal cancer, bladder cancer, lung cancer, stomach cancer, urinary tract cancer, prostate cancer and ovary cancer.

As used herein, a tumor cell that expresses E-cadherin is also referred to as an "E-cadherin-expressing tumor cell" or an "E-cadherin-positive tumor cell". A tumor cell that expresses both E-cadherin and TMTC3 is also referred to herein as an "E-cadherin-expressing and TMTC3-expressing tumor cell" or "E-cadherin- and TMTC3-expressing tumor cell" or "E-cadherin-positive and TMTC3-positive tumor cell" or "E-cadherin- and TMTC3-positive tumor cell". A cancer comprising tumor cells that express E-cadherin and TMTC3 is referred to herein as an "E-cadherin-positive and TMTC3-positive cancer".

A "subject" may be a human or animal individual. In some embodiments, a subject is a mammalian individual, such as for instance a human, a cat, a dog, a rabbit, a mouse, a rat, a cow, a goat, a horse, a pig, a monkey, an ape, or a gorilla. In particular embodiments, said subject is a human individual.

As used herein, the term "a disorder that is associated with cells that express E-cadherin and an O-mannosyltransferase" means any disease that involves the presence of disease-specific cells that express E-cadherin and an O-mannosyltransferase. In some embodiments, such cells are a causative factor of the disease, as is often the case for tumor cells that express E-cadherin and an O-mannosyltransferase. In some embodiments, the presence of such cells cause adverse symptoms, such as for instance inflammation and/or pain.

The term "treating or preventing a disorder that is associated with cells that express E-cadherin and an O-mannosyltransferase" may refer to counteracting the onset or progression of a said disorder, and/or to alleviating symptoms resulting from said disorder. For instance, the term "treating or preventing a disorder that is associated with tumor cells that express E-cadherin and an O-mannosyltransferase" may include preventing, counteracting and/or slowing down the growth of said tumor cells, and/or alleviating symptoms resulting from the presence of said tumor cells in a patient.

Some embodiments provide an antibody or antigen binding fragment or bispecific antibody or multispecific antibody or ADC or CAR T cell or nucleic acid or vector or host cell for use in a method for treating or preventing an E-cadherin-positive and TMTC3-positive cancer. An advantage of O-mannosylated E-cadherin-specific antibodies and antigen binding fragments according to the invention is their specificity for (tumor) cells that express both E-cadherin and TMTC3, while they bind to a significantly lower extent to E-cadherin-positive cells that do not express TMTC3. This enables a reduction in adverse side effects, so that higher dosages may be tolerated.

Some embodiments provide an antibody or antigen binding fragment or bispecific antibody or multispecific antibody or ADC or CAR T cell or nucleic acid or vector or host cell according to the invention for use in a method for treating or preventing an E-cadherin-positive and TMTC3-positive epithelial cancer.

Some embodiments provide an antibody or antigen binding fragment or bispecific antibody or multispecific antibody or ADC or CAR T cell or nucleic acid or vector or host cell according to the invention for use in a method for treating or preventing an E-cadherin-positive and TMTC3-positive cancer selected from the group consisting of adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive colorectal cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive colon cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive colon cancer subtype CMS1.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive colon cancer subtype CMS2.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive colon cancer subtype CMS3.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive colon cancer subtype CMS4.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive laryngeal cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive head and neck cancer Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive breast cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive pancreatic cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive esophageal cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive bladder cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive lung cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive stomach cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive urinary tract cancer.

Some embodiments provide an antibody or antigen binding fragment or bispecific antibody or multispecific antibody or ADC or CAR T cell or nucleic acid or vector or host cell according to the invention for use in a method for treating or preventing E-cadherin-positive and TMTC3-positive prostate cancer or ovary cancer.

In some embodiments, an antibody or antigen binding fragment or bispecific antibody or multispecific antibody or ADC or CAR T cell or nucleic acid or vector or host cell according to the invention is used against an E-cadherin-positive and TMTC3-positive cancer that also comprises tumor cells that express transforming growth factor beta (TGFβ), preferably TGFβ1. As used herein, a cancer that comprises E-cadherin-expressing tumor cells and TMTC3-expressing tumor cells and TGFβ-expressing tumor cells is referred to as an "E-cadherin-positive and TMTC3-positive and TGFβ-positive cancer". As shown in the Examples, an antibody or functional fragment according to the invention binds particularly well to tumor cells if TGFβ is present. A combination of an antibody or antigen binding fragment according to the invention with TGFβ is particularly suitable for inhibiting tumor cell growth and/or for increasing tumor cell death. Further provided is therefore an antibody or antigen binding fragment or bispecific antibody or multispecific antibody or ADC or CAR T cell or nucleic acid or vector or host cell according to the invention, for use in a method for treating or preventing an E-cadherin-positive and TMTC3-positive and TGFβ-positive cancer. An advantage of improved tumor cell growth inhibition in the presence of TGFβ is the possibility to use a lower dosage.

A preferred antibody for use in any of the recited methods is an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, and antigen binding fragments thereof that have the same binding specificity.

Some embodiments provide a use of an antibody or antigen binding fragment or bispecific antibody or multispecific antibody or ADC or CAR T cell or nucleic acid or vector or host cell according to the invention for the manufacture of a medicament. Some embodiments provide a use of an antibody or antigen binding fragment or bispecific antibody or multispecific antibody or ADC or CAR T cell or nucleic acid or vector or host cell according to the invention for the manufacture of a medicament for treating or preventing a disorder that is associated with cells that express E-cadherin and an O-mannosyltransferase. In particular embodiments, said cells are tumor cells. In particular embodiments, said O-mannosyltransferase is TMTC3. Some embodiments provide a use of an antibody or antigen binding fragment or bispecific antibody or multispecific antibody or ADC or CAR T cell or nucleic acid or vector or host cell according to the invention for the preparation of a medicament for treating or preventing an E-cadherin-positive and TMTC3-positive cancer. In some embodiments, said E-cadherin-positive and TMTC3-positive cancer is an epithelial cancer. In some embodiments, said E-cadherin-positive and TMTC3-positive cancer is selected from the group consisting of adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer. In some embodiments, said E-cadherin-positive and TMTC3-positive cancer is selected from the group consisting of colorectal cancer, colon cancer, colon cancer subtype CMS1, colon cancer subtype CMS2, colon cancer subtype CMS3, colon cancer subtype CMS4, laryngeal cancer, head and neck cancer, breast cancer, pancreatic cancer, esophageal cancer, bladder cancer, lung cancer, stomach cancer, urinary tract cancer, prostate cancer and ovary cancer.

Further embodiments provide a composition comprising an antibody or antigen binding fragment according to the invention. Some embodiments provide a composition comprising a bispecific antibody, a multispecific antibody, an ADC or a CAR T cell according to the invention. A composition comprising a nucleic acid molecule according to the invention is also provided, as well as a composition comprising a vector or a cell according to the invention. In some embodiments, said antibody is an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN. In some embodiments, a composition according to the invention comprises an antibody according to the invention, and another E-cadherin-specific antibody. Said other E-cadherin-specific antibody preferably binds a different E-cadherin epitope as compared to an antibody according to the invention. Such combination of different E-cadherin-specific antibodies is particularly suitable for binding and/or counteracting E-cadherin-positive cells, such as E-cadherin- and TMTC3-positive tumor cells.

In some embodiments, a composition according to the present invention is a pharmaceutical composition. Such pharmaceutical composition preferably also comprises a pharmaceutical acceptable carrier, diluent and/or excipient. Non-limiting examples of suitable carriers for instance comprise keyhole limpet haemocyanin (KLH), serum albumin (e.g. BSA or RSA) and ovalbumin. In some particular embodiments said suitable carrier comprises a solution, like for example saline. A pharmaceutical composition according to the invention is preferably suitable for human use.

The invention further provides a method for treating and/or preventing a disorder that is associated with cells, preferably but not limited to tumor cells, that express E-cadherin and an O-mannosyltransferase, comprising administering to an individual in need thereof a therapeutically effective amount of an antibody or antigen binding fragment according to the invention, and/or a bispecific antibody or multispecific antibody or ADC or CAR T cell according to the invention, and/or a nucleic acid according to the invention, and/or a vector or cell according to the invention, and/or a composition or kit of parts according to the invention. Further provided is a method for at least in part treating and/or preventing an E-cadherin-positive and TMTC3-positive cancer, comprising administering to an individual in need thereof a therapeutically effective amount of an antibody or antigen binding fragment according to the invention, and/or a bispecific antibody or multispecific antibody or ADC or CAR T cell according to the invention, and/or a nucleic acid according to the invention, and/or a vector or cell according to the invention, and/or a composition or kit of parts according to the invention. Said composition is preferably a pharmaceutical composition according to the invention. An antibody or antigen binding fragment or nucleic acid molecule or vector or ADC or CAR T cell or pharmaceutical composition according to the invention is preferably administered via one or more injections. In some embodiments, an antibody or antigen binding fragment or nucleic acid molecule or vector or ADC or CAR T cell or pharmaceutical composition according to the invention is administered by intravenous administration. Alternatively, other administration routes known in the art are used. Non-limiting examples of doses of administration of a binding compound according to the invention are between 0.1 and 10 mg per kg body weight.

Some embodiments provide an antibody or antigen binding fragment or ADC or CAR T cell or nucleic acid or vector or host cell according to the invention, which is combined with another therapeutic agent, preferably an anti-cancer therapeutic agent and/or an immunomodulatory compound. For instance, an antibody or antigen binding fragment according to the invention is combined with another agent that is useful in the treatment and/or prevention of a disorder that is associated with cells, preferably tumor cells, that express E-cadherin and an O-mannosyltransferase such as TMTC3. Provided is therefore an antibody or antigen binding fragment or bispecific antibody or multispecific antibody or ADC or CAR T cell or nucleic acid or vector or host cell according to the invention for use in a method for treating or preventing a disorder that is associated with cells, preferably tumor cells, that express E-cadherin and an O-mannosyltransferase, preferably TMTC3, whereby said antibody or antigen binding fragment or bispecific antibody or multispecific antibody or ADC or CAR T cell or nucleic acid or vector or host cell according to the invention is combined with another therapeutic agent useful in the treatment and/or prevention of said disorder that is associated with cells, preferably tumor cells, that express E-cadherin and an O-mannosyltransferase, preferably TMTC3.

Further provided is an antibody or antigen binding fragment or bispecific antibody or multispecific antibody or ADC or CAR T cell or nucleic acid or vector or host cell according to the invention for use in a method for treating or preventing an E-cadherin-positive and TMTC3-positive cancer, whereby said antibody or antigen binding fragment or bispecific antibody or multispecific antibody or ADC or CAR T cell or nucleic acid or vector or host cell according to the invention is combined with another therapeutic agent for the treatment and/or prevention of said cancer.

In some embodiments, said other therapeutic agent is a chemotherapeutic agent. In some embodiments, said other therapeutic agent is a cytostatic or cytotoxic drug.

In some embodiments, said other therapeutic agent is a therapeutic nucleic acid.

In some embodiments, said nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In some embodiments, said nucleic acid is an aptamer or a ribozyme.

In some embodiments, said other therapeutic agent comprises radiolabeled amino acids.

In some embodiments, said other therapeutic agent comprises a radioisotope or a radioisotope-containing chelate Said disorder that is associated with tumor cells that express E-cadherin and an O-mannosyltransferase is preferably an E-cadherin-positive and TMTC3-positive cancer. In some embodiments, said disorder that is associated with tumor cells that express E-cadherin and an O-mannosyltransferase is an epithelial cancer. In some embodiments, said disorder that is associated with tumor cells that express E-cadherin and an O-mannosyltransferase is a cancer selected from the group consisting of adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer. In some particular embodiments, said disorder that is associated with tumor cells that express E-cadherin and an O-mannosyltransferase is a cancer selected from the group consisting of colorectal cancer, colon cancer, colon cancer subtype CMS1, colon cancer subtype CMS2, colon cancer subtype CMS3, colon cancer subtype CMS4, laryngeal cancer, head and neck cancer, breast cancer, pancreatic cancer, esophageal cancer, bladder cancer, lung cancer, stomach cancer, urinary tract cancer, prostate cancer and ovary cancer.

Compositions and kits of parts that comprise a combination of an antibody or antigen binding fragment or ADC or CAR T cell or nucleic acid or vector or host cell according to the invention and another therapeutic agent are also provided herewith. Some embodiments provide a kit of parts or a composition, comprising an antibody or antigen binding fragment or bispecific antibody or multispecific antibody or ADC or CAR T cell or nucleic acid molecule or vector or host cell according to the invention, and another therapeutic agent for the treatment or prevention of a disorder that is associated with cells, preferably tumor cells, that express E-cadherin and an O-mannosyltransferase, preferably TMTC3. In some embodiments, said composition is a pharmaceutical composition. Said disorder is preferably an E-cadherin-positive and TMTC3-positive cancer.

In some embodiments, said composition is a pharmaceutical composition. Said disorder is preferably an E-cadherin-positive and TMTC3-positive cancer.

A kit of parts according to the invention may comprise one or more containers filled with a composition comprising an antibody or antigen binding fragment or bispecific antibody or multispecific antibody or ADC or CAR T cell or nucleic acid molecule or vector or host cell according to the invention and a composition comprising the other therapeutic agent. Said kit of part or said one or more containers further optionally comprises one or more pharmaceutically acceptable carriers, diluents or excipients. Associated with such kit of parts or container(s) can be various written materials such as instructions for use, or a notice in the form prescribed by a governmental agency regulating the manufacture, use or sale of pharmaceuticals products, which notice reflects approval by the agency of manufacture, use, or sale. In some embodiments, a kit of parts according to the invention comprises instructions for use.

Some embodiments provide a method for treating or preventing a disorder associated with cells, preferably tumor cells, that express E-cadherin and an O-mannosyltransferase, preferably TMTC3, in a human or non-human individual, the method comprising administering to said individual a therapeutically effective amount of an antibody or antigen binding fragment or bispecific antibody or multispecific antibody or ADC or CAR T cell or nucleic acid or vector or host cell or composition or kit of parts according to the invention, in combination with a further therapeutic agent or therapeutic procedure. Said further therapeutic agent is preferably an agent as described herein above.

Further Applications of E-Cadherin-Specific Antibodies

Antibodies, antigen binding fragments, ADCs and CAR T cells according to the invention are also particularly useful for detection of O-mannosylated E-cadherin-expressing cells. For instance, if an individual, preferably a human, is suspected of suffering from a disorder associated with O-mannosylated E-cadherin-expressing cells, a sample from said individual can be tested for the presence of O-mannosylated E-cadherin-expressing cells (also referred to herein as O-mannosylated E-cadherin-positive cells), using antibodies or antigen binding fragments or ADC or CAR T cells according to the invention. In some embodiments said sample is mixed with an antibody or antigen binding fragment or ADC or CAR T cell according to the invention, which will specifically bind O-mannosylated E-cadherin-positive cells, if such cells are present in said sample. O-mannosylated E-cadherin-positive cells, such as for instance O-mannosylated E-cadherin-positive tumor cells, that are bound to an antibody or antigen binding fragment or ADC or CAR T cell according to the invention can be isolated from the sample and/or detected using any method known in the art, for example, but not limited to, isolation using magnetic beads, streptavidin-coated beads, or isolation through the use of secondary antibodies immobilized on a column. Alternatively, or additionally, an antibody or antigen binding fragment or ADC or CAR T cell according to the invention is labeled in order to be able to detect it.

Such antibody or antigen binding fragment or ADC or CAR T cell is for instance fluorescently labeled, enzymatically labeled or radioactively labeled, for instance using fluorophores such as rare earth chelates, fluorescein or its derivatives, rhodamine and its derivatives, isothiocyanate, phycoerythrin, phycocyanin, allophycocyanin, o-phthaladehyde, fluorescamine, 152E u, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels or stable free radicals. In some embodiments, an antibody or antigen binding fragment or ADC or CAR T cell according to the invention is detected using a labeled secondary antibody which is directed against said antibody or antigen binding fragment or ADC or CAR T cell.

Screening assays as provided herein can be performed using methods known in the art such as for instance enzyme-linked immunosorbent assays (ELISA), radio-immuno assays (RIA), western blot assays and immunohistochemical staining assays.

Labelled antibodies or antigen binding fragments or ADCs or CAR T cells according to the invention are for instance incubated with a cell-containing sample of an individual, such as for instance a blood sample or tissue sample, where after unbound binding compounds are washed away. Subsequently, it is determined whether said labelled antibodies or antigen binding fragments or ADCs or CAR T cells according to the invention are bound to O-mannosylated E-cadherin-positive cells. In some embodiments, unlabeled antibodies or antigen binding fragments or ADCs or CAR T cells according to the invention are contacted with a cell-containing sample. After incubation, one or more washing steps are preferably performed in order to remove non-bound binding compounds. Subsequently, it is tested whether antibodies or antigen binding fragments or ADCs or CAR T cells according to the invention are bound to O-mannosylated E-cadherin-positive cells, for instance using a detecting antibody that is specifically directed against an antibody or antigen binding fragment or ADC or CAR T cell according to the invention and that is coupled to a marker, such as for instance a fluorescent compound or for instance horseradish peroxidase or alkaline phosphatase. After a further washing step, it is preferably determined whether the detecting antibody has bound, for instance by measuring light emission or by adding a substrate of horseradish peroxidase or alkaline phosphatase. These detection techniques are well known in the art.

If an antibody or antigen binding fragment or ADC or CAR T cell according to the invention appears to be bound to a component of a patient's sample, it is indicative for the presence of O-mannosylated E-cadherin-positive cells. This way, disease-specific cells like O-mannosylated E-cadherin-positive tumor cells can be detected. Furthermore, the presence of disease-specific O-mannosylated E-cadherin-positive cells like O-mannosylated E-cadherin-positive tumor cells suggests that treatment with an antibody or antigen binding fragment or ADC or CAR T cell according to the invention will have a beneficial effect. Some embodiments therefore provide a use of an antibody or antigen binding fragment or bispecific antibody or multispecific antibody or ADC or CAR T cell according to the invention for determining whether a sample comprises cells that express O-mannosylated E-cadherin. In some embodiments said antibody or antigen binding fragment or bispecific antibody or multispecific antibody or ADC or CAR T cell according to the invention is used for determining whether a sample comprises tumor cells that express O-mannosylated E-cadherin.

Also provided is a method for determining whether cells, preferably tumor cells, that express O-mannosylated E-cadherin are present in a sample, the method comprising:

contacting said sample with an antibody or antigen binding fragment or bispecific antibody or multispecific antibody or ADC or CAR T cell according to the invention, and allowing said antibody or antigen binding fragment or bispecific antibody or multispecific antibody or ADC or CAR T cell to bind to cells, preferably tumor cells, that express O-mannosylated E-cadherin, if present, and determining whether or not cells are bound to said antibody or antigen binding fragment or bispecific antibody or multispecific antibody or ADC or CAR T cell, thereby determining whether or not cells, preferably tumor cells, that express O-mannosylated E-cadherin are present in said sample. Antibodies AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, and antigen binding fragments thereof, are particularly suitable for detecting O-mannosylated E-cadherin-expressing cells, like for instance O-mannosylated E-cadherin-positive tumor cells. Further provided is therefore a use of an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, for determining whether a sample comprises O-mannosylated E-cadherin-comprising cells. Some embodiments provide a use of an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, for determining whether a sample comprises tumor cells that comprise O-mannosylated E-cadherin, like for instance O-mannosylated E-cadherin-expressing epithelial cancer cells, or cells of a cancer selected from the group consisting of adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer, preferably selected from the group consisting of colorectal cancer cells, colon cancer cells, colon cancer subtype CMS1 cells, colon cancer subtype CMS2 cells, colon cancer subtype CMS3 cells, colon cancer subtype CMS4 cells, laryngeal cancer cells, head and neck cancer, breast cancer cells, pancreatic cancer cells, esophageal cancer cells, bladder cancer cells, lung cancer cells, stomach cancer cells, urinary tract cancer cells, prostate cancer cells and ovary cancer cells.

Also provided is a method for determining whether cells, preferably tumor cells, that comprise O-mannosylated E-cadherin are present in a sample, the method comprising:

contacting said sample with an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, and allowing said antibody or antigen binding fragment to bind to cells, preferably tumor cells, that comprise O-mannosylated E-cadherin, if present, and determining whether or not cells are bound to said antibody or antigen binding fragment, thereby determining whether or not cells, preferably tumor cells, that comprise O-mannosylated E-cadherin are present in said sample.

Some embodiments provide a method according to the invention wherein said sample comprises a blood sample or a bone marrow sample or a biopsy. In some embodiments, said biopsy is from the intestines, preferably to test for gastrointestinal cancer, colorectal cancer, colon cancer, esophageal cancer or stomach cancer. In some embodiments, said biopsy is from pancreatic tissue or from lung tissue or from breast tissue or from laryngeal tissue or from squamous epithelial tissue or from liver tissue or from ovarian tissue or from prostate tissue or from urinary tract tissue or from bladder tissue or from brain tissue. In some embodiments, said sample is a blood sample, which is for instance useful for testing for the presence of multiple myeloma and/or metastases of any of the above mentioned solid tumors.

The test results of a method according to the invention are useful for typing of a sample. For instance, if a sample of an individual appears to contain malignant O-mannosylated E-cadherin-positive cells, the sample is typed as containing disease-associated cells. Such typing can subsequently be used for diagnosis of a disorder associated with O-mannosylated E-cadherin-expressing cells. Some embodiments therefore provide an antibody or antigen binding fragment or bispecific antibody or multispecific antibody or ADC or CAR T cell or nucleic acid or vector or host cell according to the invention for use as a diagnostic agent. Further provided is an antibody or antigen binding fragment or bispecific antibody or multispecific antibody or ADC or CAR T cell or nucleic acid or vector or host cell according to the invention for use in diagnosis of a disorder that is associated with cells, preferably tumor cells, that comprise O-mannosylated E-cadherin. Said disorder is preferably an epithelial cancer, preferably selected from the group consisting of adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer, more preferably selected from the group consisting of colorectal cancer, colon cancer, colon cancer subtype CMS1, colon cancer subtype CMS2, colon cancer subtype CMS3, colon cancer subtype CMS4, laryngeal cancer, head and neck cancer, breast cancer, pancreatic cancer, esophageal cancer, bladder cancer, lung cancer, stomach cancer, urinary tract cancer, prostate cancer and ovary cancer.

In some preferred embodiments, an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, is used for the above-mentioned detection and diagnosis. Also provided is therefore an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, for use in diagnosis of a disorder associated with O-mannosylated E-cadherin-comprising cells. Some embodiments provide an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, for use in diagnosis of an E-cadherin-positive and TMTC3-positive cancer selected from the group consisting of epithelial cancer, adenocarcinoma, squamous cell carcinoma, adenosquamous carcinoma, anaplastic carcinoma, large cell carcinoma, small cell carcinoma, colorectal cancer, colon cancer, stomach cancer, gastric cancer, gastroesophageal junction carcinoma, breast cancer, pancreatic cancer, esophageal cancer, gastroesophageal junction carcinoma, bladder cancer, lung cancer, small cell lung cancer, non-small cell lung cancer, lung adenocarcinoma, urinary tract cancer, prostate cancer, brain cancer, thyroid cancer, laryngeal cancer, carcinoid cancer, liver cancer, hepatocellular carcinoma, head and neck cancer, ovary cancer, cervical cancer, ovarian cancer, endometrial cancer, intraepithelial carcinoma, clear cell carcinoma, melanoma, multiple myeloma, kidney cancer, renal cell carcinoma, renal transitional cell cancer, fallopian tube cancer and peritoneal cancer, more preferably selected from the group consisting of colorectal cancer, colon cancer, colon cancer subtype CMS1, colon cancer subtype CMS2, colon cancer subtype CMS3, colon cancer subtype CMS4, laryngeal cancer, head and neck cancer, breast cancer, pancreatic cancer, esophageal cancer, bladder cancer, lung cancer, stomach cancer, urinary tract cancer, prostate cancer and ovary cancer.

Also provided is a method for determining whether a human or non-human individual is suffering from a cancer that comprises O-mannosylated E-cadherin, the method comprising:

contacting cells of said individual with an antibody or antigen binding fragment or bispecific antibody or multispecific antibody or ADC or CAR T cell according to the invention, allowing said antibody or antigen binding fragment or bispecific antibody or multispecific antibody or ADC or CAR T cell to bind tumor cells that comprise O-mannosylated E-cadherin, if present, and determining whether or not tumor cells are bound to said antibody or antigen binding fragment or bispecific antibody or multispecific antibody or ADC or CAR T cell, thereby determining whether or not said individual is suffering from a cancer that comprises O-mannosylated E-cadherin. In some embodiments, said method is an ex vivo method. In other embodiments, said method is an in vivo imaging method.

Suitable imaging techniques include SPECT imaging (single photon emission computed tomography) and PET imaging (positron emission tomography). Suitable labels include for instance iodine-123 ($^{123}I$) and technetium-99m ($9m^{9}$ Tc), for instance in conjunction with SPECT imaging or $^{11}C$, $^{13}N$, $^{15}O$ or $^{18}F$, for instance in conjunction with PET imaging or Indium-111 (See e.g., Gordon et al., (2005) International Rev. Neurobiol. 67:385-440).

Non-limiting examples of O-mannosylated E-cadherin-positive cancers are listed above. Preferably, an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, is used for said method. Some embodiments therefore provide a method for determining whether a human or non-human individual is suffering from a cancer that express O-mannosylated E-cadherin, the method comprising:

contacting cells of said individual with an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, allowing said antibody or antigen binding fragment to bind tumor cells that comprise O-mannosylated E-cadherin, if present, and determining whether or not tumor cells are bound to said antibody or antigen binding fragment, thereby determining whether or nor said individual is suffering from a cancer that comprises O-mannosylated E-cadherin.

In some embodiments it is determined whether an individual is suffering from a cancer that expresses E-cadherin and an O-mannosyltransferase, preferably TMTC3. As explained herein before, the presence of a cancer that comprises O-mannosylated E-cadherin indicates that treatment with an antibody or antigen binding fragment or ADC or CAR T cell according to the invention will have a beneficial effect. Also provided is therefore a method for determining whether an individual is suffering from a cancer that expresses E-cadherin and an O-mannosyltransferase, preferably TMTC3, comprising:

contacting a sample from said individual with an antibody or antigen binding fragment or bispecific antibody or multispecific antibody or ADC or CAR T cell according to the invention, and allowing said antibody or antigen binding fragment or bispecific antibody or multispecific antibody or ADC or CAR T cell to bind tumor cells that express E-cadherin and an O-mannosyltransferase, preferably TMTC3, if present, and determining whether or not tumor cells are bound to said antibody or antigen binding fragment or bispecific antibody or multispecific antibody or ADC or CAR T cell, thereby determining whether or nor said individual is suffering from a cancer that expresses E-cadherin and an O-mannosyltransferase, preferably TMTC3. Preferably said individual is a human.

Another aspect of the invention provides a method for determining whether treatment of a cancer patient with an antibody or antigen binding fragment or ADC or CAR T cell according to the invention has an improved chance of a positive outcome of treatment, as compared to the mean population of cancer patients, the method comprising determining whether a sample of said cancer patient comprises O-mannosylated E-cadherin-positive tumor cells. If this is the case, antibodies according to the invention like for instance an antibody selected from the group consisting of AT1636, E-C06, D-H04, D-A02, D-E09, E-A04, E-B09, C-A05, C-A03, C-B02, C-D04-A, C-D04-B, F-C08, D-G03, D-F10, C-E08, D-B06, D-G05, D-H08, C-H01, D-C12, D-C11, E-C10, AT1636-I, AT1636-Y, AT1636-E, AT1636-N, AT1636-YN, AT1636-IYN and AT1636-IYEN, or an antigen binding fragment thereof, is particularly suitable for counteracting such cancer. Therefore, if it is known that cancer cells of an individual comprise O-mannosylated E-cadherin at their surface, the chance of successful treatment is increased. Further provided is therefore a screening method comprising determining whether disease-specific cells, preferably tumor cells, of an individual comprise O-mannosylated E-cadherin at their surface. In some aspect, it is determined whether said disease-specific cells express E-cadherin and an O-mannosyltransferase, preferably TMTC3. In some aspect, it is further determined whether said disease-specific cells express TGFβ. If disease-specific cells like cancer cells express E-cadherin and an O-mannosyltransferase, preferably TMTC3, and TGFβ, the chance of successful treatment with an antibody or antigen binding fragment or ADC or CAR T cell according to the invention is even higher.

As the presence of O-mannosylated E-cadherin is typically a result of expression of E-cadherin and an O-mannosyltransferase such as for instance TMTC3, some embodiments provide a screening method comprising determining whether disease-specific cells of an individual, preferably tumor cells, express E-cadherin and an O-mannosyltransferase, particularly TMTC3. Some embodiments provide a screening method comprising determining whether disease-specific cells of an individual, preferably tumor cells, express E-cadherin and an O-mannosyltransferase, particularly TMTC3, and TGFβ.

In some embodiments such methods according to the invention comprise the steps of:

contacting a disease-specific cell-containing sample from an individual with a binding compound, preferably an antibody or antigen binding fragment, that is specific for O-mannosylated E-cadherin;

allowing said binding compound to bind disease-specific cells of said sample, and determining whether or not said binding compound is bound to disease-specific cells of said sample, wherein binding of said binding compound to disease-specific cells of said sample indicates that said patient has a significant chance of a positive outcome of treatment with an antibody or antigen binding fragment or ADC or CAR T cell according to the invention.

In some embodiments, said disease-specific cells are tumor cells.

In some embodiments, it is further determined whether said disease-specific cells also express TGFβ.

While the current application may describe features as part of the same embodiment or as parts of separate embodiments, the scope of the present invention also includes embodiments comprising any combination of all or some of the features described herein.

The invention is further explained in the following examples. These examples do not limit the scope of the invention, but merely serve to clarify the invention.

TABLE 1

Amino acid sequences referred to in the specification. Amino acids and nucleotides that differ from the AT1636 sequences are highlighted.

| Description | SEQ ID NO: | Sequence |
|---|---|---|
| AT1636 VH/ E-C10 VH | 1 | EVQLVESGGGLVKPGGSLRLSCAASGFTFSNAWMNWVRQAPGKGLEWVGRIKSKIDGGTTEYTTPVKGRFTISRDDS KDTVYLHMKRLKTEDTAVYYCTPGVGANDPYYFDRWGQGVLVTVSS |
| E-C06 VH/ D-H04 VH | 2 | EVQLVESGGGLVKPGGSLRLSCAASGF**I**FSNAWMNWVRQAPGKGLEWVGRIKSKIDGGTTEYTTPVKGRFTISRDDS KDTVYLHMK**S**LKTEDTAVYYCTPGVGANDPYYFDRWGQGVLVTVSS |
| D-A02 VH/ D-E09 VH/ E-A04 VH/ E-B09 VH/ AT1636-I VH | 3 | EVQLVESGGGLVKPGGSLRLSCAASGF**I**FSNAWMNWVRQAPGKGLEWVGRIKSKIDGGTTEYTTPVKGRFTISRDDS KDTVYLHMKRLKTEDTAVYYCTPGVGANDPYYFDRWGQGVLVTVSS |
| C-A05 VH | 4 | EVQLVESGGGLVKPGGSLRLSCAASGF**I**FSNAWMNWVRQAPGKGLEWVGRIKSKIDG**E**TTEYTTPVKGRFTISRDDS KDTVYLHMKRLKTEDTAVYYCTPGVGANDPYYFDRCGQGVLVTVSS |
| C-A03 VH/ C-B02 VH/ AT1636-E VH | 5 | EVQLVESGGGLVKPGGSLRLSCAASGFTFSNAWMNWVRQAPGKGLEWVGRIKSKIDG**E**TTEYTTPVKGRFTISRDDS KDTVYLHMKRLKTEDTAVYYCTPGVGANDPYYFDRWGQGVLVTVSS |
| C-D04-A VH/ C-D04-B VH | 6 | EVQLVESGGGLVKPGGSLRLSCAASGFTFSNAWMNWVRQAPGKGLEWVGRIKSKIDG**E**TTEYTTPVKGRFTISRDDS KDTVYLHMKRLKTEDTAVYYCTPGVGAN**N**PYYFDRWGQGVLVTVSS |
| F-C08 VH | 7 | EVQLVESGGGLVKPGGSLRLSCAASGFTFSNAWMNWVRQAPGKGLEWVGRIKSKIDGGTTEYTTPVKGRFTISRDDS KDTVYLHMKR**V**KTEDTAVYYCTPGVGAN**N**PYYFDRWGQGVLVTVSS |
| D-G03 VH/ AT1636-N VH | 8 | EVQLVESGGGLVKPGGSLRLSCAASGFTFSNAWMNWVRQAPGKGLEWVGRIKSKIDGGTTEYTTPVKGRFTISRDDS KDTVYLHMKRLKTEDTAVYYCTPGVGAN**N**PYYFDRWGQGVLVTVSS |
| D-F10 VH | 9 | EVQLVESGGGLVKPGGSLRLSCAASGFTFSNAWMNWVRQAPGKGLEWVGRIKSKIDGGTTEYTTPVKGRFTISRDDS KDTVYLHMKRLKTEDTAVYYCTPGVGTN**N**PYYFDRWGQGVLVTVSS |
| C-E08 VH / D-B06 VH / D-G05 VH / AT1636-Y VH | 10 | EVQLVESGGGLVKPGGSLRLSCAASGFTFS**Y**AWMNWVRQAPGKGLEWVGRIKSKIDGGTTEYTTPVKGRFTISRDDS KDTVYLHMKRLKTEDTAVYYCTPGVGANDPYYFDRWGQGVLVTVSS |
| D-H08 VH | 11 | EVQLVESGG**D**LVKPGGSLRLSCAASGFTFS**Y**AWMNWVRQAPGKGLEWVGRIKSKIDGGTTEYTTPVKGRFTISRDDS KDTVYLHMKRLKTEDTAVYYCTPGVGANDPYYFDRWGQGVLVTVSS |
| C-H01 VH | 12 | EVQLVESGGGLVKPGGSLRLSCAASGFTFSNAWMNWVRQAPGKGLEWVGRIKSKIDGGT**I**EYTTPVKGRFTISRDDS KDTVYLHMKRLKTEDTAVYYCTPGVGANDPYYFDRWGQGVLVTVSS |
| D-C12 VH | 13 | EVQLVESGGGLVKPGGSLRLSCAASGFTFSNAWMNWVRQAP**E**KGLEWVGRIKSKIDGGTTEYTTPVKGRFTISRDDS KDTVYLHMKRLKTEDTAVYYCTPGVGANDPYYFDRWGQGVLVTVSS |
| D-C11 VH | 14 | EVQLVESGGDLVKPGGSLRLSCAASGFTFSNAWMNWVRQAPGKGLEWVGRIKSKIDGGTTEYTTPVKGRFTISRDDS KDTVYLHMKRLK**I**EDTAVYYCTPGVGANDPYYFDRWGQGVLVTVSS |
| AT1636-YN VH | 15 | EVQLVESGGGLVKPGGSLRLSCAASGFTFS**Y**AWMNWVRQAPGKGLEWVGRIKSKIDGGTTEYTTPVKGRFTISRDDS KDTVYLHMKRLKTEDTAVYYCTPGVGAN**N**PYYFDRWGQGVLVTVSS |
| AT1636-IYN VH | 16 | EVQLVESGGGLVKPGGSLRLSCAASGF**I**FS**Y**AWMNWVRQAPGKGLEWVGRIKSKIDGGTTEYTTPVKGRFTISRDDS KDTVYLHMKRLKTEDTAVYYCTPGVGAN**N**PYYFDRWGQGVLVTVSS |
| AT1636-IYEN VH | 17 | EVQLVESGGGLVKPGGSLRLSCAASGF**I**FS**Y**AWMNWVRQAPGKGLEWVGRIKSKIDG**E**TTEYTTPVKGRFTISRDDS KDTVYLHMKRLKTEDTAVYYCTPGVGAN**N**PYYFDRWGQGVLVTVSS |
| AT1636 VL/ E-C06 VL/ D-H04 VL/ D-A02 VL/ D-E09 VL/ | 18 | DIVMTQSPDSLAVSLGERATINCRSSQSVLCRSNNKNCLAWYQQRPGQPPKLLIYWASIRESGVPDRFSGSGSGTDF TLTISSLQAEDVAVYYCQQYSNTPQTFGQGTKVEIKR |

TABLE 1-continued

Amino acid sequences referred to in the specification. Amino acids and nucleotides that differ from the AT1636 sequences are highlighted.

| Description | SEQ ID NO: | Sequence |
|---|---|---|
| E-A04 VL/<br>E-B09 VL/<br>C-A03 VL/<br>C-B02 VL/<br>F-C08 VL/<br>D-G03 VL/<br>D-F10 VL/<br>C-E08 VL/<br>D-B06 VL/<br>D-H08 VL/<br>C-H01 VL/<br>D-C12 VL/<br>D-C11 VL/<br>C-D04-A VL/<br>AT1636-I VL/<br>AT1636-Y VL/<br>AT1636-E VL/<br>AT1636-N VL/<br>AT1636-YN VL/<br>AT1636-IYN VL/<br>AT1636-IYEN VL | | |
| C-A05 VL | 19 | DIVMTQSPDSLAVSLGERATINCRSSQSVLCRSNNKNCLAWYQQRPGQPPKLLIYWASIRESGVPDRFSGSGSGTDF<br>TLTI**N**SLQAEDVAVYYCQQYSNTPQTFGQGTKVEIKR |
| C-D04-B VL | 20 | DIVMTQSPDSLAVSLGERATINCRSSQSVLCRSNNKNCLAWYQQRPGQPPKLLIYWA**C**IRESGVPDRFSGSGSGTDF<br>TLTISSLQAEDVAVYYCQQYSNTPQTFGQGTKVEIKR |
| D-G05 VL | 21 | DIVMTQSPDSLAVSLGERATINCRSSQSVLCRSNNKNCL**T**WYQQRPGQPPKLLIYWASIRESGVPDRFSGSGSGTDF<br>TLTISSLQAEDVAVYYCQQYSNTPQTFGQGTKVEIKR |
| E-C10 VL | 22 | DIVMTQSPDSLAVSLGERATINCRSSQSVLCRSNNKNCLAWYQQRPGQPPKLLIYWASIRESGVPDRFSGSGSGT**H**F<br>TLTISSLQAEDVAVYYCQQYSNTPQTFGQGTKVEIKR |

Nucleic Acid Sequences Referred to in the Specification

| Description | SEQ ID NO: | Sequence |
|---|---|---|
| AT1636 VH/<br>E-C10 VH | 23 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccggggtgggg<br>agctaatgatccgtactattttgaccgctggggccagggagtcctggtcaccgtctcctca |
| E-C06 VH/<br>D-H04 VH | 24 | gaggtgcagctggtggagtctgggggaggcttggtaaagcctggggggtcccttagactctcctgtgcagcctctgg<br>tttca**t**tttcagtaatgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaag**c**ctgaaaaccgaggacacagccgtctattactgtaccccgggggtggg<br>agctaatgatccgtactattttgaccgctggggccagggagtcctggtcaccgtctcctca |
| D-E09 VH/<br>D-A02 VH/<br>E-A04 VH/<br>E-B09 VH/<br>AT1636-I VH | 25 | gaggtgcagctggtggagtctgggggaggcttggtaaagcctggggggtcccttagactctcctgtgcagcctctgg<br>tttca**t**tttcagtaatgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaatgatccgtactattttgaccgctggggccagggagtcctggtcaccgtctcctca |
| C-A05 VH | 26 | gaggtgcagctggtggagtctgggggaggcttggtaaagcctggggggtcccttagactctcctgtgcagcctctgg<br>tttca**t**tttcagtaatgcctggatgaactgggtccgccaggctccagggaaggggctggagtgggtcggccgtatta<br>aaagcaaaattgatggtg**a**gacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaatgatccgtactattttgaccgctg**t**ggccagggagtcctggtcaccgtctcctca |
| C-A03 VH/<br>C-B02 VH/<br>AT1636-E VH | 27 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtg**a**gacaacagagtacaccacacccgtgaaaggcagattcaccatctcaagagatgattca |

-continued

| Description | SEQ ID NO: | Sequence |
|---|---|---|
| | | aaagacacagtgtacctgcacatgaaaaggctgaaaaccgaggacacagccgtctattactgtaccccgggggtggg<br>agctaatgatccgtactattttgaccgctggggccagggagtcctggtcaccgtctcctca |
| C-D04-A VH/<br>C-D04-B VH | 28 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtg**a**gacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaat**a**atccgtactattttgaccgctggggccagggagtcctggtcaccgtctcctca |
| F-C08 VH | 29 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaagg**g**tgaaaaccgaggacacagccgtctattactgtaccccgggggtggg<br>agctaat**a**atccgtactattttgaccgctggggccagggagtcctggtcaccgtctcctca |
| D-G03 VH/<br>AT1636-N VH | 30 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaat**a**atccgtactattttgaccgctggggccagggagtcctggtcaccgtctcctca |
| D-F10 VH | 31 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>a**a**ctaat**a**atccgtactattttgaccgctggggccagggagtcctggtcaccgtctcctca |
| C-E08 VH/<br>D-B06 VH/<br>D-G05 VH/<br>AT1636-Y VH | 32 | gaggtgcagctggtggagtctgggggaggcttggtaaagcctggggggtcccttagactctcctgtgcagcctctgg<br>tttcactttcagt**t**atgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaatgatccgtactattttgaccgctggggccagggagtcctggtcaccgtctcctca |
| D-H08 VH | 33 | gaggtgcagctggtggagtctgggggag**a**cttggtaaagcctggggggtcccttagactctcctgtgcagcctctgg<br>tttcactttcagt**t**atgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaatgatccgtactattttgaccgctggggccagggagtcctggtcaccgtctcctca |
| C-H01 VH | 34 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtgggacaa**t**agagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaatgatccgtactattttgaccgctggggccagggagtcctggtcaccgtctcctca |
| D-C12 VH | 35 | gaggtgcagctggtggagtctgggggaggcttggtaaagcctggggggtcccttagactctcctgtgcagcctctgg<br>tttcactttcagtaatgcctggatgaactgggtccgccaggctccag**a**gaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaatgatccgtactattttgaccgctggggccagggagtcctggtcaccgtctcctca |
| D-C11 VH | 36 | gaggtgcagctggtggagtctgggggaggcttggtaaagcctggggggtcccttagactctcctgtgcagcctctgg<br>tttcactttcagtaatgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaa**t**cgaggacacagccgtctattactgtaccccgggggtggg<br>agctaatgatccgtactattttgaccgctggggccagggagtcctggtcaccgtctcctca |
| AT1636-YN<br>VH | 37 | gaggtgcagctggtggagtctgggggaggcttggtaaagcctggggggtcccttagactctcctgtgcagcctctgg<br>tttcactttcagt**t**atgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggtggg<br>agctaat**a**atccgtactattttgaccgctggggccagggagtcctggtcaccgtctcctca |
| AT1636-IYN<br>VH | 38 | gaggtgcagctggtggagtctgggggaggcttggtaaagcctggggggtcccttagactctcctgtgcagcctctgg<br>tttca**t**tttcagt**t**atgcctggatgaactgggtccgccaggctccagggaaggggctggagtgggtcggccgtatta<br>aaagcaaaattgatggtgggacaacagagtacaccacacccgtgaaaggcagattcaccatctcaagagatgattca<br>aaagacacagtgtacctgcacatgaaaaggctgaaaaccgaggacacagccgtctattactgtaccccgggggggg<br>agctaat**a**atccgtactattttgaccgctggggccagggagtcctggtcaccgtctcctca |
| AT1636-IYEN<br>VH | 39 | gaggtgcagctggtggagtctgggggaggcttggtaaagcctggggggtcccttagactctcctgtgcagcctctgg<br>tttca**t**tttcagt**t**atgcctggatgaactgggtccgccaggctccagggaaggggctggagtgggtcggccgtatta<br>aaagcaaaattgatggtg**a**gacaacagagtacaccacacccgtgaaaggcagattcaccatctcaagagatgattca<br>aaagacacagtgtacctgcacatgaaaaggctgaaaaccgaggacacagccgtctattactgtaccccgggggggg<br>agctaat**a**atccgtactattttgaccgctggggccagggagtcctggtcaccgtctcctca |

-continued

| Description | SEQ ID NO: | Sequence |
|---|---|---|
| AT1636 VL/<br>E-C06 VL/<br>D-H04 VL/<br>D-A02 VL/<br>D-E09 VL/<br>E-A04 VL/<br>E-B09 VL/<br>C-A03 VL/<br>C-B02 VL/<br>F-C08 VL/<br>D-G03 VL/<br>D-F10 VL/<br>C-E08 VL/<br>D-B06 VL/<br>D-H08 VL/<br>C-H01 VL/<br>D-C12 VL/<br>D-C11 VL/<br>AT1636-I VH/<br>AT1636-Y VH/<br>AT1636-E VH/<br>AT1636-N VH/<br>C-D04-A VL/<br>AT1636-YN<br>VL/<br>AT1636-IYN<br>VL/<br>AT1636-IYEN<br>VL | 40 | gacatcgtgatgacccagtctccagactccctggctgtgtctctgggcgagagggccaccatcaactgcaggtccag<br>ccagagtgttttatgtcggtccaacaataagaactgcttagcttggtaccagcagagaccaggacagcctcctaaac<br>tgctcatttattgggcatctattcgggaatccggggtccctgaccgattcagtggcagcgggtctgggacagatttc<br>actctcaccatcagcagcctgcaggctgaagatgtggcagtttattactgtcagcaatattctaatactcctcagac<br>gttcggccaagggaccaaggtggaaatcaaacga |
| C-A05 VL | 41 | gacatcgtgatgacccagtctccagactccctggctgtgtctctgggcgagagggccaccatcaactgcaggtccag<br>ccagagtgttttatgtcggtccaacaataagaactgcttagcttggtaccagcagagaccaggacagcctcctaaac<br>tgctcatttattgggcatctattcgggaatccggggtccctgaccgattcagtggcagcgggtctgggacagatttc<br>actctcaccatca**a**cagcctgcaggctgaagatgtggcagtttattactgtcagcaatattctaatactcctcagac<br>gttcggccaagggaccaaggtggaaatcaaacga |
| C-D04-B VL | 42 | gacatcgtgatgacccagtctccagactccctggctgtgtctctgggcgagagggccaccatcaactgcaggtccag<br>ccagagtgttttatgtcggtccaacaataagaactgcttagcttggtaccagcagagaccaggacagcctcctaaac<br>tgctcatttattgggcat**g**tattcgggaatccggggtccctgaccgattcagtggcagcgggtctgggacagatttc<br>actctcaccatcagcagcctgcaggctgaagatgtggcagtttattactgtcagcaatattctaatactcctcagac<br>gttcggccaagggaccaaggtggaaatcaaacga |
| D-G05 VL | 43 | gacatcgtgatgacccagtctccagactccctggctgtgtctctgggcgagagggccaccatcaactgcaggtccag<br>ccagagtgttttatgtcggtccaacaataagaactgctta**a**cttggtaccagcagagaccaggacagcctcctaaac<br>tgctcatttattgggcatctattcgggaatccggggtccctgaccgattcagtggcagcgggtctgggacagatttc<br>actctcaccatcagcagcctgcaggctgaagatgtggcagtttattactgtcagcaatattctaatactcctcagac<br>gttcggccaagggaccaaggtggaaatcaaacga |
| -C10 VL | 44 | gacatcgtgatgacccagtctccagactccctggctgtgtctctgggcgagagggccaccatcaactgcaggtccag<br>ccagagtgttttatgtcggtccaacaataagaactgcttagcttggtaccagcagagaccaggacagcctcctaaac<br>tgctcatttattgggcatctattcgggaatccggggtccctgaccgattcagtggcagcgggtctgggaca**c**atttc<br>actctcaccatcagcagcctgcaggctgaagatgtggcagtttattactgtcagcaatattctaatactcctcagac<br>gttcggccaagggaccaaggtggaaatcaaacga |

TABLE 2

Amino acid classes with respect to conservative amino acid substitutions. Substitutions of amino acid residues within an Amino acid class are non-limiting examples of conservative amino acid substitutions.

| Amino acid class | Amino acid residues within a class |
|---|---|
| Aliphatic | glycine, alanine, valine, leucine, isoleucine |
| Acidic | aspartate, glutamate |
| Basic | histidine, lysine, arginine |
| Non-polar uncharged | proline, cysteine, methionine |
| Hydrophilic uncharged | serine, threonine, asparagine, glutamine |
| Aromatic | phenylalanine, tyrosine, tryptophan |

TABLE 3

Binding of AT1636 to different (cancer) cell types as determined using flow cytometry. E-Cadherin* and TMTC3* mRNA (Affy) expression data originates from the Cancer cell line Encyclopedia from the Broad Institute (https://portals.broadinstitute.org/ccle). Relative units <6 are scored negative, 6-7 are scored +/− and >7 is scored positive.

| | AT1636 Binding | E-Cadherin* | TMTC3* | Remarks (cell type, tissue, disease) |
|---|---|---|---|---|
| Colon Cancer | | | | |
| DLD-1 | + | + | + | CMS1, epithelial, colon, colorectal adenocarcinoma |
| HCT 116 | + | + | + | CMS1, epithelial, colon, colorectal carcinoma |
| SW480 | +/− | +/− | + | CMS2, epithelial, colon, colorectal adenocarcinoma |
| Caco-2 | + | + | + | CMS2, epithelial, colon, colorectal adenocarcinoma |
| HT-29 | + | + | + | CMS4, epithelial, colon, colorectal adenocarcinoma |
| HT55 | + | + | + | CMS2, epithelial, colon carcinoma |
| KM12 | + | + | + | CMS1, Colon carcinoma |
| LS-513 | + | + | + | CMS3, epithelial, cecum, colorectal carcinoma |
| SW948 | + | + | + | CMS1, epithelial, colon, colorectal adenocarcinoma |
| Lo Vo | + | + | + | Epithelial, colon; derived from metastatic site: left supraclavicular region, colorectal adenocarcinoma |
| Breast Cancer | | | | |
| MCF7 | + | + | + | Epithelial, mammary gland, breast; derived from metastatic site: pleural effusion, adenocarcinoma |
| T-47D | + | + | + | Epithelial, mammary gland; derived from metastatic site: pleural effusion, ductal carcinoma |
| ZR-75-1 | + | + | + | Epithelial, mammary gland; breast/duct; derived from metastatic site: ascites, ductal carcinoma |
| BT-20 | +/− | + | +/− | Triple negative. Epithelial, mammary gland/breast, carcinoma |
| BT-549 | − | − | +/− | Triple negative. Epithelial, mammary gland; breast, ductal carcinoma |
| MCF 10A | + | No data | No data | Ductal cell line. Epithelial, mammary gland; breast, fybrocystic disease |
| SK-BR-3 | − | − | + | Epithelial, mammary gland/breast; derived from metastatic site: pleural effusion, adenocarcinoma |
| Pancreatic Cancer | | | | |
| Capan-2 | + | + | + | Polygonal, pancreas, adenocarcinoma |
| PANC 08.13 | + | + | + | Epithelial, pancreas, adenocarcinoma |
| PDX-53 | + | No data | No data | Patient derived xenograft |
| PDX-67 | + | No data | No data | Patient derived xenograft |
| PDX-193 | − | No data | No data | Patient derived xenograft |
| Bladder Cancer | | | | |
| 5637 | + | + | + | Epithelial, urinary bladder, grade II carcinoma |
| T24 | − | − | + | (E-Cadherin negative), epithelial, urinary bladder, transitional cell carcinoma |
| UM-UC-3 | − | − | + | (E-Cadherin negative), epithelial, urinary bladder, transitional cell carcinoma |

TABLE 3-continued

Binding of AT1636 to different (cancer) cell types as determined using flow cytometry. E-Cadherin* and TMTC3* mRNA (Affy) expression data originates from the Cancer cell line Encyclopedia from the Broad Institute (https://portals.broadinstitute.org/ccle). Relative units <6 are scored negative, 6-7 are scored +/− and >7 is scored positive.

| | AT1636 Binding | E-Cadherin* | TMTC3* | Remarks (cell type, tissue, disease) |
|---|---|---|---|---|
| SW 780 | + | + | + | Epithelial, urinary bladder, transitional cell carcinoma |
| RT4 | + | + | + | Epithelial, urinary bladder, transitional cell papilloma |
| HT-1376 | + | + | + | Epithelial, urinary bladder, grade 3, carcinoma |
| Gastric Cancer | | | | |
| SNU-1 | − | − | + | (E-Cadherin negative), epithelial, stomach, gastric carcinoma |
| SNU-5 | − | − | + | (E-Cadherin negative), epithelial, stomach; derived from metastatic site: ascites, gastric carcinoma |
| AGS | − | − | + | (E-Cadherin negative), epithelial, stomach, gastric adenocarcinoma |
| NCI-N87 | + | + | + | Epithelial, stomach; derived from metastatic site: liver, gastric carcinoma |
| Fibroblasts | | | | |
| FRC | − | No data | No data | Primary Fibroblastic Riticular cells (cultured, passage 8) |
| BJ | − | No data | No data | Fibroblast, skin; foreskin, normal |
| MRC-5 | − | No data | No data | Fibroblast, lung, normal |
| Primary n = 3 | − | No data | No data | Fibroblast, skin |
| Hematological cancer | | | | |
| SH-2 | − | No data | No data | Acute Myeloid Leukemia |
| K562 | − | − | +/− | Lymphoblast, bone marrow, chronic myelogenous leukemia |
| BV-173 | − | − | +/− | B cell precursor leukemia, chronic myeloid leukemia (CML) |
| MUTZ-5 | − | No data | No data | B cell precursor leukemia, B cell precursor acute lymphoblastic leukemia (BCP-ALL) |
| MHH-CALL-2 | − | − | +/− | B cell precursor leukemia, acute lymphoblastic leukemia (cALL) |
| SUP-B15 | − | − | +/− | B lymphoblast, bone marrow, acute lymphoblastic leukemia |
| Jurkat | − | − | +/− | T lymphocyte, peripheral blood, acute T cell leukemia |
| Skin cancer | | | | |
| A431 | + | No data | No data | Epithelial, skin/epidermis, epidermoid carcinoma |
| Endometrium cancer | | | | |
| HEC-1-A | + | + | + | Epithelial, uterus; endometrium, adenocarcinoma |
| KLE | + | + | + | uterus; endometrium, adenocarcinoma |
| Lung cancer | | | | |
| NCI-H661 | − | − | + | Epithelial, lung; derived from metastatic site: lymph node, carcinoma; large cell lung cancer |
| NCI-H1299 | − | − | + | Epithelial, lung; derived from metastatic site: lymph node, carcinoma; non-small cell lung cancer |

TABLE 3-continued

Binding of AT1636 to different (cancer) cell types as determined using flow cytometry. E-Cadherin* and TMTC3* mRNA (Affy) expression data originates from the Cancer cell line Encyclopedia from the Broad Institute (https://portals.broadinstitute.org/ccle). Relative units <6 are scored negative, 6-7 are scored +/− and >7 is scored positive.

| | AT1636 Binding | E-Cadherin* | TMTC3* | Remarks (cell type, tissue, disease) |
|---|---|---|---|---|
| NCI-H1975 | + | + | + | Epithelial, lung, adenocarcinoma; non-small cell lung cancer |
| NCI-H1563 | − | − | + | Lung, adenocarcinoma; non-small cell lung cancer |
| NCI-H1573 | + | + | + | Lung, derived from metastatic site: soft tissue, adenocarcinoma (stage 4) |
| NCI-H1437 | + | + | + | lung; derived from metastatic site: pleural effusion, adenocarcinoma; non-small cell lung cancer (stage 1) |
| Oesophagus cancer | | | | |
| OE19 | + | + | +/− | Epithelial, adenocarcinoma of gastric cardia/oesophageal gastric junction |
| OE33 | + | + | + | Epithelial, adenocarcinoma of the lower oesophagus (Barrett's metaplasia) |
| Endothelium | | | | |
| HAEC | − | No data | No data | Human aortic endothelial cells, primary cells (cultured ex vivo) |
| HMEC-1 | − | No data | No data | Dermal microvascular endothelium |
| Leukocytes | | | | |
| Eosinophils | − | No data | No data | From blood |
| Granulocytes | − | No data | No data | From blood |
| NK cells | − | No data | No data | From blood |
| B cells | − | No data | No data | From tonsil & blood |
| T cells | − | No data | No data | From tonsil & blood |
| Monocytes | − | No data | No data | From tonsil & blood |
| Dendritic cells | − | No data | No data | Monocyte derived, from PBMC, differentiated in vitro |
| Langerhans cells | − | No data | No data | Monocyte derived, from PBMC, differentiated in vitro |
| Mouse/Dog | | | | |
| CMT-93 | +/− | No data | No data | Mouse, epithelial, rectum, polyploid carcinoma |
| CT26 | − | No data | No data | Mouse, fibroblast, colon, carcinoma |
| MDCK | + | No data | No data | Dog, epithelial, kidney |

TABLE 4

Calculation of the fold-increase in binding of the AT1636 variants compared to the parental AT1636 wild-type antibody to the Full-Length and p70 E-cadherin and the E-cadherin D3 mutated protein. Ratios were calculated by dividing the $EC_{50}$ values obtained from the ELISA results shown in FIG. 7c. $EC_{50}$ values were determined using Prism software. Fold increase in binding compared to AT1636 wild-type antibody

| | AT1636 variant E-cadherin variant: | | | | | | |
|---|---|---|---|---|---|---|---|
| | T29I | N36Y | G63E | D112N | YN | IYN | IYEN |
| 70 kDa | 2.0 | 6.6 | 0.2 | 4.5 | 56.5 | 67.1 | 28.6 |
| Full Length | 2.6 | 6.5 | 0.5 | 6.0 | 28.4 | 64.3 | 34.3 |

REFERENCES

Aiello, N M, Maddipati, R, Norgard, R J, Balli, D, Li, J, Yuan, S, Yamazoe, T, et al. EMT Subtype Influences Epithelial Plasticity and Mode of Cell Migration. Developmental Cell 2018; 45:681-695.e4.

Atwell, S, Ridgway, J B, Wells, J A, Carter, P. Stable heterodimers from remodeling the domain interface of a homodimer using a phage display library. Journal of Molecular Biology 1997; 270:26-35.

Baeuerle, P. A. et al. Nature Communications (2019) 10:2087

Barretina, J, Caponigro, G, Stransky, N, Venkatesan, K, Margolin, A A, Kim, S, Wilson, C J, et al. The Cancer Cell Line Encyclopedia enables predictive modelling of anti-cancer drug sensitivity. Nature 2012; 483:603-607.

Bartels M F, et al. (2016) Protein O-mannosylation in the murine brain: Occurrence of mono-O-mannosyl glycans and identification of new substrates. PLOS One 11:e0166119.

Bartels, L, de Jong, G, Gillissen, M A, Yasuda, E, Kattler, V, Bru, C, Fatmawati, C, et al. A Chemo-enzymatically Linked Bispecific Antibody Retargets T Cells to a Sialylated Epitope on CD43 in Acute Myeloid Leukemia. Cancer Research 2019; 79:3372-3382.
Bartels, L. et al. A Chemo-enzymatically Linked Bispecific Antibody Retargets T Cells to a Sialylated Epitope on CD43 in Acute Myeloid Leukemia. Methods 2019, accepted for publication
Carvalho S, et al. (2016) O-mannosylation and N-glycosylation: Two coordinated mechanisms regulating the tumour suppressor functions of E-cadherin in cancer. Oncotarget 7:65231-65246.
Chau C. et al. Lancet 2019: 394: 793-804
Chen, Y et al. (1999) J. Mol. Biol. 293:865-881
Gauthier L. et al. (2019) Cell 177, 1701-1713
De Groot, A. S. et al. (2005) Dev. Biol. 122:171-194
Guedan, S. et al. (2019) Molecular Therapy: Methods & Clinical Development. Vol 12:145-156
Hanly et al. (1995) ILAR Journal. 37(3): 93-118
Idusogie, E E et al. (2001) J. Immunol. 166:2571-2575
Junghans et al., in Cancer Chemotherapy and Biotherapy 655-686 (2d edition, Chafner and Longo, eds., Lippincott Raven (1996))
Kwakkenbos, M. J. et al. Genetic manipulation of B cells for the isolation of rare therapeutic antibodies from the human repertoire. Methods 2013; 1-6
Larsen, I S B, Narimatsu, Y, Joshi, H J, Siukstaite, L, Harrison, O J, Brasch, J, Goodman, K M, et al. Discovery of an O-mannosylation pathway selectively serving cadherins and protocadherins. Proc Natl Acad Sci USA 2017; 114:11163-11168.
Lazar, G A et al. (2006) Proc. Natl. Acad. Sci. USA 103:4005-4010
Lommel M, et al. (2013) Protein O-mannosylation is crucial for E-cadherin-mediated cell adhesion. Proc Natl Acad Sci USA 110:21024-21029.
Lund, J et al (1992) Mol. Immunol. 29:53-59
Merchant, A M, Zhu, Z, Yuan, J Q, Goddard, A, Adams, C W, Presta, L G, Carter, P. An efficient route to human bispecific IgG. Nature Biotechnology, Published online: 1 Aug. 2008; | doi:10.1038/nbt0808-886 1998; 16:677-681.
Moore, G L et al. (2010) MAbs 2(2): 181-189
Padmanaban, V, Krol, I, Suhail, Y, Szczerba, B M, Aceto, N, Bader, J S, Ewald, A J. E-cadherin is required for metastasis in multiplemodels of breast cancer. Nature 2019; 1-31.
Patnaik & Stanley (2006) Methods Enzymol. 416:159-182
Racapé, M, Duong Van Huyen, J-P, Danger, R, Giral, M, Bleicher, F, Foucher, Y, Pallier, A, et al. The Involvement of SMILE/TMTC3 in Endoplasmic Reticulum Stress Response. PLOS ONE 2011; 6:e19321.
Rafiq et al. 17 Dec. 2019, nature reviews, clinical oncology
Shields, R L et al. (2001) J. Biol Chem 276:6591-6604
Stavenhagen, J B et al. (2007) Cancer Res. 67:8882-8890
Sunryd, J C, Cheon, B, Graham, J B, Giorda, K M, Fissore, R A, Hebert, D N. TMTC1 and TMTC2 are novel endoplasmic reticulum tetratricopeptide repeat-containing adapter proteins involved in calcium homeostasis. Journal of Biological Chemistry 2014; 289:16085-16099.
Suurs F. V. et al (2019) Pharmacology & Therapeutics 201:103-119
Tauriello, D V F, Palomo-Ponce, S, Stork, D, Berenguer-Llergo, A, Badia-Ramentol, J, Iglesias, M, Sevillano, M, et al. TGFβ drives immune evasion in genetically reconstituted colon cancer metastasis. Nature 2018; 554:538-543
Tsuchikama K. et al. (2018). Protein Cell 9(1):33-46
Vester-Christensen, M B, Halim, A, Joshi, H J, Steentoft, C, Bennett, E P, Levery, S B, Vakhrushev, S Y, et al. Mining the O-mannose glycoproteome reveals cadherins as major O-mannosylated glycoproteins. Proc Natl Acad Sci USA 2013; 110:21018-21023.
Yamane-Ohnuki, N et al. (2004) Biotechnol. Bioeng 87:614-622
U.S. Pat. No. 4,681,581
U.S. Pat. No. 4,735,210
U.S. Pat. No. 5,101,827
U.S. Pat. No. 5,102,990 (US RE35,50G)
U.S. Pat. No. 5,648,471
U.S. Pat. No. 5,697,902
U.S. Pat. No. 9,534,058 (B2)
WO 2010/087994
WO 2013/081463
WO 2015/093949

EXAMPLES

Example 1 AT1636 Antibody Discovery

Patient and Healthy Human Materials

Study protocols were approved by the Medical Ethical Committee of the Academic Medical Centre, Amsterdam, The Netherlands. All participants signed informed consent. Total peripheral blood mononuclear cells (PBMC) were isolated from fresh blood after Ficoll gradient centrifugation and frozen until use.

Generation of Colon-Cancer-Specific Clone AT1636

Following procedures as described in WO 2015/093949 and by Kwakkenbos et al., Nat Med (2010), naïve and memory IgG B cells were isolated from a patient suffering from Lynch syndrome who is a carrier of a pathogenic gene variant in the MSH6 gene and had been diagnosed with stage IV colorectal cancer (CRC) and liver metastasis and that had been successfully treated with avastin, capecitabine and oxaliplatin. B cells were isolated from peripheral blood that was obtained from this patient 9 years after the last treatment. Naïve and memory IgG B cells were immortalized by retroviral transduction of Bcl6 and Bcl-xL genes and the reporter gene GFP. Next, immortalized B-cells were seeded at a concentration of 5, 10 or 20 cells per well (hereafter named microcultures) and expanded with IL-21 and CD40L. Supernatants of expanded B cell microcultures were then screened for specific antibody binding to a mix of colon cell lines: COLO-205, CACO-2 and DLD1 cells (ATCC). Bound antibodies were detected using anti-human-IgG-PE (Southern Biotech) as a secondary antibody by flow cytometry (BD).

An irrelevant control antibody (AT1002) that specifically binds the HA antigen of influenza (described in WO 2013/081463) was included as negative control in the experiments.

Microcultures for which the supernatants demonstrated specific binding to colon cell lines were selected and seeded at a concentration of 1 cell/well to obtain clonal cultures. After expansion supernatants of the clonal cultures were tested again for the presence of antibodies specifically binding to colon cell lines using flow cytometry as described above. One of the obtained colon-specific B cell clones, named 7G02, produced an IgG3 antibody that bound two of the three colon cell lines.

Cloning of Colon Carcinoma-Specific Antibody AT1636

To identify the antibody produced by 7G02, total mRNA was isolated using TriPure/chloroform method (Roche) following the manufacturer's instructions. Next cDNA was generated by Reverse Transcriptase (SuperScript III, Invitrogen) and Random Hexamers (Promega). The IgG variable domains of heavy and light chains were amplified by PCR (FastStart Taq DNA Polymerase, Roche) following the manufacturer's procedure applying leader specific primers combined with CH1 (Heavy chain) and Ckappa (Light chain) specific primers. The amplicons were used for Sänger dideoxy fluorescent sequencing (BDT, Invitrogen) using the cognate primers as used for amplification. To rule out reverse transcriptase or DNA polymerase induced mutation at least 5 clones were sequenced.

Next, synthetic codon optimized DNA fragments (GeneArt) encoding the complete heavy and light chain regions of 7G02 were subcloned into Double Gene pXC based expression vectors (Lonza). Constructs were checked for integrity by DNA sequencing. From here on the human IgG1/Kappa recombinant antibody of 7G02 is designated AT1636.

Subsequently, the pXC Double Gene vector was stably transfected into CHO-GS cells to generate a stable pool (GS Xceed platform, Lonza). The stable pool was expanded and used for shaker flask, fed-batch cell culture IgG production for 7 days. The cell cleared supernatant containing the recombinant AT1636 antibody was harvested and purified using Protein A chromatography using an AKTA purification system (General Electric Lifesciences). Antibodies were eluted using 0.1M Citrate, 150 mM NaCl, pH 3,5 buffer, subsequently neutralized in 1M Tris-HCl, pH 9,0 and then rebuffered in TBS-TS by size-exclusion chromatography. Concentration was established using NanoDrop spectrophotometer (OD280, ThermoFisher). Monomeric content of the purified antibody was confirmed >90% using size-exclusion chromatography. Integrity of purified proteins was established by SDS-PAGE.

Flow Cytometry Binding Properties of AT1636

Recombinant AT1636 antibody was tested for binding to a panel of cell lines and primary cell material using flow cytometry. In short, cells were incubated with antibody solution for 30-60 minutes at 4° C. and then washed twice with 150 μl PBS 1% BSA. Antibody binding was detected with anti-human IgG-RPE (Southern Biotech) or Alexa Fluor 647-conjugated polyclonal BCR antibody (Invitrogen) and analyzed on a FACSCanto II or LSRFortessa (Becton, Dickinson and Company). AT1636 shows binding (see Table 3) to epithelial cell lines that co-express E-Cadherin and TMCT3 (according to the cancer cell line encyclopedia, (https://portals.broadinstitute.org/ccle)).

Example 2 Target Identification of AT1636

Immunoprecipitation

To identify the target of the AT1636 antibody an immunoprecipitation (IP) of the target was performed using colon cancer cell line DLD1 (ATCC CCL-221) and cells of the T-cell line Jurkat (negative control). Cells were lysed using lysis buffer (0,5% Triton X114 (Sigma), 0.5% DOC; 0.1% SDS, 150 mM NaCl, 10 mM Tris-HCL pH7.4, 1.5 mM MgCl2) supplemented with protease and phosphatase inhibitors (Roche)). After lysis, the non-soluble fraction was removed by centrifugation. Lysates were then precleared with an irrelevant antibody (RSV antibody Palivizumab) bound to Protein-G Dynabeads (Invitrogen) and Streptavidin beads (Invitrogen) to remove non-specific binding proteins. Precleared lysates were then incubated with 50 μg Protein-G Dynabeads-bound AT1636 antibody or with the bead-bound influenza specific antibody AT1002 as a negative control for 3 hrs at 4° C. Antibody-incubated beads were washed three times with lysis buffer and bound proteins were eluted from the beads with 1×SDS-PAGE sample buffer (BioRad)+0,1M DTT. Samples were resolved on an SDS-PAGE gel. 85% of IP samples were run on a preparative SDS-PAGE and immunoprecipitated proteins were visualized with Imperial protein stain (Pierce). Differential immunoprecipitated proteins between AT1636 and AT1002 (negative control) immunoprecipitates from DLD1 vs Jurkat T-cells (as a negative control) were excised: 70 kDa and 85 kDa, see FIG. 2*a*. The bands were subjected to mass spectrometry analysis. Proteins were subjected to reduction with dithiothreitol, alkylation with iodoacetamide and in-gel trypsin digestion using a Proteineer DP digestion robot (Bruker Daltonics, Bremen, Germany). Tryptic peptides were analyzed by on-line C18 nanoHPLC MS/MS with a system consisting of an Easy nLC 1000 gradient HPLC system (Thermo, Bremen, Germany), and a LUMOS mass spectrometer (Thermo). Proteins were subsequently identified by searching the mass spectrometry data against the human Uniprot database, using the Mascot algorithm (Mascot v2.2.04, Matrix Science). A MS tolerance of 10 ppm and a MS/MS tolerance of 0.02 Da were used. Trypsin was designated as the enzyme of choice, and up to 2 missed cleavage sites were allowed. Carbamidomethylcysteine was selected as a fixed modification, and oxidation of methionine and N-terminal acetylation as a variable modification. Results from the database searches were analyzed and visualized using Scaffold (www.proteomesoftware.com). E-cadherin was found to be O-mannosylated. For the identification of O-mannosylation, modification of serine and threonine by a hexose was selected as a variable modification. Semi-trypsin was used as enzyme specificity in order to identify non-tryptic N-termini.

Mass spectrometry analysis revealed that the proteins that are immunoprecipitated by AT1636 are a truncated 70 kDa form of E-cadherin (CDH1, the truncated form being referred to herein as p70) with 24% sequence coverage of E-cadherin in the excised 70 kDa band, while Beta Catenin is found in the 85 kDa band (a 76% protein coverage). No peptides corresponding to the outermost C-terminal domains of E-cadherin were detected, indicative of a truncated protein (see cartoon of full length and truncated E-cadherin in FIG. 3). Further N-terminal acetylation experiments revealed the N-terminal residue to be glutamic acid 463 (numbering according to Uniprot P12830 entry).

Western Blot

Figure 2B:
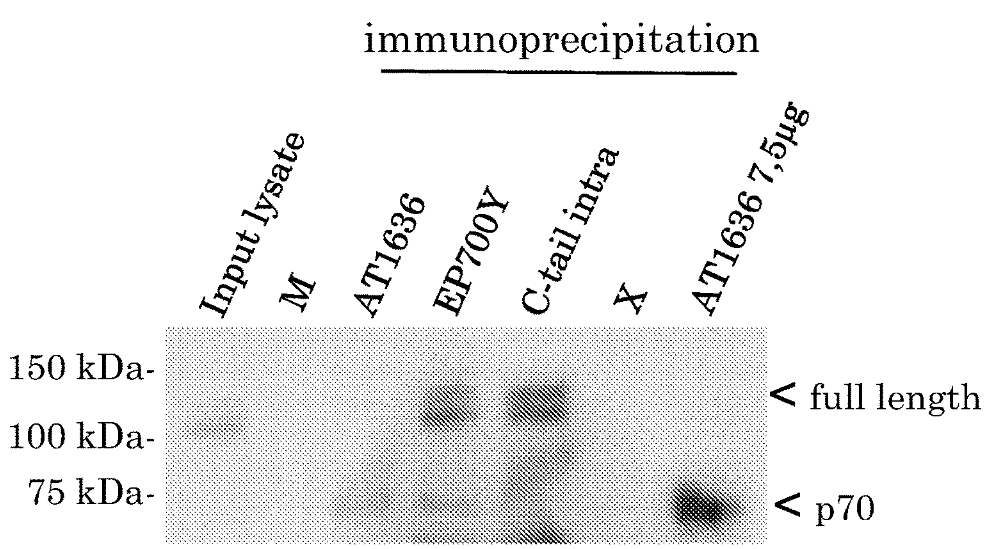

The specific binding of AT1636 to p70 E-cadherin was confirmed by western blot. AT1636 reactivity was compared to the commercially available EP700Y (Abcam, rabbit antibody) and a mouse antibody specific for the cytoplasmic domain of E-cadherin (clone 36/E, BD Biosciences). EP700Y has been shown to bind to the EC5 domain of human E-cadherin and thus will bind both full length and p70 E-cadherin, which is also true for the intracellular C-tail antibody. The E-cadherin antibody immunoprecipitation was performed from DLD1 cells with equal amounts of lysate (10 mg) and antibodies (2,5 μg). Input (40 μg) and IP samples (all) were run on SDS-PAGE and transferred to PVDF membrane (Bio-Rad) for immunoblotting. Using the antibody binding the intracellular domain of E-cadherin as well as the EP700Y antibody, the full length (120 kDa) E-cadherin as well as the 70 kDa protein were immunoprecipitated, while AT1636 mainly immunoprecipitated the 70 kDa protein (FIG. 2*b*). Thus AT1636 preferentially binds p70 over full length E-cadherin as shown by the enrichment for p70 over full length E-cadherin. Upon densitometric quantification of the signals, we find a 7-fold enrichment of p70 over full length in the AT1636 IP, compared to the EP700Y IP.

In FIG. 3 a graphic is summarizing the truncation that is found in p70, which is removing the EC1, EC2 and a large part of the EC3 domain of full-length E-cadherin and leaving a short peptide of the D3 domain plus the domains EC4 and EC5. Also depicted are the binding regions of several antibodies and the β-catenin interacting domain.

Proteolytic Cleavage of AT1636 Target

To investigate whether E-Cadherin is proteolytically cleaved to generate p70 we inhibited Furin and related convertases with a furin/convertase inhibitor added to DLD1 cells (Decanoyl-RVKR-CMK (Tocris)). Cells were cultured for 48 hrs in the absence or presence of inhibitor at indicated concentrations and refreshed once. Cells were harvested and subjected to flow cytometry with indicated antibodies (FIG. 4). Incubation of DLD1 cells with CMK reduced but did not fully abrogate the AT1636 binding to DLD1 cells (FIG. 4), indicating that p70 cleavage is in part mediated by Furin and other related convertases.

In addition to the unique cleavage of E-cadherin within the EC3 domain, it is known that E-cadherin can be O-mannosylated (I. S. B. Larsen, PNAS (2017), M. B. Vester-Christensen, PNAS (2013), M. Lommel, PNAS (2013) and S. Carvalho S, Oncotarget (2016)). Adjacent to the cleavage site and possible binding domain of AT1636 are at least two O-mannosylated Threonine (Thr residue 472 and 474) and possibly one at position 470. To study the dependence of O-mannosylation of p70 for AT1636 binding, an experiment similar to the CMK experiment was performed with a mannosyltransferase inhibitor (Mann, Oxo-2-thioxo-3-thiazolidinylacetic acid, Sigma). Shown in the two right columns in FIG. 4 is the reduction in AT1636 binding to DLD1 cells treated with Mann, indicating that p70 O-mannosylation within the AT1636 binding region is required for binding.

Example 3 Generation of a High Affinity AT1636 Variants

Production of Recombinant Soluble p70 E-Cadherin Protein

The full length E-cadherin cDNA and the p70 E-cadherin cDNA (FIG. 1) corresponding to the EC5 and EC4 domains and the part of EC3 up to the N-terminus at position 463 both excluding the intracellular and transmembrane (TM) domains were obtained from GeneArt and subsequently cloned into the pCMV3, pcDNA3 and pXC19 vectors, containing a FLAG tag on a mouse Fc-tail that was equipped with a sortase and HIS tag or the protein was produced only containing a C-tag. Vectors were transiently transfected in in Expi293 or CHO cells and recombinant proteins were purified with C-Tag affinity matrix or protein A sepharose. Eluted proteins were rebuffered in TBS-TS by size-exclusion chromatography. Concentration was established using NanoDrop spectrophotometer (OD280, ThermoFisher). Monomeric content of the purified antibody was confirmed >90% using size-exclusion chromatography. Integrity of purified proteins was established by SDS-PAGE.

Generation of GFP High Expressing 7G02 B Cells

Next to the genes for Bcl6 and Bcl-xL, the retrovirus used to transduce the 7G02 B cell also contained the gene for GFP as reporter for successful transduction of the B cells. The 7G02 B cells were subjected to a second round of retroviral transduction using the retrovirus containing the Bcl6, Bcl-xL and GFP genes. This resulted in 7G02 B cells with higher GFP expression then the original 7G02 B cells. High GFP expressing 7G02 B cells were subjected to cell sorting using a FACSAria III (BD Biosciences) to create a homogeneous population of 7G02 B cells stably expressing high levels of GFP. The sequence of the variable domains of the heavy and light antibody chains of 7G02-GFP-high cells was determined by isolating total RNA using the TriPure/chloroform (Roche/Merck), following the manufacturer's protocol. Next, cDNA was generated using reverse transcriptase (Invitrogen). cDNAs encoding the variable domains of the heavy and light antibody chains were amplified by PCR using VH and VL primers and subjected to DNA sequencing. The sequence of the variable domains of the heavy and light antibody chains of 7G02-GFP-high B cells were identical to those of the 7G02-GFP-low B cells.

Isolation of 7G02 B-Cell Clones with Increased Target Binding

Soluble E-cadherin proteins were used to select subclones with increased antigen-binding compared to the original 7G02 B cell clone by the AIMProve method as described by Kwakkenbos et al. (M. J. Kwakkenbos, Methods (2013)). In short, the 7G02 B cell GFP-high-clone was expanded and proliferated cells were incubated with recombinant soluble E-cadherin mouse-Fc fusion proteins (see above). Subsequently, cells were washed and co-incubated with Alexa Fluor 647-conjugated polyclonal antibody (Invitrogen) that specifically binds the heavy- and the light chain of the B-cell receptor (BCR) to assess BCR expression levels and with R-Phycoerythrin labeled polyclonal anti-mouse-Fc antibodies (Jackson ImmunoResearch) to visualize bound E-cadherin protein. Cells were analyzed by flow cytometry and cells that demonstrated a higher recombinant E-cadherin protein binding relative to their BCR expression compared to the average 7G02 B cell population were sorted single cell using a FACSAria III (BD Biosciences) (FIG. 5*a*). Selected clones were cultured for 2 to 3 weeks to allow expansion and then tested in an antigen competition assay (see below) for increased antigen binding compared to the parental 7G02-GFP-low clone.

Antigen Competition Assay

7G02 B cells (7G02, GFP low) were harvested and seeded at 10,000 cells per well in 96-well round bottom microwell plates. Subsequently, 10-50 μl of sorted subclones (GFP high) was added to these wells. Total cells were washed twice and incubated with E-cadherin-mouse-Fc protein for 1-3 hrs on ice. Subsequently, cells were washed twice and incubated with Alexa Fluor 647-conjugated polyclonal BCR antibody and R-Phycoerythrin labeled polyclonal anti-mouse-Fc antibodies (Jackson ImmunoResearch) for approximately 1 hour. Then cells were washed and bound antibodies were detected by flow cytometry using a FACS Canto (BD Biosciences). The amount of recombinant E-cadherin protein binding to parental 7G02-GFP-low cells is compared with the amount of recombinant E-cadherin protein bound to the subclones (GFP high). Higher binding of recombinant E-cadherin to the subclone (GFP-high) versus parental clone (GFP-low), relative to their BCR expression level is indicative of BCRs with higher binding capacity. Plotted in FIG. 5*b* are examples of 7G02-GFP-high subclones that show increased binding to E-cadherin protein compared to the parental 7G02-GFP-low B cells, relative to their BCR expression.

Cloning and Sequence Analysis of Selected Subclone Antibodies of AT1636

A panel of subclones was selected based on enhanced recombinant E-cadherin antigen binding compared to the parental 7G02 clone. Of these subclones total RNA was isolated using the TriPure/chloroform method (Roche) following the manufacturer's instructions. Next cDNA was generated by Reverse Transcriptase (SuperScript III, Invitrogen) and Random Hexamers (Promega). The IgG variable domains of heavy and light chains were amplified by PCR (FastStart Taq DNA Polymerase, Roche) following the manufacturer's procedure applying leader specific primers combined with CH1 (Heavy chain) and Ckappa (Light chain) specific primers. The amplicons were used for Sänger dideoxy fluorescent sequencing (BDT, Invitrogen) using the cognate primers as used for amplification. Table 1 is depicting the DNA and amino acid sequences of the subclones that showed increased antigen binding, relative to the amounts of BCR on the surface of the B-cell subclones. Based on this sequence data recombinant antibodies AT1636-I (VH SEQ ID NO: 3, VL SEQ ID NO: 18), AT1636-Y (VH SEQ ID NO: 10, VL SEQ ID NO: 18), AT1636-E (VH SEQ ID NO: 5, VL SEQ ID NO: 18), AT1636-N (VH SEQ ID NO: 8, VL SEQ ID NO: 18), AT1636-YN (VH SEQ ID NO: 15, VL SEQ ID NO: 18), AT1636-IYN (VH SEQ ID NO: 16, VL SEQ ID NO: 18) and AT1636-IYEN (VH SEQ ID NO: 17, VL SEQ ID NO: 18) were produced recombinant.

To produce recombinant antibodies based on the 7G02 subclones sequences, heavy and light variable regions were cloned in frame with human IgG1 and Kappa constant regions into Double Gene pXC based expression vectors (Lonza). Constructs were checked for integrity by DNA sequencing and transfected into ExpiCHO-S cells (GS Xceed platform, Lonza). The cells were expanded and used for shaker flask, fed-batch cell culture IgG production for 7 days. The cell cleared supernatants containing the recombinant AT1636 antibodies was harvested and purified using Protein A chromatography using an AKTA purification system (General Electric Lifesciences). Antibodies were eluted using 0.1M Citrate, 150 mM NaCl, pH 3,5 buffer, subsequently neutralized in 1M Tris-HCl, pH 9,0 and then rebuffered in TBS-TS by size-exclusion chromatography. Concentration was established using NanoDrop spectrophotometer (OD280, ThermoFisher). Monomeric content of the purified antibody was confirmed >90% using size-exclusion chromatography. Integrity of purified proteins was established by SDS-PAGE.

Next, the recombinant antibodies were compared for flow cytometry binding to different cell lines including colon DLD1, mouse CMT93, breast MCF10a, skin A431 and lung A547 (FIGS. 6*a* and 6*b*). From these experiments we could conclude that the AT1636-IYN antibody, that combines 3 mutations (VH SEQ ID NO: 16, VL SEQ ID NO: 18), bound these cells more efficient compared to AT1636 and the other AT1636 variants.

Example 4 Analysis of AT1636 High Affinity Variants

Binding of AT1636 High Affinity Variants Using SPR

The AT1636 recombinant antibody and AT1636-YN (also referred to herein as -NY; VH SEQ ID: 15 and VL SEQ ID: 18) and AT1636-IYN (also referred to herein as -IYN; VH SEQ ID: 16 and VL SEQ ID: 18) variants were tested for binding to recombinant p70 E-cadherin and compared to antibody EP700Y E-cadherin antibody using the IBIS Mx96 (IBIS Technologies) and CFM Spotter (Wasatch Microfluidics). Results were analyzed using Sprint software (version 11.0.24, IBIS). Binding curves were fitted using Scrubber2 software (Biologic software).

A SensEye G-STREP chip (Ssens B V, Enschede, Netherlands) is coated with a concentration series (0.2-2.0 μg/ml) of human p70 E-cadherin-mouseFc-biotin (see Example 3). Binding was assessed under a flow speed of 2 μl/min (during association+dissociation), 8 μl/min (regeneration steps) both at a temperature of 25° C. Anti-rabbit IgG (goat anti-rabbit H+L, Jackson), anti-mouse IgG (goat anti-mouse H+L, Jackson), EP700Y (Abcam), AT1636 and variants-IYN and -NY were subsequently injected in a concentration series of 0.5-20 μg/ml, in duplicate. Binding is established by the IBIS multiplex SPR imaging.

Figure 7A:
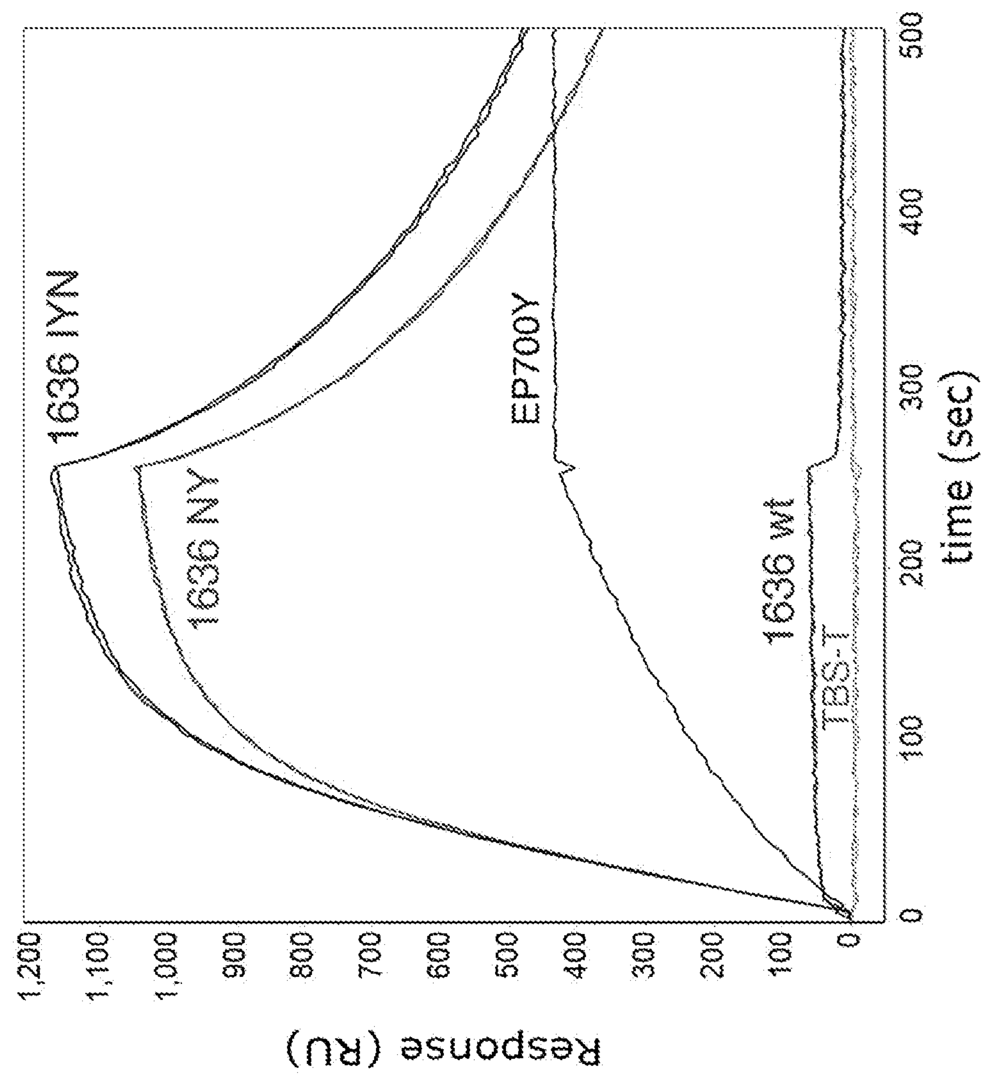

As shown in FIG. 7*a* binding of AT1636 and the variants-YN and -IYN to soluble p70 E-cadherin was demonstrated. AT1636 NY shows greatly improved binding compared to AT1636 and shows approximately equal binding compared to AT1636 IYN. Of the AT1636 antibodies especially the on-rate is increased, the off-rate remained unchanged.

Steady-State Binding of AT1636 Variants by ELISA

Figure 7B:
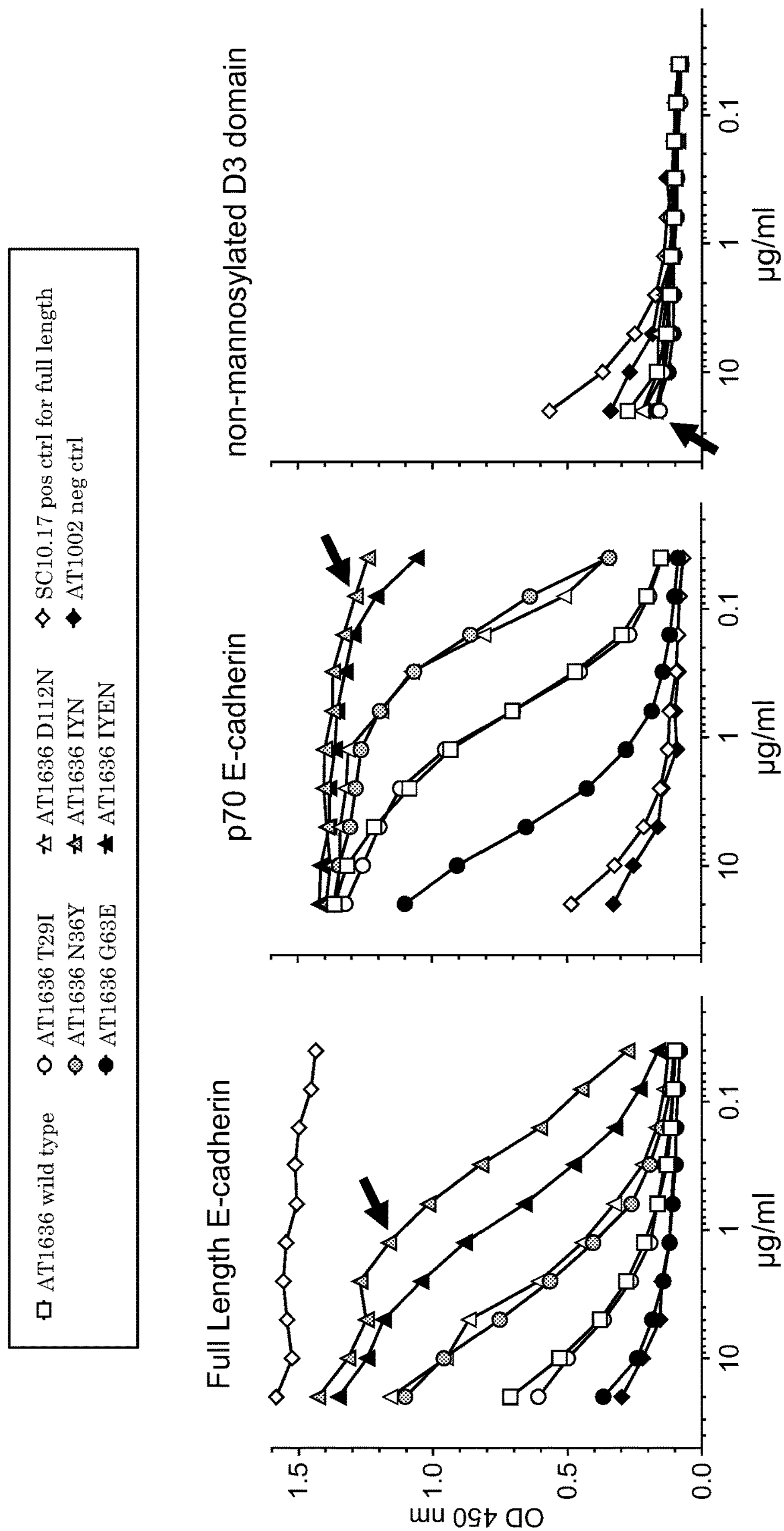

Recombinant E-cadherin mFc proteins were captured on 96-well plates (Costar) using goat-anti-mouse IgG Fcy antibodies (Jackson). After blocking with TBS/5% BSA/0.05% Tween 20, washing twice with PBS/0,05% Tween, captures and washing twice with PBS/0,05% Tween, AT1636 and AT1636 affinity variants were added (at 4 degree) and binding of these antibodies was detected after 2 washes with PBS/0,05% Tween using a goat a-human IgG H+L-HRP (Jackson). Bound antibodies were visualized using a TMB substrate (Sigma) and the reaction was stopped with $H_2SO_4$ (Merck) and quantified by OD450 measurement using an Envision plate reader (Perkin Elmer). As shown in FIG. 7*b* (two left panels), similar increased binding of AT1636-YN and -IYN antibody variants in comparison to AT1636 antibody was observed by ELISA to full length E-cadherin and p70. Again the AT1636 IYN variant shows stronger binding than-YN and the AT1636 antibody. Here SC10.17, a humanized EC1 domain specific E-cadherin antibody binds full length E-cadherin but not the p70 truncated variant. Of note, all tested antibodies AT1636 variants, as well as AT1636 wild type, bind the truncated 70 kDa form of E-cadherin better than full length E-cadherin.

In another ELISA we tested the binding of AT1636 and its variants to a D3-mouseFc protein containing an Alanine substitutions of residue Thr470. Since AT1636 binding is dependent on O-mannosylated p70, shown by the mannosyltransferase inhibition using Oxo-2-thioxo-3-thiazolidinylacetic acid in Example 2, FIG. 4, we made a substitution that would abolish O-mannosylation. Residue 470 is located central in the AT1636 epitope and probably mannosylated. Indeed, we could show that AT1636 almost completely lost binding to this Thr470Ala D3 variant (FIG. 7*b*, right panel). The AT1636 variants were, albeit their increased binding capacity to p70 compared to AT1636-wt, still dependent on proper O-mannosylation within their binding epitope.

To assess binding preference for p70 over full length E-cadherin we tested a wide concentration range of AT1636 and its variants, for binding to full length E-cadherin, p70 and to the D3-mouseFc protein containing an alanine substitution of residue Thr470, a variant to which AT1636 binding is strongly reduced (shown in FIG. 7*b*).

Figure 7C:
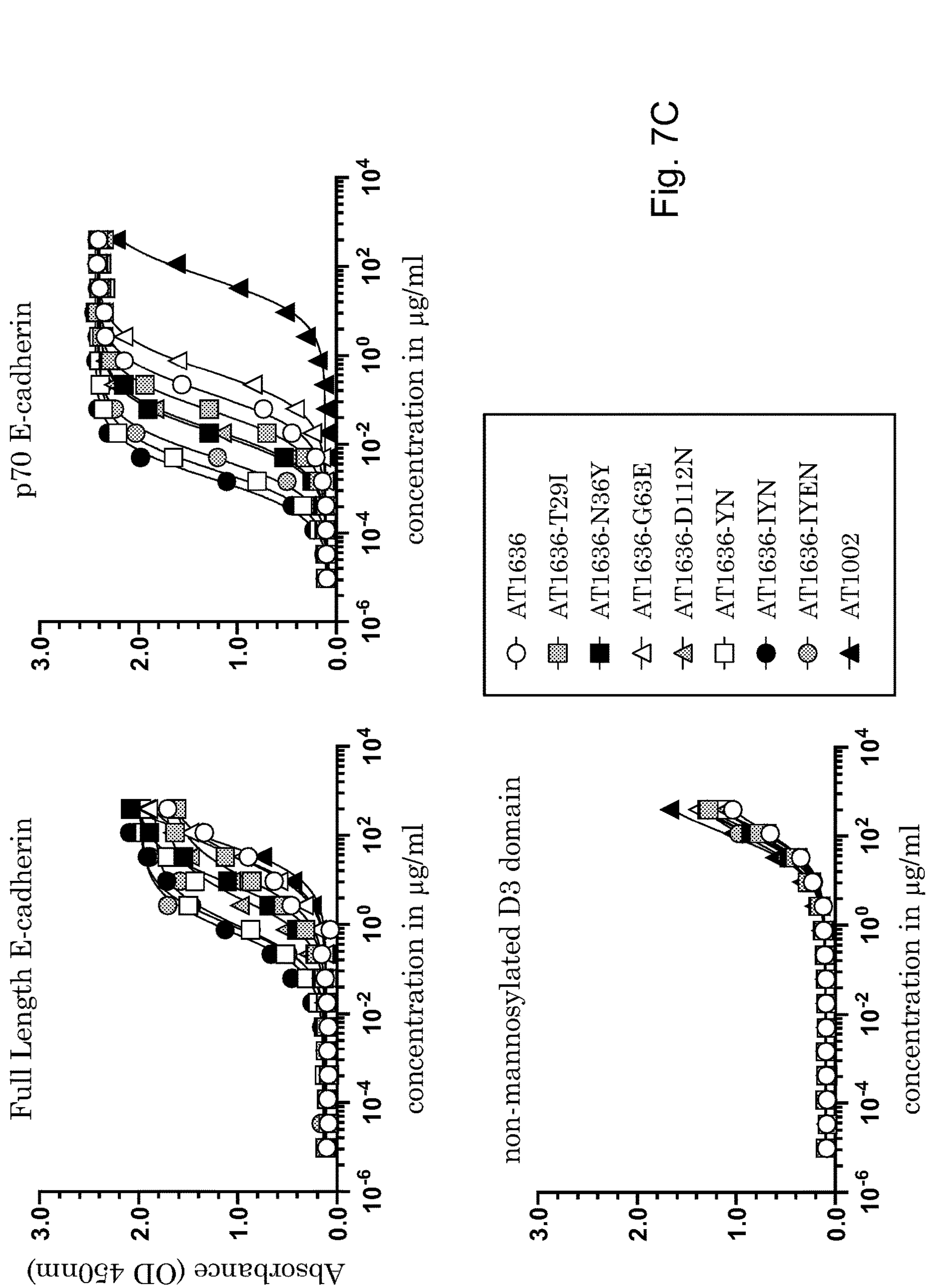

As shown in FIG. 7*c* and Table 4 the increase in binding compared to AT1636 wild-type is most pronounced for the -IYN and -YN variants. Importantly, they retain preferred binding to the p70 form of E-cadherin compared to Full Length E-cadherin (56,5-fold for YN and 67.1-fold for IYN) and (28.4-fold for YN and 64.3-fold for IYN), respectively.

Example 5 Epitope Mapping p70 E-Cadherin Binding to AT1636 is Mannose Dependent

Figure 8A:
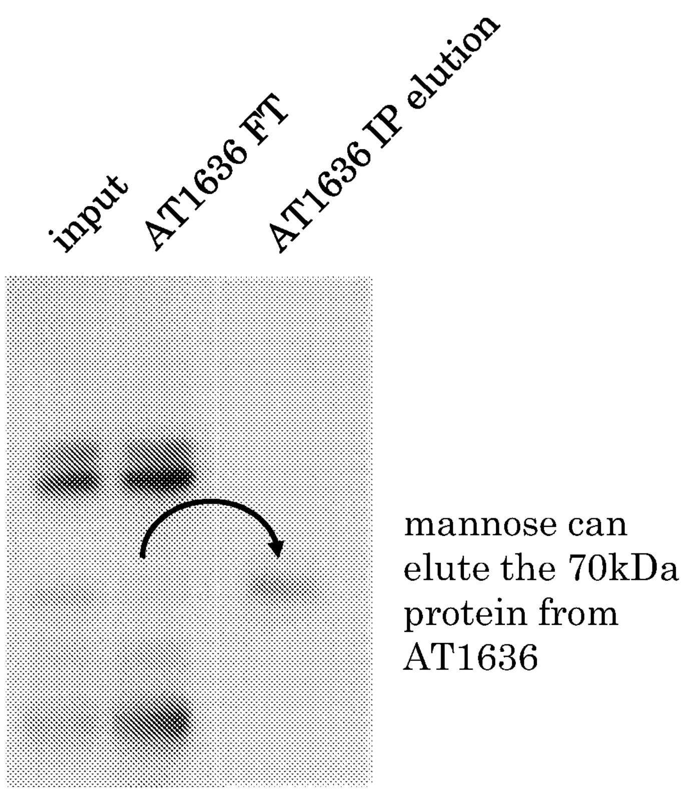
Figure 8B:
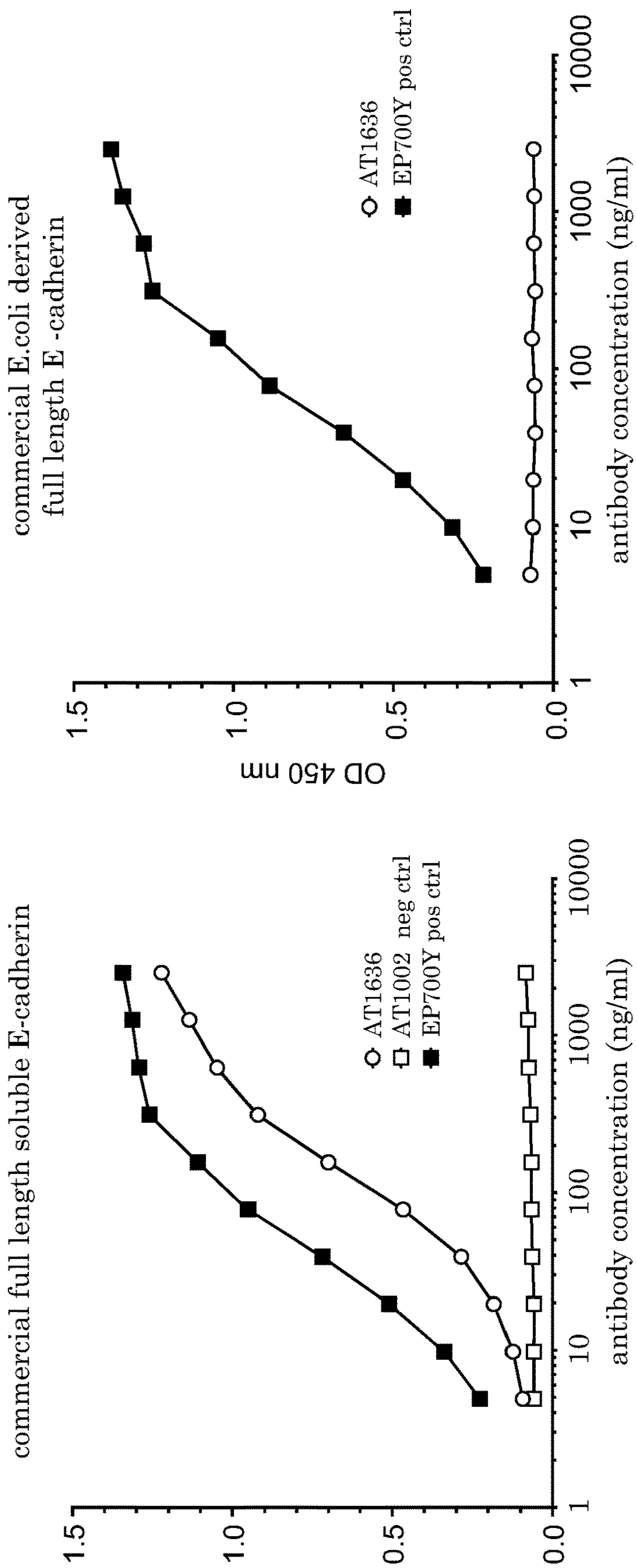

DLD1 cells (ATCC CCL-221) were lysed using lysis buffer (0,5% Triton X114 (Sigma), 0.5% DOC; 0.1% SDS, 150 mM NaCl, 10 mM Tris-HCL pH7.4, 1.5 mM MgCl2 supplemented with protease and phosphatase inhibitors (Roche)) for 3 hrs at 4° C. After lysis non-soluble fraction was removed by centrifugation. Next, lysates were pre-cleared with an irrelevant antibody (RSV antibody Palivizumab) captured to Protein-G Dynabeads (Invitrogen) and Streptavidin beads (Invitrogen) to remove non-specific binding proteins. Precleared lysates were then incubated with AT1636 antibody captured to protein-G Dynabeads (Invitrogen) for 3 hrs. at 4° C., washed three times in lysis buffer and bound proteins were eluted from the beads with 450 mM Methyl a-D-mannopyranoside (Sigma). Eluates were analyzed by SDS-PAGE gel in 1×SDS-PAGE sample buffer (BioRad)+0,1M DTT followed by western blotting onto PVDF membranes. After blocking of the membranes with TBST/5% BSA, membranes were incubated with rabbit-anti-E-cadherin (EP700Y, Abcam) to detect E-cadherin protein. As shown in FIG. 8*a* p70 E-cadherin was eluted from AT1636 by high mannose addition, indicating that one or more mannose groups form an intrinsic part of the binding epitope of AT1636. Mannose dependency of the binding of AT1636 to E-cadherin was confirmed by ELISA. Recombinant E-cadherin proteins were captured on 96-well plates (Costar) using goat-anti-mouse IgG Fcy antibodies (Jackson). Full length E-cadherin (Sino Biologics) derived from HEK cells and full length E-cadherin derived from *E. coli* (LSbio) were captured. After captures and washing with TBS/0,05% Tween for 2 times, AT1636 and EP700Y (Abcam) and AT1002 as a negative control were added in a dose-concentration. Binding of these antibodies was detected after two washes with TBS/0,05% Tween using a goat anti-Human IgG Fc(y)-HRP (Jackson) or anti-Rabbit IgG-HRP (Dako). Bound antibodies were visualized using a TMB substrate (Sigma) and the reaction was stopped with H2SO4 (Merck) and quantified by OD450 measurement using an Envision plate reader (Perkin Elmer). While EP700Y, a rabbit antibody, against the EC5 domain of E-cadherin binds both E-cadherin recombinant proteins, AT1636 does not bind *E. coli* derived E-cadherin (carrying no post-translational modifications) where it does bind the HEK produced recombinant E-cadherin (see FIG. 8B).

Several Ser/Thr residues have been reported to be mannosylated; five in the EC2 domain, four in the EC3, four in EC4 and one in EC5 of E-cadherin (Larsen, PNAS (2017), Vester-Christensen, PNAS (2013) and Lommel, PNAS (2015)). In FIG. 3 putative O-mannosylated sites on E-cadherin are indicated in black. In the mass spectrometry analysis of the AT1636 immunoprecipitated p70 E-cadherin protein Ser/Thr residues were found to be single O-mannosylated.

Binding of AT1636 to Alanine Mutated EC3 E-Cadherin Domain

To determine the exact binding epitope of the AT1636 antibody within the truncated E-cadherin p70 domain multiple alanine mutations were generated within the truncated-recombinant extracellular domain 3 (D3). First, a truncated extracellular domain D3-only domain was generated consisting of the amino acid residues EVSLTTSTATVTVDVLDVNEAPIF (FIG. 3). In addition single alanine mutations of each residue were designed. cDNAs encoding D3 and alanine mutants thereof were cloned into pcDNA3 vector fused to a FLAG tag and mouse Fc-tail that was equipped with a sortase and HIS tag. Vectors were transiently transfected in Expi293 or CHO cells and supernatants containing the recombinant proteins were harvested after 7 days. Recombinant D3 protein or alanine mutants thereof were captured via the mouse Fc-domain on anti-mouse IgG H+L (5 μg/ml, Jackson) coated 384-well spectra plates HB (Perkin Elmer). After incubation and twice washing with TBS/0,05% Tween, AT1636-YN or control Ab AT1002 were added and binding of these antibodies was detected after two washes with TBS/0,05% Tween using a secondary goat a-human IgG Fc(y)-HRP (Jackson). Bound antibodies were visualized using a TMB substrate and the reaction was stopped with $H_2SO_4$. Quantification of bound antibodies was established by OD450 measurement on Envision plate reader (Perkin Elmer).

Alanine substitutions resulted in partial abrogation of binding of AT1636-YN in comparison to wild-type E-cadherin: E463A, S465A, T467A, S469A, T472A and V477A. The substitutions of T468A and T470A/G/N/D completely abrogated AT1636-YN binding. The importance of residue 470 was also illustrated in Example 4, FIG. 7*b*, right panel, where AT1636 and its variants were not able to bind to the D3-protein variant that has an alanine mutation at position 470. Altogether, especially 4 central threonines (467, 468, 470, and 472 to a lesser extent) seem to govern binding of AT1636 to E-cadherin and p70 E-cadherin (see FIG. 9).

Example 6 Binding of AT1636 Corresponds to TMTC3 and E-Cadherin Co-Expression

Larsen and coworkers reported that E-cadherin mannosylation is dependent on the presence of tetra-trico-peptide repeat (TPR) repeat-containing proteins (TMTC1-4) (M. Racape M, PLOS One (2011), Bartels MF, PLOS One (2016), J. C. Sunryd, J Biol Chem (2014) and I. S. B. Larsen, PNAS (2017)). Using mRNA expression of full length E-cadherin and TMTC3 in >1100 cell lines retrieved from the Cancer Cell Line Encyclopedia mRNA database from the Broad Institute (https://portals.broadinstitute.org/ccle), a strong correlation between co-expression of E-cadherin and TMTC3 was established, while for none of the other TMTC1, 2 and 4 such a correlation could be established. In addition, a correlation between E-cadherin, TMTC3 and binding of AT1636 could be established (Table 3). Using a cut-off of 7 for mRNA expression for TMTC3 and E-cadherin, all cell lines that show ≥7 mRNA expression of TMTC3 and E-cadherin were predicted positive for AT1636 binding. The percentage of cell lines derived from different tumor types that are predicted positive for AT1636 binding is depicted in FIG. 10. Several solid tumors express both genes at high level suggesting that a large percentage of tumor cell lines including tumors from the upper-(aero) digestive tract, esophagus, breast, colon, prostate, pancreas, stomach, urinary tract, ovary and lung bind AT1636 or AT1636 high affinity variants.

Expression of Full-Length E-Cadherin in a TMTC3 Expressing E-Cadherin Negative Cell Line The E-cadherin full coding sequence was obtained from Geneart and subcloned into the pHEF lentiviral vector containing an IRES-GFP. Lentiviral particles were produced with a VSV-G envelope and SK-MEL-5 target cells (ATCC HTB-70) were transduced with virus and sorted for GFP expression after expansion for at least one week using a FACS Aria (BD). Isolated cells were subjected to flow cytometry with AT1002 as a negative control antibody, AT1636 and EP700Y E-cadherin antibodies using goat anti-human-Alexa647 (Invitrogen) and goat anti-rabbit-Alexa647 (Jackson) antibody as detection reagent (FIG. 11). Overexpression of full length E-cadherin in the TMTC3 expressing but normally E-cadherin negative cell SK-MEL-5 results in binding of the AT1636 antibody.

AT1636 Binding is Dependent on TMTC3

Several shRNAs were designed to target the TMTC3 mRNA (NCBI Reference Sequence: NM_181783.4). Ultimately the selected shTMTC3 targets the last coding exon (14):

22_mer: AGGAGACATTCTGATGAATCAA. The selected shRNA was subcloned into the pTRIPZ vector (Thermo Scientific) and lentiviral particles with a VSV-G envelope were generated following the manufacturer's instructions. DLD1 cells (ATCC CCL-221) were transduced and expression of the shRNAs was induced upon addition of 1 μg/ml Doxycylin (Sigma). After 4 to 7 days in culture, cells were subjected to flow cytometry analysis for binding of AT1636 and AT1002 antibodies, using goat anti-human-Alexa647 (Invitrogen) antibody as to detect bound antibodies. In parallel, RNA was isolated using Tripure isolation reagent (Roche) and cDNA was generated with SuperscriptIII Reverse Transcriptase kit (Invitrogen) with Oligo-dT primers. A quantitative PCR was performed on an ICycler (BioRAD) with IQ Sybrgreen supermix (BioRad) to detect TMTC3 mRNA using TMTC3 qPCR Forward Primer 5'-GGTGTGGTTACTGCCTGCTAT-3' and Reverse Primer 5'-GGACGGTAAGACTTGTGGCT-3' and using GAPDH control to quantify mRNA transcripts.

As shown in FIG. 12, following shRNA knock down of TMTC3, AT1636 binding to DLD1 cells is strongly reduced.

Figure 13A:
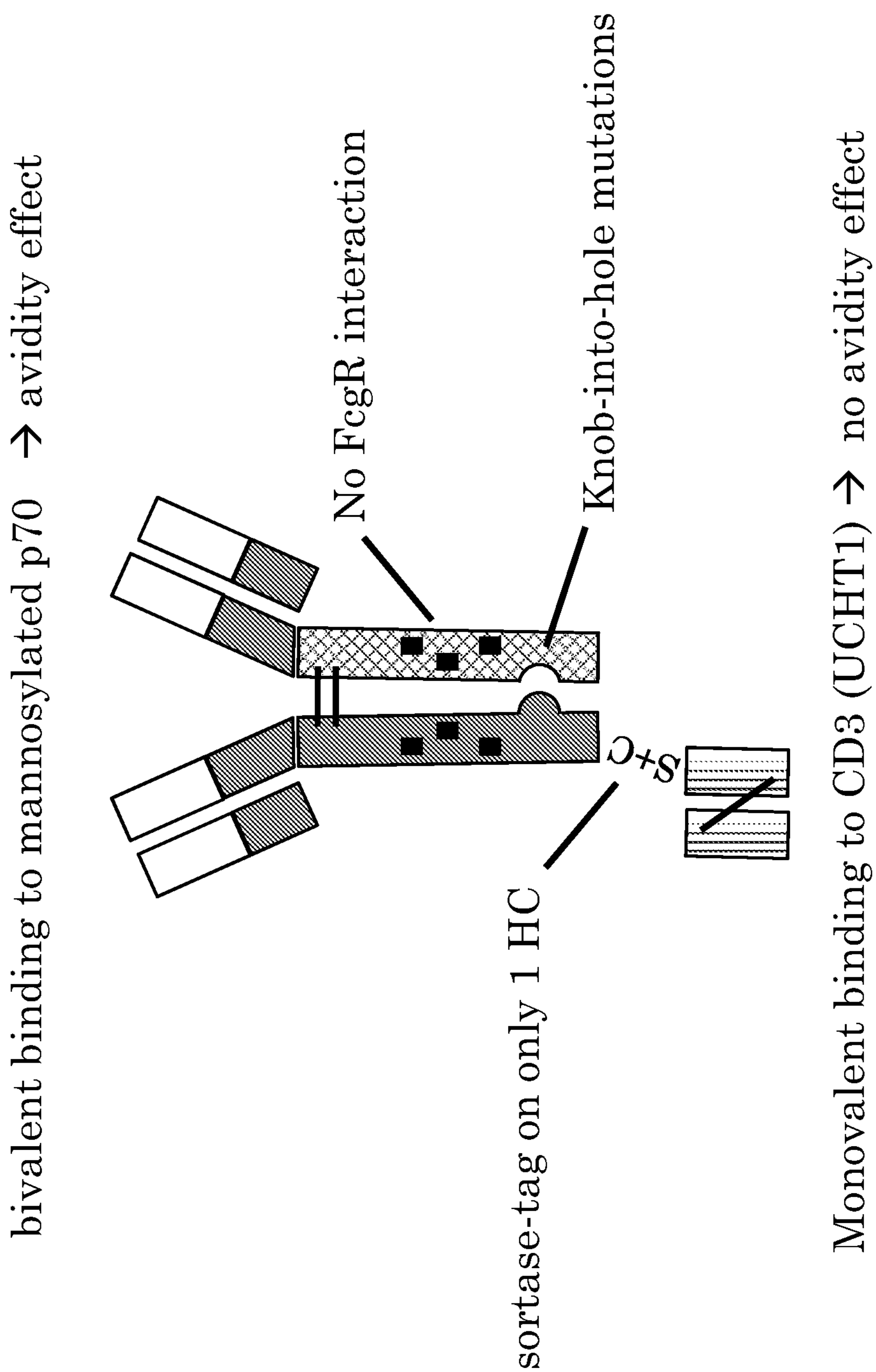

Example 7 A T-Cell Engager Targeting p70 E-Cadherin Induces Cytotoxicity on Tumor Cell Lines Generation of T-Cell Engaging Antibodies T-cell engaging antibodies (TCEs) were generated in a TCE format bivalent for p70 and monovalent for CD38 binding (mTCE) (FIG. 13*a*; S. Atwell, Journal of Molecular Biology (1997) and A. M. Merchant, Nature Biotechnology (1998)). To obtain antibodies that can be equipped with a single anti-CD3 fragment on only one heavy chain C-terminus, sequences of AT1636 and AT1636-IYN encoding the 'knob' mutations S354C and T366W (SEQ ID) in one and the 'hole' mutations Y349C, T366S, L368A, Y407V (SEQ ID) in the other heavy chain Fc region were used. Additionally, in the heavy chain sequence containing the 'knob' mutations, the C-terminal lysine residues were replaced with a C-terminal ST-tag (amino acid sequence: GGGGSLPETGGHHHHHH). Antibodies were expressed in CHO cells transient transfection with three different vectors encoding a) the light chain, b) the 'knob' mutated ST-tag containing heavy chain and c) the 'hole' mutated heavy chain. mTCEs were generated and purified according to methods described by L. Bartels et al. Cancer Res (2019) and L. Bartels et al. Methods (2019). After 7 days of culture recombinant antibodies were harvested and purified from the culture supernatant using Protein A chromatography using an AKTA purification system (General Electric Lifesciences). Antibodies were eluted using 0.1M Citrate, 150 mM NaCl, pH 3,5 buffer, subsequently neutralized in 1M Tris-HCl, pH 9,0 and then rebuffered in TBS-TS by size-exclusion chromatography. Concentration was established using NanoDrop spectrophotometer (OD280, ThermoFisher). Monomeric content of the purified antibody was confirmed >90% using size-exclusion chromatography. Integrity of purified proteins was established by SDS-PAGE.

Next, ST-tag modified heavy chain C-termini were equipped with methyltetrazine click handles using sortase-catalyzed transpeptidation and conjugated to an anti-CD3 single chain variable fragment based on antibody UCHT1 which had been modified by sortase-catalyzed transpeptidation analogous to the full-length antibodies, but with the complimentary click handle trans-cyclooctene.

A control mTCE based on the antibody AT1002 (specific for hemagglutinin proteins of group 2 influenza viruses) was prepared analogously.

Endotoxins potentially remaining in mTCE preparations were removed using Pierce High Capacity Endotoxin Removal Spin Columns (ThermoFisher) and final endotoxin levels were confirmed with EndoZyme Assay kits (Hyglos).

In another experiment we generated a T-cell engager monovalent for both E-cadherin and CD3e. AT1636 variants were reformatted into a Knob-in-Hole (KiH) bispecific format consisting of one heavy and light chain of AT1636, AT1636-IYN or AT1002 and a single chain anti-CD38 fragment fused to a Fc-tail (FIG. 13*c*). Antibodies were expressed in CHO cells transient transfected with three different vectors encoding a) the light chain of AT1636, AT1636-IYN or AT1002, b) the 'knob' mutated heavy chain carrying the mutations S354C, and T366W of AT1636, AT1636-IYN or AT1002 and c) a heavy chain carrying the 'hole' mutations Y349C, T366S, L368A, and Y407V in which the VH-CH1 region had been replaced by the UCHT1 single chain variable fragment (scFv). KiH bispecifics were purified using HiTrap MabSelect Sure columns (GE Healthcare) as the other antibodies (described above).

CD3 T-Cell Engager of AT1636 and -IYN Induced Cell Cytotoxicity of Tumor Cells mTCE variants of AT1636 and AT1636-IYN were assessed in a luciferase-based cytotoxicity assay. First, DLD1, HCT116 and HT29 (all CRC cell lines) were transduced with a lentiviral vector encoding firefly luciferase followed by ZsGreen fluorescent protein controlled by a pHIV or pHCMV promoter (Addgene). Green fluorescent cells were sorted using a FACS ARIA system (BD). Transfected and isolated cells were pre-incubated in flat bottom tissue culture plates overnight with various concentrations of mTCE and with Peripheral Blood Mononuclear Cells as effector cells in an effector to target cell ratio of approximately 10:1. After assay incubation for 40-44 hrs, cells were lysed using ONE-Glo, a luciferin containing lysis solution (Promega). Luminescence was acquired using an EnVision plate reader (Perkin Elmer).

Figure 13B:
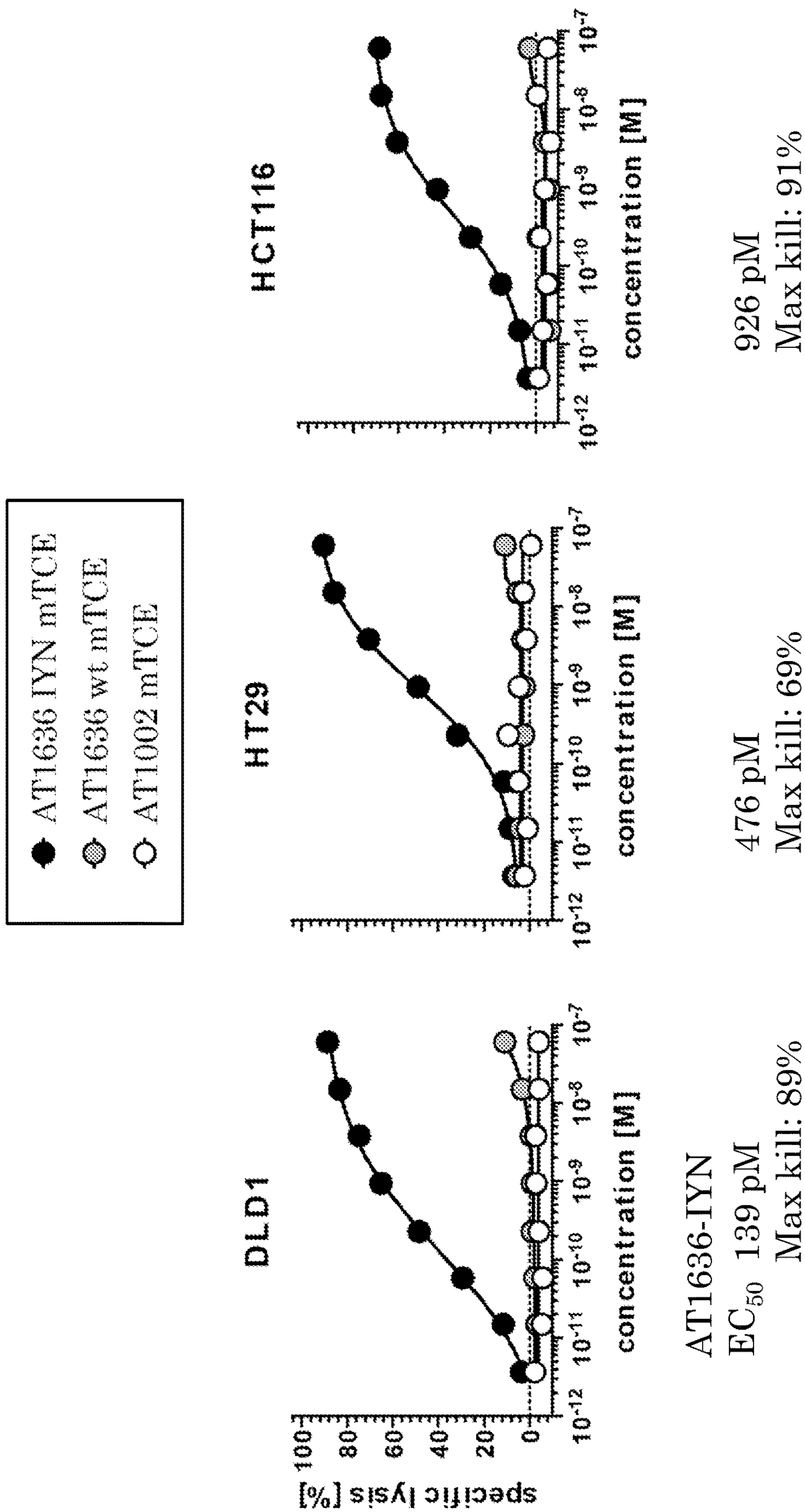
Figure 13C:
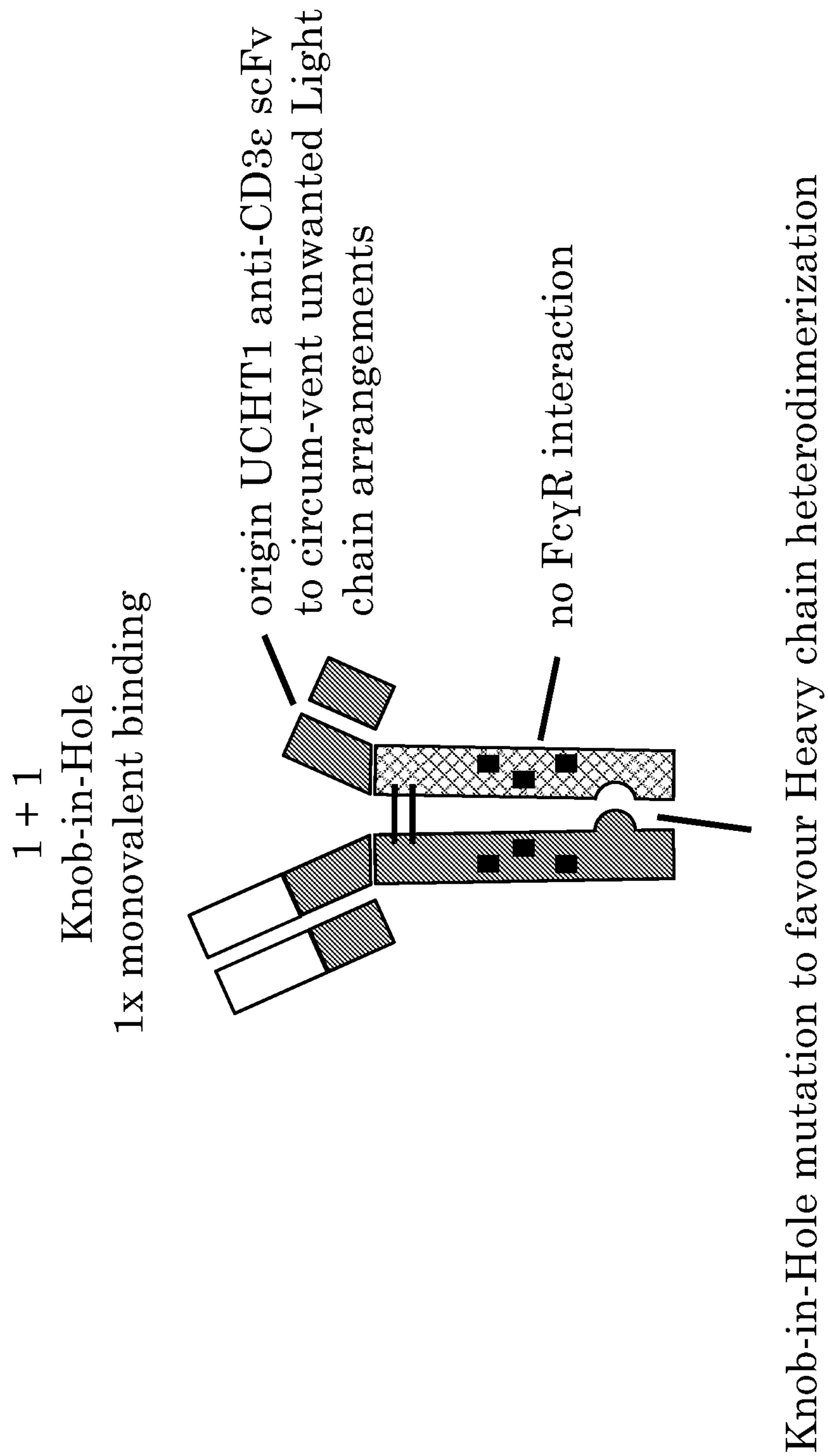

In the T-cell engagement assay, AT1636-IYN mTCE induced cytotoxicity against DLD1, HT29 and HCT116 target cells with EC50 values of 139 μM, 476 μM, and 926 μM, respectively (FIG. 13*b*). Maximal target cell lysis ranged from 69 to 91%. AT1636 mTCE induced target cell lysis at higher concentrations and no lysis was observed after incubation with negative control AT1002 mTCE.

Figure 13D:
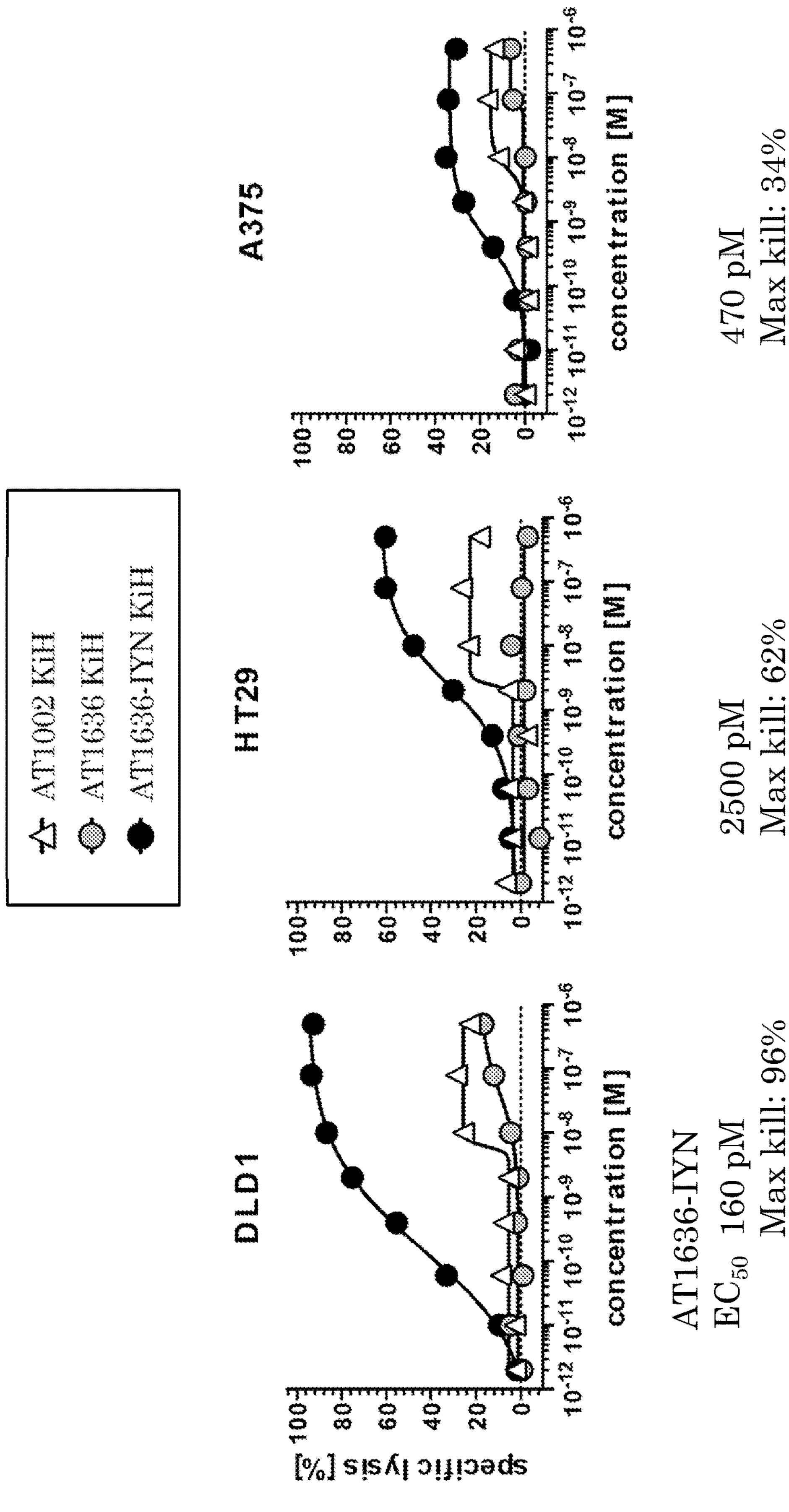

The AT1636-IYN KiH induced cytotoxicity against DLD1, HT29 and A375 target cells with EC50 values of 160 μM, 2500 μM, and 470 μM, respectively (FIG. 13*d*). Maximal target cell lysis ranged from 34 to 96%. AT1636 and AT1002 KiH only induced target cell lysis at higher concentrations.

Example 8. Overexpression of p70 E-Cadherin Functions as a De-Adhesive Molecule The E-cadherin full length open reading frame and p70 E-cadherin coding sequences were obtained from Geneart and subcloned into the pHEF lentiviral vector containing an IRES-GFP. Lentiviral particles were produced with a VSV-G envelope and target cells were transduced with virus. Transduced cells were selected for GFP expression and seeded in equal amounts. After 48 hours cells overexpressing the p70 E-cadherin protein demonstrated an aberrant, rounded cell morphology as depicted in FIG. 14, suggestive of less strong cell-cell interactions and more single cells and of epithelial to mesenchymal transition (EMT) (V. Padmanaban, Nature (2019) and N. M. Aiello, Developmental Cell (2018)).

Example 9. Binding of AT1636 on Epithelial Cell Lines is Increased in the Presence of TGFβ

TGFβ is a well-known factor to promote for its epithelial to mesenchymal transition. TGFβ (Prospec, Rehovot, Israel) (V. Padmanaban, Nature (2019), D. V. F. Tauriello, Nature (2018) and N. M. Aiello, Developmental Cell (2018)) was added at 10 to 40 ng/ml to human CRC cell line DLD1, mouse colon CMT93, human skin A431 and the human breast MCF7, a cell line for 6 to 7 days. TGFβ was added every other day and at day 4 culture medium was refreshed. Cells were cultured in 24 well plates at low cell density either on tissue culture treated plastic or in wells coated with fibronectin. In addition, where applicable AT1636 or AT1636-IYN was added (at concentration between 10 and 50 μg/ml) in presence or absence of TGF. Cell morphology and cell density was monitored by Operetta (Perkin Elmer) and AT1636 or AT1636-IYN binding to cell lines was monitored by flow cytometry (MFI per cell).

In FIG. 15 the binding ratio of AT1636-IYN between cell lines cultured in the presence or absence of TGFβ is shown. Prolonged culture in the presence of TGFβ 3-4 fold increased binding of AT1636-IYN to the A431 and CMT93, while a smaller induction was found for MCF7 as determined by flow cytometry. A small change in binding of AT1636 to HT29 cells in the presence of TGFβ was observed.

During co-culture with TGFβ and AT1636-IYN antibody for 5-7 days as described above, a decrease in cell growth and number of cells attached to the well surface was observed for A431 cells (see FIG. 16*a* (10× magnification) & 16b (20× magnification)). This effect was observed in settings were cells were cultured either directly on plastic or on fibronectin coated wells.

Example 10. Internalization of AT1636 and High Affinity Variants 8,000 DLD1 cells were seeded per well in 100 μl in a 96-well plate and cultured O/N. AT1636, AT1636 high affinity variants, AT1002 and SC10.17 antibodies were conjugated with goat anti-human Fc Fab labelled Zenon pHrodo iFL dye (Invitrogen) during a 15 minute incubation following the manufacturer's instructions. Next, antibodies were added to DLD1 cells and internalization of pHrodo-conjugated antibodies was monitored over time by detection every hour in the Incucyte (Essenbio) for max 60 hrs.

In FIG. 17 the acidic environment induced pHrodo dye fluorescence is depicted indicating that AT1636 and AT1636 high affinity variants are internalized into DLD1 cells. The AT1636-IYN antibody is most efficient in being internalized as compared to the AT1636-YN, AT1636 or SC10.17 antibodies. AT1002 as negative control in contrast is not internalized.

Example 11. Interaction of Full Length and p70 E-Cadherin with CD103 on CD8+ T Cells Fresh PBMC were obtained from blood collected in Lithium-Heparin tubes using Ficoll gradient centrifugation and CD8+ T cells were isolated using MagniSort™ Human CD8 T cell Enrichment Kit (Thermo Fisher) following the manufacturer's instructions. Subsequently CD8+ cells were cultured in RPMI 10% FCS pen/strep in the presence of 10 μg/ml PHA, 6000 U/mL IL-2 and 10 ng/ml TGFβ at a cell density of $1\times10^6$ PBMCs in 1 ml. After approximately 10 days CD103 expression on the CD8 cells is determined by flow cytometry (Ber ACT 8 clone, BD, FITC labeled).

To analyze the interaction of CD103 on the CD8+ T cells with plate bound E-cadherin proteins, full length and p70 E-cadherin is coated O/N in DPBS containing 1 mM Ca2+ and Mg2+ and CD103 expressing CD8+ T cells are labelled with 5 μM Celltrace-CFSE (Thermo Fisher) for 5 min at RT. Next, cells are resuspended in culture medium with 1 mM Mn2+ at a concentration of $1\times10^5$/ml and pre-incubated for 30 min with 10 μg/ml of AT1002 negative control antibody, the anti-CD103 antibody and AT1636 and its-IYN variant for 30 minutes. After adding 50.000 cells (100 μl) for 30 min at 37° C. to each well containing the E-cadherin proteins, the wells are emptied by reverting the plate, washed with DPBS and fixed with 3.7% Formalin in DPBS before being analyzed in a fluorescence microscope.

In FIG. 18 is depicted the well coverage by CFSE labeled CD103+ CD8+ T cells. When cells were preincubated with the CD103 specific antibody MCA708, the cells did not adhere to the full length E-cadherin. When cells were preincubated with AT1636 and the -IYN variant cells could still attach, indicating the AT1636 is not interacting with the CD103 protein on the cells. In addition we observed that CD103+ CD8+ T cells did not attach to the p70 E-cadherin protein.

The content of the ASCII text file of the sequence listing named "Substitute-Sequence-Listing-20885-6101", having a size of 69.0 kb and a creation date of 13 Jan. 2013, and electronically submitted via EFS-Web on 18 Jan. 2023, is incorporated herein by reference in its entirety.

The invention claimed is:

1. A synthetic or recombinant IgG1 antibody or antigen binding fragment thereof that is able to bind O mannosylated E cadherin, wherein said antibody or antigen binding fragment comprises each of:

a. a heavy chain variable region CDR1 comprising the amino acid sequence GF$X_1$FS$X_2$AW (SEQ ID NO: 59), wherein $X_1$ is T or I and wherein $X_2$ is N or Y;

b. a heavy chain variable region CDR2 comprising the amino acid sequence IKSKIDG $X_1$T $X_2$ (SEQ ID NO: 60), wherein $X_1$ is G or E and wherein $X_2$ is T or I;

c. a heavy chain variable region CDR3 comprising the amino acid sequence TPGVG$X_1$N$X_2$PYYFDR (SEQ ID NO: 61), wherein $X_1$ is A or T and wherein $X_2$ is D or N;

d. a light chain variable region CDR1 comprising the amino acid sequence QSVLCRSNNKNC (SEQ ID NO: 62);

e. a light chain variable region CDR2 comprising the amino acid sequence WA$X_1$, wherein $X_1$ is S or C; and f. a light chain variable region CDR3 comprising the amino acid sequence QQYSNTPQT (SEQ ID NO: 63).

2. The synthetic or recombinant antibody or antigen binding fragment according to claim 1, wherein said antibody or antigen binding fragment comprises:

a. a heavy chain CDR1 comprising the sequence GFTFSNAW (SEQ ID NO: 69) and a heavy chain CDR2 comprising the sequence IKSKIDGGTT (SEQ ID NO: 70) and a heavy chain CDR3 comprising the sequence TPGVGANDPYYFDR (SEQ ID NO: 71) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or b. a heavy chain CDR1 comprising the sequence GFIFSNAW (SEQ ID NO: 72) and a heavy chain CDR2 comprising the sequence IKSKIDGGTT (SEQ ID NO: 73) and a heavy chain CDR3 comprising the sequence TPGVGANDPYYFDR (SEQ ID NO: 74) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or c. a heavy chain CDR1 comprising the sequence GFIFSNAW (SEQ ID NO: 75) and a heavy chain CDR2 comprising the sequence IKSKIDGETT (SEQ ID NO: 76) and a heavy chain CDR3 comprising the sequence TPGVGANDPYYFDR (SEQ ID NO: 77) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or d. a heavy chain CDR1 comprising the sequence GFTFSNAW (SEQ ID NO: 78) and a heavy chain CDR2 comprising the sequence IKSKIDGETT (SEQ ID NO: 79) and a heavy chain CDR3 comprising the sequence TPGVGANDPYYFDR (SEQ ID NO: 80) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or e. a heavy chain CDR1 comprising the sequence GFTFSNAW (SEQ ID NO: 81) and a heavy chain CDR2 comprising the sequence IKSKIDGETT (SEQ ID NO: 82) and a heavy chain CDR3 comprising the sequence TPGVGANNPYYFDR (SEQ ID NO: 83) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or f. a heavy chain CDR1 comprising the sequence GFTFSNAW (SEQ ID NO: 84) and a heavy chain CDR2 comprising the sequence IKSKIDGETT (SEQ ID NO: 85) and a heavy chain CDR3 comprising the sequence TPGVGANNPYYFDR (SEQ ID NO: 86) and a light chain CDR1 comprising the sequence QSVLCRSNNKNC (SEQ ID NO: 62) and a light chain CDR2 comprising the sequence WAC and a light chain CDR3 comprising the sequence QQYSNTPQT (SEQ ID NO: 63); or g. a heavy chain CDR1 comprising the sequence GFTFSNAW (SEQ ID NO: 87) and a heavy chain CDR2 comprising the sequence IKSKIDGGTT (SEQ ID NO: 88) and a heavy chain CDR3 comprising the sequence TPGVGANNPYYFDR (SEQ ID NO: 89) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or h. a heavy chain CDR1 comprising the sequence GFTFSNAW (SEQ ID NO: 90) and a heavy chain CDR2 comprising the sequence IKSKIDGGTT (SEQ ID NO: 91) and a heavy chain CDR3 comprising the sequence TPGVGTNNPYYFDR (SEQ ID NO: 92) and a light chain CDR1 comprising the sequence QSVL-CRSNNKNC (SEQ ID NO: 62) and a light chain CDR2 comprising the sequence WAS and a light chain CDR3 comprising the sequence QQYSNTPQT (SEQ ID NO: 63); or i. a heavy chain CDR1 comprising the sequence GFTFSYAW (SEQ ID NO: 93) and a heavy chain CDR2 comprising the sequence IKSKIDGGTT (SEQ ID NO: 94) and a heavy chain CDR3 comprising the sequence TPGVGANDPYYFDR (SEQ ID NO: 95) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or j. a heavy chain CDR1 comprising the sequence GFTFSNAW (SEQ ID NO: 96) and a heavy chain CDR2 comprising the sequence IKSKIDGGTI (SEQ ID NO: 97) and a heavy chain CDR3 comprising the sequence TPGVGANDPYYFDR (SEQ ID NO: 98) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or k. a heavy chain CDR1 comprising the sequence GFTFSYAW (SEQ ID NO: 99) and a heavy chain CDR2 comprising the sequence IKSKIDGGTT (SEQ ID NO: 100) and a heavy chain CDR3 comprising the sequence TPGVGANNPYYFDR (SEQ ID NO: 101) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or l. A heavy chain CDR1 comprising the sequence GFIFSYAW (SEQ ID NO: 102) and a heavy chain CDR2 comprising the sequence IKSKIDGGTT (SEQ ID NO: 103) and a heavy chain CDR3 comprising the sequence TPGVGANNPYYFDR (SEQ ID NO: 104) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or m. a heavy chain CDR1 comprising the sequence GFIFSYAW (SEQ ID NO: 105) and a heavy chain CDR2 comprising the sequence IKSKIDGETT (SEQ ID NO: 106) and a heavy chain CDR3 comprising the sequence TPGVGANNPYYFDR (SEQ ID NO: 107) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63).

3. The synthetic or recombinant antibody or antigen binding fragment according to claim 1, comprising:

a heavy chain variable region comprising a sequence having at least 90% sequence identity with a VH sequence selected from the group consisting of SEQ ID NOs: 1-17; and/or a light chain variable region comprising a sequence having at least 90% sequence identity with a VL sequence selected from the group consisting of SEQ ID NOs: 18-22.

4. The synthetic or recombinant antibody or antigen binding fragment according to claim 1, comprising:

a VH sequence as depicted in SEQ ID NO: 1 and a VL sequence as depicted in SEQ ID NO: 18, or sequences having at least 90% sequence identity thereto; or a VH sequence as depicted in SEQ ID NO: 1 and a VL sequence as depicted in SEQ ID NO: 22, or sequences having at least 90% sequence identity thereto; or a VH sequence as depicted in SEQ ID NO: 2 and a VL sequence as depicted in SEQ ID NO: 18, or sequences having at least 90% sequence identity thereto; or a VH sequence as depicted in SEQ ID NO: 3 and a VL sequence as depicted in SEQ ID NO: 18, or sequences having at least 90% sequence identity thereto; or a VH sequence as depicted in SEQ ID NO: 4 and a VL sequence as depicted in SEQ ID NO: 19, or sequences having at least 90% sequence identity thereto; or a VH sequence as depicted in SEQ ID NO: 5 and a VL sequence as depicted in SEQ ID NO: 18, or sequences having at least 90% sequence identity thereto; or a VH sequence as depicted in SEQ ID NO: 6 and a VL sequence as depicted in SEQ ID NO: 18, or sequences having at least 90% sequence identity thereto; or a VH sequence as depicted in SEQ ID NO: 6 and a VL sequence as depicted in SEQ ID NO: 20, or sequences having at least 90% sequence identity thereto; or a VH sequence as depicted in SEQ ID NO: 7 and a VL sequence as depicted in SEQ ID NO: 18, or sequences having at least 90% sequence identity thereto; or a VH sequence as depicted in SEQ ID NO: 8 and a VL sequence as depicted in SEQ ID NO: 18, or sequences having at least 90% sequence identity thereto; or a VH sequence as depicted in SEQ ID NO: 9 and a VL sequence as depicted in SEQ ID NO: 18, or sequences having at least 90% sequence identity thereto; or a VH sequence as depicted in SEQ ID NO: 10 and a VL sequence as depicted in SEQ ID NO: 18, or sequences having at least 90% sequence identity thereto; or a VH sequence as depicted in SEQ ID NO: 10 and a VL sequence as depicted in SEQ ID NO: 21, or sequences having at least 90% sequence identity thereto; or a VH sequence as depicted in SEQ ID NO: 11 and a VL sequence as depicted in SEQ ID NO: 18, or sequences having at least 90% sequence identity thereto; or a VH sequence as depicted in SEQ ID NO: 12 and a VL sequence as depicted in SEQ ID NO: 18, or sequences having at least 90% sequence identity thereto; or a VH sequence as depicted in SEQ ID NO: 13 and a VL sequence as depicted in SEQ ID NO: 18, or sequences having at least 90% sequence identity thereto; or a VH sequence as depicted in SEQ ID NO: 14 and a VL sequence as depicted in SEQ ID NO: 18, or sequences having at least 90% sequence identity thereto; or a VH sequence as depicted in SEQ ID NO: 15 and a VL sequence as depicted in SEQ ID NO: 18, or sequences having at least 90% sequence identity thereto; or a VH sequence as depicted in SEQ ID NO: 16 and a VL sequence as depicted in SEQ ID NO: 18, or sequences having at least 90% sequence identity thereto; or a VH sequence as depicted in SEQ ID NO: 17 and a VL sequence as depicted in SEQ ID NO: 18, or sequences having at least 90% sequence identity thereto.

5. The synthetics or recombinant antibody or antigen binding fragment according to claim 1, wherein said antibody or antigen binding fragment has one or more, and preferably each of, the following characteristics:

binds to the extracellular (EC) 3 domain of O mannosylated E cadherin;

binds to O mannosylated truncated 70 kDa E cadherin with higher affinity than to O mannosylated full length E cadherin; and binds tumor cells that co-express E cadherin and an O mannosyltransferase.

6. A bispecific antibody or antigen binding fragment thereof that is able to bind O mannosylated E cadherin, comprising:

one Fab fragment of the synthetic or recombinant antibody or antigen binding fragment according to claim 1; and one Fab fragment of another antibody, specific for a T cell, a natural killer cell (NK cell), a natural killer T cell (NKT cell) or a gamma-delta T cell.

7. A bispecific antibody or antigen binding fragment thereof that is able to bind O mannosylated E cadherin, comprising:

one Fab fragment of the synthetic or recombinant antibody or antigen binding fragment according to claim 1; and one Fab fragment of another antibody, specific for TGFβ.

8. A chimeric antigen receptor (CAR) T cell that is able to bind O mannosylated E cadherin, wherein the CAR T cell comprises the heavy chain CDR1, CDR2 and CDR3 sequences and the light chain CDR1, CDR2 and CDR3 sequences of the synthetic or recombinant antibody according to claim 1.

9. A synthetic or recombinant nucleic acid that is codon optimized for a non-human cell, and that encodes the synthetic or recombinant antibody or antigen binding fragment according to claim 1, or encoding at least the heavy chain CDR1, CDR2 and CDR3 sequences of the synthetic or recombinant antibody or antigen binding fragment thereof according to claim 1, or encoding at least the heavy chain CDR1, CDR2 and CDR3 sequences and the light chain CDR1, CDR2 and CDR3 sequences of an antibody according to claim 1, or encoding at least the heavy chain variable region and/or the light chain variable region of the synthetic or recombinant antibody or antigen binding fragment according to claim 1.

10. A vector comprising a nucleic acid encoding the synthetic or recombinant antibody or antigen binding fragment according to claim 5, or encoding at least the heavy chain CDR1, CDR2 and CDR3 sequences of the synthetic or recombinant antibody or antigen binding fragment thereof according to claim 1, or encoding at least the heavy chain CDR1, CDR2 and CDR3 sequences and the light chain CDR1, CDR2 and CDR3 sequences of an antibody according to claim 1, or encoding at least the heavy chain variable region and/or the light chain variable region of the synthetic or recombinant antibody or antigen binding fragment according to claim 1.

11. An isolated or recombinant host cell, or a non-human animal, comprising the vector according to claim 10.

12. A vector, wherein said vector is a CAR T cell vector comprising a nucleic acid sequence encoding a T cell activating domain and a nucleic acid sequence encoding an antigen recognition domain, wherein said antigen recognition domain comprises at least the heavy chain CDR1, CDR2 and CDR3 sequences of the synthetic or recombinant antibody or antigen binding fragment thereof according to claim 1.

13. A composition comprising the synthetic or recombinant antibody or antigen binding fragment according to claim 1.

14. A kit of parts comprising the synthetic or recombinant antibody or antigen binding fragment according to claim 1 and another therapeutic agent for the treatment or prevention of a disorder that is associated with cells that comprise O mannosylated E cadherin.

15. A method for producing the synthetic or recombinanat antibody or antigen binding fragment according to claim 1, the method comprising culturing a cell comprising a nucleic acid encoding the synthetic or recombinant antibody or antigen binding fragment according to claim 1 and allowing said cell to translate said nucleic acid, thereby producing said antibody or antigen binding fragment according to claim 1.

16. A method for determining whether cells that comprise O mannosylated E cadherin are present in a sample, the method comprising:

contacting said sample with the synthetic or recombinant antibody or antigen binding fragment according to claim 1, and allowing said antibody or antigen binding fragment to bind to cells that comprise O mannosylated E cadherin, if present, and determining whether or not cells are bound to said antibody or antigen binding fragment, thereby determining whether or not cells that comprise O mannosylated E cadherin are present in said sample.

17. A method for determining whether a human or non-human individual is suffering from a cancer that is positive for O mannosylated E cadherin, the method comprising:

contacting tumor cells of said individual with the synthetic or recombinant antibody or antigen binding fragment according to claim 1, allowing said antibody or antigen binding fragment or bispecific antibody to bind tumor cells that comprise O mannosylated E cadherin, if present, and determining whether or not tumor cells are bound to said antibody or antigen binding fragment, thereby determining whether or nor said individual is suffering from a cancer that comprises O mannosylated E cadherin and an O mannosyltransferase.

18. A method for treating a disorder associated with tumor cells that comprise O mannosylated E cadherin, the method comprising administering to an individual in need thereof a therapeutically effective amount of the synthetic or recombinant antibody or antigen binding fragment according to claim 1.

19. The synthetic or recombinant antibody or antigen binding fragment according to claim 1, wherein said antigen binding fragment is selected from the group consisting of a single chain variable fragment (scFv), an Fv fragment, a diabody, an Fab fragment, and an $F(ab')_2$ fragment.

20. A nucleic acid that encodes the antibody or antigen binding fragment according to claim 1.

21. A synthetic or recombinant antibody or antigen binding fragment thereof that is able to bind O mannosylated E cadherin, wherein said antibody or antigen binding fragment comprises each of:

a. a heavy chain variable region CDR1 comprising the amino acid sequence $GFX_1FSX_2AW$ (SEQ ID NO: 59), wherein $X_1$ is T or I and wherein $X_2$ is N or Y;

b. a heavy chain variable region CDR2 comprising the amino acid sequence IKSKIDG $X_1T$ $X_2$ (SEQ ID NO: 60), wherein $X_1$ is G or E and wherein $X_2$ is T or I;

C. a heavy chain variable region CDR3 comprising the amino acid sequence $TPGVGX_1NX_2PYYFDR$ (SEQ ID NO: 61), wherein $X_1$ is A or T and wherein $X_2$ is D or N;

d. a light chain variable region CDR1 comprising the amino acid sequence QSVLCRSNNKNC (SEQ ID NO: 62);

e. a light chain variable region CDR2 comprising the amino acid sequence $WAX_1$, wherein $X_1$ is S or C; and f. a light chain variable region CDR3 comprising the amino acid sequence QQYSNTPQT (SEQ ID NO: 63);

and wherein the antibody or antigen binding fragment is afucosylated or hypergalactosylated or wherein said antibody or antigen binding fragment has a modified Fc region, and wherein said modified Fc region comprises an amino acid mutation selected from the group consisting of:

S298A, E333A, K334A;
S239D, I332E;
S239D, I332E, A330L;
L235V, F243L, R292P, Y300L, P396L;
K326W;
E333S;
K326W, E333S;
E345R;
E345K;
E430G;
E345K, E430G;
S267E, H268F, S324T;
S267E, H268F, S324T, G236A, I332E;
L235E;
L234A, L235A;
L234A, L235A, P329G;
S228P, L235E; and
S228P, L235E, P329G.

22. A synthetic or recombinant antibody or antigen binding fragment thereof that is able to bind O mannosylated E cadherin, wherein said antibody or antigen binding fragment comprises each of:

a. a heavy chain variable region CDR1 comprising the amino acid sequence $GFX_1FSX_2AW$ (SEQ ID NO: 59), wherein $X_1$ is T or I and wherein $X_2$ is N or Y;

b. a heavy chain variable region CDR2 comprising the amino acid sequence IKSKIDG $X_1T$ $X_2$ (SEQ ID NO: 60), wherein $X_1$ is G or E and wherein $X_2$ is T or I;

C. a heavy chain variable region CDR3 comprising the amino acid sequence $TPGVGX_1NX_2PYYFDR$ (SEQ ID NO: 61), wherein $X_1$ is A or T and wherein $X_2$ is D or N;

d. a light chain variable region CDR1 comprising the amino acid sequence QSVLCRSNNKNC (SEQ ID NO: 62);

e. a light chain variable region CDR2 comprising the amino acid sequence $WAX_1$, wherein $X_1$ is S or C; and f. a light chain variable region CDR3 comprising the amino acid sequence QQYSNTPQT (SEQ ID NO: 63);

and wherein the antibody or antigen binding fragment is covalently linked to a cell-binding agent, a cytokine, a second antibody or antigen binding part thereof, a detectable label, a drug, a cytotoxic agent, a hormone, an enzyme, or a nucleic acid.

23. The synthetic or recombinant antibody or antigen binding fragment according to claim 22, wherein the antibody or antigen binding fragment is covalently coupled to a CD3-specific binding compound or a TGFβ-specific binding compound.

24. A synthetic or recombinant antibody or antigen binding fragment thereof that is able to bind O mannosylated E cadherin, wherein said antibody or antigen binding fragment comprises each of:

a heavy chain variable region CDR1 comprising the amino acid sequence $GFX_1FSX_2AW$ (SEQ ID NO: 59), wherein $X_1$ is T or I and wherein $X_2$ is N or Y;

and a heavy chain variable region CDR2 comprising the amino acid sequence IKSKIDG $X_1T$ $X_2$ (SEQ ID NO: 60), wherein $X_1$ is G or E and wherein $X_2$ is T or I;

and a heavy chain variable region CDR3 comprising the amino acid sequence $TPGVGX_1NX_2PYYFDR$ (SEQ ID NO: 61), wherein $X_1$ is A or T and wherein $X_2$ is D or N;

and a light chain variable region CDR1 comprising the amino acid sequence QSVLCRSNNKNC (SEQ ID NO: 62); and a light chain variable region CDR2 comprising the amino acid sequence $WAX_1$, wherein $X_1$ is S or C; and and a light chain variable region CDR3 comprising the amino acid sequence QQYSNTPQT (SEQ ID NO: 63);

and wherein the synthetic or recombinant antibody or antigen binding fragment thereof is a variant of antibody AT1636.

25. The synthetic or recombinant antibody or antigen binding fragment according to claim 24, wherein the antibody or antigen binding fragment does not comprise one or more of a heavy chain CDR1 comprising the sequence GFTFSNAW (SEQ ID NO: 69), and a heavy chain CDR2 comprising the sequence IKSKIDGGTT (SEQ ID NO: 70) and a heavy chain CDR3 comprising the sequence TPGVGANDPYYFDR (SEQ ID NO: 71) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63).

26. The synthetic or recombinant antibody according to claim 24, comprising:

a heavy chain CDR1 comprising the sequence GFIFSNAW (SEQ ID NO: 72) and a heavy chain CDR2 comprising the sequence IKSKIDGGTT (SEQ ID NO: 73) and a heavy chain CDR3 comprising the sequence TPGVGANDPYYFDR (SEQ ID NO: 74) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFIFSNAW (SEQ ID NO: 75) and a heavy chain CDR2 comprising the sequence IKSKIDGETT (SEQ ID NO: 76) and a heavy chain CDR3 comprising the sequence TPGVGANDPYYFDR (SEQ ID NO: 77)

and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFTFSNAW (SEQ ID NO: 78) and a heavy chain CDR2 comprising the sequence IKSKIDGETT (SEQ ID NO: 79) and a heavy chain CDR3 comprising the sequence TPGVGANDPYYFDR (SEQ ID NO: 80) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFTFSNAW (SEQ ID NO: 81) and a heavy chain CDR2 comprising the sequence IKSKIDGETT (SEQ ID NO: 82) and a heavy chain CDR3 comprising the sequence TPGVGANNPYYFDR (SEQ ID NO: 83) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFTFSNAW (SEQ ID NO: 84) and a heavy chain CDR2 comprising the sequence IKSKIDGETT (SEQ ID NO: 85) and a heavy chain CDR3 comprising the sequence TPGVGANNPYYFDR (SEQ ID NO: 86) and a light chain CDR1 comprising the sequence QSVLCRSNNKNC (SEQ ID NO: 62) and a light chain CDR2 comprising the sequence WAC and a light chain CDR3 comprising the sequence QQYSNTPQT (SEQ ID NO: 63); or a heavy chain CDR1 comprising the sequence GFTFSNAW (SEQ ID NO: 87) and a heavy chain CDR2 comprising the sequence IKSKIDGGTT (SEQ ID NO: 88) and a heavy chain CDR3 comprising the sequence TPGVGANNPYYFDR (SEQ ID NO: 89) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFTFSNAW (SEQ ID NO: 90) and a heavy chain CDR2 comprising the sequence IKSKIDGGTT (SEQ ID NO: 91) and a heavy chain CDR3 comprising the sequence TPGVGTNNPYYFDR (SEQ ID NO: 92) and a light chain CDR1 comprising the sequence QSVL-CRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFTFSYAW (SEQ ID NO: 93) and a heavy chain CDR2 comprising the sequence IKSKIDGGTT (SEQ ID NO: 94) and a heavy chain CDR3 comprising the sequence TPGVGANDPYYFDR (SEQ ID NO: 95) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFTFSNAW (SEQ ID NO: 96) and a heavy chain CDR2 comprising the sequence IKSKIDGGTI (SEQ ID NO: 97) and a heavy chain CDR3 comprising the sequence TPGVGANDPYYFDR (SEQ ID NO: 98) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFTFSYAW (SEQ ID NO: 99) and a heavy chain CDR2 comprising the sequence IKSKIDGGTT (SEQ ID NO: 100) and a heavy chain CDR3 comprising the sequence TPGVGANNPYYFDR (SEQ ID NO: 101) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFIFSYAW (SEQ ID NO: 102) and a heavy chain CDR2 comprising the sequence IKSKIDGGTT (SEQ ID NO: 103) and a heavy chain CDR3 comprising the sequence TPGVGANNPYYFDR (SEQ ID NO: 104) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63); or a heavy chain CDR1 comprising the sequence GFIFSYAW (SEQ ID NO: 105) and a heavy chain CDR2 comprising the sequence IKSKIDGETT (SEQ ID NO: 106) and a heavy chain CDR3 comprising the sequence TPGVGANNPYYFDR (SEQ ID NO: 107) and a light chain CDR1 comprising the sequence QSVLCRSNNKNC (SEQ ID NO: 62) and a light chain CDR2 comprising the sequence WAS and a light chain CDR3 comprising the sequence QQYSNTPQT (SEQ ID NO: 63).

27. A nucleic acid that encodes the synthetic or recombinant antibody or antigen binding fragment according to claim 26, or encoding at least the heavy chain CDR1, CDR2 and CDR3 sequences of the synthetic or recombinant antibody or antigen binding fragment thereof according to claim 26, or encoding at least the heavy chain CDR1, CDR2 and CDR3 sequences and the light chain CDR1, CDR2 and CDR3 sequences of an antibody according to claim 26, or encoding at least the heavy chain variable region and/or the light chain variable region of the synthetic or recombinant antibody or antigen binding fragment according to claim 26.

* * * * *

SEQUENCE LISTING

```
<160> NUMBER OF SEQ ID NOS: 114

<210> SEQ ID NO 1
<211> LENGTH: 123
<212> TYPE: PRT
<213> ORGANISM: Artificial Sequence
<220> FEATURE:
<223> OTHER INFORMATION: AT1636 VH / E-C10 VH

<400> SEQUENCE: 1
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110

Trp Gly Gln Gly Val Leu Val Thr Val Ser Ser
        115                 120


<210> SEQ ID NO 2
<211> LENGTH: 123
<212> TYPE: PRT
<213> ORGANISM: Artificial Sequence
<220> FEATURE:
<223> OTHER INFORMATION: E-C06 VH / D-H04 VH

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Ser Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110

Trp Gly Gln Gly Val Leu Val Thr Val Ser Ser
        115                 120


<210> SEQ ID NO 3
<211> LENGTH: 123
<212> TYPE: PRT
<213> ORGANISM: Artificial Sequence
<220> FEATURE:
<223> OTHER INFORMATION: D-A02 VH /D-E09 VH /E-A04 VH /E-B09 VH /AT1636-
      I VH

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Thr Glu Tyr Thr Thr
```

```
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110

Trp Gly Gln Gly Val Leu Val Thr Val Ser Ser
        115                 120


<210> SEQ ID NO 4
<211> LENGTH: 123
<212> TYPE: PRT
<213> ORGANISM: Artificial Sequence
<220> FEATURE:
<223> OTHER INFORMATION: C-A05 VH

<400> SEQUENCE: 4

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Glu Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110

Cys Gly Gln Gly Val Leu Val Thr Val Ser Ser
        115                 120


<210> SEQ ID NO 5
<211> LENGTH: 123
<212> TYPE: PRT
<213> ORGANISM: Artificial Sequence
<220> FEATURE:
<223> OTHER INFORMATION: C-A03 VH /C-B02 VH /AT1636-E VH

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Glu Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110
```

Trp Gly Gln Gly Val Leu Val Thr Val Ser Ser
115 120

<210> SEQ ID NO 6
<211> LENGTH: 123
<212> TYPE: PRT
<213> ORGANISM: Artificial Sequence
<220> FEATURE:
<223> OTHER INFORMATION: C-D04 A VH /C D04 B VH

<400> SEQUENCE: 6

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Asn Trp Val Arg Gln Ala Pro Gly Lys Gly Leu Glu Trp Val
35 40 45

Gly Arg Ile Lys Ser Lys Ile Asp Gly Glu Thr Thr Glu Tyr Thr Thr
50 55 60

Pro Val Lys Gly Arg Phe Thr Ile Ser Arg Asp Asp Ser Lys Asp Thr
65 70 75 80

Val Tyr Leu His Met Lys Arg Leu Lys Thr Glu Asp Thr Ala Val Tyr
85 90 95

Tyr Cys Thr Pro Gly Val Gly Ala Asn Asn Pro Tyr Tyr Phe Asp Arg
100 105 110

Trp Gly Gln Gly Val Leu Val Thr Val Ser Ser
115 120

<210> SEQ ID NO 7
<211> LENGTH: 123
<212> TYPE: PRT
<213> ORGANISM: Artificial Sequence
<220> FEATURE:
<223> OTHER INFORMATION: F-C08 VH

<400> SEQUENCE: 7

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Asn Trp Val Arg Gln Ala Pro Gly Lys Gly Leu Glu Trp Val
35 40 45

Gly Arg Ile Lys Ser Lys Ile Asp Gly Gly Thr Thr Glu Tyr Thr Thr
50 55 60

Pro Val Lys Gly Arg Phe Thr Ile Ser Arg Asp Asp Ser Lys Asp Thr
65 70 75 80

Val Tyr Leu His Met Lys Arg Val Lys Thr Glu Asp Thr Ala Val Tyr
85 90 95

Tyr Cys Thr Pro Gly Val Gly Ala Asn Asn Pro Tyr Tyr Phe Asp Arg
100 105 110

Trp Gly Gln Gly Val Leu Val Thr Val Ser Ser
115 120

<210> SEQ ID NO 8
<211> LENGTH: 123
<212> TYPE: PRT
<213> ORGANISM: Artificial Sequence
<220> FEATURE:
<223> OTHER INFORMATION: D-G03 VH /AT1636-N VH -continued

<400> SEQUENCE: 8

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asn Pro Tyr Tyr Phe Asp Arg
            100                 105                 110

Trp Gly Gln Gly Val Leu Val Thr Val Ser Ser
        115                 120
```

<210> SEQ ID NO 9
<211> LENGTH: 123
<212> TYPE: PRT
<213> ORGANISM: Artificial Sequence
<220> FEATURE:
<223> OTHER INFORMATION: D-F10 VH

<400> SEQUENCE: 9

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Thr Asn Asn Pro Tyr Tyr Phe Asp Arg
            100                 105                 110

Trp Gly Gln Gly Val Leu Val Thr Val Ser Ser
        115                 120
```

<210> SEQ ID NO 10
<211> LENGTH: 123
<212> TYPE: PRT
<213> ORGANISM: Artificial Sequence
<220> FEATURE:
<223> OTHER INFORMATION: C-E08 VH /D-B06 VH /D-G05 VH /AT1636-Y VH

<400> SEQUENCE: 10

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ala
            20                  25                  30

Trp Met Asn Trp Val Arg Gln Ala Pro Gly Lys Gly Leu Glu Trp Val
        35                  40                  45
```

-continued

```
Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110

Trp Gly Gln Gly Val Leu Val Thr Val Ser Ser
        115                 120


<210> SEQ ID NO 11
<211> LENGTH: 123
<212> TYPE: PRT
<213> ORGANISM: Artificial Sequence
<220> FEATURE:
<223> OTHER INFORMATION: D-H08 VH

<400> SEQUENCE: 11

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Tyr Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110

Trp Gly Gln Gly Val Leu Val Thr Val Ser Ser
        115                 120


<210> SEQ ID NO 12
<211> LENGTH: 123
<212> TYPE: PRT
<213> ORGANISM: Artificial Sequence
<220> FEATURE:
<223> OTHER INFORMATION: C-H01 VH

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Ile Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110
```

```
Trp Gly Gln Gly Val Leu Val Thr Val Ser Ser
        115                 120


<210> SEQ ID NO 13
<211> LENGTH: 123
<212> TYPE: PRT
<213> ORGANISM: Artificial Sequence
<220> FEATURE:
<223> OTHER INFORMATION: D-C12 VH

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Glu Lys Gly Leu Glu Trp Val
        35                  40                  45

Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asp Pro Tyr Tyr Phe Asp Arg
            100                 105                 110

Trp Gly Gln Gly Val Leu Val Thr Val Ser Ser
        115                 120


<210> SEQ ID NO 14
<211> LENGTH: 123
<212> TYPE: PRT
<213> ORGANISM: Artificial Sequence
<220> FEATURE:
<223> OTHER INFORMATION: D-C11 VH

<400> SEQUENCE: 14

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Ile Asp Gly Gly Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Ile Glu Asp Thr Ala Val Tyr
                85                  90                  95

Tyr Cys Thr Pro Gly Val Gly Ala Asn Asp Pro Tyr Tyr Phe Asp Arg
            100                 105                 110

Trp Gly Gln Gly Val Leu Val Thr Val Ser Ser
        115                 120


<210> SEQ ID NO 15
<211> LENGTH: 123
<212> TYPE: PRT
<213> ORGANISM: Artificial Sequence
<220> FEATURE:
<223> OTHER INFORMATION: AT1636-YN VH
```

<400> SEQUENCE: 15

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Tyr Ala
20 25 30

Trp Met Asn Trp Val Arg Gln Ala Pro Gly Lys Gly Leu Glu Trp Val
35 40 45

Gly Arg Ile Lys Ser Lys Ile Asp Gly Gly Thr Thr Glu Tyr Thr Thr
50 55 60

Pro Val Lys Gly Arg Phe Thr Ile Ser Arg Asp Asp Ser Lys Asp Thr
65 70 75 80

Val Tyr Leu His Met Lys Arg Leu Lys Thr Glu Asp Thr Ala Val Tyr
85 90 95

Tyr Cys Thr Pro Gly Val Gly Ala Asn Asn Pro Tyr Tyr Phe Asp Arg
100 105 110

Trp Gly Gln Gly Val Leu Val Thr Val Ser Ser
115 120

<210> SEQ ID NO 16
<211> LENGTH: 123
<212> TYPE: PRT
<213> ORGANISM: Artificial Sequence
<220> FEATURE:
<223> OTHER INFORMATION: AT1636-IYN VH

<400> SEQUENCE: 16

Glu Val Gln Leu Val Glu Ser Gly Gly Gly Leu Val Lys Pro Gly Gly
1 5 10 15

Ser Leu Arg Leu Ser Cys Ala Ala Ser Gly Phe Ile Phe Ser Tyr Ala
20 25 30

Trp Met Asn Trp Val Arg Gln Ala Pro Gly Lys Gly Leu Glu Trp Val
35 40 45

Gly Arg Ile Lys Ser Lys Ile Asp Gly Gly Thr Thr Glu Tyr Thr Thr
50 55 60

Pro Val Lys Gly Arg Phe Thr Ile Ser Arg Asp Asp Ser Lys Asp Thr
65 70 75 80

Val Tyr Leu His Met Lys Arg Leu Lys Thr Glu Asp Thr Ala Val Tyr
85 90 95

Tyr Cys Thr Pro Gly Val Gly Ala Asn Asn Pro Tyr Tyr Phe Asp Arg
100 105 110

Trp Gly Gln Gly Val Leu Val Thr Val Ser Ser
115 120

<210> SEQ ID NO 17
<211> LENGTH: 123
<212> TYPE: PRT
<213> ORGANISM: Artificial Sequence
<220> FEATURE:
<223> OTHER INFORMATION: AT1636-IYEN VH

<400> SEQUENCE: 17

Glu Val Gln Leu Val Glu Ser Gly Gly Gly Leu Val Lys Pro Gly Gly
1 5 10 15

Ser Leu Arg Leu Ser Cys Ala Ala Ser Gly Phe Ile Phe Ser Tyr Ala
20 25 30

Trp Met Asn Trp Val Arg Gln Ala Pro Gly Lys Gly Leu Glu Trp Val
35 40 45

-continued

```
Gly Arg Ile Lys Ser Lys Ile Asp Gly Glu Thr Thr Glu Tyr Thr Thr
    50                  55                  60

Pro Val Lys Gly Arg Phe Thr Ile Ser Arg Asp Asp Ser Lys Asp Thr
65                  70                  75                  80

Val Tyr Leu His Met Lys Arg Leu Lys Thr Glu Asp Thr Ala Val Tyr
                85                  90                  95

Tyr Cys Thr Pro Gly Val Gly Ala Asn Asn Pro Tyr Tyr Phe Asp Arg
            100                 105                 110

Trp Gly Gln Gly Val Leu Val Thr Val Ser Ser
        115                 120


<210> SEQ ID NO 18
<211> LENGTH: 114
<212> TYPE: PRT
<213> ORGANISM: Artificial Sequence
<220> FEATURE:
<223> OTHER INFORMATION: AT1636 VL

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Cys Arg
            20                  25                  30

Ser Asn Asn Lys Asn Cys Leu Ala Trp Tyr Gln Gln Arg Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Asn Thr Pro Gln Thr Phe Gly Gln Gly Thr Lys Val Glu Ile
            100                 105                 110

Lys Arg


<210> SEQ ID NO 19
<211> LENGTH: 114
<212> TYPE: PRT
<213> ORGANISM: Artificial Sequence
<220> FEATURE:
<223> OTHER INFORMATION: C-A05 VL

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Cys Arg
            20                  25                  30

Ser Asn Asn Lys Asn Cys Leu Ala Trp Tyr Gln Gln Arg Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Ser Asn Thr Pro Gln Thr Phe Gly Gln Gly Thr Lys Val Glu Ile
            100                 105                 110
```

Lys Arg

<210> SEQ ID NO 20
<211> LENGTH: 114
<212> TYPE: PRT
<213> ORGANISM: Artificial Sequence
<220> FEATURE:
<223> OTHER INFORMATION: C-D04 B VL

<400> SEQUENCE: 20

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Cys Arg
            20                  25                  30

Ser Asn Asn Lys Asn Cys Leu Ala Trp Tyr Gln Gln Arg Pro Gly Gln
        35                  40                  45

Pro Pro Lys Leu Leu Ile Tyr Trp Ala Cys Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Asn Thr Pro Gln Thr Phe Gly Gln Gly Thr Lys Val Glu Ile
            100                 105                 110

Lys Arg
```

<210> SEQ ID NO 21
<211> LENGTH: 114
<212> TYPE: PRT
<213> ORGANISM: Artificial Sequence
<220> FEATURE:
<223> OTHER INFORMATION: D-G05 VL

<400> SEQUENCE: 21

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Cys Arg
            20                  25                  30

Ser Asn Asn Lys Asn Cys Leu Thr Trp Tyr Gln Gln Arg Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Asn Thr Pro Gln Thr Phe Gly Gln Gly Thr Lys Val Glu Ile
            100                 105                 110

Lys Arg
```

<210> SEQ ID NO 22
<211> LENGTH: 114
<212> TYPE: PRT
<213> ORGANISM: Artificial Sequence
<220> FEATURE:
<223> OTHER INFORMATION: E-C10 VL

<400> SEQUENCE: 22

-continued

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Cys Arg
            20                  25                  30

Ser Asn Asn Lys Asn Cys Leu Ala Trp Tyr Gln Gln Arg Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr His Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Asn Thr Pro Gln Thr Phe Gly Gln Gly Thr Lys Val Glu Ile
            100                 105                 110

Lys Arg
```

<210> SEQ ID NO 23
<211> LENGTH: 369
<212> TYPE: DNA
<213> ORGANISM: Artificial Sequence
<220> FEATURE:
<223> OTHER INFORMATION: AT1636 VH /E-C10 VH

<400> SEQUENCE: 23

```
gaggtgcagc tggtggagtc tgggggaggc ttggtaaagc ctggggggtc ccttagactc     60

tcctgtgcag cctctggttt cactttcagt aatgcctgga tgaactgggt ccgccaggct    120

ccagggaagg ggctggagtg ggtcggccgt attaaaagca aaattgatgg tgggacaaca    180

gagtacacca cacccgtgaa aggcagattc accatctcaa gagatgattc aaaagacaca    240

gtgtacctgc acatgaaaag gctgaaaacc gaggacacag ccgtctatta ctgtaccccg    300

ggggtgggag ctaatgatcc gtactatttt gaccgctggg gccagggagt cctggtcacc    360

gtctcctca                                                            369
```

<210> SEQ ID NO 24
<211> LENGTH: 369
<212> TYPE: DNA
<213> ORGANISM: Artificial Sequence
<220> FEATURE:
<223> OTHER INFORMATION: E-C06 VH / D H04 VH

<400> SEQUENCE: 24

```
gaggtgcagc tggtggagtc tgggggaggc ttggtaaagc ctggggggtc ccttagactc     60

tcctgtgcag cctctggttt cattttcagt aatgcctgga tgaactgggt ccgccaggct    120

ccagggaagg ggctggagtg ggtcggccgt attaaaagca aaattgatgg tgggacaaca    180

gagtacacca cacccgtgaa aggcagattc accatctcaa gagatgattc aaaagacaca    240

gtgtacctgc acatgaaaag cctgaaaacc gaggacacag ccgtctatta ctgtaccccg    300

ggggtgggag ctaatgatcc gtactatttt gaccgctggg gccagggagt cctggtcacc    360

gtctcctca                                                            369
```

<210> SEQ ID NO 25
<211> LENGTH: 369
<212> TYPE: DNA
<213> ORGANISM: Artificial Sequence
<220> FEATURE:
<223> OTHER INFORMATION: D-E09 VH /D A02 VH /E A04 VH / E B09 VH
/AT1636-I VH

<400> SEQUENCE: 25
gaggtgcagc tggtggagtc tgggggaggc ttggtaaagc ctgggggtc ccttagactc 60 tcctgtgcag cctctggttt cattttcagt aatgcctgga tgaactgggt ccgccaggct 120
ccagggaagg ggctggagtg ggtcggccgt attaaaagca aaattgatgg tgggacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaatgatcc gtactatttt gaccgctggg gccagggagt cctggtcacc 360
gtctcctca 369

<210> SEQ ID NO 26
<211> LENGTH: 369
<212> TYPE: DNA
<213> ORGANISM: Artificial Sequence
<220> FEATURE:
<223> OTHER INFORMATION: C-A05 VH

<400> SEQUENCE: 26
gaggtgcagc tggtggagtc tgggggaggc ttggtaaagc ctgggggtc ccttagactc 60 tcctgtgcag cctctggttt cattttcagt aatgcctgga tgaactgggt ccgccaggct 120
ccagggaagg ggctggagtg ggtcggccgt attaaaagca aaattgatgg tgagacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaatgatcc gtactatttt gaccgctgtg gccagggagt cctggtcacc 360
gtctcctca 369

<210> SEQ ID NO 27
<211> LENGTH: 369
<212> TYPE: DNA
<213> ORGANISM: Artificial Sequence
<220> FEATURE:
<223> OTHER INFORMATION: C-A03 VH /C B02 VH /AT1636-E VH

<400> SEQUENCE: 27
gaggtgcagc tggtggagtc tgggggaggc ttggtaaagc ctgggggtc ccttagactc 60 tcctgtgcag cctctggttt cactttcagt aatgcctgga tgaactgggt ccgccaggct 120
ccagggaagg ggctggagtg ggtcggccgt attaaaagca aaattgatgg tgagacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaatgatcc gtactatttt gaccgctggg gccagggagt cctggtcacc 360
gtctcctca 369

<210> SEQ ID NO 28
<211> LENGTH: 369
<212> TYPE: DNA
<213> ORGANISM: Artificial Sequence
<220> FEATURE:
<223> OTHER INFORMATION: C-D04 A VH /C-D04 B VH

<400> SEQUENCE: 28
gaggtgcagc tggtggagtc tgggggaggc ttggtaaagc ctgggggtc ccttagactc 60 tcctgtgcag cctctggttt cactttcagt aatgcctgga tgaactgggt ccgccaggct 120
ccagggaagg ggctggagtg ggtcggccgt attaaaagca aaattgatgg tgagacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaataatcc gtactatttt gaccgctggg gccagggagt cctggtcacc 360
gtctcctca 369

<210> SEQ ID NO 29
<211> LENGTH: 369
<212> TYPE: DNA
<213> ORGANISM: Artificial Sequence
<220> FEATURE:
<223> OTHER INFORMATION: F-C08 VH

<400> SEQUENCE: 29
gaggtgcagc tggtggagtc tgggggaggc ttggtaaagc ctgggggggtc ccttagactc 60 tcctgtgcag cctctggttt cactttcagt aatgcctgga tgaactgggt ccgccaggct 120
ccagggaagg ggctggagtg ggtcggccgt attaaaagca aaattgatgg tgggacaaca 180
gagtacacca cacccgtgaa aggcagattc accatctcaa gagatgattc aaaagacaca 240
gtgtacctgc acatgaaaag ggtgaaaacc gaggacacag ccgtctatta ctgtaccccg 300
ggggtgggag ctaataatcc gtactatttt gaccgctggg gccagggagt cctggtcacc 360
gtctcctca 369

<210> SEQ ID NO 30
<211> LENGTH: 369
<212> TYPE: DNA
<213> ORGANISM: Artificial Sequence
<220> FEATURE:
<223> OTHER INFORMATION: D-G03 VH /AT1636-N VH

<400> SEQUENCE: 30
gaggtgcagc tggtggagtc tgggggaggc ttggtaaagc ctgggggggtc ccttagactc 60 tcctgtgcag cctctggttt cactttcagt aatgcctgga tgaactgggt ccgccaggct 120
ccagggaagg ggctggagtg ggtcggccgt attaaaagca aaattgatgg tgggacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaataatcc gtactatttt gaccgctggg gccagggagt cctggtcacc 360
gtctcctca 369

<210> SEQ ID NO 31
<211> LENGTH: 369
<212> TYPE: DNA
<213> ORGANISM: Artificial Sequence
<220> FEATURE:
<223> OTHER INFORMATION: D-F10 VH

<400> SEQUENCE: 31
gaggtgcagc tggtggagtc tgggggaggc ttggtaaagc ctgggggggtc ccttagactc 60 tcctgtgcag cctctggttt cactttcagt aatgcctgga tgaactgggt ccgccaggct 120
ccagggaagg ggctggagtg ggtcggccgt attaaaagca aaattgatgg tgggacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggaa ctaataatcc gtactatttt gaccgctggg gccagggagt cctggtcacc 360
gtctcctca 369

<210> SEQ ID NO 32
<211> LENGTH: 369
<212> TYPE: DNA
<213> ORGANISM: Artificial Sequence
<220> FEATURE:
<223> OTHER INFORMATION: C-E08 VH /D-B06 VH /D-G05 VH/ AT1636-Y VH

<400> SEQUENCE: 32
gaggtgcagc tggtggagtc tgggggaggc ttggtaaagc ctggggggtc ccttagactc 60
tcctgtgcag cctctggttt cactttcagt tatgcctgga tgaactgggt ccgccaggct 120
ccagggaagg ggctggagtg ggtcggccgt attaaaagca aaattgatgg tgggacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaatgatcc gtactatttt gaccgctggg gccagggagt cctggtcacc 360
gtctcctca 369

<210> SEQ ID NO 33
<211> LENGTH: 369
<212> TYPE: DNA
<213> ORGANISM: Artificial Sequence
<220> FEATURE:
<223> OTHER INFORMATION: D-H08 VH

<400> SEQUENCE: 33
gaggtgcagc tggtggagtc tgggggagac ttggtaaagc ctggggggtc ccttagactc 60
tcctgtgcag cctctggttt cactttcagt tatgcctgga tgaactgggt ccgccaggct 120
ccagggaagg ggctggagtg ggtcggccgt attaaaagca aaattgatgg tgggacaaca 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaatgatcc gtactatttt gaccgctggg gccagggagt cctggtcacc 360
gtctcctca 369

<210> SEQ ID NO 34
<211> LENGTH: 369
<212> TYPE: DNA
<213> ORGANISM: Artificial Sequence
<220> FEATURE:
<223> OTHER INFORMATION: C-H01 VH

<400> SEQUENCE: 34
gaggtgcagc tggtggagtc tgggggaggc ttggtaaagc ctggggggtc ccttagactc 60
tcctgtgcag cctctggttt cactttcagt aatgcctgga tgaactgggt ccgccaggct 120
ccagggaagg ggctggagtg ggtcggccgt attaaaagca aaattgatgg tgggacaata 180
gagtacacca cacccgtgaa aggcagattc accatctcaa gagatgattc aaaagacaca 240
gtgtacctgc acatgaaaag gctgaaaacc gaggacacag ccgtctatta ctgtaccccg 300
ggggtgggag ctaatgatcc gtactatttt gaccgctggg gccagggagt cctggtcacc 360
gtctcctca 369

<210> SEQ ID NO 35
<211> LENGTH: 369
<212> TYPE: DNA

<213> ORGANISM: Artificial Sequence
<220> FEATURE:
<223> OTHER INFORMATION: D-C12 VH

<400> SEQUENCE: 35

```
gaggtgcagc tggtggagtc tgggggaggc ttggtaaagc ctgggggggtc ccttagactc      60

tcctgtgcag cctctggttt cactttcagt aatgcctgga tgaactgggt ccgccaggct     120

ccagagaagg ggctggagtg ggtcggccgt attaaaagca aaattgatgg tgggacaaca     180

gagtacacca cacccgtgaa aggcagattc accatctcaa gagatgattc aaaagacaca     240

gtgtacctgc acatgaaaag gctgaaaacc gaggacacag ccgtctatta ctgtaccccg     300

ggggtgggag ctaatgatcc gtactatttt gaccgctggg gccagggagt cctggtcacc     360

gtctcctca                                                            369
```

<210> SEQ ID NO 36
<211> LENGTH: 369
<212> TYPE: DNA
<213> ORGANISM: Artificial Sequence
<220> FEATURE:
<223> OTHER INFORMATION: D-C11 VH

<400> SEQUENCE: 36

```
gaggtgcagc tggtggagtc tgggggaggc ttggtaaagc ctgggggggtc ccttagactc      60

tcctgtgcag cctctggttt cactttcagt aatgcctgga tgaactgggt ccgccaggct     120

ccagggaagg ggctggagtg ggtcggccgt attaaaagca aaattgatgg tgggacaaca     180

gagtacacca cacccgtgaa aggcagattc accatctcaa gagatgattc aaaagacaca     240

gtgtacctgc acatgaaaag gctgaaaatc gaggacacag ccgtctatta ctgtaccccg     300

ggggtgggag ctaatgatcc gtactatttt gaccgctggg gccagggagt cctggtcacc     360

gtctcctca                                                            369
```

<210> SEQ ID NO 37
<211> LENGTH: 369
<212> TYPE: DNA
<213> ORGANISM: Artificial Sequence
<220> FEATURE:
<223> OTHER INFORMATION: AT1636-YN VH

<400> SEQUENCE: 37

```
gaggtgcagc tggtggagtc tgggggaggc ttggtaaagc ctgggggggtc ccttagactc      60

tcctgtgcag cctctggttt cactttcagt tatgcctgga tgaactgggt ccgccaggct     120

ccagggaagg ggctggagtg ggtcggccgt attaaaagca aaattgatgg tgggacaaca     180

gagtacacca cacccgtgaa aggcagattc accatctcaa gagatgattc aaaagacaca     240

gtgtacctgc acatgaaaag gctgaaaacc gaggacacag ccgtctatta ctgtaccccg     300

ggggtgggag ctaataatcc gtactatttt gaccgctggg gccagggagt cctggtcacc     360

gtctcctca                                                            369
```

<210> SEQ ID NO 38
<211> LENGTH: 369
<212> TYPE: DNA
<213> ORGANISM: Artificial Sequence
<220> FEATURE:
<223> OTHER INFORMATION: AT1636-IYN VH

<400> SEQUENCE: 38

```
gaggtgcagc tggtggagtc tgggggaggc ttggtaaagc ctgggggggtc ccttagactc      60
```

-continued

```
tcctgtgcag cctctggttt cattttcagt tatgcctgga tgaactgggt ccgccaggct    120

ccagggaagg ggctggagtg ggtcggccgt attaaaagca aaattgatgg tgggacaaca    180

gagtacacca cacccgtgaa aggcagattc accatctcaa gagatgattc aaaagacaca    240

gtgtacctgc acatgaaaag gctgaaaacc gaggacacag ccgtctatta ctgtaccccg    300

ggggtgggag ctaataatcc gtactatttt gaccgctggg gccagggagt cctggtcacc    360

gtctcctca                                                             369
```

<210> SEQ ID NO 39
<211> LENGTH: 369
<212> TYPE: DNA
<213> ORGANISM: Artificial Sequence
<220> FEATURE:
<223> OTHER INFORMATION: AT1636-IYEN VH

<400> SEQUENCE: 39

```
gaggtgcagc tggtggagtc tggggggaggc ttggtaaagc ctggggggtc ccttagactc     60

tcctgtgcag cctctggttt cattttcagt tatgcctgga tgaactgggt ccgccaggct    120

ccagggaagg ggctggagtg ggtcggccgt attaaaagca aaattgatgg tgagacaaca    180

gagtacacca cacccgtgaa aggcagattc accatctcaa gagatgattc aaaagacaca    240

gtgtacctgc acatgaaaag gctgaaaacc gaggacacag ccgtctatta ctgtaccccg    300

ggggtgggag ctaataatcc gtactatttt gaccgctggg gccagggagt cctggtcacc    360

gtctcctca                                                             369
```

<210> SEQ ID NO 40
<211> LENGTH: 342
<212> TYPE: DNA
<213> ORGANISM: Artificial Sequence
<220> FEATURE:
<223> OTHER INFORMATION: AT1636 VL /E C06 VL /D H04 VL /D A02 VL /D E09
      VL

<400> SEQUENCE: 40

```
gacatcgtga tgacccagtc tccagactcc ctggctgtgt ctctgggcga gagggccacc     60

atcaactgca ggtccagcca gagtgtttta tgtcggtcca acaataagaa ctgcttagct    120

tggtaccagc agagaccagg acagcctcct aaactgctca tttattgggc atctattcgg    180

gaatccgggg tccctgaccg attcagtggc agcgggtctg ggacagattt cactctcacc    240

atcagcagcc tgcaggctga agatgtggca gtttattact gtcagcaata ttctaatact    300

cctcagacgt tcggccaagg gaccaaggtg gaaatcaaac ga                        342
```

<210> SEQ ID NO 41
<211> LENGTH: 342
<212> TYPE: DNA
<213> ORGANISM: Artificial Sequence
<220> FEATURE:
<223> OTHER INFORMATION: C-A05 VL

<400> SEQUENCE: 41

```
gacatcgtga tgacccagtc tccagactcc ctggctgtgt ctctgggcga gagggccacc     60

atcaactgca ggtccagcca gagtgtttta tgtcggtcca acaataagaa ctgcttagct    120

tggtaccagc agagaccagg acagcctcct aaactgctca tttattgggc atctattcgg    180

gaatccgggg tccctgaccg attcagtggc agcgggtctg ggacagattt cactctcacc    240

atcaacagcc tgcaggctga agatgtggca gtttattact gtcagcaata ttctaatact    300
```

cctcagacgt tcggccaagg gaccaaggtg gaaatcaaac ga 342

<210> SEQ ID NO 42
<211> LENGTH: 342
<212> TYPE: DNA
<213> ORGANISM: Artificial Sequence
<220> FEATURE:
<223> OTHER INFORMATION: C-D04 B VL

<400> SEQUENCE: 42
gacatcgtga tgacccagtc tccagactcc ctggctgtgt ctctgggcga gagggccacc 60
atcaactgca ggtccagcca gagtgtttta tgtcggtcca acaataagaa ctgcttagct 120
tggtaccagc agagaccagg acagcctcct aaactgctca tttattgggc atgtattcgg 180
gaatccgggg tccctgaccg attcagtggc agcgggtctg ggacagattt cactctcacc 240
atcagcagcc tgcaggctga agatgtggca gtttattact gtcagcaata ttctaatact 300
cctcagacgt tcggccaagg gaccaaggtg gaaatcaaac ga 342

<210> SEQ ID NO 43
<211> LENGTH: 342
<212> TYPE: DNA
<213> ORGANISM: Artificial Sequence
<220> FEATURE:
<223> OTHER INFORMATION: D-G05 VL

<400> SEQUENCE: 43
gacatcgtga tgacccagtc tccagactcc ctggctgtgt ctctgggcga gagggccacc 60
atcaactgca ggtccagcca gagtgtttta tgtcggtcca acaataagaa ctgcttaact 120
tggtaccagc agagaccagg acagcctcct aaactgctca tttattgggc atctattcgg 180
gaatccgggg tccctgaccg attcagtggc agcgggtctg ggacagattt cactctcacc 240
atcagcagcc tgcaggctga agatgtggca gtttattact gtcagcaata ttctaatact 300
cctcagacgt tcggccaagg gaccaaggtg gaaatcaaac ga 342

<210> SEQ ID NO 44
<211> LENGTH: 342
<212> TYPE: DNA
<213> ORGANISM: Artificial Sequence
<220> FEATURE:
<223> OTHER INFORMATION: E-C10 VL

<400> SEQUENCE: 44
gacatcgtga tgacccagtc tccagactcc ctggctgtgt ctctgggcga gagggccacc 60
atcaactgca ggtccagcca gagtgtttta tgtcggtcca acaataagaa ctgcttagct 120
tggtaccagc agagaccagg acagcctcct aaactgctca tttattgggc atctattcgg 180
gaatccgggg tccctgaccg attcagtggc agcgggtctg ggacacattt cactctcacc 240
atcagcagcc tgcaggctga agatgtggca gtttattact gtcagcaata ttctaatact 300
cctcagacgt tcggccaagg gaccaaggtg gaaatcaaac ga 342

<210> SEQ ID NO 45
<211> LENGTH: 882
<212> TYPE: PRT
<213> ORGANISM: Homo sapiens

<400> SEQUENCE: 45

Met Gly Pro Trp Ser Arg Ser Leu Ser Ala Leu Leu Leu Leu Leu Gln
1 5 10 15

```
Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430
```

-continued

```
Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
    530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Ile Asp Ala Asp Leu Pro Pro Asn Thr Ser
    610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Gly Glu Glu Asp Gln Asp Phe Asp
        755                 760                 765

Leu Ser Gln Leu His Arg Gly Leu Asp Ala Arg Pro Glu Val Thr Arg
    770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
```

```
    850                 855                 860

Trp Gly Asn Arg Phe Lys Lys Leu Ala Asp Met Tyr Gly Gly Gly Glu
865                 870                 875                 880

Asp Asp


<210> SEQ ID NO 46
<211> LENGTH: 27
<212> TYPE: PRT
<213> ORGANISM: Homo sapiens

<400> SEQUENCE: 46

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro
            20                  25


<210> SEQ ID NO 47
<211> LENGTH: 127
<212> TYPE: PRT
<213> ORGANISM: Homo sapiens

<400> SEQUENCE: 47

Cys His Pro Gly Phe Asp Ala Glu Ser Tyr Thr Phe Thr Val Pro Arg
1               5                   10                  15

Arg His Leu Glu Arg Gly Arg Val Leu Gly Arg Val Asn Phe Glu Asp
            20                  25                  30

Cys Thr Gly Arg Gln Arg Thr Ala Tyr Phe Ser Leu Asp Thr Arg Phe
        35                  40                  45

Lys Val Gly Thr Asp Gly Val Ile Thr Val Lys Arg Pro Leu Arg Phe
    50                  55                  60

His Asn Pro Gln Ile His Phe Leu Val Tyr Ala Trp Asp Ser Thr Tyr
65                  70                  75                  80

Arg Lys Phe Ser Thr Lys Val Thr Leu Asn Thr Val Gly His His His
                85                  90                  95

Arg Pro Pro Pro His Gln Ala Ser Val Ser Gly Ile Gln Ala Glu Leu
            100                 105                 110

Leu Thr Phe Pro Asn Ser Ser Pro Gly Leu Arg Arg Gln Lys Arg
        115                 120                 125


<210> SEQ ID NO 48
<211> LENGTH: 108
<212> TYPE: PRT
<213> ORGANISM: Homo sapiens

<400> SEQUENCE: 48

Asp Trp Val Ile Pro Pro Ile Ser Cys Pro Glu Asn Glu Lys Gly Pro
1               5                   10                  15

Phe Pro Lys Asn Leu Val Gln Ile Lys Ser Asn Lys Asp Lys Glu Gly
            20                  25                  30

Lys Val Phe Tyr Ser Ile Thr Gly Gln Gly Ala Asp Thr Pro Pro Val
        35                  40                  45

Gly Val Phe Ile Ile Glu Arg Glu Thr Gly Trp Leu Lys Val Thr Glu
    50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
                85                  90                  95
```

```
Thr Val Thr Asp Gln Asn Asp Asn Lys Pro Glu Phe
            100                 105


<210> SEQ ID NO 49
<211> LENGTH: 113
<212> TYPE: PRT
<213> ORGANISM: Homo sapiens

<400> SEQUENCE: 49

Thr Gln Glu Val Phe Lys Gly Ser Val Met Glu Gly Ala Leu Pro Gly
1               5                   10                  15

Thr Ser Val Met Glu Val Thr Ala Thr Asp Ala Asp Asp Asp Val Asn
            20                  25                  30

Thr Tyr Asn Ala Ala Ile Ala Tyr Thr Ile Leu Ser Gln Asp Pro Glu
        35                  40                  45

Leu Pro Asp Lys Asn Met Phe Thr Ile Asn Arg Asn Thr Gly Val Ile
    50                  55                  60

Ser Val Val Thr Thr Gly Leu Asp Arg Glu Ser Phe Pro Thr Tyr Thr
65                  70                  75                  80

Leu Val Val Gln Ala Ala Asp Leu Gln Gly Glu Gly Leu Ser Thr Thr
                85                  90                  95

Ala Thr Ala Val Ile Thr Val Thr Asp Thr Asn Asp Asn Pro Pro Ile
            100                 105                 110

Phe


<210> SEQ ID NO 50
<211> LENGTH: 111
<212> TYPE: PRT
<213> ORGANISM: Homo sapiens

<400> SEQUENCE: 50

Asn Pro Thr Thr Tyr Lys Gly Gln Val Pro Glu Asn Glu Ala Asn Val
1               5                   10                  15

Val Ile Thr Thr Leu Lys Val Thr Asp Ala Asp Ala Pro Asn Thr Pro
            20                  25                  30

Ala Trp Glu Ala Val Tyr Thr Ile Leu Asn Asp Asp Gly Gly Gln Phe
        35                  40                  45

Val Val Thr Thr Asn Pro Val Asn Asn Asp Gly Ile Leu Lys Thr Ala
    50                  55                  60

Lys Gly Leu Asp Phe Glu Ala Lys Gln Gln Tyr Ile Leu His Val Ala
65                  70                  75                  80

Val Thr Asn Val Val Pro Phe Glu Val Ser Leu Thr Thr Ser Thr Ala
                85                  90                  95

Thr Val Thr Val Asp Val Leu Asp Val Asn Glu Ala Pro Ile Phe
            100                 105                 110


<210> SEQ ID NO 51
<211> LENGTH: 109
<212> TYPE: PRT
<213> ORGANISM: Homo sapiens

<400> SEQUENCE: 51

Val Pro Pro Glu Lys Arg Val Glu Val Ser Glu Asp Phe Gly Val Gly
1               5                   10                  15

Gln Glu Ile Thr Ser Tyr Thr Ala Gln Glu Pro Asp Thr Phe Met Glu
            20                  25                  30

Gln Lys Ile Thr Tyr Arg Ile Trp Arg Asp Thr Ala Asn Trp Leu Glu
        35                  40                  45
```

```
Ile Asn Pro Asp Thr Gly Ala Ile Ser Thr Arg Ala Glu Leu Asp Arg
    50                  55                  60

Glu Asp Phe Glu His Val Lys Asn Ser Thr Tyr Thr Ala Leu Ile Ile
65                  70                  75                  80

Ala Thr Asp Asn Gly Ser Pro Val Ala Thr Gly Thr Gly Thr Leu Leu
                85                  90                  95

Leu Ile Leu Ser Asp Val Asn Asp Asn Ala Pro Ile Pro
            100                 105


<210> SEQ ID NO 52
<211> LENGTH: 110
<212> TYPE: PRT
<213> ORGANISM: Homo sapiens

<400> SEQUENCE: 52

Glu Pro Arg Thr Ile Phe Phe Cys Glu Arg Asn Pro Lys Pro Gln Val
1               5                   10                  15

Ile Asn Ile Ile Asp Ala Asp Leu Pro Pro Asn Thr Ser Pro Phe Thr
            20                  25                  30

Ala Glu Leu Thr His Gly Ala Ser Ala Asn Trp Thr Ile Gln Tyr Asn
        35                  40                  45

Asp Pro Thr Gln Glu Ser Ile Ile Leu Lys Pro Lys Met Ala Leu Glu
    50                  55                  60

Val Gly Asp Tyr Lys Ile Asn Leu Lys Leu Met Asp Asn Gln Asn Lys
65                  70                  75                  80

Asp Gln Val Thr Thr Leu Glu Val Ser Val Cys Asp Cys Glu Gly Ala
                85                  90                  95

Ala Gly Val Cys Arg Lys Ala Gln Pro Val Glu Ala Gly Leu
            100                 105                 110


<210> SEQ ID NO 53
<211> LENGTH: 26
<212> TYPE: PRT
<213> ORGANISM: Homo sapiens

<400> SEQUENCE: 53

Gln Ile Pro Ala Ile Leu Gly Ile Leu Gly Gly Ile Leu Ala Leu Leu
1               5                   10                  15

Ile Leu Ile Leu Leu Leu Leu Leu Phe Leu
            20                  25


<210> SEQ ID NO 54
<211> LENGTH: 71
<212> TYPE: PRT
<213> ORGANISM: Homo sapiens

<400> SEQUENCE: 54

Arg Arg Arg Ala Val Val Lys Glu Pro Leu Leu Pro Pro Glu Asp Asp
1               5                   10                  15

Thr Arg Asp Asn Val Tyr Tyr Tyr Asp Glu Glu Gly Gly Gly Glu Glu
            20                  25                  30

Asp Gln Asp Phe Asp Leu Ser Gln Leu His Arg Gly Leu Asp Ala Arg
        35                  40                  45

Pro Glu Val Thr Arg Asn Asp Val Ala Pro Thr Leu Met Ser Val Pro
    50                  55                  60

Arg Tyr Leu Pro Arg Pro Ala
65                  70
```

<210> SEQ ID NO 55
<211> LENGTH: 80
<212> TYPE: PRT
<213> ORGANISM: Homo sapiens

<400> SEQUENCE: 55

```
Asn Pro Asp Glu Ile Gly Asn Phe Ile Asp Glu Asn Leu Lys Ala Ala
1               5                   10                  15

Asp Thr Asp Pro Thr Ala Pro Pro Tyr Asp Ser Leu Leu Val Phe Asp
            20                  25                  30

Tyr Glu Gly Ser Gly Ser Glu Ala Ala Ser Leu Ser Ser Leu Asn Ser
        35                  40                  45

Ser Glu Ser Asp Lys Asp Gln Asp Tyr Asp Tyr Leu Asn Glu Trp Gly
    50                  55                  60

Asn Arg Phe Lys Lys Leu Ala Asp Met Tyr Gly Gly Gly Glu Asp Asp
65                  70                  75                  80
```

<210> SEQ ID NO 56
<211> LENGTH: 420
<212> TYPE: PRT
<213> ORGANISM: Homo sapiens

<400> SEQUENCE: 56

```
Glu Val Ser Leu Thr Thr Ser Thr Ala Thr Val Thr Val Asp Val Leu
1               5                   10                  15

Asp Val Asn Glu Ala Pro Ile Phe Val Pro Pro Glu Lys Arg Val Glu
            20                  25                  30

Val Ser Glu Asp Phe Gly Val Gly Gln Glu Ile Thr Ser Tyr Thr Ala
        35                  40                  45

Gln Glu Pro Asp Thr Phe Met Glu Gln Lys Ile Thr Tyr Arg Ile Trp
    50                  55                  60

Arg Asp Thr Ala Asn Trp Leu Glu Ile Asn Pro Asp Thr Gly Ala Ile
65                  70                  75                  80

Ser Thr Arg Ala Glu Leu Asp Arg Glu Asp Phe Glu His Val Lys Asn
                85                  90                  95

Ser Thr Tyr Thr Ala Leu Ile Ile Ala Thr Asp Asn Gly Ser Pro Val
            100                 105                 110

Ala Thr Gly Thr Gly Thr Leu Leu Leu Ile Leu Ser Asp Val Asn Asp
        115                 120                 125

Asn Ala Pro Ile Pro Glu Pro Arg Thr Ile Phe Phe Cys Glu Arg Asn
    130                 135                 140

Pro Lys Pro Gln Val Ile Asn Ile Ile Asp Ala Asp Leu Pro Pro Asn
145                 150                 155                 160

Thr Ser Pro Phe Thr Ala Glu Leu Thr His Gly Ala Ser Ala Asn Trp
                165                 170                 175

Thr Ile Gln Tyr Asn Asp Pro Thr Gln Glu Ser Ile Ile Leu Lys Pro
            180                 185                 190

Lys Met Ala Leu Glu Val Gly Asp Tyr Lys Ile Asn Leu Lys Leu Met
        195                 200                 205

Asp Asn Gln Asn Lys Asp Gln Val Thr Thr Leu Glu Val Ser Val Cys
    210                 215                 220

Asp Cys Glu Gly Ala Ala Gly Val Cys Arg Lys Ala Gln Pro Val Glu
225                 230                 235                 240

Ala Gly Leu Gln Ile Pro Ala Ile Leu Gly Ile Leu Gly Gly Ile Leu
                245                 250                 255
```

-continued

```
Ala Leu Leu Ile Leu Ile Leu Leu Leu Leu Leu Phe Leu Arg Arg Arg
            260                 265                 270

Ala Val Val Lys Glu Pro Leu Leu Pro Pro Glu Asp Asp Thr Arg Asp
        275                 280                 285

Asn Val Tyr Tyr Tyr Asp Glu Glu Gly Gly Gly Glu Glu Asp Gln Asp
    290                 295                 300

Phe Asp Leu Ser Gln Leu His Arg Gly Leu Asp Ala Arg Pro Glu Val
305                 310                 315                 320

Thr Arg Asn Asp Val Ala Pro Thr Leu Met Ser Val Pro Arg Tyr Leu
                325                 330                 335

Pro Arg Pro Ala Asn Pro Asp Glu Ile Gly Asn Phe Ile Asp Glu Asn
            340                 345                 350

Leu Lys Ala Ala Asp Thr Asp Pro Thr Ala Pro Pro Tyr Asp Ser Leu
        355                 360                 365

Leu Val Phe Asp Tyr Glu Gly Ser Gly Ser Glu Ala Ala Ser Leu Ser
    370                 375                 380

Ser Leu Asn Ser Ser Glu Ser Asp Lys Asp Gln Asp Tyr Asp Tyr Leu
385                 390                 395                 400

Asn Glu Trp Gly Asn Arg Phe Lys Lys Leu Ala Asp Met Tyr Gly Gly
                405                 410                 415

Gly Glu Asp Asp
            420


<210> SEQ ID NO 57
<211> LENGTH: 15
<212> TYPE: PRT
<213> ORGANISM: Artificial Sequence
<220> FEATURE:
<223> OTHER INFORMATION: truncated D3 domain

<400> SEQUENCE: 57

Glu Val Ser Leu Thr Thr Ser Thr Ala Thr Val Thr Val Asp Val
1               5                   10                  15


<210> SEQ ID NO 58
<211> LENGTH: 19
<212> TYPE: PRT
<213> ORGANISM: Artificial Sequence
<220> FEATURE:
<223> OTHER INFORMATION: D3 protein variant

<400> SEQUENCE: 58

Glu Val Ser Leu Thr Thr Ser Thr Ala Thr Val Thr Val Asp Val Leu
1               5                   10                  15

Asp Val Asn


<210> SEQ ID NO 59
<211> LENGTH: 8
<212> TYPE: PRT
<213> ORGANISM: Artificial Sequence
<220> FEATURE:
<223> OTHER INFORMATION: CDR1
<220> FEATURE:
<221> NAME/KEY: MISC_FEATURE
<222> LOCATION: (3)..(3)
<223> OTHER INFORMATION: X is T or I
<220> FEATURE:
<221> NAME/KEY: MISC_FEATURE
<222> LOCATION: (6)..(6)
<223> OTHER INFORMATION: X is N or Y

<400> SEQUENCE: 59
```

Gly Phe Xaa Phe Ser Xaa Ala Trp
1 5

<210> SEQ ID NO 60
<211> LENGTH: 10
<212> TYPE: PRT
<213> ORGANISM: Artificial Sequence
<220> FEATURE:
<223> OTHER INFORMATION: CDR2
<220> FEATURE:
<221> NAME/KEY: MISC_FEATURE
<222> LOCATION: (8)..(8)
<223> OTHER INFORMATION: X is G or E
<220> FEATURE:
<221> NAME/KEY: MISC_FEATURE
<222> LOCATION: (10)..(10)
<223> OTHER INFORMATION: X is T or I

<400> SEQUENCE: 60

Ile Lys Ser Lys Ile Asp Gly Xaa Thr Xaa
1 5 10

<210> SEQ ID NO 61
<211> LENGTH: 14
<212> TYPE: PRT
<213> ORGANISM: Artificial Sequence
<220> FEATURE:
<223> OTHER INFORMATION: CDR3
<220> FEATURE:
<221> NAME/KEY: MISC_FEATURE
<222> LOCATION: (6)..(6)
<223> OTHER INFORMATION: X is A or T
<220> FEATURE:
<221> NAME/KEY: MISC_FEATURE
<222> LOCATION: (8)..(8)
<223> OTHER INFORMATION: X is D or N

<400> SEQUENCE: 61

Thr Pro Gly Val Gly Xaa Asn Xaa Pro Tyr Tyr Phe Asp Arg
1 5 10

<210> SEQ ID NO 62
<211> LENGTH: 12
<212> TYPE: PRT
<213> ORGANISM: Artificial Sequence
<220> FEATURE:
<223> OTHER INFORMATION: CDR1

<400> SEQUENCE: 62

Gln Ser Val Leu Cys Arg Ser Asn Asn Lys Asn Cys
1 5 10

<210> SEQ ID NO 63
<211> LENGTH: 9
<212> TYPE: PRT
<213> ORGANISM: Artificial Sequence
<220> FEATURE:
<223> OTHER INFORMATION: CDR3

<400> SEQUENCE: 63

Gln Gln Tyr Ser Asn Thr Pro Gln Thr
1 5

<210> SEQ ID NO 64
<211> LENGTH: 4
<212> TYPE: PRT
<213> ORGANISM: Artificial Sequence
<220> FEATURE:
<223> OTHER INFORMATION: Ab seq

<400> SEQUENCE: 64

Thr Thr Ser Thr
1

<210> SEQ ID NO 65
<211> LENGTH: 5
<212> TYPE: PRT
<213> ORGANISM: Artificial Sequence
<220> FEATURE:
<223> OTHER INFORMATION: ab seq

<400> SEQUENCE: 65

Ser Thr Thr Ser Thr
1 5

<210> SEQ ID NO 66
<211> LENGTH: 6
<212> TYPE: PRT
<213> ORGANISM: Artificial Sequence
<220> FEATURE:
<223> OTHER INFORMATION: ab seq

<400> SEQUENCE: 66

Ser Thr Thr Ser Thr Thr
1 5

<210> SEQ ID NO 67
<211> LENGTH: 7
<212> TYPE: PRT
<213> ORGANISM: Artificial Sequence
<220> FEATURE:
<223> OTHER INFORMATION: ab seq

<400> SEQUENCE: 67

Glu Ser Thr Thr Ser Thr Thr
1 5

<210> SEQ ID NO 68
<211> LENGTH: 8
<212> TYPE: PRT
<213> ORGANISM: Artificial Sequence
<220> FEATURE:
<223> OTHER INFORMATION: ab seq

<400> SEQUENCE: 68

Glu Ser Thr Thr Ser Thr Thr Val
1 5

<210> SEQ ID NO 69
<211> LENGTH: 8
<212> TYPE: PRT
<213> ORGANISM: Artificial Sequence
<220> FEATURE:
<223> OTHER INFORMATION: CDR1

<400> SEQUENCE: 69

Gly Phe Thr Phe Ser Asn Ala Trp
1 5

<210> SEQ ID NO 70
<211> LENGTH: 10
<212> TYPE: PRT
<213> ORGANISM: Artificial Sequence
<220> FEATURE:
<223> OTHER INFORMATION: CDR2

<400> SEQUENCE: 70

Ile Lys Ser Lys Ile Asp Gly Gly Thr Thr
1 5 10

<210> SEQ ID NO 71
<211> LENGTH: 14
<212> TYPE: PRT
<213> ORGANISM: Artificial Sequence
<220> FEATURE:
<223> OTHER INFORMATION: CDR3

<400> SEQUENCE: 71

Thr Pro Gly Val Gly Ala Asn Asp Pro Tyr Tyr Phe Asp Arg
1 5 10

<210> SEQ ID NO 72
<211> LENGTH: 8
<212> TYPE: PRT
<213> ORGANISM: Artificial Sequence
<220> FEATURE:
<223> OTHER INFORMATION: CDR1

<400> SEQUENCE: 72

Gly Phe Ile Phe Ser Asn Ala Trp
1 5

<210> SEQ ID NO 73
<211> LENGTH: 10
<212> TYPE: PRT
<213> ORGANISM: Artificial Sequence
<220> FEATURE:
<223> OTHER INFORMATION: CDR2

<400> SEQUENCE: 73

Ile Lys Ser Lys Ile Asp Gly Gly Thr Thr
1 5 10

<210> SEQ ID NO 74
<211> LENGTH: 14
<212> TYPE: PRT
<213> ORGANISM: Artificial Sequence
<220> FEATURE:
<223> OTHER INFORMATION: CDR3

<400> SEQUENCE: 74

Thr Pro Gly Val Gly Ala Asn Asp Pro Tyr Tyr Phe Asp Arg
1 5 10

<210> SEQ ID NO 75
<211> LENGTH: 8
<212> TYPE: PRT
<213> ORGANISM: Artificial Sequence
<220> FEATURE:
<223> OTHER INFORMATION: CDR1

<400> SEQUENCE: 75

Gly Phe Ile Phe Ser Asn Ala Trp
1 5

<210> SEQ ID NO 76
<211> LENGTH: 10
<212> TYPE: PRT
<213> ORGANISM: Artificial Sequence
<220> FEATURE:
<223> OTHER INFORMATION: CDR2

<400> SEQUENCE: 76

Ile Lys Ser Lys Ile Asp Gly Glu Thr Thr
1 5 10

<210> SEQ ID NO 77
<211> LENGTH: 14
<212> TYPE: PRT
<213> ORGANISM: Artificial Sequence
<220> FEATURE:
<223> OTHER INFORMATION: CDR3

<400> SEQUENCE: 77

Thr Pro Gly Val Gly Ala Asn Asp Pro Tyr Tyr Phe Asp Arg
1 5 10

<210> SEQ ID NO 78
<211> LENGTH: 8
<212> TYPE: PRT
<213> ORGANISM: Artificial Sequence
<220> FEATURE:
<223> OTHER INFORMATION: CDR1

<400> SEQUENCE: 78

Gly Phe Thr Phe Ser Asn Ala Trp
1 5

<210> SEQ ID NO 79
<211> LENGTH: 10
<212> TYPE: PRT
<213> ORGANISM: Artificial Sequence
<220> FEATURE:
<223> OTHER INFORMATION: CDR2

<400> SEQUENCE: 79

Ile Lys Ser Lys Ile Asp Gly Glu Thr Thr
1 5 10

<210> SEQ ID NO 80
<211> LENGTH: 14
<212> TYPE: PRT
<213> ORGANISM: Artificial Sequence
<220> FEATURE:
<223> OTHER INFORMATION: CDR3

<400> SEQUENCE: 80

Thr Pro Gly Val Gly Ala Asn Asp Pro Tyr Tyr Phe Asp Arg
1 5 10

<210> SEQ ID NO 81
<211> LENGTH: 8
<212> TYPE: PRT
<213> ORGANISM: Artificial Sequence
<220> FEATURE:
<223> OTHER INFORMATION: CDR1

<400> SEQUENCE: 81

Gly Phe Thr Phe Ser Asn Ala Trp
1 5

<210> SEQ ID NO 82
<211> LENGTH: 10
<212> TYPE: PRT
<213> ORGANISM: Artificial Sequence
<220> FEATURE:
<223> OTHER INFORMATION: CDR2

<400> SEQUENCE: 82

Ile Lys Ser Lys Ile Asp Gly Glu Thr Thr 1 5 10

<210> SEQ ID NO 83
<211> LENGTH: 14
<212> TYPE: PRT
<213> ORGANISM: Artificial Sequence
<220> FEATURE:
<223> OTHER INFORMATION: CDR3

<400> SEQUENCE: 83

Thr Pro Gly Val Gly Ala Asn Asn Pro Tyr Tyr Phe Asp Arg
1 5 10

<210> SEQ ID NO 84
<211> LENGTH: 8
<212> TYPE: PRT
<213> ORGANISM: Artificial Sequence
<220> FEATURE:
<223> OTHER INFORMATION: CDR1

<400> SEQUENCE: 84

Gly Phe Thr Phe Ser Asn Ala Trp
1 5

<210> SEQ ID NO 85
<211> LENGTH: 10
<212> TYPE: PRT
<213> ORGANISM: Artificial Sequence
<220> FEATURE:
<223> OTHER INFORMATION: CDR2

<400> SEQUENCE: 85

Ile Lys Ser Lys Ile Asp Gly Glu Thr Thr
1 5 10

<210> SEQ ID NO 86
<211> LENGTH: 14
<212> TYPE: PRT
<213> ORGANISM: Artificial Sequence
<220> FEATURE:
<223> OTHER INFORMATION: CDR3

<400> SEQUENCE: 86

Thr Pro Gly Val Gly Ala Asn Asn Pro Tyr Tyr Phe Asp Arg
1 5 10

<210> SEQ ID NO 87
<211> LENGTH: 8
<212> TYPE: PRT
<213> ORGANISM: Artificial Sequence
<220> FEATURE:
<223> OTHER INFORMATION: CDR1

<400> SEQUENCE: 87

Gly Phe Thr Phe Ser Asn Ala Trp
1 5

<210> SEQ ID NO 88
<211> LENGTH: 10
<212> TYPE: PRT
<213> ORGANISM: Artificial Sequence
<220> FEATURE:
<223> OTHER INFORMATION: CDR2

<400> SEQUENCE: 88

Ile Lys Ser Lys Ile Asp Gly Gly Thr Thr
1 5 10

<210> SEQ ID NO 89
<211> LENGTH: 14
<212> TYPE: PRT
<213> ORGANISM: Artificial Sequence
<220> FEATURE:
<223> OTHER INFORMATION: CDR3

<400> SEQUENCE: 89

```
Thr Pro Gly Val Gly Ala Asn Asn Pro Tyr Tyr Phe Asp Arg
1               5                   10
```

<210> SEQ ID NO 90
<211> LENGTH: 8
<212> TYPE: PRT
<213> ORGANISM: Artificial Sequence
<220> FEATURE:
<223> OTHER INFORMATION: CDR1

<400> SEQUENCE: 90

```
Gly Phe Thr Phe Ser Asn Ala Trp
1               5
```

<210> SEQ ID NO 91
<211> LENGTH: 10
<212> TYPE: PRT
<213> ORGANISM: Artificial Sequence
<220> FEATURE:
<223> OTHER INFORMATION: CDR2

<400> SEQUENCE: 91

```
Ile Lys Ser Lys Ile Asp Gly Gly Thr Thr
1               5                   10
```

<210> SEQ ID NO 92
<211> LENGTH: 14
<212> TYPE: PRT
<213> ORGANISM: Artificial Sequence
<220> FEATURE:
<223> OTHER INFORMATION: CDR3

<400> SEQUENCE: 92

```
Thr Pro Gly Val Gly Thr Asn Asn Pro Tyr Tyr Phe Asp Arg
1               5                   10
```

<210> SEQ ID NO 93
<211> LENGTH: 8
<212> TYPE: PRT
<213> ORGANISM: Artificial Sequence
<220> FEATURE:
<223> OTHER INFORMATION: CDR1

<400> SEQUENCE: 93

```
Gly Phe Thr Phe Ser Tyr Ala Trp
1               5
```

<210> SEQ ID NO 94
<211> LENGTH: 10
<212> TYPE: PRT
<213> ORGANISM: Artificial Sequence
<220> FEATURE:
<223> OTHER INFORMATION: CDR2

<400> SEQUENCE: 94

```
Ile Lys Ser Lys Ile Asp Gly Gly Thr Thr
1               5                   10
```

<210> SEQ ID NO 95
<211> LENGTH: 14
<212> TYPE: PRT
<213> ORGANISM: Artificial Sequence
<220> FEATURE:
<223> OTHER INFORMATION: CDR3

<400> SEQUENCE: 95

Thr Pro Gly Val Gly Ala Asn Asp Pro Tyr Tyr Phe Asp Arg
1 5 10

<210> SEQ ID NO 96
<211> LENGTH: 8
<212> TYPE: PRT
<213> ORGANISM: Artificial Sequence
<220> FEATURE:
<223> OTHER INFORMATION: CDR1

<400> SEQUENCE: 96

Gly Phe Thr Phe Ser Asn Ala Trp
1 5

<210> SEQ ID NO 97
<211> LENGTH: 10
<212> TYPE: PRT
<213> ORGANISM: Artificial Sequence
<220> FEATURE:
<223> OTHER INFORMATION: CDR2

<400> SEQUENCE: 97

Ile Lys Ser Lys Ile Asp Gly Gly Thr Ile
1 5 10

<210> SEQ ID NO 98
<211> LENGTH: 14
<212> TYPE: PRT
<213> ORGANISM: Artificial Sequence
<220> FEATURE:
<223> OTHER INFORMATION: CDR3

<400> SEQUENCE: 98

Thr Pro Gly Val Gly Ala Asn Asp Pro Tyr Tyr Phe Asp Arg
1 5 10

<210> SEQ ID NO 99
<211> LENGTH: 8
<212> TYPE: PRT
<213> ORGANISM: Artificial Sequence
<220> FEATURE:
<223> OTHER INFORMATION: CDR1

<400> SEQUENCE: 99

Gly Phe Thr Phe Ser Tyr Ala Trp
1 5

<210> SEQ ID NO 100
<211> LENGTH: 10
<212> TYPE: PRT
<213> ORGANISM: Artificial Sequence
<220> FEATURE:
<223> OTHER INFORMATION: CDR2

<400> SEQUENCE: 100

Ile Lys Ser Lys Ile Asp Gly Gly Thr Thr
1 5 10

<210> SEQ ID NO 101
<211> LENGTH: 14
<212> TYPE: PRT
<213> ORGANISM: Artificial Sequence
<220> FEATURE:
<223> OTHER INFORMATION: CDR3

<400> SEQUENCE: 101

Thr Pro Gly Val Gly Ala Asn Asn Pro Tyr Tyr Phe Asp Arg
1 5 10

<210> SEQ ID NO 102
<211> LENGTH: 8
<212> TYPE: PRT
<213> ORGANISM: Artificial Sequence
<220> FEATURE:
<223> OTHER INFORMATION: CDR1

<400> SEQUENCE: 102

Gly Phe Ile Phe Ser Tyr Ala Trp
1 5

<210> SEQ ID NO 103
<211> LENGTH: 10
<212> TYPE: PRT
<213> ORGANISM: Artificial Sequence
<220> FEATURE:
<223> OTHER INFORMATION: CDR2

<400> SEQUENCE: 103

Ile Lys Ser Lys Ile Asp Gly Gly Thr Thr
1 5 10

<210> SEQ ID NO 104
<211> LENGTH: 14
<212> TYPE: PRT
<213> ORGANISM: Artificial Sequence
<220> FEATURE:
<223> OTHER INFORMATION: CDR3

<400> SEQUENCE: 104

Thr Pro Gly Val Gly Ala Asn Asn Pro Tyr Tyr Phe Asp Arg
1 5 10

<210> SEQ ID NO 105
<211> LENGTH: 8
<212> TYPE: PRT
<213> ORGANISM: Artificial Sequence
<220> FEATURE:
<223> OTHER INFORMATION: CDR1

<400> SEQUENCE: 105

Gly Phe Ile Phe Ser Tyr Ala Trp
1 5

<210> SEQ ID NO 106
<211> LENGTH: 10
<212> TYPE: PRT
<213> ORGANISM: Artificial Sequence
<220> FEATURE:
<223> OTHER INFORMATION: CDR2

<400> SEQUENCE: 106

Ile Lys Ser Lys Ile Asp Gly Glu Thr Thr
1 5 10

<210> SEQ ID NO 107

<211> LENGTH: 14
<212> TYPE: PRT
<213> ORGANISM: Artificial Sequence
<220> FEATURE:
<223> OTHER INFORMATION: CDR3

<400> SEQUENCE: 107

Thr Pro Gly Val Gly Ala Asn Asn Pro Tyr Tyr Phe Asp Arg
1 5 10

<210> SEQ ID NO 108
<211> LENGTH: 6
<212> TYPE: PRT
<213> ORGANISM: Artificial Sequence
<220> FEATURE:
<223> OTHER INFORMATION: sortase recognition site

<400> SEQUENCE: 108

Leu Pro Glu Thr Gly Gly
1 5

<210> SEQ ID NO 109
<211> LENGTH: 5
<212> TYPE: PRT
<213> ORGANISM: Artificial Sequence
<220> FEATURE:
<223> OTHER INFORMATION: seq

<400> SEQUENCE: 109

Gly Gly Gly Gly Ser
1 5

<210> SEQ ID NO 110
<211> LENGTH: 24
<212> TYPE: PRT
<213> ORGANISM: Artificial Sequence
<220> FEATURE:
<223> OTHER INFORMATION: trunc D3 domain

<400> SEQUENCE: 110

Glu Val Ser Leu Thr Thr Ser Thr Ala Thr Val Thr Val Asp Val Leu
1 5 10 15

Asp Val Asn Glu Ala Pro Ile Phe
20

<210> SEQ ID NO 111
<211> LENGTH: 22
<212> TYPE: DNA
<213> ORGANISM: Artificial Sequence
<220> FEATURE:
<223> OTHER INFORMATION: last coding exon

<400> SEQUENCE: 111
aggagacatt ctgatgaatc aa 22

<210> SEQ ID NO 112
<211> LENGTH: 21
<212> TYPE: DNA
<213> ORGANISM: Artificial Sequence
<220> FEATURE:
<223> OTHER INFORMATION: fw primer

<400> SEQUENCE: 112
ggtgtggtta ctgcctgcta t 21

<210> SEQ ID NO 113

-continued

```
<211> LENGTH: 20
<212> TYPE: DNA
<213> ORGANISM: Artificial Sequence
<220> FEATURE:
<223> OTHER INFORMATION: rv primer

<400> SEQUENCE: 113

ggacggtaag acttgtggct                                          20


<210> SEQ ID NO 114
<211> LENGTH: 17
<212> TYPE: PRT
<213> ORGANISM: Artificial Sequence
<220> FEATURE:
<223> OTHER INFORMATION: ST-tag

<400> SEQUENCE: 114

Gly Gly Gly Gly Ser Leu Pro Glu Thr Gly Gly His His His His His
1               5                   10                  15

His
```